US008071751B2

(12) United States Patent
Delwart et al.

(10) Patent No.: US 8,071,751 B2
(45) Date of Patent: Dec. 6, 2011

(54) HUMAN PARVOVIRUS: BOCAVIRUS

(75) Inventors: Eric Delwart, San Francisco, CA (US); Amit Kapoor, Pacifica, CA (US)

(73) Assignee: Blood Systems, Inc., Scottsdale, AZ (US)

( * ) Notice: Subject to any disclaimer, the term of this patent is extended or adjusted under 35 U.S.C. 154(b) by 0 days.

(21) Appl. No.: 12/426,173

(22) Filed: Apr. 17, 2009

(65) Prior Publication Data

US 2009/0297557 A1    Dec. 3, 2009

Related U.S. Application Data

(60) Provisional application No. 61/045,926, filed on Apr. 17, 2008.

(51) Int. Cl.
  *C07H 21/04*    (2006.01)
  *C12P 19/34*    (2006.01)
(52) U.S. Cl. .................................. 536/24.32; 435/91.2
(58) Field of Classification Search ........................ None
  See application file for complete search history.

(56) References Cited

U.S. PATENT DOCUMENTS

2007/0160983 A1    7/2007    Paul et al.
2008/0053205 A1    3/2008    Pollack et al.

FOREIGN PATENT DOCUMENTS

WO    WO 2007/057062 A1    5/2007
WO    WO2007057062    *    5/2007

OTHER PUBLICATIONS

Human bocavirus 2 strain W153, complete genome GenBank EU0822131, 2009.*
Hernandez J. Virol, 2000, vol. 74(9), pp. 4220-4228.*
International Search Report from WO 2009/117615 A3, Dec. 30, 2009, Blood Systems, Inc.
Allander et al., "A virus discovery method incorporating DNase treatment and its application to the identification of two bovine parvovirus species", *Proc. Natl. Acad. Sci. U.S.A.*, 98(20):11609-11614 (2001).
Allander et al., "Cloning of a human parvovirus by molecular screening of respiratory tract samples", *Proc. Natl. Acad. Sci. U.S.A.*, 102(36):12891-12896 (2005).
Breitbart et al., "Genomic analysis of uncultured marine viral communities", *Proc. Natl. Acad. Sci. U.S.A.*, 99(22):14250-14255 (2002).
Breitbart et al., "Metagenomic analyses of an uncultured viral community from human feces", *J Bacteriol.*, 185(20):6220-6223 (2003).
Cox-Foster et al., "A metagenomic survey of microbes in honey bee colony collapse disorder", *Science* (New York, N. Y.), 318(5848):283-287 (2007).
Culley et al., "High diversity of unknown picorna-like viruses in the sea", *Nature*, 424(6952):1054-1057 (2003).
Duke et al., "Sequence and structural elements that contribute to efficient encephalomyocarditis virus RNA translation", *J Virol.*, 66(3):1602-1609 (1992).

Edwards & Rohwer, "Viral metagenomics", *Nat. Rev. Microbiol*., 3(6):504-510 (2005).
Fauquet et al., "Virus taxonomy", *8th reports of the International Committee on Taxonomy of Viruses (Academic Press)*, p. 1162 (2005).
Feng et al., "Clonal integration of a polyomavirus in human Merkel cell carcinoma", *Science* (New York, N. Y.), 319(5866):1096-1100 (2008).
Finkbeiner et al., "Metagenomic analysis of human diarrhea: viral detection and discovery", *PLoS Pathogens*, 4(2):e 1000011 (2008).
GenBank: DQ401688.1. Theiler's encephalomyelitis virus, complete genome (Mar. 2, 2007). Retrieved from the Internet Aug. 17, 2009 at:<http://www.ncbi.nlm.nih.gov/nuccore/89280778> (nucleotides 5192-5206; 6924-6939; 7227-7239; 7304-7317).
Hales et al., "Complete genome sequence analysis of Seneca Valley virus-001, a novel oncolytic picornavirus", *The Journal of General Virology*, 89(Pt 5):1265-1275 (2008).
Hellen & de Breyne, "A distinct group of hepacivirus/pestivirus-like internal ribosomal entry sites in members of diverse picornavirus genera: evidence for modular exchange of functional noncoding RNA elements by recombination", *J. Virol.*, 81(11):5850-5863 (2007).
Hinton & Crabb, "The novel picornavirus Equine rhinitis B virus contains a strong type U internal ribosomal entry site which functions similarly to that of Encephalomyocarditis virus", *The Journal of general virology*, 82(Pt 9):2257-2269 (2001).
Hinton et al., "Internal ribosomal entry site-mediated translation initiation in equine rhinitis A virus: similarities to and differences from that of foot-and-mouth disease virus", *J. Virol.*, 74(24):11708-11716 (2000).
Holtz et al., "Identification of a novel picornavirus related to cosaviruses in a child with acute diarrhea", *Virology Journal*, 2008, 5:159 (http://www.virologyj.com/content/5/1/159).
Jones et al., "New DNA viruses identified in patients with acute viral infection syndrome", *J. Virol.*, 79(13):8230-8236 (2005).
Jones et al., "Discovery of a novel human picornavirus in a stool sample from a pediatric patient presenting with fever of unknown origin", *Journal of Clinical Microbiology*, 45(7):2144-2150 (2007).
Kapoor et al., "A highly divergent picornavirus in a marine mammal", *J. Virol.*, 82(1):311-320 (2008).
Kapoor et al., "A highly prevalent and genetically diversified Picornaviridae genus in South Asian children", *Proc. Natl. Acad. Sci. U.S.A.*, 105(51):20482-20487 (2008).
Kistler et al., "Pan-viral screening of respiratory tract infections in adults with and without asthma reveals unexpected human coronavirus and human rhinovirus diversity", *The Journal of Infectious Diseases*, 196(6):817-825 (2007).
Koonin & Dolja, "Evolution and taxonomy of positive-strand RNA viruses: implications of comparative analysis of amino acid sequences", *Crit. Rev. Biochem. Mol. Biol.*, 28(5):375-430 (1993).
Kozak M., "Point mutations define a sequence flanking the AUG initiator codon that modulates translation by eukaryotic ribosomes", *Cell*, 44(2):283-292 (1986).

(Continued)

*Primary Examiner* — Bao Li
(74) *Attorney, Agent, or Firm* — DLA Piper LLP (US)

(57) ABSTRACT

Provided herein are sequences of the genomes and encoded proteins of a new human parvovirus, Bocavirus-2, and variants thereof. Also provided are methods of detecting the Bocavirus-2 and diagnosing Bocavirus-2 infection, methods of treating or preventing Bocavirus-2 infection, and methods for identifying anti-Bocavirus-2 compounds.

11 Claims, 57 Drawing Sheets

OTHER PUBLICATIONS

Lamson et al., "MassTag polymerase-chain-reaction detection of respiratory pathogens, including a new rhinovirus genotype, that caused influenza-like illness in New York State during 2004-2005", *The Journal of Infectious Diseases*, 194(10):1398-1402 (2006).

Lopez de Quinto & Martinez-Salas, "Interaction of the eIF4G initiation factor with the aphthovirus IRES is essential for internal translation initiation in vivo", *RNA* (New York, N.Y.), 6(10):1380-1392 (2000).

Martinez-Salas et al., "New insights into internal ribosome entry site elements relevant for viral gene expression", *The Journal of General Virology*, 89(Pt 3):611-626 (2008).

Mason et al., "Identification and characterization of a cis-acting replication element (cre) adjacent to the internal ribosome entry site of foot-and-mouth disease virus", *J. Virol.*, 76(19):9686-9694 (2002).

Modlin J.F., "Enterovirus déjà vu", *The New England Journal of Medicine*, 356(12):1204-1205 (2007).

Morens & Pallansch, "Human enterovirus infections", *Epidemiology*, ed Rotbart HA (ASM Press, Washington, D.C.), pp. 3-23 (1995).

Oberste et al., "Molecular evolution of the human enteroviruses: correlation of serotype with VP1 sequence and application to picornavirus classification", *J. Virol.*, 73(3):1941-1948 (1999).

Palacios et al., "A new arenavirus in a cluster of fatal transplant-associated diseases", *The New England Journal of Medicine*, 358(10):991-998 (2008).

Pallansch & Roos, "Enteroviruses: polioviruses, coxsackieviruses, echoviruses, and newer enteroviruses", *Fields Virology* (*Lippincott Williams and Wilkins*, Philadelphia, PA) 4th Ed. pp. 723-775 (2001).

Saeed et al., "Epidemiology and clinical findings associated with enteroviral acute flaccid paralysis in Pakistan", *BMC Infectious Diseases*, 7:6 (2007).

Saleh et al., "Functional interaction of translation initiation factor eIF4G with the foot-and-mouth disease virus internal ribosome entry site", *The Journal of General Virology*, 82(Pt 4):757-763 (2001).

Simmonds et al, "Detection of genome-scale ordered RNA structure (GORS) in genomes of positive-stranded RNA viruses: Implications for virus evolution and host persistence", *RNA* (New York, N.Y.), 10(9):1337-1351 (2004).

Solomon & Willison, "Infectious causes of acute flaccid paralysis", *Current Opinion in Infectious Diseases*, 16(5):375-381 (2003).

Strikas et al., "Temporal and geographic patterns of isolates of nonpolio enterovirus in the United States, 1970-1983", *The Journal of Infectious Diseases*, 153(2):346-351 (1986).

van den Hoogen et al., "A newly discovered human pneumovirus isolated from young children with respiratory tract disease", *Nat. Med.*, 7(6):719-724 (2001).

van Der Hoek et al., "Identification of a new human coronavirus", *Nat. Med.*, 10(4):368-373 (2004).

Welch et al., "Detection of enterovirus viraemia in blood donors", *Vox Sanguinis*, 80(4):211-215 (2001).

Witso et al., "High prevalence of human enterovirus a infections in natural circulation of human enteroviruses", *Journal of Clinical Microbiology*, 44(11):4095-4100 (2006).

Zhang et al, "RNA Viral Community in Human Feces: Prevalence of Plant Pathogenic Viruses", *PLoS Biology*, 4(I):e3 (2005).

\* cited by examiner

>HBoV2A-PK5510
GGAGTGGCTACGTATGGGGTGATCATAAACACGCCCAGGAAGTGACGTATGTCAACCAATCAGCATCG
AGCATATATCCT
ATATAAGCCGATGCACTYCCGCATCTCGTCAGACTGCATCCGGTCTCCGGCGAGTGAACATCTCTGGG
AAGAGCTCCACG
CACGTGGTGAGTGACACTATGGCCTTTTCTGCTCCTGTAATTAGAGCTTTTTCTCAACCTGCTTTTAC
TTATGTTGTTAA
ATTTCCATATGAAAACTGGAAAGAGGAAGAGCACTTACTATGGAGCTTACTTGCTCCTGGGACTGAAC
GTCTCATGATTC
AACTAAGAAACTGCGCACCACATCCTGAAGATGATCCTGTCAGGGAAGATATTTTATGCTCACTAGCA
GATCAACACTAT
GGTGCTATTTTTGCTAAAGCTTGCTACATAGCTACAACTACACTAATGGGGCAGAAACAGAGAACACC
TTTTCCACGCTG
CGACATTATATGCCAATCTGAAATTGGTTCAGAACATCTACATTGTCACATACTTGTTGGAGGAGCCG
GTCTCAGCAAAA
GAAATGCTAAAATTTCACGTGCTACACTTCTGGGTCTTGTGATGGCTGAACTAACACAACGCTGCAAA
CAGCTTCTTGCG
CTTCGTCCATTTGAACCAGCTGAGGCTAATATTTTTCATCTCCTCAAGCGCATTGAACGCGAAGCATG
GTCAGGGCATAC
TGGTAACTGGGTTCAAATTCTTCAATACAAAGATAAGCGAGGTGATCTTCACGCTCAACCAATTGATC
CTTTACGCTTTT
TAAAGCATTACATACTACCAAAAAATCGATTGATTTCTCCTTCCAGCAAACCTGACGTCTGCACTACT
CCAGATAACTGG
TTCATTCTAGCTGACAAAACATACGCTCACACTATTATTAATGGGCTTCCGCTGCTAGAACATAACAG
AAAAGCCTATCT
ACAAGAGTTAGAAAGTGAAGTCATCCCGGGGCCTTCTACCATGGCCTTTGGGGACGTGGTGCGTGGG
AACAACTTCCTG
AGGTAGGAGAACAACGCTTAATTACTTCTAATGCTTCTACTGCTTATAAAGCTAACAAAAAAGAAAAA
TTAATGCTAAAT
TTACTTGATAAATGTGATGAACTTAATTTACTTGTTTATGAAGACTTAGTTAGTGCTTGTCCTGACCT
TTTACTTATGCT
TGAAGGTCAGCCAGGTGGTGCACGCCTAATTGAACAGGTGCTTGGCATGCATCATATTAAGGTGTGTG
CTAAATACACTG
CATTAACATTTTTATTTCATTTACATCCGGATCAATTATTAACTTCTAACAATAAAGCTTTAAAACTA
CTGTTGATTCAA
GGGTACAACCCACTTCAAGTAGGGCATGCCATCTGTTGTGTACTTAACAAACAGATGGGCAAGCAGAA
CACTATCTGCTT
TTATGGTCCTGCTTCAACAGGCAAAACAAACTTTGCAAAAGCAATAGTTCAAGGTGTTCGCCTTTATG
GCTGTGTTAATC
ATTTAAACAAAGGGTTTGTCTTTAACGATTGCAGACAACGCCTTATAATTTGGTGGGAAGAGTGTTTA
ATGCACCAAGAT
TGGGTGGAACCTGCTAAATGCATTTTAGGCGGAACTGAATGTAGAATTGATGTTAAACATAAAGACAG
TGTTCTTCTTCA
ACAAACACCAGTAATTATTTCCACTAACCATGACATCTACTCTGTAGTTGGTGGCAATACTGTTTCTC
ATGTTCATGCAG
CACCATTAAAAGAGCGAGTCCTTCAGCTAAATTTCATGAAACAACTGCCACAAACATTTGGAGAAATT
TCTCCAGTTGAA
ATTGCAGAACTATTGCAATGGTGCTTTAATGAGTACGAATGTACTCTTACTGGCTTTAAACAAAATG
GAACTTAGATAA
AGTTCCAAACTCATTTCCTCTTGGAGACCTTTGTCCTACACATTCACAGGACTACACGCTTCACGAAA
ACGGATTCTGCA

FIG. 1

```
CTGACTGTGGCGGCTATCTTCCTCATAGTGCTGACGATTTTGTCTACACTGACGTGGCTAGCGAAACA
ACAAGCGGAGAC
TGCGACCCAGGTAGGCTTTAATACATTTGCTTAATTAAATTATATATTTGCACTTTGCTTATGTATTA
ACTCCTACAGGT
AACCTGGGGGATACGGACGGAGAGGACTCCAAGTCAGAGGCATCGGAAGTGGACTTTCGTCCATCCAA
GAAGAGGCGTGT
GATTTCAGCAACTCCACCAAGCAGTCCAGTAAGTGGTCCAAGCCTTTCTACCTTTTTAGATACTTGGC
AGTCACAACCTA
GGGACGAAGATGAGCTCCGAATCTATGAAGAACAAGCATCGCAACTCCAAAAGAACACCAAGTCCACT
CCAGAAAGAGAG
GAGGCGCAACTGGGAGAGCCACAAGAGCCGCAGCCGGAGCCCGATCCGACGGCATGGGAGAAAAACT
TGGAGTATGCTC
ATCACAGCAACCAGGAGAACCGCCAGTCGTCTTATACTGCTTTGAAGACCTCAGACCAAGCGACGAAG
ACGAAGGAGAAA
ACATCGGGGGGAATAGAACCAATCCTTATACTGTATTCAGTCAACACAGGGCTAATCATTCAGATGC
TCCTGGATGGTG
TGGGTTTTACTGGCATTCTACTAGACTTGCTAGAGATGGGACTAATTGTATCTTTAATGAAATGAAAC
AAGAATTTCAAG
AATTACAAATAAATGGAAAAATTACTTGGGACAATGCTAGAGAACTATTGTTTAGTCAGAAAAAAAAG
CTAGATCAAAAA
TACAGAAACATGCTGTATCATTTCAGACACAGTCCTGATTGTCCTAGATGTGATTATTGGGATAATGT
ATACCGTAGACA
CTTAGCTCATGTCTCTTCACAGGAATCAGAGGAGGTTACAGACGAAGAAATGCTTTCTGCTGTTGAAA
GCATGGATACAA
ATGCCTCCAATTAAACGCCAGCCTGGAGGGTGGGTGCTTCCTGGTTATAAATACCTTGGTCCATTCAA
TCCTCTTGAAAA
CGGTGAACCAGTTAATAAAGCTGATCGTGCTGCTCAAGCTCATGATAAATCATATTCTGAAATAATAA
AAAGTGGAAAAA
ATCCTTACTTGTATTTCAATAAAGCTGATGAAAAATTCATTGACGATTTGAAAAACGACTGGTCTCTT
GGTGGCATTATT
GGCTCAAGTTTCTTTAAACTTAAGCGCGCCGTGGCTCCTGCTCTAGGAAATAAAGAGCGAGCTCAAAA
AAGACATTTTTA
CTTTGCAAACTCAAATAAAGGTGCTAAAAAACCAAAAAATAACGAGCCTAAACCAGGCACATCAAAAA
TGTCTGAAAATG
AAATCCAAGACCAACAACCATCTGGCTCCATGGAGGAGCGAGGAGGCGGAGGAGGTGCGGTCGGTAGT
GTGGGAGGGGGG
AAAGGTTCTAGTGTGGGTATATCCACAGGCGGCTGGGTTGGAGGCAGCTACTTTACTGACTCATATGT
CATAACAAAGAA
CACTAGACAGTTCTTAGTTAAAATACAAAATGACCACAAATACAGAACAGAGAATATAATTCCAAGCA
ACGCAGGAGGAA
AATCCCAGCGATGCGTAAGCACACCTTGGTCATACTTTAACTTCAATCAATACAGCAGTCACTTCTCA
CCACAAGACTGG
CAGCATTTAACAAATGAATATAAACGCTTTAAGCCTAGAAAAATGCATGTAAAAATTTACAACTTACA
AATAAAACAAAT
ACTCTCAAATGGTGCTGACACTACATACAACAACGACCTAACAGCTGGTGTTCACATCTTTTGTGATG
GTGAACACGCAT
ATCCAAATGCAACACATCCATGGGATGAAGATGTCATGCCAGAACTTCCATATGAAACATGGTATTTG
TTTCAATATGGA
TACATTCCAGTTATTCATGAACTGGCTGAAATGGAAGACGCAAATGCTGTAGAAAAGCTATAGCACT
ACAAATACCCTT
```
FIG. 1 (continued)

```
TTTCATGCTTGAAAACAGCGACCATGAAGTGTTAAGAACAGGAGAAAGCACAGAATTCACTTTTGACT
TTGACTGTGAAT
GGATAAACAACGAAAGAGCATACATTCCTCCTGGATTAATGTTTAATCCAAAAGTTCCTACAAGAAGA
GCTCAATACATC
AGACAGCACGGAAACACAGCATCCAGCAACACCAGAATTCAACCATATGCAAAACCTACAAGCTGGAT
GACAGGACCAGG
TCTACTCAGCGCACAAAGAGTAGGACCAGCTGGCTCAGACACTGCATCATGGATGGTTGTTGTCAATC
CAGACGGAGCTG
CAGTTAACTCAGGAATGGCAGGAGTTGGTTCAGGATTTGATCCTCCTTCAGGATCTCTAAGACCAACT
GACTTAGAATAC
AAAATACAATGGTACCAAACTCCTGCAGGTACCAACAGTGATGGAAACATCATTTCAAATCCACCACT
ATCCATGCTCAG
AGATCAAGCTCTCTACAGAGGAAATCAAACAACCTACAACCTATGCTCAGATGTGTGGATGTTCCCAA
ATCAAATTTGGG
ACAGATATCCAATAACCAGAGAAAATCCAATCTGGTGTAAAAAACCAAGATCAGACAAAAACACAATA
ATTGATCCTTTC
GATGGAACACTTGCAATGGATCATCCGCCAGGAACAATCTTCATAAAAATGGCAAAAATTCCAGTTCC
TTCAAACAACAA
CGCAGACTCATACCTAAACATCTACTGCACTGGACAAGTCAGCTGCGAAATTGTCTGGGAAGTTGAAA
GATACGCAACAA
AGAACTGGAGACCAGAAAGAAGACACACCGCACTTGGTCTTGGAATTGGAGGAGAAGAAAACGTAAAT
CCAACTTATCAT
GTAGACAAAAATGGAAAATACATTCAACCAACAACTTGGGACATGTGCTATCCTATCAAAACAAACAT
CAATAAAGTGTT
GTAATCTCTTAAGCCTGTTCATTGCTTATGCTTATAAGTTCCTCTCCAATGGACAAGAGGAAAGAAAA
GGGTGACTGTAA
TCCCGAGCTCATGAGTTCGAGGCTACAGTCCGATGGCAGTGGTGTTGCCGTCTCGAACCTAGCCGGTA
CACCCTTGTGCA
TTGTGGGAGGAGCTGTTTTGCTTACGCAATCGCGAAATTTTATATATTTAATGTAGTGTTGTACTGCG
TCAGGCAT
```

FIG. 1 (continued)

>HBoV2A- PK 5510-NS1
M
AFSAPVIRAFSQPAFTYVVKFPYENWKEEEHLLWSLLAPGTERLMIQLRNCAPHPEDDPV
REDILCSLADQHYGAIFAKACYIATTTLMGQKQRTPFPRCDIICQSEIGSEHLHCHILVG
GAGLSKRNAKISRATLLGLVMAELTQRCKQLLALRPFEPAEANIFHLLKRIEREAWSGHT
GNWVQILQYKDKRGDLHAQPIDPLRFLKHYILPKNRLISPSSKPDVCTTPDNWFILADKT
YAHTIINGLPLLEHNRKAYLQELESEVIPGPSTMAFGGRGAWEQLPEVGEQRLITSNAST
AYKANKKEKLMLNLLDKCDELNLLVYEDLVSACPDLLLMLEGQPGGARLIEQVLGMHHIK
VCAKYTALTFLFHLHPDQLLTSNNKALKLLLIQGYNPLQVGHAICCVLNKQMGKQNTICF
YGPASTGKTNFAKAIVQGVRLYGCVNHLNKGFVFNDCRQRLIIWWEECLMHQDWVEPAKC
ILGGTECRIDVKHKDSVLLQQTPVIISTNHDIYSVVGGNTVSHVHAAPLKERVLQLNFMK
QLPQTFGEISPVEIAELLQWCFNEYECTLTGFKQKWNLDKVPNSFPLGDLCPTHSQDYTL
HENGFCTDCGGYLPHSADDFVYTDVASETTSGDCDPGRL

>HBoV2A-PK5510-NS2
M
AFSAPVIRAFSQPAFTYVVKFPYENWKEEEHLLWSLLAPGTERLMIQLRNCAPHPEDDPV
REDILCSLADQHYGAIFAKACYIATTTLMGQKQRTPFPRCDIICQSEIGSEHLHCHILVG
GAGLSKRNAKISRATLLGLVMAELTQRCKQLLALRPFEPAEANIFHLLKRIEREAWSGHT
GNWVQILQYKDKRGDLHAQPIDPLRFLKHYILPKNRLISPSSKPDVCTTPDNWFILADKT
YAHTIINGLPLLEHNRKAYLQELESEVIPGPSTMAFGGRGAWEQLPEVGEQRLITSNAST
AYKANKKEKLMLNLLDKCDELNLLVYEDLVSACPDLLLMLEGQPGGARLIEQVLGMHHIK
VCAKYTALTFLFHLHPDQLLTSNNKALKLLLIQGYNPLQVGHAICCVLNKQMGKQNTICF
YGPASTGKTNFAKAIVQGVRLYGCVNHLNKGFVFNDCRQRLIIWWEECLMHQDWVEPAKC
ILGGTECRIDVKHKDSVLLQQTPVIISTNHDIYSVVGGNTVSHVHAAPLKERVLQLNFMK
QLPQTFGEISPVEIAELLQWCFNEYECTLTGFKQKWNLDKVPNSFPLGDLCPTHSQDYTL
HENGFCTDCGGYLPHSADDFVYTDVASETTSGDCDPGNLGDTDGEDSKSEASEVDFRPSK
KRRVISATPPSSPVSGPSLSTFLDTWQSQPRDEDELRIYEEQASQLQKNTKSTPEREEAQ
LGEPQEPQPEPDPTAWGEKLGVCSSQQPGEPPVVLYCFEDLRPSDEDEGENIGGE

FIG. 2

>HBoV2A-PK5510-NP1
MSSE
SMKNKHRNSKRTPSPLQKERRRNWESHKSRSRSPIRRHGEKNLEYAHHSNQENRQSSYTA
LKTSDQATKTKEKTSGGNRTNPYTVFSQHRANHSDAPGWCGFYWHSTRLARDGTNCIFNE
MKQEFQELQINGKITWDNARELLFSQKKKLDQKYRNMLYHFRHSPDCPRCDYWDNVYRRH
LAHVSSQESEEVTDEEMLSAVESMDTNASN

FIG. 3

>HBoV2A-PK5510-VP1
MPPIKRQPGGWVLPGYKYLGPFNPLENGEPVNKA
DRAAQAHDKSYSEIIKSGKNPYLYFNKADEKFIDDLKNDWSLGGIIGSSFFKLKRAVAPA
LGNKERAQKRHFYFANSNKGAKKPKNNEPKPGTSKMSENEIQDQQPSGSMEERGGGGAV
GSVGGGKGSSVGISTGGWVGGSYFTDSYVITKNTRQFLVKIQNDHKYRTENIIPSNAGGK
SQRCVSTPWSYFNFNQYSSHFSPQDWQHLTNEYKRFKPRKMHVKIYNLQIKQILSNGADT
TYNNDLTAGVHIFCDGEHAYPNATHPWDEDVMPELPYETWYLFQYGYIPVIHELAEMEDA
NAVEKAIALQIPFFMLENSDHEVLRTGESTEFTFDFDCEWINNERAYIPPGLMFNPKVPT
RRAQYIRQHGNTASSNTRIQPYAKPTSWMTGPGLLSAQRVGPAGSDTASWMVVVNPDGAA
VNSGMAGVGSGFDPPSGSLRPTDLEYKIQWYQTPAGTNSDGNIISNPPLSMLRDQALYRG
NQTTYNLCSDVWMFPNQIWDRYPITRENPIWCKKPRSDKNTIIDPFDGTLAMDHPPGTIF
IKMAKIPVPSNNNADSYLNIYCTGQVSCEIVWEVERYATKNWRPERRHTALGLGIGGEEN
VNPTYHVDKNGKYIQPTTWDMCYPIKTNINKVL

>HBoV2A-PK5510-VP2
MSENEIQDQQPSGSMEERGGGGAV
GSVGGGKGSSVGISTGGWVGGSYFTDSYVITKNTRQFLVKIQNDHKYRTENIIPSNAGGK
SQRCVSTPWSYFNFNQYSSHFSPQDWQHLTNEYKRFKPRKMHVKIYNLQIKQILSNGADT
TYNNDLTAGVHIFCDGEHAYPNATHPWDEDVMPELPYETWYLFQYGYIPVIHELAEMEDA
NAVEKAIALQIPFFMLENSDHEVLRTGESTEFTFDFDCEWINNERAYIPPGLMFNPKVPT
RRAQYIRQHGNTASSNTRIQPYAKPTSWMTGPGLLSAQRVGPAGSDTASWMVVVNPDGAA
VNSGMAGVGSGFDPPSGSLRPTDLEYKIQWYQTPAGTNSDGNIISNPPLSMLRDQALYRG
NQTTYNLCSDVWMFPNQIWDRYPITRENPIWCKKPRSDKNTIIDPFDGTLAMDHPPGTIF
IKMAKIPVPSNNNADSYLNIYCTGQVSCEIVWEVERYATKNWRPERRHTALGLGIGGEEN
VNPTYHVDKNGKYIQPTTWDMCYPIKTNINKVL

FIG. 4

```
HBoV2    ------GGAGTGGCTACGTATGGGGTGATC-ATAAACACGCCCAGGAAGTGACGTATGTC  53
HBoV1    CAAGGAGGAGTGGTTA--TATGATGTAATCCATAACCACTCCCAGGAAATGACGTATGAT  58
               ******* **  ****  ** *** **** *** ********* *********

HBoV2    AACCAATCAGCATCGAGCATATATCCTATATAAGCCGATGCACTYCCGCATCTCGTCAGA  113
HBoV1    AGCCAATCAGAATTGAGTATTGAACCTATATAAGCTGCTGCACTTCCTGATTCAATCAGA  118
          * ******** ** *** **  * ********** * ****** **  **     *****

HBoV2    CTGCATCCGGTCTCCGGCGAGTGAACATCTCTGGGAAGAGCTCCACGCACGTGGTGAGTG  173
HBoV1     CTGCATCCGGTCTCCGGCGAGTGAACATCTCTGGAAAAAGCTCCACGCTTGTGGTGAGTC  178
          ********************************** ********** * *********

HBoV2    ACACTATGGCCTTTTCTGCTCCTGTAATTAGAGCTTTTTCTCAACCTGCTTTTACTTATG  233
HBoV1    -TACTATGGCTTTCAATCCTCCTGTGATTAGAGCTTTTTCTCAACCTGCTTTTACTTATG  237
          ******** **    * ******* ***********************************

HBoV2    TTGTTAAATTTCCATATGAAAACTGGAAAGAGGAAGAGCACTTACTATGGAGCTTACTTG  293
HBoV1    TCTTCAAATTTCCATATCCACAATGGAAAGAAAAAGAATGGCTGCTTCATGCACTTTTAG  297
          *   * ************   *  *  ********     *  **      * *   * * *

HBoV2    CTCCTGGGACTGAACGTCTCATGATTCAACTAAGAAACTGCGCACCACATCCTGAAGATG  353
HBoV1    CTCATGGAACTGAACAATCTATGATACAATTAAGAAACTGCGCTCCTCATCCGGATGAAG  357
         *** *** ******      ***** ***  ************  ** ***** **  ** *

HBoV2    ATCCTGTCAGGGAAGATATTTTATGCTCACTAGCAGATCAACACTATGGTGCTATTTTTG  413
HBoV1    ACATAATCCGTGATGACTTGCTTATTTCTTTAGAAGATCGCCATTTTGGGGCTGTTCTCT  417
          *        ** *  ** **   *   ** *** *****  ** * *** *** **  * *

HBoV2    CTAAAGCTTGCTACATAGCTACAACTACACTAATGGGGCAGAAACAGAGAACACCTTTTC  473
HBoV1    GCAAGGCTGTTTACATGGCAACAACTACTCTCATGTCACACAAACAAGGAATATGTTTC  477
          ** ***   ***** ** ********  ** ***    ** *****  *      ****

HBoV2    CACGCTGCGACATTATATGCCAATCTGAAATTGGTTCAGAACATCTACATTGTCACATAC  533
HBoV1    CTCGTTGTGACATCATAGTTCAGTCTGAGCTAGGAGAGAAAAAACTTACACTGCCATATTA  537
          * ** ** *****  ***   **  ****  *  *   ** *  **** **  **  **

HBoV2    TTGTTGGAGGAGCCGGTCTCAGCAAAAGAAATGCTAAAATTTCACGTGCTACACTTCTGG  593
HBoV1    TAGTTGGGGGAGAAGGACTAAGCAAGAGGAATGCTAAATCATCCTGTGCTCAGTTCTATG  597
          * *****  ** ** ** ** *****  ********   **   ****** *   * *

HBoV2    GTCTTGTGATGGCTGAACTAACACAACGCTGCAAACAGCTTCTTGCGCTTCGTCCATTTG  653
HBoV1    GTTTAATACTAGCTGAAATAATTCAACGCTGCAAATCTCTTCTGGCTACACGTCCTTTTG  657
         **  *   *  ******  *   ************   ***** **      **** ****

HBoV2    AACCAGCTGAGGCTAATATTTTTCATCTCCTCAAGCGCATTGAACGCGAAGCATGGTCAG  713
HBoV1    AACCTGAAGAGGCTGACATATTTCACACTTTAAAAAAGGCTGAGCGAGAGGCATGGGGTG  717
         ****  * ****** *  ** ****   *  **     *** ** ** ****** * *

HBoV2    GGCATACTGGTAACTGGGTTCAAATTCTTCAATACAAAGATAAGCGAGGTGATCTTCACG  773
HBoV1    GAGTTACTGGCGGCAACATGCAAATCCTTCAATATAGAGATCGCAGAGGAGACCTTCATG  777
          *  ******  *   *  ***** ******** *  ****    **** ** ***** *

HBoV2    CTCAACCAATTGATCCTTTACGCTTTTTAAAGCATTACATACTACCAAAAAATCGATTGA  833
HBoV1    CACAAACAGTGGATCCTCTTCGCTTCTTCAAAAACTACCTTTTACCTAAAAATAGATGTA  837
         * *** ** * ******* * ***** ** *** ** **   **** ****** ***  *

HBoV2    TTTCTCCTTCCAGCAAACCTGACGTCTGCACTACTCCAGATAACTGGTTCATTCTAGCTG  893
HBoV1    TTTCATCTTACAGCAAACCTGATGTTTGTACTTCTCCTGACAACTGGTTCATTTTAGCTG  897
         ****  *** *********** ** ** **** **** ** *********** ******

HBoV2    ACAAAACATACGCTCACACTATTATTAATGGGCTTCCGCTGCTAGAACATAACAGAAAAG  953
HBoV1    AAAAAACTTACTCTCACACTCTTATTAACGGGCTGCCGCTTCCAGAACATTACAGAAAAA  957
         * ***** *** ******** ******* ***** ***** * ******  ********

HBoV2    CCTATCTACAAGAGTTAGAAAGTGAAGTCATCCCGGGGCCTTCTACCATGGCCTTTGGGG  1013
HBoV1    ACTACCACGCAACCCTAGATAACGAAGTCATTCCAGGGCCTCAAACAATGGCCTATGGAG  1017
          ** *  *   ****  ******** ** ****** **  ******* *** *
```

FIG. 5

```
HBoV2    GACGTGGTGCGTGGGAACAACTTCCTGAGGTAGGAGAACAACGCTTAATTACTTCTAATG 1073
HBoV1    GACGTGGTCCGTGGGAACATCTTCCTGAGGTAGGAGATCAGCGCCTAGCTGCGTCTTCTG 1077
         ******* ********* ****************** ** *** **  * * *** **

HBoV2    CTTCTACTGCTTATAAAGCTAACAAAAAAGAAAAATTAATGCTAAATTTACTTGATAAAT 1133
HBoV1    TTAGCACTACTTATAAACCTAACAAAAAAGAAAAACTTATGCTAAACTTGCTAGACAAAT 1137
          *   *** ******** ****************** * ******** ** ** ** ****

HBoV2    GTGATGAACTTAATTTACTTGTTTATGAAGACTTAGTTAGTGCTTGTCCTGACCTTTTAC 1193
HBoV1    GTAAAGAGCTAAATCTATTAGTTTATGAAGACTTAGTAGCTAATTGTCCTGAACTACTCC 1197
         ** * ** ** *** **  ****************   * ********* **  * *

HBoV2    TTATGCTTGAAGGTCAGCCAGGTGGTGCACGCCTAATTGAACAGGTGCTTGGCATGCATC 1253
HBoV1    TTATGCTTGAAGGTCAACCAGGAGGGGCACGCCTTATAGAACAAGTCTTGGGCATGCACC 1257
         ****************  **** ** ******** **  ****** ** * ******** *

HBoV2    ATATTAAGGTGTGTGCTAAATACACTGCATTAACATTTTTATTTCATTTACATCCGGATC 1313
HBoV1    ATATTAATGTTTGTTCTAACTTTACAGCTCTCACATATCTTTTTCATCTACATCCTGTTA 1317
         ******* ** *** ****  *  ** **  * **** * * ****** ******* * *

HBoV2    AATTATTAACTTCTAACAATAAAGCTTTAAAACTACTGTTGATTCAAGGGTACAACCCAC 1373
HBoV1    CTTCGCTTGACTCAGACAATAAAGCTTTACAGCTTTTGTTGATTCAAGGCTATAATCCTC 1377
          *  *   ** ** ** ************  ** ** ************ ** ** ** *

HBoV2    TTCAAGTAGGGCATGCCATCTGTTGTGTACTTAACAAACAGATGGGCAAGCAGAACACTA 1433
HBoV1    TAGCCGTTGGTCACGCCCTGTGCTGTGTCCTGAACAAACAATTCGGGAAACAAAACACTG 1437
         *  ** ** ** *** * ** * ** ***** *******   ** ** ** ** ******

HBoV2    TCTGCTTTTATGGTCCTGCTTCAACAGGCAAAACAAACTTTGCAAAAGCAATAGTTCAAG 1493
HBoV1    TTTGCTTTTACGGGCCTGCCTCAACAGGTAAAACAAATATGGCCAAGGCAATCGTCCAAG 1497
         * ********  ** ***** ******** *******  * **  ** ***** ** ****

HBoV2    GTGTTCGCCTTTATGGCTGTGTTAATCATTTAAACAAAGGGTTTGTCTTTAACGATTGCA 1553
HBoV1    GGATTAGACTTTATGGGTGTGTTAATCATTTGAACAAAGGATTTGTATTTAATGACTGCA 1557
         *  ** * ******** ************** ******* ***** ***** ** ****

HBoV2    GACAACGCCTTATAATTTGGTGGGAAGAGTGTTTAATGCACCAAGATTGGGTGGAACCTG 1613
HBoV1    GACAACGCTTAGTTGTTTGGTGGGAGGAGTGCTTAATGCACCAGGATTGGGTGGAACCTG 1617
         ********  *   * ********* ***** ********** ****************

HBoV2    CTAAATGCATTTTAGGCGGAACTGAATGTAGAATTGATGTTAAACATAAAGACAGTGTTC 1673
HBoV1    CAAAGTGTATCTTGGGCGGGACAGAATGCAGAATTGACGTCAAGCATAGAGACAGTGTAC 1677
         * ** **  ** ** ****** ** ****** ****** ** ** **** ******** *

HBoV2    TTCTTCAACAAACACCAGTAATTATTTCCACTAACCATGACATCTACTCTGTAGTTGGTG 1733
HBoV1    TTTTAACTCAAACACCTGTAATTATATCCACTAACCACGATATCTACGCGGTTGTTGGTG 1737
         ** *   ******** ******** ************ ** ****** * ** *******

HBoV2    GCAATACTGTTTCTCATGTTCATGCAGCACCATTAAAAGAGCGAGTCCTTCAGCTAAATT 1793
HBoV1    GCAATTCTGTTTCTCATGTTCACGCGGCTCCATTAAAAGAAGTGATTCAGCTAAATT 1797
         ***** **************** ** ** ** ********      ****  ************

HBoV2    TCATGAAACAACTGCCACAAACATTTGGAGAAATTTCTCCAGTTGAAATTGCAGAACTAT 1853
HBoV1    TTATGAAACAACTTCCTCAAACATTTGGAGAAATCACTGCTACTGAGATTGCAGCTCTTC 1857
         * *********** **  **************** ** *   *** ******* **

HBoV2    TGCAATGGTGCTTTAATGAGTACGAATGTACTCTTACTGGCTTTAAACAAAAATGGAACT 1913
HBoV1    TACAGTGGTGTTTCAATGAGTACGACTGTACTCTGACAGGATTTAAACAAAAATGGAATT 1917
         * ** ***** ** *********** ******** ** ** ***************** *

HBoV2    TAGATAAAGTTCCAAACTCATTTCCTCTTGGAGACCTTTGTCCTACACATTCACAGGACT 1973
HBoV1    TAGATAAAATTCCAAACTCATTTCCTCTTGGGGTCCTTTGTCCTACTCATTCACAGGACT 1977
         ********  ****************** * * ************ ************

HBoV2    ACACGCTTCACGAAAACGGATTCTGCACTGACTGTGGCGGCTATCTTCCTCATAGTGCTG 2033
HBoV1    TTACACTTCACGAAAACGGATACTGCACTGATTGCGGTGGTTACCTTCCTCATAGTGCTG 2037
           *** *************** ********* ** ** ** ** ****************
```

FIG. 5 (continued)

```
HBoV2    ACGATTTTGTCTACACTGACGTGGCTAGCGAAACAACAAGCGGAGACTGCGACCCAGGTA 2093
HBoV1    ACAATTCTATGTACACTGATCGCGCAAGCGAAACTAGCACAGGAGACATCACACCAAGTA 2097
         ** ***  * * ********   ** ********  *  *  ******   *   *** ***

HBoV2    GGCTTTAATACATTTGCTTAATTAAATTATATATTTGCACTTTGCT-TATGTATTAACTC 2152
HBoV1    AG--TAAATACGCATGCGCAAGTAATTCTTTTACTTTCACTTCGCTATTTTTACCAATTT 2155
         *  * ***** *** **  ** ***  *  * ** ** ***** *** * ** ** *

HBoV2    CTAC----AGGTAACCTGGGGGATACGGACGGAGAGGACTCCAAGTCAGAGGCATCGGAA 2208
HBoV1    TTACTTTTAGGTGACTTGGGGGATTCGGACGGAGAAGACACCGAGCCTGAGACATCGCAA 2215
         ***     **** **  ******** ********** *** **  ** *  ***** **

HBoV2    GTGGACTTTCGTCCATCCAAGAAGAGGCGTGTGATT---TCAGCAACTCCACCAAGCAGT 2265
HBoV1    GTGGACTATTGTCCACCCAAGAAACGTCGTCTAACTGCTCCAGCAAGTCCTCCAAACTCA 2275
         ******* * ***** *******  * *** * * *      ****** ***  ****  *

HBoV2    CCAGTAAGTGGTCCAAGCCTTTCTACCTTTTTAGATACTTGGCAGTCACAACCTAGGGAC 2325
HBoV1    CCTGCGAGCTCTGTAAGTACTATTACTTTCTTTAACACTTGGCACGCACAGCCACGTGAC 2335
         ** * **   * * ***  *  *** ** **  * ********  ****  ** * ***

HBoV2    GAAGATGAGCTCCGAATCTATGAAGAACAAGCATCGCAACTCCAAAAGAACACCAAGTCC 2385
HBoV1    GAAGATGAGCTCAGGGAATATGAAAGACAAGCATCGCTCCTACAAAAGAAAAGGGAGTCC 2395
         ************ *   ******  **********  **  ******** *    *****

HBoV2    ACTCCAGAAAGAGAGGAGGCGCAACTGGGAGA------GCCACAAGAGCCGCAGCCGGAG 2439
HBoV1    AGAAAGAGGGGAGAGGAAGAGACACTGGCAGACAACTCATCACAGGAGCAGGAGCCGCAG 2455
         *       *******  *  *  ***** ***          **** ****  * ***** **

HBoV2    CCCGATCCGACGGCATGGGGAGAAAAACTTGGAGTATGCTCATCACAGCAACCAGGAGAA 2499
HBoV1    CCCGATCCGACACAGTGGGGAGAGAGGCTCGGGCTCATATCATCAGGAACACCCAATCAG 2515
         ***********    * ******** *   ** *   * *  ****** ***   *         *

HBoV2    CCGCCAGTCGTCTTATACTGCTTTGAAGACCTCAGACCAAGCGACGAAGACGAAGGAGAA 2559
HBoV1    CCACCTATCGTCTTGCACTGCTTCGAAGACCTCAGACCAAGTGATGAAGACGAGGGAGAG 2575
         ** **  *******   ******* ****************** ** ********  *****

HBoV2    AACATCGGGGGGGAA------TAGAACCAATCCTTATACTGTATTCAGTCAACACAGGGC 2613
HBoV1    TACATCGGGGAAAAAGACAATAGAACAAATCCATACACTGTATTCAGTCAACACAGAGC 2635
         *********  **      ****** ***** ** ********************** **

HBoV2    TAATCATTCAGATGCTCCTGGATGGTGTGGGTTTTACTGGCATTCTACTAGACTTGCTAG 2673
HBoV1    TTCCAATCCTGAAGCTCCAGGGTGGTGTGGGTTCTACTGGCACTCTACTCGCATTGCTAG 2695
         *   ** * **  ***** ** *********** ******** ****** ** *******

HBoV2    AGATGGGACTAATTGTATCTTTAATGAAATGAAACAAGAATTTCAAGAATTACAAATAAA 2733
HBoV1    AGATGGTACTAATTCAATCTTTAATGAAATGAAACAACAGTTTCAACAGCTACAAATTGA 2755
         ****** *******  ******************** *  ****** *  ******* *

HBoV2    TGGAAAAATTACTTGGGACAATGCTAGAGAACTATTGTTTAGTCAGAAAAAAAAGCTAGA 2793
HBoV1    TAATAAAATAGGATGGGATAACACTAGAGAACTATTGTTTAATCAAAAGAAAACACTAGA 2815
         *  ***** *  ** *** **  ****************** *** **  ***  *****

HBoV2    TCAAAAATACAGAAACATGCTGTATCATTTCAGACACAGTCCTGATTGTCCTAGATGTGA 2853
HBoV1    TCAAAAATACAGAAATATGTTCTGGCACTTTAGAAATAACTCTGATTGTGAAAGATGTAA 2875
         *************** ***  *  ** ** ** *   * ******** *     ***** *

HBoV2    TTATTGGGATAATGTATACCGTAGACACTTAGCTCATGTCTCTTCACAG---GAATCAGA 2910
HBoV1    TTACTGGGATGATGTGTACCGTAGGCACTTAGCTAATGTTTCCTCACAGACAGAAGCAGA 2935
         *** ****** **** ********  ******** ***** ** *******    *** ****

HBoV2    GGAGGTTACAGACGAAGAAATGCTTTCTGCTGTTGAAAGCATGGATACAAATGCCTCCAA 2970
HBoV1    CGAGATAACTGACGAGGAAATGCTTTCTGCTGCTGAAAGCATGGAAGCAGATGCCTCCAA 2995
         *** *  ** ***** **************** *************   **********

HBoV2    TTAAACGCCAGCCTGGAGGGTGGGTGCTTCCTGGTTATAAATACCTTGGTCCATTCAATC 3030
HBoV1    TTAAGAGACAGCCTAGAGGGTGGGTGCTGCCTGGATACAGATATCTTGGGCCATTTAATC 3055
         ****  * ****** ************ ***** ** * *** ***** ***** *****
```

FIG. 5 (continued)

```
HBoV2    CTCTTGAAAACGGTGAACCAGTTAATAAAGCTGATCGTGCTGCTCAAGCTCATGATAAAT 3090
HBoV1    CACTTGATAACGGTGAACCTGTAAATAACGCTGATCGCGCTGCTCAATTACATGATCACG 3115
         * ***** *********** ** ***** ******** *********   ****** *

HBoV2    CATATTCTGAAATAATAAAAAGTGGAAAAAATCCTTACTTGTATTTCAATAAAGCTGATG 3150
HBoV1    CCTACTCTGAACTAATAAAGAGTGGTAAAAATCCATACCTGTATTTCAATAAAGCTGATG 3175
         *  ** ****** ******   ****  ****** *** *** ****************

HBoV2    AAAAATTCATTGACGATTTGAAAAACGACTGGTCTCTTGGTGGCATTATTGGCTCAAGTT 3210
HBoV1    AAAAATTCATTGATGATCTAAAAGACGATTGGTCAATTGGTGGAATTATTGGATCCAGTT 3235
         ************* *** * *** **** *****  ******* ******** ** ****

HBoV2    TCTTTAAACTTAAGCGCGCCGTGGCTCCTGCTCTAGGAAATAAAGAGCGAGCTCAAAAAA 3270
HBoV1    TTTTTAAAATAAAGCGCGCCGTGGCTCCTGCTCTGGGAAATAAAGAGAGAGCCCAAAAAA 3295
         * ****** * ********************** *************  **** *******

HBoV2    GACATTTTTACTTTGCAAACTCAAATAAAGGTGCTAAAAAACCAAAAAATAACGAGCCTA 3330
HBoV1    GACACTTTTACTTTGCTAACTCAAATAAAGGTGCAAAAAAAACAAAAAAAAGTGAACCTA 3355
         **** *********** ***************** ******  *******    ** ****

HBoV2    AACCAGGCACATCAAAAATGTCTGAAAATGAAATCCAAGACCAACAACCATCTGGCTCCA 3390
HBoV1    AACCAGGAACCTCAAAAATGTCTGACACTGACATTCAAGACCAACAACC---TGATACTG 3412
         ******* ** ************ * *** ** **************    **   *

HBoV2    TGGAGGAGCGAGGAGGCGG---AGGAGGTGCGGTCGGTAGTGTGGGAGGGGGGAAAGGTT 3447
HBoV1    TGGACGCACCACAGAACGCCTCAGGGGGAGGAACAGGAAGTATTGGAGGAGGAAAAGGAT 3472
         ****  *  *  *    **    *** ** *    ** *** * ***** ***** *

HBoV2    CTAGTGTGGGTATATCCACAGGCGGCTGGGTTGGAGGCAGCTACTTTACTGACTCATATG 3507
HBoV1    CTGGTGTGGGGATTTCCACTGGAGGGTGGGTCGGAGGTTCTCACTTTTCAGACAAATATG 3532
         ** ******* **  **** ** ** ***** *****    ***** * ***    ****

HBoV2    TCATAACAAAGAACACTAGACAGTTCTTAGTTAAAATACAAAATGACCACAAATACAGAA 3567
HBoV1    TGGTTACTAAAAACACAAGACAATTTATAACCACAATTCAGAATGGTCACCTCTACAAAA 3592
         *   * ** ** ***** **** **   **   *   * *** ***  ***   **** **

HBoV2    CAGAGAATATAATTCCAAGCAACGCAGGAGGAAAATCCCAGCGATGCGTAAGCACACCTT 3627
HBoV1    CAGAGGCCATTGAAACAACAAACCAAAGTGGAAATCACAGCGCTGCGTCACAACTCCAT 3652
         *****     **   ***  *  * ******* ***** *  ****** *  ** ** *

HBoV2    GGTCATACTTTAACTTCAATCAATACAGCAGTCACTTCTCACCACAAGACTGGCAGCATT 3687
HBoV1    GGACATACTTTAACTTTAATCAATACAGCTGTCACTTCTCACCACAAGATTGGCAGCGCC 3712
         ** ************* *********** ******************* *******

HBoV2    TAACAAATGAATATAAACGCTTTAAGCCTAGAAAAATGCATGTAAAAATTTACAACTTAC 3747
HBoV1    TTACAAATGAATATAAGCGCTTCAGACCTAAAGCAATGCAAGTAAAGATTTACAACTTGC 3772
         * ************** ***** *  **** * * ***** ***** *********** *

HBoV2    AAATAAAACAAATACTCTCAAATGGTGCTGACACTACATACAACAACGACCTAACAGCTG 3807
HBoV1    AAATAAAACAAATACTTTCAAATGGTGCTGACACAACATACAACAATGACCTCACAGCTG 3832
         **************** **************** *********** ***** *******

HBoV2    GTGTTCACATCTTTTGTGATGGTGAACACGCATATCCAAATGCAACACATCCATGGGATG 3867
HBoV1    GCGTTCACATCTTTTGTGATGGAGAGCATGCTTACCCAAATGCATCTCATCCATGGGATG 3892
         * ******************** ** ** **  * ********* * *************

HBoV2    AAGATGTCATGCCAGAACTTCCATATGAAACATGGTATTTGTTTCAATATGGATACATTC 3927
HBoV1    AGGACGTCATGCCTGATCTTCCATACAAGACCTGGAAACTTTTTCAATATGGATATATTC 3952
         * ** ******** ** ********  * ** *** *  * * ************ ****

HBoV2    CAGTTATTCATGAACTGGCTGAAATGGA---AGACGCA--------AATGCTGTAGAAA 3975
HBoV1    CTATTGAAAATGAACTAGCAGATCTTGATGGAAATGCAGCTGGAGGCAATGCTACAGAAA 4012
         * **   ******* ** **  *   *    * *** ******  *****

HBoV2    AAGCTATAGCACTACAAATACCCTTTTTCATGCTTGAAAACAGCGACCATGAAGTGTTAA 4035
HBoV1    AAGCACTTCTGTATCAGATGCCTTTTTTTCTACTTGAAAACAGTGACCACCAAGTACTTA 4072
         ****    *   ** * ** ** ****** * *********** ***** **** * **
```

FIG. 5 (continued)

```
HBoV2        GAACAGGAGAAAGCACAGAATTCACTTTTGACTTTGACTGTGAATGGATAAACAACGAAA 4095
HBoV1        GAACTGGTGAGAGCACTGAATTTACTTTTAACTTTGACTGTGAATGGGTTAATAATGAAA 4132
             ****  ** ** ***** ***** ****** ***************  ** ** ****

HBoV2        GAGCATACATTCCTCCTGGATTAATGTTTAATCCAAAAGTTCCTACAAGAAGAGCTCAAT 4155
HBoV1        GAGCATACATTCCTCCTGGATTGATGTTCAATCCAAAAGTTCCAACAAGAAGAGTTCAGT 4192
             **********************  ***** ************* ********** *** *

HBoV2        ACATCAGACAGCACGGAAACACAGCATCCAGCAACACCAGAATTCAACCATATGCAAAAC 4215
HBoV1        ACATAAGACAAAACGGAAGCACAGCAGCCAGCACAGGCAGAATTCAGCCATACTCAAAAC 4252
             ****  ***** ** ***** ****** ****** *  ********  ***** ******

HBoV2        CTACAAGCTGGATGACAGGACCAGGTCTACTCAGCGCACAAAGAGTAGGACCAGCTGGCT 4275
HBoV1        CAACAAGCTGGATGACAGGACCTGGCCTGCTCAGTGCACAGAGAGTAGGACCACAGTCAT 4312
             * ******************** **  ** ***** ***** **************        *

HBoV2        CAGACACTGCATCATGGATGGTTGTTGTCAATCCAGACGGAGCTGCAGTTAACTCAGGAA 4335
HBoV1        CAGACACTGCTCCATTCATGGTTTGCACTAACCCAGAAGGAACACACATAAACACAGGTG 4372
             **********  ***  ****** *  *** *  ***** *** *     * *** ****

HBoV2        TGGCAGGAGTTGGTTCAGGATTTGATCCTCCTTCAGGATCTCTAAGACCAACTGACTTAG 4395
HBoV1        CTGCAGGATTTGGATCTGGCTTTGATCCTCCAAGCGGATGTCTGGCACCAACTAACCTAG 4432
              ****** **** **  ** *********** **** *** ******* ** ***

HBoV2        AATACAAAATACAATGGTACCAAACTCCTGCAGGTACCAACAGTGATGGAAACATCATTT 4455
HBoV1        AATACAAACTTCAGTGGTACCAGACACCAGAAGGAACAGGAAATAATGGAAACATAATTG 4492
             ********  * ** ********  ** ** *  ***    * * ********** ***

HBoV2        CAAATCCACCACTATCCATGCTCAGAGATCAAGCTCTCTACAGAGGAAATCAAACAACCT 4515
HBoV1        CAAACCCATCACTCTCAATGCTTAGAGACCAACTCCTATACAAAGGAAACCAGACCACAT 4552
             ****  *** **** ** *****  ***   **  ** ****** **** ** ** **  *

HBoV2        ACAACCTATGCTCAGATGTGTGGATGTTCCCAAATCAAATTTGGGACAGATATCCAATAA 4575
HBoV1        ACAATCTAGTGGGGGACATATGGATGTTTCCAAATCAAGTCTGGGACAGATTTCCTATCA 4612
             **** ***        **  * ********  *  ******** * ** ********  *** ** *

HBoV2        CCAGAGAAAATCCAATCTGGTGTAAAAAACCAAGATCAGACAAAAACACAATAATTGATC 4635
HBoV1        CCAGAGAAAATCCAATCTGGTGCAAAAAACCAAGGGCTGACAAACACACAATCATGGATC 4672
             ********************** ***********    * ****** *  ******* ** ****

HBoV2        CTTTCGATGGAACACTTGCAATGGATCATCCGCCAGGAACAATCTTCATAAAAATGGCAA 4695
HBoV1        CATTTGATGGATCCATTGCAATGGATCATCCTCCAGGCACTATTTTTATAAAAATGGCAA 4732
             * ** ****** *  **************** ***** ** ** ** **  ***********

HBoV2        AAATTCCAGTTCCTTCAAACAACAACGCAGACTCATACCTAAACATCTACTGCACTGGAC 4755
HBoV1        AAATTCCAGTACCAACTGCAACAAATGCAGACTCATATCTAAACATATACTGTACTGGAC 4792
             **********  **  *     *  ** ********* ******** *****  *******

HBoV2        AAGTCAGCTGCGAAATTGTCTGGGAAGTTGAAAGATACGCAACAAAGAACTGGAGACCAG 4815
HBoV1        AAGTCAGCTGTGAAATTGTATGGGAAGTAGAAAGATACGCAACAAAGAACTGGCGTCCAG 4852
             ********** ******** ******** ************************ * ****

HBoV2        AAAGAAGACACACCGCACTTGGTCTTGGAATTGGAGGAGAAGAAAACGTAAATCCAACTT 4875
HBoV1        AAAGAAGACATACTGCACTCGGGATGTCACTGGGAGGAGAGAGCAACTACACGCCTACAT 4912
             **********  ** ***** **      *  * ** ******** *  ***   * ** ** *

HBoV2        ATCATGTAGACAAAAATGGAAAATACATTCAACCAACAACTTGGGACATGTGCTATCCTA 4935
HBoV1        ACCACGTGGATCCAACAGGAGCATACATCCAGCCCACGTCTATATGATCAGTGTATGCCAG 4972
             * ** ** **    ** ** *** *** ****  ** **  * **    ***   ***   **

HBoV2        TCAAAACAAACATCAATAAAGTGTTGTAATCTCTTAAGCCTGTTCATTGCTTATGCTTAT 4995
HBoV1        TAAAAACAAACATCAATAAAGTGTTGTAATCTTATAAGCCTCTTTTTTGCTTCTGCTTAC 5032
             * ***************************  * ******* **  ****** *****

HBoV2        AAGTTCCTCTCCAATGGACAAGAGGAAAGAAAAGGGTGACTGTAATCCCGAGCTCATGAG 5055
HBoV1        AAGTTCCTCCTCAATGGACAAGCGGAAAGTGAAGGGTGACTGTAGTCCTGAGCTCATGGG 5092
             *********  *********** ******  ************* *** ********* *
```

FIG. 5 (continued)

```
HBoV2      TTCGAGGCTACAGTCCGATGGCAGTGGTGTTGCCGTCTCGAACCTAGCCGGTACACCCTT 5115
HBoV1      TTCAAGACCACAGCCCGATGGTAGTGGTGTTACCGTCTCGAACCTAGCCGACA-GCCCTT 5151
           *** ** * **** ****** ******** ******************  *   *****

HBoV2      GTGCATTGTGGGAGGAGCTGTTTTG----CTTACGCAATCGCGAAATTTTATATATTT-A 5170
HBoV1      GTACATTGTGGGGGAGCTGTTTTGTTTGCTTATGCAATCGCGAAACTCTATATCTTTTA 5211
           ** ******** ************    **** ************ * ***** *** *

HBoV2      ATGTAGTGTTGTACTGCGTCAGGCAT 5196
HBoV1      ATGTGT-------------------- 5217
           ****
```

FIG. 5 (continued)

```
HBoV2        MAFSAPVIRAFSQPAFTYVVKFPYENWKEEEHLLWSLLAPGTERLMIQLR  50
HBoV1        MAFNPPVIRAFSQPAFTYVFKFPYPQWKEKEWLLHALLAHGTEQSMIQLR  50
             ***..*************.****.:***:*.**.:***.***.:.*****

HBoV2        NCAPHPEDDPVREDILCSLADQHYGAIFAKACYIATTTLMGQKQRTPFPR  100
HBoV1        NCAPHPDEDIIRDDLLISLEDRHFGAVLCKAVYMATTTLMSHKQRNMFPR  100
             ******::*..:*.:*:*.**.*:*:**::..**.*:******.:***..***

HBoV2        CDIICQSEIGSEHLHCHILVGGAGLSKRNAKISRATLLGLVMAELTQRCK  150
HBoV1        CDIIVQSELGEKNLHCHIIVGGEGLSKRNAKSSCAQFYGLILAEIIQRCK  150
             ****.***:*..::*****:***.********.*.*...**.:.**:.****

HBoV2        QLLALRPFEPAEANIFHLLKRIEREAWSGHTGNWVQILQYKDKRGDLHAQ  200
HBoV1        SLLATRPFEPEEADIFHTLKKAEREAWGGVTGGNMQILQYRDRRGDLHAQ  200
             .*** *****.**:***.**:.******.*.**..:*****:*:*******

HBoV2        PIDPLRFLKHYILPKNRLISPSSKPDVCTTPDNWFILADKTYAHTIINGL  250
HBoV1        TVDPLRFFKNYLLPKNRCISSYSKPDVCTSPDNWFILAEKTYSHTLINGL  250
             .:*****:*:*:*****.**...*****.:*********:.***:**.****

HBoV2        PLLEHNRKAYLQELESEVIPGPSTMAFGGRGAWEQLPEVGEQRLITSNAS  300
HBoV1        PLPEHYRKNYHATLDNEVIPGPQTMAYGGRGPWEHLPEVGDQRLAASSVS  300
             **.**.**.*.....*:.******.***.****.******:***.:..*

HBoV2        TAYKANKKEKLMLNLLDKCDELNLLVYEDLVSACPDLLLMLEGQPGGARL  350
HBoV1        TTYKPNKKEKLMLNLLDKCKELNLLVYEDLVANCPELLLMLEGQPGGARL  350
             *:**.**************.************:.**:*************

HBoV2        IEQVLGMHHIKVCAKYTALTFLFHLHPDQLLTSNNKALKLLLIQGYNPLQ  400
HBoV1        IEQVLGMHHINVCSNFTALTYLFHLHPVTSLDSDNKALQLLLIQGYNPLA  400
             **********:**::.****:******...*..:****:**********.

HBoV2        VGHAICCVLNKQMGKQNTICFYGPASTGKTNFAKAIVQGVRLYGCVNHLN  450
HBoV1        VGHALCCVLNKQFGKQNTVCFYGPASTGKTNMAKAIVQGIRLYGCVNHLN  450
             ****:*******:*****:***********:******:**********

HBoV2        KGFVFNDCRQRLIIWWEECLMHQDWVEPAKCILGGTECRIDVKHKDSVLL  500
HBoV1        KGFVFNDCRQRLVVWWEECLMHQDWVEPAKCILGGTECRIDVKHRDSVLL  500
             ************::******************************:*****

HBoV2        QQTPVIISTNHDIYSVVGGNTVSHVHAAPLKERVLQLNFMKQLPQTFGEI  550
HBoV1        TQTPVIISTNHDIYAVVGGNSVSHVHAAPLKERVIQLNFMKQLPQTFGEI  550
             .*************:*****.*************:***************

HBoV2        SPVEIAELLQWCFNEYECTLTGFKQKWNLDKVPNSFPLGDLCPTHSQDYT  600
HBoV1        TATEIAALLQWCFNEYDCTLTGFKQKWNLDKIPNSFPLGVLCPTHSQDFT  600
             :..***.*********:*************:*******.********:*

HBoV2        LHENGFCTDCGGYLPHSADDFVYTDVASETTSGDCDPGRL  640
HBoV1        LHENGYCTDCGGYLPHSADNSMYTDRASETSTGDITPSK-  639
             *****:*************:..***.****:***.**..
```

FIG. 6A

```
HBoV2      MSSESMKNKHRNSKRTPSPLQKERRRNWES--HKSRSRSPIRRHGEKNLE  48
HBoV1      MSSGNMKDKHRSYKRKGSPERGERKRHWQTTHHRSRSRSPIRHSGERGSG  50
           ***.**:***_.**_.**_:_**:*:*::___*:********:_**:_.

HBoV2      YAHHSNQENRQSSYTALKTSDQATKTKEKTSG--GNRTNPYTVFSQHRAN  96
HBoV1      SYHQEHPISHLSSCTASKTSDQVMKTRESTGKKDNRTNPYTVFSQHRAS  100
           *:_.:__.:_**_**_*****_.**:*_***___.*************_*.

HBoV2      HSDAPGWCGFYWHSTRLARDGTNCIFNEMKQEFQELQINGKITWDNAREL 146
HBoV1      NPEAPGWCGFYWHSTRIARDGTNSIFNEMKQQFQQLQIDNKIGWDNTREL 150
           :_.:**************:******_.*******:**:***_:_**_***:***

HBoV2      LFSQKKKLDQKYRNMLYHFRHSPDCPRCDYWDNVYRRHLAHVSSQ-ESEE 195
HBoV1      LFNQKKTLDQKYRNMFWHFRNNSDCERCNYWDDVYRRHLANVSSQTEADE 200
           **.***.********:.***:_.._**_**:***:********_****_*:_:*

HBoV2      VTDEEMLSAVESMDTNASN 214
HBoV1      ITDEEMLSAAESMEADASN 219
           :********.***:_:_:***
```

FIG. 6B

```
HBoV2    MSLHRNQRRLQTKKCFLLLKAWIQMPPIKRQPGGWVLPGYKYLGPFNPLE  50
HBoV1    ----------------------MPPIKRQPRGWVLPGYRYLGPFNPLD  26
                               ******** ****** ********.:

HBoV2    NGEPVNKADRAAQAHDKSYSEIIKSGKNPYLYFNKADEKFIDDLKNDWSL  100
HBoV1    NGEPVNNADRAAQLHDHAYSELIKSGKNPYLYFNKADEKFIDDLKDDWSI  76
         ******:****** **:.***:**********************:.***:

HBoV2    GGIIGSSFFKLKRAVAPALGNKERAQKRHFYFANSNKGAKKPKNNEPKPG  150
HBoV1    GGIIGSSFFKIKRAVAPALGNKERAQKRHFYFANSNKGAKKTKKSEPKPG  126
         **********:******************************.*:.*****

HBoV2    TSKMSENEIQDQQPSGSMEERGGGGGAVGSVGGGKGSSVGISTGGWVGGS  200
HBoV1    TSKMSDTDIQDQQPDTVDAPQNASGGGTGSIGGGKGSGVGISTGGWVGGS  176
         *****..:******.. :...**..**.******.*************

HBoV2    YFTDSYVITKNTRQFLVKIQNDHKYRTENIIPSNAGGKSQRCVSTPWSYF  250
HBoV1    HFSDKYVVTKNTRQFITTIQNGHLYKTEAIETTNQSGKSQRCVTTPWTYF  226
         :*:*.**.********:..***.* *:** * ..:* .*******:***:**

HBoV2    NFNQYSSHFSPQDWQHLTNEYKRFKPRKMHVKIYNLQIKQILSNGADTTY  300
HBoV1    NFNQYSCHFSPQDWQRLTNEYKRFRPKAMQVKIYNLQIKQILSNGADTTY  276
         ******.********:********:*: *:********************

HBoV2    NNDLTAGVHIFCDGEHAYPNATHPWDEDVMPELPYETWYLFQYGYIPVIH  350
HBoV1    NNDLTAGVHIFCDGEHAYPNASHPWDEDVMPDLPYKTWKLFQYGYIPIEN  326
         *********************:*********:***:**:*********: :

HBoV2    ELAEMED----ANAVEKAIALQIPFFMLENSDHEVLRTGESTEFTFDFDC  396
HBoV1    ELADLDGNAAGGNATEKALLYQMPFFLLENSDHQVLRTGESTEFTFNFDC  376
         ***::.     .**.***:  :***:*******:************.***

HBoV2    EWINNERAYIPPGLMFNPKVPTRRAQYIRQHGNTASSNTRIQPYAKPTSW  446
HBoV1    EWVNNERAYIPPGLMFNPKVPTRRVQYIRQNGSTAASTGRIQPYSKPTSW  426
         **:*********************.*****:*.**:*. *****:*****

HBoV2    MTGPGLLSAQRVGPAGSDTASWMVVVNPDGAAVNSGMAGVGSGFDPPSGS  496
HBoV1    MTGPGLLSAQRVGPQSSDTAPFMVCTNPEGTHINTGAAGFGSGFDPPSGC  476
         ************** .****. :** .**:*:  *..** ********.

HBoV2    LRPTDLEYKIQWYQTPAGTNSDGNIISNPPLSMLRDQALYRGNQTTYNLC  546
HBoV1    LAPTNLEYKLQWYQTPEGTNNGNIIANPSLSMLRDQLLYKGNQTTYNLV  526
         * **:****:****** **..:****:**.*******..**:*********

HBoV2    SDVWMFPNQIWDRYPITRENPIWCKKPRSDKNTIIDPFDGTLAMDHPPGT  596
HBoV1    GDIWMFPNQVWDRFPITRENPIWCKKPRADKHTIMDPFDGSIAMDHPPGT  576
         .*:******:***:**************:**:**:*****::********

HBoV2    IFIKMAKIPVPSNNNADSYLNIYCTGQVSCEIVWEVERYATKNWRPERRH  646
HBoV1    IFIKMAKIPVPTATNADSYLNIYCTGQVSCEIVWEVERYATKNWRPERRH  626
         **********:. .***********************************

HBoV2    TALGLGIGGEENVNPTYHVDKNGKYIQPTTWDMCYPIKTNINKVL  691
HBoV1    TALGMSLGGESNYTPTYHVDPTGAYIQPTSYDQCMPVKTNINKVL  671
         ****:. :***.*  * ****** .*  ****:. * *:********
```

FIG. 6C

>HBoV4-TU210-07
GTGGTGAGTCACATTATGGCTTTCAATCCACCTGTTATTAGAGCATTCTCTTCACCTGCTTTTACTTA
TGTCTTCAAATT
TCCATATCCATCATGGAAAGAAAAAGAATGGCTTCTTCATGCACTTCTGGCTCATGGTACCGAGCAAG
CCATGATCCAGC
TGAGAAACTGTGTTCCTCATCCGGATGAAGATATAATCCGTGATGACTTACTACTTTCTCTAGAAGAT
CGCCATTTTGGG
GCAATTCTCTGCAAGGCTGTCTATATGGCTACTACTACTTTTATGTCACAGAAACAAAGAAATATGTT
TCCTCGCTGTGA
CATAATAGTCCAATCTGAGCTTGGGGAGACAAACCTACACTGCCATATTATAGTTGGGGGAGAAGGCT
TAAGCAAGAGAA
ATGCAAAAACATCATGTCCTCAACTATATGGACTGATACTAGGGGAATTAATCCAACGCTGCAAAACT
CTTCTGGCTACG
CGTCCTTTTGAACCGGAAGAGGCAGAAATTTATCATGCTTTAAAACGAGCTGAGCGAGAAGCTTGGGG
TGGAGTTACTAG
CGGCAACCTACAAATTCTCCAATACAGAGATCGCAGAGGAGACCTTCACGCACAACAAGTGGATGCTC
TTCGCTTCTTCA
AAAACTACCTATTGCCTAAAAATAGATGCATTACATCTTACAGCAGACCTGATGTCTGTACTTCTCCA
GAAAACTGGTTT
GTTTTAGCTGAAAAAACTTACTGTCACACTCTTGTTAACGGGCTGCCGCTTCCAGAACATTACAGAAA
ACACTACCACGC
AACCCTAGATAACGAAGTTCTACCAGGGCCTCAGACAATGGCCTTTGGGGACGTGGTCCGTGGGAAC
ATCTTCCTGAGG
TAGGAGATCAACGTTTAGCTGCTTCTTCTGTTAGTACAACATATAAACCAAACAAAAAGAAAAACTT
ATGCTTAACTTA
CTAGATAAATGCAGCGAATTAAATCTTTTAGTTTATGAAGACTTAGTAGCTAACTGTCCTGAACTTTT
GCTTATGCTTGA
AGGTCAACCAGGTGGGGCACGCTTAATAGAACAAGTCCTAGGCATGCACCATATTAATGTTTGCTCTA
ACTTTACTGCTC
TTAGTTATCTCTTTCACCTTTACCCTGGCACAACCTTATCTTCAGATAACAAGGCTTTGCAGCTGTTG
TTGATACAAGGT
TACAACCCATTAATGGTTGGTCACGCCTTGTGCTGTGTACTCAACAAGCAATTTGGCAAACAAAACAC
TGTTTGCTTTTA
TGGACCAGCTTCTACTGGTAAAACAAACATGGCAAAGGCCATAGTCCAAGGCATTAGACTATATGGCT
GTGTTAATCATT
TAAACAAAGGGTTTGTCTTTAATGATTGCAGACAACGCCTAGTTGTTTGGTGGGAGGAGTGCTTAATG
CACCAGGATTGG
GTGGAACCAGCAAAGTGTATCTTGGGTGGAACTGAGTGTAGAATTGACGTCAAACACAGAGATAGTGT
ATTATTGACACA
AACTCCAGTAATTATTTCCACTAACCACGATATCTACGCGGTTGTTGGTGGTAATTCTGTTTCTCATG
TTCATGCGGCTC
CATTAAAAGAAGAGTGATTCAGCTAAATTTTATGAAACAACTTCCTCAAACATTTGGAGAGATCACT
CCAGAAGAAATT
GCAGCTCTACTGCAATGGTGTTTCAATGAGTACGAATGTACTCTGACAGGCTTTAAAACAAAATGGAG
CCTAGATAAAAT
TCCAAACTCATTTCCTCTTGGGGTCCTTTGTCCTACTCATTCACAGGACTTCATACTCCACGAAAACG
GATACTGCACTG
ATTGTGGTGGTTACCTTGCTCATAGCGCTGACGATTCTGTGTACACTGATCGTGCAAGCGACACTAGC
AAAGAAGCCATC
GACGCAGGTAAGTTTACGTTCTCCAGGCACTTTATATATATCCTATACACAACACTAAAACATATGTT
TAATTACAGGTG

FIG. 7A

ACTTGGGGGATACGGACGGAGAGGACTCCGAGTCAGAAGCATCGGAAGTGGGTGTTCGTCCATCCAAG
AAGCGACGCATA
ACTATTCCTGCAACTCCACCAAATTCTCCTGGCAGCTCTGTGAGTACTTCTGCCTTCTTTGATAATTG
GTGCGCACAACC
GCGAGACGAAGATGAGCTCAGGGAATACGAAAGACAAGCATCGCGCCTACAAAAGAAAAGGGAGTCCA
GGGAGAGACGAG
AAGAAACGCCCATGGCAACCTCGTCACAGGAGTCGGAGTCGGAGCCCAATCCGACGCAGTGGGGAGAC
AAGCTCGGGGTC
ATACCGTCAGGAACACCAGATCAGCCACCTATCGTCTTGCACTGCTTCGAAGATCTCAGACCCAGTGA
CGAAGACGAAGG
AGAATACATCGGGAAGAGAGACTCTAGAACTAATCCATACACTGTATTCAGCCAGCATAAAGCCTCA
CATCCTGATGCT
CCAGGATGGTGTGGGTTCTATTGGCATTCTACTAGAATTGCTAGAAATGGTACTAATGCAATCTTTAA
TGAAATGAAACA
GCAGTTCCAACAACTGCAGCTAGACAACAAAATTGGCTGGGATAATGCTAGAGAATTATTGTTTAGTC
AGAAAAAATCAC
TAGATCAACAATACAGAAATATGTTCTGGCACTTTAGAAATGCTTCTGATTGTGAACGTTGTAATTAC
TGGGACAATGTA
TACCGTATGCACTTAGCTCATGTTTCCTCTCAGACAGAATCAGAAGAAATAACTGACGAGGAAATGCT
TTCTGCTGCTGA
AAGTATGGAAACAGATGCCTCCAATTAAAAGGCAACCTGGAGGGTGGGTGCTTCCTGGTTACAAATAC
CTTGGTCCATTT
AATCCTCTTGATAACGGTGAACCAGTTAATAAAGCTGATCGTGCTGCTCAATCTCATGATAAATCATA
TTCTGAATTAAT
AAAAAGTGGAAAAAATCCTTACTTATATTTCAATAAAGCTGATGAAAAATTCATTGACGATTTGAAAA
ACGACTGGTCTC
TTGGTGGCATTATTGGCTCAAGTTTCTTTAAACTTAAGCGCGCCGTGGCTCCTGCTCTAGGAAATAAA
GAGCGAGCTCAA
AAAAGACACTTTTATTTTCCAAACTCAAATAAAGGTGCTAAAAAATCAAAAAACAACGAACCTAAACC
AAACACCTCAAA
AATGTCTGAAAATGAAATTCAAGATCAACAGCCATCAGAACCTAATGATGGCCAACGAGGAGGGGGAG
GAGGTGCGACCG
GCAGTGTGGGAGGGGGGAAAGGTTCTGGTGTGGGTATATCCACAGGTGGATGGGTAGGAGGCAGCTAC
TTTACTGACTCC
TATGTCATAACAAAAAACACCAGACAATTTCTGGTTAAAATCCAAAACAACCATCAATATAAAACTGA
AAATATAATTCC
TTCCAATGGAGGAGGAAAATCACAAAGATGTGTCAGCACACCATGGTCATACTTTAACTTTAATCAAT
ACAGCAGTCATT
TCTCACCACAGGACTGGCAGCGCCTAACAAATGAATACAAAAGATTCAGACCTAAAGGTATGCATGTT
AAAATCTACAAT
TTACAAATAAAACAGATTTTATCAAATGGTGCTGATGTTACATACAACAACGACCTAACAGCAGGAGT
ACACATCTTTTG
TGATGGCGAACATGCATATCCAAACGCTACACATCCATGGGACGAAGATGTAATGCCAGAACTTCCTT
ACCAAACATGGT
ATCTGTTTCAATATGGATACATACCTACCATTCATGAACTTGCAGAAATGGAAGACTCCAATGCAGTA
GAAAAAGCAATT
GCTTTACAGATACCATTCTTCATGCTTGAAAACAGCGACCATGAAGTTCTAAGAACTGGAGAAAGTGC
AGAATTTAACTT
CAACTTTGACTGTGAATGGATTAACAATGAAAGAGCATTCATTCCTCCAGGACTGATGTTTAATCCAT
TGGTACCAACAA

FIG. 7A (continued)

GAAGAGCTCAATACATACGAAGAAATGGAAACACTCAAGCAAGTACATCACGAATTCAACCCTATGCT
AAACCTACAAGC
TGGATGACTGGGCCAGGTTTACTCAGTGCACAACGAGTAGGTCCAGCTGCTTCTGACACAGCTGCATG
GATGGTTGGTGT
AGATCCAGAAGGCGCAAACATCAACTCAGGAAGAGCAGGAGTTAGCAGTGGATTTGATCCTCCAGCTG
GATCACTCAGAC
CTACAGATCTAGAATACAAAGTACAATGGTACCAAACTCCAGCTGGAACAAACAACGATGGAAACATC
ATTTCAAATCCA
CCTTTATCAATGCTTAGAGATCAAACTCTCTACAGAGGAAACCAAACAACCTACAACTTATGCTCAGA
TGTATGGATGTT
TCCAAATCAAATTTGGGACAGATACCCAGTAACAAGAGAAAATCCTATTTGGTGCAAACAACCAAGAT
CAGACAAACACA
CAACAATTGATCCTTTTGACGGATCAATAGCCATGGATCATCCACCAGGCACAATTTTCATCAAAATG
GCAAAAATTCCA
GTTCCTTCAAACAACAACGCAGACTCATACTTAAACATCTACTGCACTGGACAAGTCAGCTGCGAAAT
TGTCTGGGAAGT
CGAAAGATATGCAACAAAGAACTGGAGACCAGAAAGAAGACACACAGCACTCGGCCTTGGAATTGGAG
GGGCAGATGAAA
TCAACCCAACATACCATGTTGACAAAAACGGAGCATACATTCAACCTACAACATGGGACATGTGCTTT
CCAGTTAAAACA
AACATTAATAAAGTGTTGTAATCTCTTAAGCCTCTTTATTGCTTACGCTTGTAAGTTCCTCTCCAATG
GACAAGTGGAAA
GAAAAGGGTGACTGTAATCCCGAGCTCATGAGTTCGAGGCTACAGTCCGATGGCAGTGGTGTTGCCGT
CTCGAACCTAGC
CGTTACACCCTT

FIG. 7A (continued)

>HBoV4-TU210-07-NS1
MAFNPPVIRAFSSPAFTYVFKFPYPSWKEKEWLLHALLAHGTEQAMIQLRNCVPH
PDEDIIRDDLLLSLEDRHFGAILCKAVYMATTTFMSQKQRNMFPRCDIIVQSELGETNLH
CHIIVGGEGLSKRNAKTSCPQLYGLILGELIQRCKTLLATRPFEPEEAEIYHALKRAERE
AWGGVTSGNLQILQYRDRRGDLHAQQVDALRFFKNYLLPKNRCITSYSRPDVCTSPENWF
VLAEKTYCHTLVNGLPLPEHYRKHYHATLDNEVLPGPQTMAFGGRGPWEHLPEVGDQRLA
ASSVSTTYKPNKKEKLMLNLLDKCSELNLLVYEDLVANCPELLLMLEGQPGGARLIEQVL
GMHHINVCSNFTALSYLFHLYPGTTLSSDNKALQLLLIQGYNPLMVGHALCCVLNKQFGK
QNTVCFYGPASTGKTNMAKAIVQGIRLYGCVNHLNKGFVFNDCRQRLVVWWEECLMHQDW
VEPAKCILGGTECRIDVKHRDSVLLTQTPVIISTNHDIYAVVGGNSVSHVHAAPLKERVI
QLNFMKQLPQTFGEITPEEIAALLQWCFNEYECTLTGFKTKWSLDKIPNSFPLGVLCPTH
SQDFILHENGYCTDCGGYLAHSADDSVYTDRASDTSKEAIDAGKFTFSRHFIYILYTTLK
HMFNYR

>HBoV4-TU210-07-NS2
MAFNPPVIRAFSSPAFTYVFKFPYPSWKEKEWLLHALLAHGTEQAMIQLRNCVPH
PDEDIIRDDLLLSLEDRHFGAILCKAVYMATTTFMSQKQRNMFPRCDIIVQSELGETNLH
CHIIVGGEGLSKRNAKTSCPQLYGLILGELIQRCKTLLATRPFEPEEAEIYHALKRAERE
AWGGVTSGNLQILQYRDRRGDLHAQQVDALRFFKNYLLPKNRCITSYSRPDVCTSPENWF
VLAEKTYCHTLVNGLPLPEHYRKHYHATLDNEVLPGPQTMAFGGRGPWEHLPEVGDQRLA
ASSVSTTYKPNKKEKLMLNLLDKCSELNLLVYEDLVANCPELLLMLEGQPGGARLIEQVL
GMHHINVCSNFTALSYLFHLYPGTTLSSDNKALQLLLIQGYNPLMVGHALCCVLNKQFGK
QNTVCFYGPASTGKTNMAKAIVQGIRLYGCVNHLNKGFVFNDCRQRLVVWWEECLMHQDW
VEPAKCILGGTECRIDVKHRDSVLLTQTPVIISTNHDIYAVVGGNSVSHVHAAPLKERVI
QLNFMKQLPQTFGEITPEEIAALLQWCFNEYECTLTGFKTKWSLDKIPNSFPLGVLCPTH
SQDFILHENGYCTDCGGYLAHSADDSVYTDRASDTSKEAIDAGDLGDTDGEDSESEASEV
GVRPSKKRRITIPATPPNSPGSSVSTSAFFDNWCAQPRDEDELREYERQASRLQKKRESR
ERREETPMATSSQESESEPNPTQWGDKLGVIPSGTPDQPPIVLHCFEDLRPSDEDEGEYI
GKERL

FIG. 7B

>HBoV4-TU210-07-NP1
MSSGNTKDKHRAYKRKGSPGRDEKKRPWQPRHRSRSRSPIRRSGETSSGSYRQEHQI
SHLSSCTASKISDPVTKTKENTSGKRDSRTNPYTVFSQHKASHPDAPGWCGFYWHSTRIA
RNGTNAIFNEMKQQFQQLQLDNKIGWDNARELLFSQKKSLDQQYRNMFWHFRNASDCERC
NYWDNVYRMHLAHVSSQTESEEITDEEMLSAAESMETDASN

FIG. 7C

>HBoV4-TU210-07-VP1
MPPIKRQPGGWVLPGYKYLGPF
NPLDNGEPVNKADRAAQSHDKSYSELIKSGKNPYLYFNKADEKFIDDLKNDWSLGGIIGS
SFFKLKRAVAPALGNKERAQKRHFYFPNSNKGAKKSKNNEPKPNTSKMSENEIQDQQPSE
PNDGQRGGGGGATGSVGGGKGSGVGISTGGWVGGSYFTDSYVITKNTRQFLVKIQNNHQY
KTENIIPSNGGGKSQRCVSTPWSYFNFNQYSSHFSPQDWQRLTNEYKRFRPKGMHVKIYN
LQIKQILSNGADVTYNNDLTAGVHIFCDGEHAYPNATHPWDEDVMPELPYQTWYLFQYGY
IPTIHELAEMEDSNAVEKAIALQIPFFMLENSDHEVLRTGESAEFNFNFDCEWINNERAF
IPPGLMFNPLVPTRRAQYIRRNGNTQASTSRIQPYAKPTSWMTGPGLLSAQRVGPAASDT
AAWMVGVDPEGANINSGRAGVSSGFDPPAGSLRPTDLEYKVQWYQTPAGTNNDGNIISNP
PLSMLRDQTLYRGNQTTYNLCSDVWMFPNQIWDRYPVTRENPIWCKQPRSDKHTTIDPFD
GSIAMDHPPGTIFIKMAKIPVPSNNNADSYLNIYCTGQVSCEIVWEVERYATKNWRPERR
HTALGLGIGGADEINPTYHVDKNGAYIQPTTWDMCFPVKTNINKVL

>HBoV4-TU210-07-VP2
MSENEIQDQQPSE
PNDGQRGGGGGATGSVGGGKGSGVGISTGGWVGGSYFTDSYVITKNTRQFLVKIQNNHQY
KTENIIPSNGGGKSQRCVSTPWSYFNFNQYSSHFSPQDWQRLTNEYKRFRPKGMHVKIYN
LQIKQILSNGADVTYNNDLTAGVHIFCDGEHAYPNATHPWDEDVMPELPYQTWYLFQYGY
IPTIHELAEMEDSNAVEKAIALQIPFFMLENSDHEVLRTGESAEFNFNFDCEWINNERAF
IPPGLMFNPLVPTRRAQYIRRNGNTQASTSRIQPYAKPTSWMTGPGLLSAQRVGPAASDT
AAWMVGVDPEGANINSGRAGVSSGFDPPAGSLRPTDLEYKVQWYQTPAGTNNDGNIISNP
PLSMLRDQTLYRGNQTTYNLCSDVWMFPNQIWDRYPVTRENPIWCKQPRSDKHTTIDPFD
GSIAMDHPPGTIFIKMAKIPVPSNNNADSYLNIYCTGQVSCEIVWEVERYATKNWRPERR
HTALGLGIGGADEINPTYHVDKNGAYIQPTTWDMCFPVKTNINKVL

FIG. 7D

>HBoV2A-TU114-06
TGGTGAGTGACACTATGGCCTTTTCTGCTCCTGTAATTAGAGCTTTTTCTCAACCTGCTTTCACTTAT
GTTGTTAAATTT
CCATATGATAACTGGAAAGAGGAAGAACACTTACTATGGAGCTTACTTGCTCCTGGGACTGAACGTCT
CATGATCCAACT
AAGAAACTGCGCACCACATCCTGAAGATGATCCTGTCAGGGAAGATATTTTATGCTCACTAGCAGACC
AACACTATGCTG
CTATTTTCACCAAGGCTTGCTACATGGCTGTAACTTCACTCATGGGGCAGAAACAGAGAACACACTTT
CCACGATGCGAC
ATAATATGCCAGGCTGAGATCGGCTCAGAATATCTACACTGTCACATACTTGTTGGAGGAGCAGGTCT
GAGCAAGAGAAA
TGCTAAAATTTCATGTGCTACGCTCTTAGGCCTTGTGATGGCTGAATTAACACAACGCTGCAAACTAC
TTCTTACACAGC
GTCCATTTGAACCAGATGAAGCTAGAATATTCCATCTACTCAGACGCGTTGAACGCGAAGCATGGTCA
GGGCACACTGGT
AACTGGGTTCAAATTCTTCAATACAGAGACAAGCGAGGTGACCTTCATGCTCAACACATTGATCCTTT
ACGCTTTTTCAA
ACACTACCTGCTGCCAAAAAATCGATTGATCTCTCCTTCCAGCAAGCCTGACGTCTGCACTACTCCAG
ATAACTGGTTTG
TCCTAGCTGATAAAACATACGCTCACACTATTGTTAATGGGCTTCCGCTGCTAGAACATAACAGAAAG
GCCTATCTACAA
GAGTTAGAGAGTGAAGTCATCCCGGGGCCTTCTACCATGGCCTTTGGGGACGTGGTGCGTGGGAACA
TCTGCCTGAGGT
AGGAGAACAACGCCTAATTACTTCTAATACTTCTACTGCTTATAAAGCTAACAAAAAGAAAAATTAA
TGCTAAACTTAC
TTGATAAATGTGATGAACTTAACTTACTTGTGTATGAAGACTTAGTTAGTGCTTGTCCTGACCTTTTA
CTTATGCTTGAA
GGTCAACCAGGTGGTGCACGCCTAATTGAACAGGTGCTTGGCATGCATCATATTAAAGTATGTGCTAA
TTACACAGCATT
ATCTTTCTTATTTCATTTACATCCTAATCAATTATTAACTTCTAGCAATAAAGCACTAAAACTATTGT
TGATTCAAGGGT
ACAACCCATTACAGGTAGGGCACGCCATCTGCTGTGTACTTAACAAACAGATGGGCAAGCAGAACACT
ATCTGCTTTTAT
GGTCCTGCTTCAACAGGTAAAACAAATATTGCAAAGGCCATAGTCCAAGGCGTTCGCCTTTATGGCTG
TGTTAATCATCT
AAACAAAGGGTTTGTCTTTAACGATTGCAGACAACGCCTTATAATTTGGTGGGAGGAATGTTTAATGC
ATCAAGATTGGG
TTGAACCTGCTAAATGCATTTTAGGTGGAACTGAATGTAGAATTGATGTTAAACACAAAGACAGTGTT
CTTCTTCAACAA
ACACCAGTAATTATTTCCACTAACCATGACATCTACTCTGTAGTTGGTGGCAATACTGTATCTCATGT
TCATGCAGCGCC
CTTAAAAGAGCGAATTCTTCAACTAAATTTTATGAAACAACTGCCACAAACATTTGGAGAGATTTCTC
CAGTTGAAATTG
CAGAGTTGCTGCAATGGTGCTTTAATGAGTACGAATGTACTCTTACTGGCTTTAAACAAAAATGGAAC
TTAGATAAAGTT
CCAAACTCATTTCCTCTTGGGGACCTTTGTCCTACACATTCACAGGACTACGTGCTTCACGAAAACGG
ATTCTGCACTGA
CTGCGGCGGCTATATTCCTCATAGTGCTGACGACTCTGTGTATACTGACGTGGCTAGCGAGACATCAA
TCAGCAGCTGCG
ACCCAGGTAGGCATTAATACATTAGCCTTTTAATATACTACTTTCTAGATGCTTATGTATTAACTCCT
ACAGGTGACTTG

FIG. 8A

GGGGATACGGACGGAGAGAACTCCCAGCCGGAGACATCGAACGTGGATAATCGTCCATCCAAGAAGCG
ACGTGTGATTCC
AGAAACTCCACCAAACAGTCCAGTAAGTCGCCAAAGCCTTTCTAGCTTTTTAGATACGTGGCAGTCAC
AACCTAGAGACG
AAGATGAGCTCCGAATCTATGAAGCACAGGCATCGCGCATCAAAGAGAACACCGAGTCCACTCCGGAG
AGAGAGAAGACA
CCAGTGGGAGAACCACAAGAAGAGTCGCAGGCGGAGCCCGATCCGACAGCATGGGGAGAAAAGCTTGG
AGTCTACTCCTC
GCTGCAACCAGGAGAGCCGCCAATCGTCTTACACTGCTTCGAAGACCTCAGACCAAGCGACGAAGACG
AAGGAGAAAACA
TCGGGGGGAATAGAACCAATCCTTATACTGTGTTCAGTCAACACAGGGCTAATCATCCAGATGCTCC
TGGATGGTGTGG
GTTTTACTGGCATTCTACTAGGCTTGCTAGAGATGGCACTAATTGTATCTTTAATGAAATGAAACAAG
AATTTCAAGAAT
TGCAAATAAATGGGAAAATTACCTGGGACAATGTTAGAGAACTATTGTTTAGCCAGAAAAAAAGCTA
GATCAAAAATAC
AGAAACATGCTGTACCATTTCAGACATAATGCTGATTGTCCTAGATGTGATTATTGGGATGATGTCTA
CCGTAAACACTT
AGCTCATGTCTCTTCACAGGAATCAGAGGAGGTAACAGACGAAGAAATGCTTTCTGCTGTTGAAAGCA
TGGAAACAAATG
CCTCCAATTAAACGCCAACCTGGAGGGTGGGTGCTTCCTGGTTATAAATACCTTGGTCCATTTAATCC
TCTTGAGAACGG
TGAACCAGTTAATAAAGCTGATCGTGCTGCTCAAGCTCATGATAAATCATATTCTGAGTTAATAAAGA
GTGGAAAAAATC
CTTACTTGTATTTCAATAAAGCTGATGAGAAATTCATTGACGATTTGAAAAACGACTGGTCTCTTGGT
GGCATTATTGGC
TCAAGTTTCTTTAAACTTAAGCGCGCCGTGGCTCCTGCTCTAGGAAATAAAGAGCGAGCTCAAAAAAG
ACATTTTTACTT
TGCAAACTCAAATAAAGGTGCTAAAAAACCAAAAAATAACGAGCCTAAACCAGGCACTTCAAAAATGT
CTGAAAATGAAA
TCCAAGACCAACAACCATCTGGCTCGATGGACGAACAGCGAGGAGGCGGAGGGGGCGCCGTTGGCAGT
GTGGGAGGGGGG
AAAGGTTCTGGTGTGGGTATATCCACAGGTGGCTGGGTAGGAGGCAGCTATTTCACTGACTCATATGT
CATAACAAAAAA
CACCAGACAATTTCTGGTAAAAATACAAAATGACCACAAATACAGAACTGAAAATATTATTCCAAGCA
ATGCTGGAGGAA
AATCACAAAGGTGCGTCAGCACACCATGGTCATATTTCAACTTCAATCAATACAGCAGTCATTTTTCA
CCACAAGACTGG
CAACGCCTAACAAATGAATATAAACGCTTTAAACCTAGAAAAATGCATGTAAAAATTTACAATCTACA
AATAAAACAAAT
ACTTTCAAATGGTGCTGACACTACATACAACAACGACCTAACAGCTGGTGTTCACATATTTTGTGATG
GTGAACACGCAT
ATCCAAATGCAACACATCCATGGGATGAAGACGTCATGCCAGAACTTCCATATGAAACATGGTATCTG
TTTCAATATGGA
TACATTCCAGTTATTCATGAACTTGCTGAAATGGAAGACGCAAATGCTGTAGAAAAGCTATAGCACT
ACAAATACCATT
CTTCATGCTTGAAAACAGTGACCATGAAGTTCTAAGAACTGGAGAAAGCACAGAATTCACTTTTGATT
TTGACTGTGAGT
GGATCAACAACGAAAGAGCATACATTCCTCCTGGATTAATGTTTAATCCAAAAGTTCCTACGAGAAGA
GCTCAATACATT

FIG. 8A (continued)

```
AGACAGCACGGAAACACAGCATCAAGCAACACCAGAATTCAACCATATGCAAAACCTACAAGCTGGAT
GACAGGACCAGG
TCTACTCAGTGCACAAAGAGTAGGACCAGCTGGCTCAGACACTGCATCATGGATGGTTGTTGTTAATC
CAGACGGAACTG
CCGTTAACTCAGGAATGGCAGGAGTTGGATCAGGATTTGATCCTCCTTCAGGATCTCTAAGACCAACT
GACTTAGAATAC
AAAATACAATGGTACCAAACTCCTGAAGGTACCAACAGTGATGGAAACATAATTTCAAATCCACCACT
GTCCATGCTTAG
AGATCAAGCTCTCTACAGAGGAAATCAAACAACCTATAACCTATGCTCAGATGTATGGATGTTCCCAA
ATCAAATTTGGG
ACAGATATCCAATAACCAGAGAAAATCCAATCTGGTGCAAAAAACCAAGATCAGATAAAAGCACAGTA
ATTGATCCTTTC
GATGGAACACTCGCAATGGATCATCCTCCTGGAACAATCTTCATAAAAATGGCAAAAATTCCAGTTCC
TTCAAACAACAA
CGCAGACTCATACCTAAACATCTACTGCACAGGACAAGTCAGCTGCGAAATTGTCTGGGAAGTTGAAA
GATACGCAACAA
AGAACTGGAGACCAGAGAGAAGACACACCGCACTTGGTCTTGGAATCGGAGGAGAAGAAAACATAAAT
CCAACTTACCAT
GTAGACAAAAATGGAAAATACATTCAGCCAACAACATGGGACATGTGCTATCCTATCAAAACAAACAT
CAATAAAGTGTT
GTAATCTCTTAAGCCTATTCATTGCTTATGCTTATAAGTTCCTCTCCAATGGACAAGAGGAAAGAAAA
GGGTGACTGTAA
TCCCGAGCTCATGAGTTCGAGGCTACAGTCCGATGGCAGTGGTGTTGCCGTCTCGAACCTAGCCGTTA
CACCCTTGTGCA
TTGTGG
```

FIG. 8A (continued)

>HBoV2A-TU114-06-NS1
MAFSAPVIRAFSQPAFTYVVKFPYDNWKEEEHLLWSLLAPGTERLMIQLRNCAPHP
EDDPVREDILCSLADQHYAAIFTKACYMAVTSLMGQKQRTHFPRCDIICQAEIGSEYLHC
HILVGGAGLSKRNAKISCATLLGLVMAELTQRCKLLLTQRPFEPDEARIFHLLRRVEREA
WSGHTGNWVQILQYRDKRGDLHAQHIDPLRFFKHYLLPKNRLISPSSKPDVCTTPDNWFV
LADKTYAHTIVNGLPLLEHNRKAYLQELESEVIPGPSTMAFGGRGAWEHLPEVGEQRLIT
SNTSTAYKANKKEKLMLNLLDKCDELNLLVYEDLVSACPDLLLMLEGQPGGARLIEQVLG
MHHIKVCANYTALSFLFHLHPNQLLTSSNKALKLLLIQGYNPLQVGHAICCVLNKQMGKQ
NTICFYGPASTGKTNIAKAIVQGVRLYGCVNHLNKGFVFNDCRQRLIIWWEECLMHQDWV
EPAKCILGGTECRIDVKHKDSVLLQQTPVIISTNHDIYSVVGGNTVSHVHAAPLKERILQ
LNFMKQLPQTFGEISPVEIAELLQWCFNEYECTLTGFKQKWNLDKVPNSFPLGDLCPTHS
QDYVLHENGFCTDCGGYIPHSADDSVYTDVASETSISSCDPGRH

>HBoV2A-TU114-06-NS2
MAFSAPVIRAFSQPAFTYVVKFPYDNWKEEEHLLWSLLAPGTERLMIQLRNCAPHP
EDDPVREDILCSLADQHYAAIFTKACYMAVTSLMGQKQRTHFPRCDIICQAEIGSEYLHC
HILVGGAGLSKRNAKISCATLLGLVMAELTQRCKLLLTQRPFEPDEARIFHLLRRVEREA
WSGHTGNWVQILQYRDKRGDLHAQHIDPLRFFKHYLLPKNRLISPSSKPDVCTTPDNWFV
LADKTYAHTIVNGLPLLEHNRKAYLQELESEVIPGPSTMAFGGRGAWEHLPEVGEQRLIT
SNTSTAYKANKKEKLMLNLLDKCDELNLLVYEDLVSACPDLLLMLEGQPGGARLIEQVLG
MHHIKVCANYTALSFLFHLHPNQLLTSSNKALKLLLIQGYNPLQVGHAICCVLNKQMGKQ
NTICFYGPASTGKTNIAKAIVQGVRLYGCVNHLNKGFVFNDCRQRLIIWWEECLMHQDWV
EPAKCILGGTECRIDVKHKDSVLLQQTPVIISTNHDIYSVVGGNTVSHVHAAPLKERILQ
LNFMKQLPQTFGEISPVEIAELLQWCFNEYECTLTGFKQKWNLDKVPNSFPLGDLCPTHS
QDYVLHENGFCTDCGGYIPHSADDSVYTDVASETSISSCDPGDLGDTDGENSQPETSNVD
NRPSKKRRVIPETPPNSPVSRQSLSSFLDTWQSQPRDEDELRIYEAQASRIKENTESTPE
REKTPVGEPQEESQAEPDPTAWGEKLGVYSSLQPGEPPIVLHCFEDLRPSDEDEGENIGG
E

FIG. 8B

>HBoV2A-TU114-06-NP1
MSSESMKHRHRASKRTPSPLRRERRHQWENHKKSRRRSPIRQHGEKSLESTPRCNQESR
QSSYTASKTSDQATKTKEKTSGGNRTNPYTVFSQHRANHPDAPGWCGFYWHSTRLARDGT
NCIFNEMKQEFQELQINGKITWDNVRELLFSQKKKLDQKYRNMLYHFRHNADCPRCDYWD
DVYRKHLAHVSSQESEEVTDEEMLSAVESMETNASN

FIG. 8C

>HBoV2A-TU114-06-VP1
MPPIKRQPGGWVLPGYKYLGPFNPLENG
EPVNKADRAAQAHDKSYSELIKSGKNPYLYFNKADEKFIDDLKNDWSLGGIIGSSFFKLK
RAVAPALGNKERAQKRHFYFANSNKGAKKPKNNEPKPGTSKMSENEIQDQQPSGSMDEQR
GGGGGAVGSVGGGKGSGVGISTGGWVGGSYFTDSYVITKNTRQFLVKIQNDHKYRTENII
PSNAGGKSQRCVSTPWSYFNFNQYSSHFSPQDWQRLTNEYKRFKPRKMHVKIYNLQIKQI
LSNGADTTYNNDLTAGVHIFCDGEHAYPNATHPWDEDVMPELPYETWYLFQYGYIPVIHE
LAEMEDANAVEKAIALQIPFFMLENSDHEVLRTGESTEFTFDFDCEWINNERAYIPPGLM
FNPKVPTRRAQYIRQHGNTASSNTRIQPYAKPTSWMTGPGLLSAQRVGPAGSDTASWMVV
VNPDGTAVNSGMAGVGSGFDPPSGSLRPTDLEYKIQWYQTPEGTNSDGNIISNPPLSMLR
DQALYRGNQTTYNLCSDVWMFPNQIWDRYPITRENPIWCKKPRSDKSTVIDPFDGTLAMD
HPPGTIFIKMAKIPVPSNNNADSYLNIYCTGQVSCEIVWEVERYATKNWRPERRHTALGL
GIGGEENINPTYHVDKNGKYIQPTTWDMCYPIKTNINKVL

>HBoV2A-TU114-06-VP2
MSENEIQDQQPSGSMDEQR
GGGGGAVGSVGGGKGSGVGISTGGWVGGSYFTDSYVITKNTRQFLVKIQNDHKYRTENII
PSNAGGKSQRCVSTPWSYFNFNQYSSHFSPQDWQRLTNEYKRFKPRKMHVKIYNLQIKQI
LSNGADTTYNNDLTAGVHIFCDGEHAYPNATHPWDEDVMPELPYETWYLFQYGYIPVIHE
LAEMEDANAVEKAIALQIPFFMLENSDHEVLRTGESTEFTFDFDCEWINNERAYIPPGLM
FNPKVPTRRAQYIRQHGNTASSNTRIQPYAKPTSWMTGPGLLSAQRVGPAGSDTASWMVV
VNPDGTAVNSGMAGVGSGFDPPSGSLRPTDLEYKIQWYQTPEGTNSDGNIISNPPLSMLR
DQALYRGNQTTYNLCSDVWMFPNQIWDRYPITRENPIWCKKPRSDKSTVIDPFDGTLAMD
HPPGTIFIKMAKIPVPSNNNADSYLNIYCTGQVSCEIVWEVERYATKNWRPERRHTALGL
GIGGEENINPTYHVDKNGKYIQPTTWDMCYPIKTNINKVL

FIG. 8D

>HBoV2B-NI213
CGCACGTGGTGAGTGACACTATGGCCTTTTCTGCTCCTGTAATTAGAGCTTTTTCTCAACCTGCTTTC
ACTTATGTTGTT
AAATTTCCATATGATAACTGGAAAGAGGAAGAGCACTTACTATGGAGCTTACTTGCTCCTGGGACTGA
ACGTCTCATGAT
CCAACTAAGAAACTGCGCACCACATCCTGAAGATGATCCTGTCAGGGAAGATATTTTATGCTCACTAG
CAGACCAACACT
ATGCTGCTATTTTCACCAAAGCTTGCTACATGGCTGTAACTTCACTCATGGGGCAGAAACAGAGAACA
CACTTTCCACGA
TGCGACATAATTTGCCAGGCTGAGATCGGCTCAGAATATCTACACTGTCACATACTTGTTGGAGGAGC
AGGTCTGAGCAA
GAGAAATGCTAAAATTTCATGTGCTACGCTCCTAGGCCTTGTGATGGCTGAATTAACACAACGCTGCA
AACTACTTCTTG
CACAGCGTCCATTTGAACCAGATGAAGCTAGAATATTTCATCTACTCAGACGCGTTGAACGCGAAGCA
TGGTCAGGGCAC
ACTGGTAACTGGGTTCAAATTCTTCAATACAGAGACAAGCGAGGTGACCTTCATGCTCAACACATTGA
TCCTTTACGCTT
TTTCAAACACTACCTGCTGCCAAAAAATCGGTTGATCTCTCCTTCCAGCAAGCCTGACGTCTGCACTA
CTCCAGATAACT
GGTTTGTCCTAGCTGAAAAAACATACGCTCACACTATTGTTAATGGGCTTCCGCTGCTAGAACATAAC
AGAAAGGCCTAT
CTACAAGAGTTAGAAAGTGAAGTCATCCCAGGGCCTTCTACCATGGCCTTTGGGGACGTGGTGCGTG
GAACATCTGCC
TGAGGTAGGAGAACAACGCCTAATAACTTCTAATACTTCTACTGCTTATAAAGCTAACAAAAAAGAAA
AATTAATGCTAA
ACTTACTTGATAAATGTGATGAACTTAACTTACTTGTGTATGAAGACTTAGTTAGTGCTTGTCCTGAC
CTTTTACTTATG
CTTGAAGGTCAGCCAGGTGGTGCACGCCTAATTGAACAGGTGCTTGGCATGCATCATATTAAAGTGTG
TGCTAATTACAC
AGCGTTATCTTTCTTGTTTCATCTACATCCTGATCAATTATTAACTTCTAGCAATAAAGCACTAAAAC
TATTGTTGATTC
AAGGGTACAACCCATTGCAAGTAGGCCACGCCATCTGTTGTGTTCTTAACAAACAGATGGGCAAGCAG
AACACAATTTGC
TTTTATGGCCCTGCTTCAACAGGCAAAACAAATATTGCAAAGGCCATAGTTCAAGGCGTTCGTCTGTA
TGGCTGTGTTAA
TCATTTAAACAAAGGGTTTGTCTTTAACGATTGCAGACAACGCCTCATAATCTGGTGGGAGGAGTGTT
TAATGCACCAAG
ACTGGGTGGAACCTGCTAAATGCATTCTAGGTGGAACTGAATGTAGAATTGATGTTAAACATAAGGAC
AGTGTTCTTCTT
CAACAAACACCAGTAATTATTTCCACTAACCATGACATCTACTCTGTAGTTGGTGGCAATACTGTATC
TCATGTTCATGC
AGCGCCCTTAAAAGAGCGAATCCTTCAGCTAAATTTTATGAAACAACTGCCACAAACATTTGGAGAAA
TTTCTCCAGTTG
AGATTGCAGAATTACTGCAATGGTGCTTTAATGAGTACGACTGTACTCTTACTGGCTTTAAACAAAAA
TGGAACTTAGAT
AAAGTTCCAAACTCATTTCCTCTTGGGGACCTTTGTCCTACACATTCACAGGACTACGTGCTTCACGA
AAACGGATTCTG
CACTGACTGCGGCGGCTATATTCCTCATAGTGCTGACGACTCTGTGTACACTGACGTGGCTAGCGAAA
CATCAATCAGCA
GCGACGACCCAGGTAGGCATTAATACATTAGCCTTTTAATATACTACCTTCCAAGTGCTTATGTATTA
ACTCCTACAGGT

FIG. 9A

GACTTGGGGGATACGGACGGAGAGAACTCCCAGCCGGAGACATCGAACGTGGATAATCGTCCATCCAAGAAGAGACGTGT
GATTCCAGAAACTCCACCAAACAGTCCAGTAAGTCGCCAAAGCCTTTCTAGCTTTTTAGATACGTGGCAGTCACAACCTA
GAGACGAAGATGAGCTCCGAATCTATGAAGCACAGGCATCGCGCATCAAAGAGAACGCCGAGTCCACTCCGGAGAGAGAG
AAGACACCAGTGGGAGAACCACAAGAAGAGTCGCAGTCGGAGCCCGATCCGACAGCATGGGGAGAAAAGCTTGGAGTCTA
CTCCTCGCTACAACCAGGAGAGCCGCCAATCGTCTTACACTGCTTCGAAGACCTCAGACCAAGCGACGAAGACGAAGGAG
AGAACATCGGGGGGGAATAGAACCAATCCTTATACTGTGTTCAGTCAACACAGGGCTAATCATCCAGATGCTCCTGGATG
GTGTGGGTTTTACTGGCATTCTACTCGGCTTGCTAGAGATGGCACTAATTGTATCTTTAATGAAATGAAACAAGAATTTC
AAGAACTACAAATAAATGGAAAAATTACTTGGGATAATGTTAGAGAATTGCTGTTTAGCCAGAAAAAGAAACTAGATCAG
AAATATAGAAATATGCTGTATCATTTCAGACATAACACTGATTGTCCTAGATGTGATTATTGGGATGATGTATACCGTAA
ACACTTAGCTCATGTCTCTTCACAGGAATCAGAGGAGGTAACAGACGAAGAAATGCTTTCTGCTGTTGAAAGCATGGAAA
CAAATGCCTCCAATTAAACGCCAACCTGGAGGGTGGGTGCTTCCTGGTTATAAATACCTTGGTCCATTTAATCCTCTTGA
AAACGGTGAACCAGTTAATAAAGCTGATCGTGCTGCTCAAGCTCATGATAAATCATATTCTGAATTAATAAAGAGTGGAA
AAAACCCTTACTTATATTTTAATAAAGCTGATGAAAAATTCATTGACGATTTGAAAAACGACTGGTCTGTTGGTGGCATT
ATTGGCTCAAGTTTCTTTAAACTTAAGCGCGCCGTGGCTCCTGCTCTAGGAAATAAAGAGCGAGCTCAAAAAAGACATTT
TTACTTTGCAAACTCAAATAAAGGTGCTAAAAGATCAAAAAACAGCGAACCTAAGCCAAGCACTTCAAAAATGTCTGAAA
ATGAAATTCAAGACCAACAACCATCAGACTCTATGGATGGACAACGAGGGGGCGGAGGAGGTGCGACTGGCAGTGTGGGA
GGGGGGAAAGGTTCTGGTGTGGGTATATCCACAGGCGGATGGGTAGGAGGCAGCTACTTTACTGACTCATATGTCATAAC
AAAAAACACCAGACAATTTCTAGTAAAGATACAAAATGACCACAAATACAGAACAGAAAATATTATTCCAAGCAATGCTG
GAGGAAAATCACAAAGATGCGTCAGCACACCGTGGTCATATTTTAACTTCAATCAATACAGCAGTCACTTTTCACCACAA
GACTGGCAGCGCCTAACAAATGAATACAAGCGCTTTAAACCTAGAAAATGCATGTAAAAATTTACAACCTACAAATAAA
ACAAATACTGTCAAATGGTGCTGACACTACATACAACAACGACCTAACAGCTGGTGTTCACATCTTCTGTGATGGTGAGC
ATGCGTATCCAAACGCCACACACCCATGGGACGAAGATGTAATGCCAGAACTTCCATATGAGACATGGTATCTGTTTCAA
TATGGATACATTCCAGTTATTCATGAACTTGCTGAAATGGAAGATGCAAATGCTGTAGAAAAGCTATAGCACTACAAAT
ACCATTCTTCATGCTTGAAAACAGTGACCATGAAGTTCTAAGAACTGGAGAAAGCACAGAATTCACTTTTGACTTTGACT
GTGAATGGATCAATAACGAAAGAGCATACATTCCTCCTGGATTAATGTTTAATCCAAAGGTTCCTACAAGAAGAGCTCAA

FIG. 9A (continued)

```
TACATAAGACAACACGGAAGCACAGCATCAAGCAACACCAGAATTCCACCATATGCAAAACCTACAAG
CTGGATGACAGG
ACCAGGTCTACTCAGCGCACAGAGAGTAGGACCAGCTGCTTCAGACTCAGCAGCATGGATGGTTGTTG
TAAATCCAGACG
GAGCTGCTATTAACTCAGGAATGGCAGGAATTGGTACAGGCTTTGATCCTCCTGGTGGATCTTTAAGA
CCAACTGATTTA
GAATATAAAATACAATGGTACCAAACTCCTGCAGGTACAAACAGCGATGGAAACATCATTTCAAATCC
ATCATTATCCAT
GCTTAGAGATCAAGCTCTCTACAGAGGAAACCAGACAACATATAACCTATGTTCAGACGTATGGATGT
TCCCAAATCAAA
TTTGGGACAGATATCCAATAACCAGAGAAAATCCAATCTGGTGTAAAAAACCAAGATCAGACAAAAGC
ACAATAATTGAT
CCATTCGATGGATCAATTGCAATGGATCATCCTCCAGGAACAATTTTCATAAAAATGGCAAAAATTCC
AGTTCCTTCAAA
CAACAATGCAGACTCATACTTAAACATCTACTGCACTGGACAAGTCAGCTGCGAAATTGTCTGGGAAG
TTGAAAGATATG
CAACAAAGAACTGGAGACCAGAAAGAAGACACACGGCACTTGGCCTTGGGATTGGAGGAGAAGAGAAT
GTAAATCCAACT
TACCATGTTGACAAAAATGGAAAATACATTCAGCCAACAACATGGGACATGTGCTATCCTATCAAAAC
AAACATCAATAA
AGTGTTGTAACCTTGTAAGCCTCTTTTTTGCTTATGCTTGTAAGTTCCTCTCCAATGGACAAGTGGAA
AGAAAAGGGTGA
CTGTAATCCCGAGCTCATAAGTTCGAGGCTACAGTCCGATGGCAGTGGTGTTGCCGTCTCGAACCTAG
CCGTTACACC
```

FIG. 9A (continued)

>HBoV2B-NI213-NS1
MAFSAPVIRAFSQPAFTYVVKFPYDNWKEEEHLLWSLLAPGTERLMIQLRNCAP
HPEDDPVREDILCSLADQHYAAIFTKACYMAVTSLMGQKQRTHFPRCDIICQAEIGSEYL
HCHILVGGAGLSKRNAKISCATLLGLVMAELTQRCKLLLAQRPFEPDEARIFHLLRRVER
EAWSGHTGNWVQILQYRDKRGDLHAQHIDPLRFFKHYLLPKNRLISPSSKPDVCTTPDNW
FVLAEKTYAHTIVNGLPLLEHNRKAYLQELESEVIPGPSTMAFGGRGAWEHLPEVGEQRL
ITSNTSTAYKANKKEKLMLNLLDKCDELNLLVYEDLVSACPDLLLMLEGQPGGARLIEQV
LGMHHIKVCANYTALSFLFHLHPDQLLTSSNKALKLLLIQGYNPLQVGHAICCVLNKQMG
KQNTICFYGPASTGKTNIAKAIVQGVRLYGCVNHLNKGFVFNDCRQRLIIWWEECLMHQD
WVEPAKCILGGTECRIDVKHKDSVLLQQTPVIISTNHDIYSVVGGNTVSHVHAAPLKERI
LQLNFMKQLPQTFGEISPVEIAELLQWCFNEYDCTLTGFKQKWNLDKVPNSFPLGDLCPT
HSQDYVLHENGFCTDCGGYIPHSADDSVYTDVASETSISSDDPGRH

>HBoV2B-NI213-NS2
MAFSAPVIRAFSQPAFTYVVKFPYDNWKEEEHLLWSLLAPGTERLMIQLRNCAP
HPEDDPVREDILCSLADQHYAAIFTKACYMAVTSLMGQKQRTHFPRCDIICQAEIGSEYL
HCHILVGGAGLSKRNAKISCATLLGLVMAELTQRCKLLLAQRPFEPDEARIFHLLRRVER
EAWSGHTGNWVQILQYRDKRGDLHAQHIDPLRFFKHYLLPKNRLISPSSKPDVCTTPDNW
FVLAEKTYAHTIVNGLPLLEHNRKAYLQELESEVIPGPSTMAFGGRGAWEHLPEVGEQRL
ITSNTSTAYKANKKEKLMLNLLDKCDELNLLVYEDLVSACPDLLLMLEGQPGGARLIEQV
LGMHHIKVCANYTALSFLFHLHPDQLLTSSNKALKLLLIQGYNPLQVGHAICCVLNKQMG
KQNTICFYGPASTGKTNIAKAIVQGVRLYGCVNHLNKGFVFNDCRQRLIIWWEECLMHQD
WVEPAKCILGGTECRIDVKHKDSVLLQQTPVIISTNHDIYSVVGGNTVSHVHAAPLKERI
LQLNFMKQLPQTFGEISPVEIAELLQWCFNEYDCTLTGFKQKWNLDKVPNSFPLGDLCPT
HSQDYVLHENGFCTDCGGYIPHSADDSVYTDVASETSISSDDPGDLGDTDGENSQPETSN
VDNRPSKKRRVIPETPPNSPVSRQSLSSFLDTWQSQPRDEDELRIYEAQASRIKENAEST
PEREKTPVGEPQEESQSEPDPTAWGEKLGVYSSLQPGEPPIVLHCFEDLRPSDEDEGENI
GGE

FIG. 9B

>HBoV2B-NI213-NP1
MSSESMKHRHRASKRTPSPLRRERRHQWENHKKSRSRSPIRQHGEKSLESTPRYNQE
SRQSSYTASKTSDQATKTKERTSGGNRTNPYTVFSQHRANHPDAPGWCGFYWHSTRLARD
GTNCIFNEMKQEFQELQINGKITWDNVRELLFSQKKKLDQKYRNMLYHFRHNTDCPRCDY
WDDVYRKHLAHVSSQESEEVTDEEMLSAVESMETNASN

FIG. 9C

```
>HBoV2B-NI213-VP1
MPPIKRQPGGWVLPGYKYLGPFNPLE
NGEPVNKADRAAQAHDKSYSELIKSGKNPYLYFNKADEKFIDDLKNDWSVGGIIGSSFFK
LKRAVAPALGNKERAQKRHFYFANSNKGAKRSKNSEPKPSTSKMSENEIQDQQPSDSMDG
QRGGGGGATGSVGGGKGSGVGISTGGWVGGSYFTDSYVITKNTRQFLVKIQNDHKYRTEN
IIPSNAGGKSQRCVSTPWSYFNFNQYSSHFSPQDWQRLTNEYKRFKPRKMHVKIYNLQIK
QILSNGADTTYNNDLTAGVHIFCDGEHAYPNATHPWDEDVMPELPYETWYLFQYGYIPVI
HELAEMEDANAVEKAIALQIPFFMLENSDHEVLRTGESTEFTFDFDCEWINNERAYIPPG
LMFNPKVPTRRAQYIRQHGSTASSNTRIPPYAKPTSWMTGPGLLSAQRVGPAASDSAAWM
VVVNPDGAAINSGMAGIGTGFDPPGGSLRPTDLEYKIQWYQTPAGTNSDGNIISNPSLSM
LRDQALYRGNQTTYNLCSDVWMFPNQIWDRYPITRENPIWCKKPRSDKSTIIDPFDGSIA
MDHPPGTIFIKMAKIPVPSNNNADSYLNIYCTGQVSCEIVWEVERYATKNWRPERRHTAL
GLGIGGEENVNPTYHVDKNGKYIQPTTWDMCYPIKTNINKVL

>HBoV2B-NI213-VP2
MSENEIQDQQPSDSMDG
QRGGGGGATGSVGGGKGSGVGISTGGWVGGSYFTDSYVITKNTRQFLVKIQNDHKYRTEN
IIPSNAGGKSQRCVSTPWSYFNFNQYSSHFSPQDWQRLTNEYKRFKPRKMHVKIYNLQIK
QILSNGADTTYNNDLTAGVHIFCDGEHAYPNATHPWDEDVMPELPYETWYLFQYGYIPVI
HELAEMEDANAVEKAIALQIPFFMLENSDHEVLRTGESTEFTFDFDCEWINNERAYIPPG
LMFNPKVPTRRAQYIRQHGSTASSNTRIPPYAKPTSWMTGPGLLSAQRVGPAASDSAAWM
VVVNPDGAAINSGMAGIGTGFDPPGGSLRPTDLEYKIQWYQTPAGTNSDGNIISNPSLSM
LRDQALYRGNQTTYNLCSDVWMFPNQIWDRYPITRENPIWCKKPRSDKSTIIDPFDGSIA
MDHPPGTIFIKMAKIPVPSNNNADSYLNIYCTGQVSCEIVWEVERYATKNWRPERRHTAL
GLGIGGEENVNPTYHVDKNGKYIQPTTWDMCYPIKTNINKVL
```

FIG. 9D

>HBoV2B-NI327
GTGACACTATGGCCTTTTCTGCTCCTGTAATTAGAGCTTTTTCTCAACCTGCTTTCACTTATGTTGTT
AAATTTCCATAT
GATAACTGGAAAGAGGAAGAGCACTTACTATGGAGCTTACTTGCTCCTGGGACTGAACGTCTCATGAT
CCAACTAAGAAA
CTGCGCACCACATCCTGAAGATGATCCTGTCAGGGAAGATATTTTATGCTCACTAGCAGACCAACACT
ATGCTGCTATTT
TCACCAAAGCTTGCTACATGGCTGTAACTTCACTCATGGGGCAGAAACAGAGAACACACTTTCCACGA
TGCGACATAATT
TGCCAGGCTGAGATCGGCTCAGAATATCTACACTGTCACATACTTGTTGGAGGAGCAGGTCTGAGCAA
GAGAAATGCTAA
AATTTCATGTGCTACGCTCCTAGGCCTTGTGATGGCTGAATTAACACAACGCTGCAAACTACTTCTTG
CACAGCGTCCAT
TTGAACCAGATGAAGCTAGAATATTTCATCTACTCAGACGCGTTGAACGCGAAGCATGGTCAGGGCAC
ACTGGTAACTGG
GTTCAAATTCTTCAATACAGAGACAAGCGAGGTGACCTTCATGCTCAACACATTGATCCTTTACGCTT
TTTCAAACACTA
CCTGCTGCCAAAAAATCGGTTGATCTCTCCTTCCAGCAAGCCTGACGTCTGCACTACTCCAGATAACT
GGTTTGTCCTAG
CTGAAAAAACATACGCTCACACTATTGTTAATGGGCTTCCGCTGCTAGAACATAACAGAAAGGCCTAT
CTACAAGAGTTA
GAAAGTGAAGTCATCCCAGGGCCTTCTACCATGGCCTTTGGGGACGTGGTGCGTGGGAACATCTGCC
TGAGGTAGGAGA
ACAACGCCTAATAACTTCTAATACTTCTACTGCTTATAAAGCTAACAAAAAGAAAAATTAATGCTAA
ACTTACTTGATA
AATGTGATGAACTTAACTTACTTGTGTATGAAGACTTAGTTAGTGCTTGTCCTGACCTTTTACTTATG
CTTGAAGGTCAG
CCAGGTGGTGCACGCCTAATTGAACAGGTGCTTGGCATGCATCATATTAAAGTGTGTGCTAATTACAC
AGCGTTATCTTT
CTTATTTCATCTACATCCTGATCAATTATTAACTTCTAGCAATAAAGCACTAAAACTATTGTTGATTC
AAGGGTACAACC
CATTGCAAGTAGGCCACGCCATCTGTTGTGTCCTTAACAAACAGATGGGCAAACAGAACACAATTTGC
TTTTATGGCCCT
GCTTCAACAGGCAAAACAAATATTGCAAAGGCCATAGTTCAAGGCGTTCGTCTGTATGGCTGTGTTAA
TCATTTAAACAA
AGGGTTTGTCTTTAACGATTGCAGACAACGCCTCATAATCTGGTGGGAGGAGTGTTTAATGCACCAAG
ACTGGGTAGAAC
CTGCTAAATGCATTCTAGGTGGAACTGAATGTAGAATTGATGTTAAACATAAGGACAGTGTTCTTCTT
CAACAAACACCA
GTAATTATTTCCACTAACCATGACATCTACTCTGTAGTTGGTGGCAATACTGTATCTCATGTTCATGC
AGCGCCCTTAAA
AGAGCGAATCCTTCAGCTAAATTTTATGAAACAACTGCCACAAACATTTGGAGAAATTTCTCCAGTTG
AAATTGCAGAAT
TACTGCAATGGTGCTTTAATGAGTACGACTGTACTCTTACTGGCTTTAAACAAAAATGGAACTTAGAT
AAAGTTCCAAAC
TCATTTCCTCTTGGGGACCTTTGTCCTACACATTCACAGGACTACGTGCTTCACGAAAACGGATTCTG
CACTGACTGCGG
CGGCTATATTCCTCATAGTGCTGACGACTCTGTGTACACTGACGTGGCTAGCGAGACATCAATCAGCA
GCGACGACCCAG
GTAGGCATTAATACATTAGCCTTTTAATATACTACCTTCCAAGTGCTTATGTATTAACTCCTACAGGT
GACTTGGGGGAT

FIG. 10A

```
ACGGACGGAGAGAACTCCCAGCCGGAGACATCGAACGTGGATAATCGTCCATCCAAGAAGAGACGTGT
GATTCCAGAAAC
TCCACCAAACAGTCCAGTAAGTCGCCAAAGCCTTTCTAGCTTTTTAGATACGTGGCAGTCACAACCTA
GAGACGAAGATG
AGCTCCGAATCTATGAAGCACAGGCATCGCGCATCAAAGAGAACGCCGAGTCCACTCCGGAGAGAGAG
AAGACACCAGTG
GGAGAACCACAAGAAGAGTCGCAGTCGGAGCCCGATCCGACAGCATGGGGAGAAAAGCTTGGAGTCTA
CTCCTCGCTACA
ACCAGGAGAGCCGCCAATCGTCTTACACTGCTTCGAAGACCTCAGACCAAGCGACGAAGACGAAGGAG
AGAACATCGGGG
GGGAATAGAACCAATCCTTATACTGTGTTCAGTCAACACAGGGCTAATCATCCAGATGCTCCTGGATG
GTGCGGGTTTTA
CTGGCATTCTACTCGGCTTGCTAGAGATGGCACTAATTGTATCTTTAATGAAATGAAACAAGAATTTC
AAGAACTACAAA
TAAATGGAAAAATTACTTGGGATAATGTTAGAGAATTGCTGTTTAGCCAGAAAAAGAAACTAGATCAG
AAATATAGAAAT
ATGCTGTATCATTTCAGACATAACACTGATTGTCCTAGATGTGATTATTGGGATGATGTATACCGTAA
ACACTTAGCTCA
TGTCTCTTCACAGGAATCAGAGGAGGTAACAGACGAAGAAATGCTTTCTGCTGTTGAAAGCATGGAAA
CAAATGCCTCCA
ATTAAACGCCAACCTGGAGGGTGGGTGCTTCCTGGTTATAAATACCTTGGTCCATTTAATCCTCTTGA
AAACGGTGAACC
AGTTAATAAAGCTGATCGTGCTGCTCAAGCTCATGATAAATCATATTCTGAATTAATAAAGAGTGGAA
AAAACCCTTACT
TATATTTTAATAAAGCTGATGAAAAATTCATTGACGATTTGAAAAACGACTGGTCTGTTGGTGGCATT
ATTGGCTCAAGT
TTCTTTAAACTTAAGCGCGCCGTGGCTCCTGCTCTAGGAAATAAAGAGCGAGCTCAAAAAGACATTT
TTACTTTGCAAA
CTCAAATAAAGGTGCTAAAAAATCAAAAAACAGCGAACCTAAGCCAGGCACTTCAAAAATGTCTGAAA
ATGAAATTCAAG
ACCAACAACCATCAGACTCTATGGATGGACAACGAGGGGGCGGAGGAGGTGCGGCTGGCAGTGTGGGA
GGGGGGAAAGGT
TCTGGTGTGGGTATATCCACAGGCGGATGGGTAGGAGGCAGCTACTTTACTGACTCATATGTCATAAC
AAAAAACACCAG
ACAATTTCTAGTAAAAATACAAAATGACCACAAATACAGAACAGAAAATATTATTCCAAGCAATGCTG
GAGGAAAATCAC
AAAGATGCGTCAGCACACCGTGGTCATATTTTAACTTCAATCAATACAGCAGTCACTTTTCACCACAA
GACTGGCAGCGC
CTAACAAATGAATACAAGCGCTTTAAGCCTAGAAAAATGCATGTAAAAATTTACAACCTACAAATAAA
ACAAATACTGTC
AAATGGTGCTGACACTACATACAACAACGACCTAACAGCTGGTGTTCACATCTTCTGTGATGGTGAGC
ATGCGTATCCAA
ACGCCACACACCCATGGGACGAAGATGTAATGCCAGAACTTCCATATGAGACATGGTATCTGTTTCAA
TATGGATACATT
CCAGTTATTCATGAACTTGCTGAAATGGAAGATGCAAATGCTGTAGAAAAGCTATAGCACTACAAAT
ACCATTCTTCAT
GCTTGAAAACAGTGACCATGAAGTTCTAAGAACTGGAGAAAGCACAGAATTCACTTTTGACTTTGACT
GTGAATGGATCA
ACAACGAAAGAGCATACATTCCTCCTGGATTAATGTTTAATCCAAAGGTTCCTACAAGAAGAGCTCAA
TACATAAGACAA
```

FIG. 10A (continued)

```
CACGGAAGCACAGCATCAAGCAACACCAGAATTCCACCATATGCAAAACCTACAAGCTGGATGACAGG
ACCAGGTCTACT
CAGCGCACAGAGAGTAGGACCAGCTGCTTCAGACTCAGCAGCATGGATGGTTGTTGTAAATCCAGACG
GAGCTGCTATTA
ACTCAGGAATGGCAGGAATTGGTACAGGCTTTGATCCTCCTGGTGGATCTTTAAGACCAACTGATTTA
GAATATAAAATA
CAATGGTACCAAACTCCTGCAGGTACAAACAGCGATGGAAACATCATTTCAAATCCATCATTATCCAT
GCTTAGAGATCA
AGCTCTCTACAGAGGAAACCAGACAACATATAACCTATGTTCAGACGTATGGATGTTCCCAAATCAAA
TTTGGGACAGAT
ATCCAATAACAAGAGAAAATCCAATCTGGTGTAAAAAACCAAGATCAGACAAAAGCACAATAATTGAT
CCATTCGATGGA
TCAATTGCAATGGATCATCCTCCAGGAACAATTTTCATAAAAATGGCAAAAATTCCAGTTCCTTCAAA
CAACAATGCAGA
CTCATACTTAAACATATACTGCACTGGACAAGTCAGCTGCGAAATTGTCTGGGAAGTTGAAAGATATG
CAACAAAGAACT
GGAGACCAGAAAGAAGACACACGGCACTTGGCCTTGGGATTGGAGGAGAAGAAAATGTAAATCCAACT
TACCATGTTGAC
AAAAATGGTAAATACATTCAGCCAACAACTTGGGACATGTGCTATCCTATCAAAACAAACATCAATAA
AGTGTTGTAATC
TCTTAAGCCTGTTCATTGCTTATGCTTATAAGTTCCTCTCCAATGGACAAGAGGAAAGAAAAGGGTGA
CTGTAATCCCGA
GCTCATGAGTTCGAGGCTACAGTCCGATGGCAGTGGTGTTGCCGTCTCGAACCTAGCCGTTACACCCT
```

FIG. 10A (continued)

>HBoV2B-NI327-NS1
MAFSAPVIRAFSQPAFTYVVKFPYDNWKEEEHLLWSLLAPGTERLMIQLRNCAPHPED
DPVREDILCSLADQHYAAIFTKACYMAVTSLMGQKQRTHFPRCDIICQAEIGSEYLHCHI
LVGGAGLSKRNAKISCATLLGLVMAELTQRCKLLLAQRPFEPDEARIFHLLRRVEREAWS
GHTGNWVQILQYRDKRGDLHAQHIDPLRFFKHYLLPKNRLISPSSKPDVCTTPDNWFVLA
EKTYAHTIVNGLPLLEHNRKAYLQELESEVIPGPSTMAFGGRGAWEHLPEVGEQRLITSN
TSTAYKANKKEKLMLNLLDKCDELNLLVYEDLVSACPDLLLMLEGQPGGARLIEQVLGMH
HIKVCANYTALSFLFHLHPDQLLTSSNKALKLLLIQGYNPLQVGHAICCVLNKQMGKQNT
ICFYGPASTGKTNIAKAIVQGVRLYGCVNHLNKGFVFNDCRQRLIIWWEECLMHQDWVEP
AKCILGGTECRIDVKHKDSVLLQQTPVIISTNHDIYSVVGGNTVSHVHAAPLKERILQLN
FMKQLPQTFGEISPVEIAELLQWCFNEYDCTLTGFKQKWNLDKVPNSFPLGDLCPTHSQD
YVLHENGFCTDCGGYIPHSADDSVYTDVASETSISSDDPGRH

>HBoV2B-NI327-NS2
MAFSAPVIRAFSQPAFTYVVKFPYDNWKEEEHLLWSLLAPGTERLMIQLRNCAPHPED
DPVREDILCSLADQHYAAIFTKACYMAVTSLMGQKQRTHFPRCDIICQAEIGSEYLHCHI
LVGGAGLSKRNAKISCATLLGLVMAELTQRCKLLLAQRPFEPDEARIFHLLRRVEREAWS
GHTGNWVQILQYRDKRGDLHAQHIDPLRFFKHYLLPKNRLISPSSKPDVCTTPDNWFVLA
EKTYAHTIVNGLPLLEHNRKAYLQELESEVIPGPSTMAFGGRGAWEHLPEVGEQRLITSN
TSTAYKANKKEKLMLNLLDKCDELNLLVYEDLVSACPDLLLMLEGQPGGARLIEQVLGMH
HIKVCANYTALSFLFHLHPDQLLTSSNKALKLLLIQGYNPLQVGHAICCVLNKQMGKQNT
ICFYGPASTGKTNIAKAIVQGVRLYGCVNHLNKGFVFNDCRQRLIIWWEECLMHQDWVEP
AKCILGGTECRIDVKHKDSVLLQQTPVIISTNHDIYSVVGGNTVSHVHAAPLKERILQLN
FMKQLPQTFGEISPVEIAELLQWCFNEYDCTLTGFKQKWNLDKVPNSFPLGDLCPTHSQD
YVLHENGFCTDCGGYIPHSADDSVYTDVASETSISSDDPGDLGDTDGENSQPETSNVDNR
PSKKRRVIPETPPNSPVSRQSLSSFLDTWQSQPRDEDELRIYEAQASRIKENAESTPERE
KTPVGEPQEESQSEPDPTAWGEKLGVYSSLQPGEPPIVLHCFEDLRPSDEDEGENIGGE

FIG. 10B

>HBoV2B-NI327-NP1
M
SSESMKHRHRASKRTPSPLRRERRHQWENHKKSRSRSPIRQHGEKSLESTPRYNQESRQS
SYTASKTSDQATKTKERTSGGNRTNPYTVFSQHRANHPDAPGWCGFYWHSTRLARDGTNC
IFNEMKQEFQELQINGKITWDNVRELLFSQKKKLDQKYRNMLYHFRHNTDCPRCDYWDDV
YRKHLAHVSSQESEEVTDEEMLSAVESMETNASN

FIG. 10C

>HBoV2B-NI327-VP1
MPPIKRQPGGWVLPGYKYLGPFNPLENGEP
VNKADRAAQAHDKSYSELIKSGKNPYLYFNKADEKFIDDLKNDWSVGGIIGSSFFKLKRA
VAPALGNKERAQKRHFYFANSNKGAKKSKNSEPKPGTSKMSENEIQDQQPSDSMDGQRGG
GGGAAGSVGGGKGSGVGISTGGWVGGSYFTDSYVITKNTRQFLVKIQNDHKYRTENIIPS
NAGGKSQRCVSTPWSYFNFNQYSSHFSPQDWQRLTNEYKRFKPRKMHVKIYNLQIKQILS
NGADTTYNNDLTAGVHIFCDGEHAYPNATHPWDEDVMPELPYETWYLFQYGYIPVIHELA
EMEDANAVEKAIALQIPFFMLENSDHEVLRTGESTEFTFDFDCEWINNERAYIPPGLMFN
PKVPTRRAQYIRQHGSTASSNTRIPPYAKPTSWMTGPGLLSAQRVGPAASDSAAWMVVVN
PDGAAINSGMAGIGTGFDPPGGSLRPTDLEYKIQWYQTPAGTNSDGNIISNPSLSMLRDQ
ALYRGNQTTYNLCSDVWMFPNQIWDRYPITRENPIWCKKPRSDKSTIIDPFDGSIAMDHP
PGTIFIKMAKIPVPSNNNADSYLNIYCTGQVSCEIVWEVERYATKNWRPERRHTALGLGI
GGEENVNPTYHVDKNGKYIQPTTWDMCYPIKTNINKVL

>HBoV2B-NI327-VP2
MSENEIQDQQPSDSMDGQRGG
GGGAAGSVGGGKGSGVGISTGGWVGGSYFTDSYVITKNTRQFLVKIQNDHKYRTENIIPS
NAGGKSQRCVSTPWSYFNFNQYSSHFSPQDWQRLTNEYKRFKPRKMHVKIYNLQIKQILS
NGADTTYNNDLTAGVHIFCDGEHAYPNATHPWDEDVMPELPYETWYLFQYGYIPVIHELA
EMEDANAVEKAIALQIPFFMLENSDHEVLRTGESTEFTFDFDCEWINNERAYIPPGLMFN
PKVPTRRAQYIRQHGSTASSNTRIPPYAKPTSWMTGPGLLSAQRVGPAASDSAAWMVVVN
PDGAAINSGMAGIGTGFDPPGGSLRPTDLEYKIQWYQTPAGTNSDGNIISNPSLSMLRDQ
ALYRGNQTTYNLCSDVWMFPNQIWDRYPITRENPIWCKKPRSDKSTIIDPFDGSIAMDHP
PGTIFIKMAKIPVPSNNNADSYLNIYCTGQVSCEIVWEVERYATKNWRPERRHTALGLGI
GGEENVNPTYHVDKNGKYIQPTTWDMCYPIKTNINKVL

FIG. 10D

>HBoV4-NI374
TCCACCTGTTATTAGAGCATTCTCTTCCCCTGCTTTTACTTATGTCTTCAAATTTCCATATCGATCAT
GGAAAGAAAAG
AATGGCTTCTTCATGCGCTTCTAGCTCATGGTACCGAGCAAGCCATGATCCAGCTGAGAAACTGTGTT
CCTCATCCGGAT
GAAGATATAATCCGTGATGACTTACTGCTTTCTCTAGAAGATCGCCATTTTGGGGCAATTCTCTGCAA
AGCTGTTTATAT
GGCTACTACTACTTTCATGTCACAGAAACAAAGAAATATGTTTCCTCGCTGTGACATAATAGTCCAGT
CTGAGCTTGGGG
AGACAAACCTACACTGCCATATTATAGTTGGGGAGAAGGCTTAAGCAAGAGAAATGCAAAACATCA
TGTCCTCAACTA
TATGGACTGATACTAGGGGAATTAATCCAACGCTGCAAAACTCTTCTGGCTACGCGTCCTTTCGAACC
GGAAGAGGCAGA
AATTTATCATGCTTTAAAACGAGCTGAGCGAGAAGCTTGGGGTGGAGTTACTAGCGGCAACCTACAAA
TTCTCCAATACA
GAGATCGCAGAGGAGACCTTCACGCACAACAAGTGGATGCTCTTCGCTTCTTCAAAAACTACCTATTG
CCTAAAAATAGA
TGCATTACATCTTACAGCAGACCTGATGTCTGTACTTCTCCAGAAAACTGGTTTGTTTTAGCTGAAAA
AACTTACTGTCA
CACTCTTGTTAACGGGCTGCCGCTTCCAGAACATTACAGAAAACACTACCACGCAACCCTAGATAACG
AAGTTCTACCGG
GGCCTCAGACAATGGCCTTTGGGGACGTGGTCCGTGGGAACATCTTCCTGAGGTAGGAGATCAACGT
TTAGCTGCCTCT
TCTGTTAGTACAACATATAAACCAAACAAAAAGAAAAACTTATGCTTAACTTACTAGATAAATGCAG
CGAATTAAACCT
TTTAGTTTATGAAGACTTAGTAGCTAACTGTCCTGAACTTTTGCTTATGCTTGAAGGTCAACCAGGTG
GAGCACGCCTAA
TAGAACAAGTCCTAGGCATGCACCATATTAATGTTTGCTCTAACTTTACTGCTCTTAGTTATCTCTTT
CACCTTTACCCT
AGCACAACTTTATCTTCAGATAACAAGGCTTTGCAGCTGTTGTTGATACAAGGTTACAACCCATTAAT
GGTTGGTCACGC
CTTGTGCTGTGTACTCAACAAGCAGTTTGGCAAACAGAACACTGTTTGCTTTTATGGACCAGCTTCTA
CTGGTAAAACAA
ACATGGCAAAGGCCATAGTCCAAGGCATTCGACTATATGGCTGTGTTAATCATTTAAACAAAGGGTTT
GTCTTTAATGAT
TGCAGACAACGCCTAGTTGTTTGGTGGGAGGAGTGCTTAATGCACCAGGATTGGGTGGAACCAGCAAA
GTGTATCTTGGG
TGGAACTGAGTGTAGAATTGACGTCAAACACAGAGATAGTGTATTATTGACACAAACTCCAGTAATTA
TTTCCACTAACC
ACGATATCTACGCGGTTGTTGGTGGTAATTCTGTTTCTCATGTTCATGCGGCTCCATTAAAAGAAAGA
GTGATTCAGCTA
AATTTTATGAAACAACTTCCTCAAACCTTTGGAGAGATCACTCCAGAAGAAATTGCAGCTCTACTGCA
ATGGTGTTTCAA
TGAGTACGAGTGTACTCTGACAGGCTTTAAAACAAAATGGAGCCTAGATAAGATTCCAAACTCATTTC
CTCTTGGGGTCC
TTTGTCCTACTCATTCACAGGACTTCATACTCCACGAAAACGGATACTGCACTGATTGTGGTGGTTAC
CTTGCTCATAGC
GCTGACGATTCTGTGTACACTGATCGTGCAAGCGACACTAGCAAAGAAGCCATCGACGCAGGTAAGTT
TACATTCTCCAG

FIG. 11A

```
ACACTTCATATATATCCTACACACCACACTAAAACATATGTTTAATTACAGGTGACTTGGGGGATACG
GACGGAGAGGAC
TCCGAGTCTGAAGCATCGGAAGTGGGTGTTCGTCCATCCAAGAAGCGACGCATAACTATTCCTGCAAC
TCCACCAAATTC
TCCTGGCAGCTCTGTGAGTACTTCTGCCTTCTTTGATAATTGGTGCGCACAACCGCGAGACGAAGATG
AGCTCAGGGAAT
ACAAAAGACAAGCATCGCGCCTACAAAAGAAAAGGGAGTCCAGGGAGAGACGAGAGGAAACGCCCATG
GCAACCTCGTCA
CAGGAGTCGGAGCCGGAGCCCAATCCGACGCAGTGGGAAGACAAGCTCGGGGTCATACCGTCAGGAAC
ACCAGATCAGCC
ACCTATCGTCTTGCACTGCTTCGAAGATCTCAGACCCAGTGACGAAGACGAAGGAGAATACATCGGGG
AAGAGAGACTCT
AGAACTAATCCATATACTGTATTCAGCCAGCATAAAGCTTCAAATCCTGATGCTCCAGGGTGGTGTGG
GTTTTATTGGCA
CTCTACTAGAATTGCTAGAAATGGTACTAATGCAATCTTTAATGAAATGAAACAGCAGTTTCAACAAC
TGCAACTAGACA
ACAAGATTGGCTGGGATAATGCTAGAGAACTATTGTTTAGCCAGAAAAAATCACTAGATCAACAATAC
AGAAATATGTTT
TGGCACTTTAGAAATGCTCCTGATTGTGAACGCTGTAATTACTGGGATAATGTGTACCGTATGCACTT
AGCTCATGTTTC
CTCTCAGGCAGAATCAGAAGAAATAACTGACGAGGAAATGCTTTCTGCTGCTGAAAGTATGGAAACAG
ATGCCTCCAATT
AAAAGGCAACCTGGAGGGTGGGTACTTCCTGGTTACAAATACCTTGGTCCATTTAATCCTCTTGATAA
CGGTGAACCAGT
TAATAAAGCTGATCGTGCTGCTCAAGCTCATGATAAATCATATTCTGAATTAATAAAAAAGTGGAAAA
AAATCCTTACTT
GTATTTTCAATAAAGCTGATGAAAAATTCATTGACGATTTGAAAAACGACTGGTCTCTTGGTGGCATT
ATTGGCTCAAAT
TTCTTTAAACTTAAGCGCGCCGTGGCTCCTGCTCTAGGAAATAAAGAGCGAGCTCAAAAAAGACATTT
TTATTTTGCAAA
CTCAAATAAAGGTGCTAAAAAATCAAAAAACAACGAACCTAAACCAAGCACCTCAAAAATGTCTGAAA
ATGAAATTCAAG
ACCAACAGCCATCAGAACCTAATGATGGCCAGCGAGGAGGGGCGGAGGTACAACCGGCAGTGTGGGA
GGGGGGAAAGGT
TCTGGTGTGGGTATATCCACAGGTGGATGGGTAGGAGGCAGCTACTTTACTGACTCATATGTCATAAC
AAAAAACACCAG
ACAATTTCTGGTTAAAATCCAAAACAACCATCAATATAAAACTGAAAATATAATTCCTTCTAATGGAG
GAGGAAAATCAC
AAAGATGTGTCAGCACACCATGGTCATACTTTAACTTTAATCAATACAGCAGCCATTTCTCACCACAA
GACTGGCAGCGC
CTAACAAATGAATACAAAAGATTCAGACCTAAAGGTATGCATGTTAAAATCTACAATTTACAGATAAA
ACAAATTTTATC
AAATGGTGCTGATGTTACATACAACAACGACCTAACAGCAGGAGTACACATCTTTTGTGATGGCGAAC
ATGCATATCCAA
ACGCTACACATCCATGGGACGAAGATGTGATGCCAGAGCTTCCTTACCAAACATGGTATCTATTTCAA
TATGGATACATA
CCTACAATTCATGAACTTGCAGAAATGGAAGACTCCAATGCAGTAGAAAAGCAATTGCTTTACAAAT
ACCATTCTTCAT
GCTTGAAAACAGCGACCATGAAGTTCTAAGAACTGGAGAAAGTGCAGAATTCAACTTTAACTTTGATT
GTGAATGGATTA
```

FIG. 11A (continued)

```
ACAATGAAAGAGCATTCATTCCTCCAGGACTGATGTTCAATCCATTGGTACCAACAAGAAGAGCTCAA
TACATAAGAAGA
AATGGAAACACTCAAGCAAGTACCACAAGAATCCAACCTTACTCAAAACCAACAAGTTGGATGACTGG
ACCAGGTCTACT
CAGTGCGCAACGAGTAGGTCCAGCTGCTTCAGACACAGCTGCATGGATGGTTGGAATAGATCTAGACG
GTGCAAACGTAA
ACTCAGGAAGAGCAGGAGTCAGCACAGGCTTTGATCCTCCAGCAGGTTCACTTAGACCTACAGATCTA
GAATACAAAATA
CAATGGTACCAGACTCCAGCTGGAACAAACAATGATGGAAACATCATATCAAATCCACCTCTTTCAAT
GCTCAGAGATCA
AACTCTATACAAAGGAAACCAAACAACCTACAACTTATGCTCAGATGTATGGATGTTCCCAAATCAAA
TTTGGGACAGAT
ACCCAATAACCAGAGAAAATCCTATTTGGTGCAAACAACCAAGATCAGACAAACACACTGTCATTGAT
CCGTTCGATGGA
TCTCTTGCAATGGATCATCCTCCAGGAACAATTTTTATCAAAATGGCAAAAATTCCAGTTCCTTCAAG
CAACAACGCAGA
CTCATACTTAAACATCTACTGCACTGGACAAGTCAGCTGCGAAATTGTCTGGGAAGTCGAAAGATATG
CAACAAAGAACT
GGAGACCAGAAAGAAGACACACGGCACTCGGCCTTGGAATTGGAGGAGCAGATGAAATCAACCCAACA
TACCATGTTGAC
AAAAACGGAGCCTACATTCAACCAACATCATGGGACATGTGCTTTCCAGTTAAAACAAACATCAATAA
AGTGTTGTAATC
TCTTAAGCCTCTTTATTGCTCACGCTTGTAAGTTCCTCTCCAATGGACAAGTGGAAAGAAAAGGGTGA
CTGTAATCCCGA
GCTCATGAGTTCGAGGCTACAGTCCGATGGCAGTGGTGTTGCCGTCTCGAACCTAGCCGTTAAACCCT
```

FIG. 11A (continued)

>HBoV4-NI374-NS1
PPVIRAFSSPAFTYVFKFPYRSWKEKEWLLHALLAHGTEQAMIQLRNCVPHPDEDIIRDD
LLLSLEDRHFGAILCKAVYMATTTFMSQKQRNMFPRCDIIVQSELGETNLHCHIIVGGEG
LSKRNAKTSCPQLYGLILGELIQRCKTLLATRPFEPEEAEIYHALKRAEREAWGGVTSGN
LQILQYRDRRGDLHAQQVDALRFFKNYLLPKNRCITSYSRPDVCTSPENWFVLAEKTYCH
TLVNGLPLPEHYRKHYHATLDNEVLPGPQTMAFGGRGPWEHLPEVGDQRLAASSVSTTYK
PNKKEKLMLNLLDKCSELNLLVYEDLVANCPELLLMLEGQPGGARLIEQVLGMHHINVCS
NFTALSYLFHLYPSTTLSSDNKALQLLLIQGYNPLMVGHALCCVLNKQFGKQNTVCFYGP
ASTGKTNMAKAIVQGIRLYGCVNHLNKGFVFNDCRQRLVVWWEECLMQDWVEPAKCILG
GTECRIDVKHRDSVLLTQTPVIISTNHDIYAVVGGNSVSHVHAAPLKERVIQLNFMKQLP
QTFGEITPEEIAALLQWCFNEYECTLTGFKTKWSLDKIPNSFPLGVLCPTHSQDFILHEN
GYCTDCGGYLAHSADDSVYTDRASDTSKEAIDAGKFTFSRHFIYILHTTLKHMFNYR

>HBoV4-NI374-NS2
PPVIRAFSSPAFTYVFKFPYRSWKEKEWLLHALLAHGTEQAMIQLRNCVPHPDEDIIRDD
LLLSLEDRHFGAILCKAVYMATTTFMSQKQRNMFPRCDIIVQSELGETNLHCHIIVGGEG
LSKRNAKTSCPQLYGLILGELIQRCKTLLATRPFEPEEAEIYHALKRAEREAWGGVTSGN
LQILQYRDRRGDLHAQQVDALRFFKNYLLPKNRCITSYSRPDVCTSPENWFVLAEKTYCH
TLVNGLPLPEHYRKHYHATLDNEVLPGPQTMAFGGRGPWEHLPEVGDQRLAASSVSTTYK
PNKKEKLMLNLLDKCSELNLLVYEDLVANCPELLLMLEGQPGGARLIEQVLGMHHINVCS
NFTALSYLFHLYPSTTLSSDNKALQLLLIQGYNPLMVGHALCCVLNKQFGKQNTVCFYGP
ASTGKTNMAKAIVQGIRLYGCVNHLNKGFVFNDCRQRLVVWWEECLMQDWVEPAKCILG
GTECRIDVKHRDSVLLTQTPVIISTNHDIYAVVGGNSVSHVHAAPLKERVIQLNFMKQLP
QTFGEITPEEIAALLQWCFNEYECTLTGFKTKWSLDKIPNSFPLGVLCPTHSQDFILHEN
GYCTDCGGYLAHSADDSVYTDRASDTSKEAIDAGDLGDTDGEDSESEASEVGVRPSKKRR
ITIPATPPNSPGSSVSTSAFFDNWCAQPRDEDELREYKRQASRLQKKRESRERREETPMA
TSSQESEPEPNPTQWEDKLGVIPSGTPDQPPIVLHCFEDLRPSDEDEGEYIGEERL

FIG. 11B

>HBoV4-NI374-NP1
MSSGN
TKDKHRAYKRKGSPGRDERKRPWQPRHRSRSRSPIRRSGKTSSGSYRQEHQISHLSSCTA
SKISDPVTKTKENTSGKRDSRTNPYTVFSQHKASNPDAPGWCGFYWHSTRIARNGTNAIF
NEMKQQFQQLQLDNKIGWDNARELLFSQKKSLDQQYRNMFWHFRNAPDCERCNYWDNVYR
MHLAHVSSQAESEEITDEEMLSAAESMETDASN

FIG. 11C

>HBoV4-NI374-VP1
MPPIKRQPGGWVLPGYKYLGPFNPLDNGEPV
NKADRAAQAHDKSYSELIKKWKKILTCIFNKADEKFIDDLKNDWSLGGIIGSNFFKLKRA
VAPALGNKERAQKRHFYFANSNKGAKKSKNNEPKPSTSKMSENEIQDQQPSEPNDGQRGG
GGGTTGSVGGGKGSGVGISTGGWVGGSYFTDSYVITKNTRQFLVKIQNNHQYKTENIIPS
NGGGKSQRCVSTPWSYFNFNQYSSHFSPQDWQRLTNEYKRFRPKGMHVKIYNLQIKQILS
NGADVTYNNDLTAGVHIFCDGEHAYPNATHPWDEDVMPELPYQTWYLFQYGYIPTIHELA
EMEDSNAVEKAIALQIPFFMLENSDHEVLRTGESAEFNFNFDCEWINNERAFIPPGLMFN
PLVPTRRAQYIRRNGNTQASTTRIQPYSKPTSWMTGPGLLSAQRVGPAASDTAAWMVGID
LDGANVNSGRAGVSTGFDPPAGSLRPTDLEYKIQWYQTPAGTNNDGNIISNPPLSMLRDQ
TLYKGNQTTYNLCSDVWMFPNQIWDRYPITRENPIWCKQPRSDKHTVIDPFDGSLAMDHP
PGTIFIKMAKIPVPSSNNADSYLNIYCTGQVSCEIVWEVERYATKNWRPERRHTALGLGI
GGADEINPTYHVDKNGAYIQPTSWDMCFPVKTNINKVL

>HBoV4-NI374-VP2
MSENEIQDQQPSEPNDGQRGG
GGGTTGSVGGGKGSGVGISTGGWVGGSYFTDSYVITKNTRQFLVKIQNNHQYKTENIIPS
NGGGKSQRCVSTPWSYFNFNQYSSHFSPQDWQRLTNEYKRFRPKGMHVKIYNLQIKQILS
NGADVTYNNDLTAGVHIFCDGEHAYPNATHPWDEDVMPELPYQTWYLFQYGYIPTIHELA
EMEDSNAVEKAIALQIPFFMLENSDHEVLRTGESAEFNFNFDCEWINNERAFIPPGLMFN
PLVPTRRAQYIRRNGNTQASTTRIQPYSKPTSWMTGPGLLSAQRVGPAASDTAAWMVGID
LDGANVNSGRAGVSTGFDPPAGSLRPTDLEYKIQWYQTPAGTNNDGNIISNPPLSMLRDQ
TLYKGNQTTYNLCSDVWMFPNQIWDRYPITRENPIWCKQPRSDKHTVIDPFDGSLAMDHP
PGTIFIKMAKIPVPSSNNADSYLNIYCTGQVSCEIVWEVERYATKNWRPERRHTALGLGI
GGADEINPTYHVDKNGAYIQPTSWDMCFPVKTNINKVL

FIG. 11D

>HBoV3-NI385
ACTATGGCCTTTTCTGCTCCTGTACTTAGAGCTTTTTCTCAACCTACTTTTACCTATGTTATTAAATT
TCCATATAATAA
CTGGAAAGAAGATGAACACTTACTATGGAGCTTACTTGCTCCTGGGACTGAAAGTCTCATGATTCAAC
TAAAAAACTGCG
CACCACATCCTGAAGATGATCCTATCAGGGAAGATATTTTATGCTCACTAGCAGATCTACACTATGGT
GCTGTTTTTGCC
AAAGCTTGCTACATAGCTACATCTACACTAATGGGGCAGAAACAAAGAACACTCTTTCCACGCTGCGA
CATTGTTTGCCA
GTCTGAAATTGGCTCAGACTTTCTACACTGTCACATACTTGTTGGAGGAGCCGGTCTTAGCAAGAGAA
ATGCTAAAATTT
CACGCGCTACACTTTTGGGTCTTGTGATGGCTGAACTAACACAACGCTGCAAGCTACTTCTTGCACAT
CGTCCATTTGAA
CCAGCTGAAGCTACTATCTATCATGAACTTAAACGCATTGAACGCGAAGCATGGTCAGGGCATACTGG
TAACTGGGTTCA
GATTCTTCAATACAAAGATAAACGAGGTGATCTTCACGCTCAACCAATTGATCCCTTACGCTTTCTAA
ACATTACATTC
TACCAAAAAATCGATTGATTTCTCCTTCCAGCAAACCTGACGTCTGCACTTCTCCAGATAACTGGTTT
ATTCTAGCTGAC
AAAACATACTCTCACACTATTATTAATGGGCTTCCGCTGCTAGAACGTAACAGAAAAGCCTATCTACA
AGAGTTAGAAAG
TGAAGTCATCCCGGGGCCTTCTGCCATGGCCTTTGGGGACGTGGTGCGTGGGAACAACTTCCTGAGG
TAGGAGAACAAC
GCCTAATTACTTCTAATACTTCTACTGCTTATAAAGCTAACAAAAAGAAAAATTAATGTTAAATTTA
CTTGATAAATGT
GATGAACTTAATTTGCTTGTATATGAAGACTTAGTTAGTGCTTGTCCTGACCTTTTACTAATGCTTGA
AGGACAACCGGG
TGGAGCACGACTAATTGAACAGGTGCTTGGCATGCACCATATTAAAGTATGTGCTAAACATACTGCCT
TATCTTTTTAT
TTCACTTACATCCTGATCAATTATTAACTTCTAGCAATAAAGCACTAAAACTACTATTGATTCAAGGA
TACAACCCATTA
CAAGTAGGGCATGCCATCTGTTGTGTACTTAACAAACAGATGGGCAAGCAGAACACTATTTGCTTTTA
TGGCCCTGCTTC
AACAGGCAAAACAAACTTTGCAAAAGCTATAGTTCAGGGCGTTCGCCTTTATGGCTGTGTTAATCATT
TAAACAAGGGGT
TTGTTTTTAACGATTGCAGACAACGCCTTATAATTTGGTGGGAAGAATGTTTAATGCATCAAGATTGG
GTAGAACCTGCT
AAATGTATTTTAGGCGGAACTGAATGTAGAATTGATGTTAAACATAAAGATAGTGTTCTCCTTCAACA
AACACCAGTAAT
CATTTCCACTAACCATGACATCTACTCTGTAGTTGGTGGCAATACTGTTTCTCATGTTCATGCAGCAC
CATTAAAAGAAC
GAGTTCTTCAGCTAAATTTTATGAAACAACTACCACAAACATTTGGAGAAATCTCTCCAAGTGAAATT
GCAGAACTTTTG
CAATGGTGCTTTAATGAGTACGACTGTACTCTTGCTGGCTTTAAACAAAATGGAACTTAGACAAAGT
TCCAAACTCATT
TCCTATTGGAGACCTTTGTCCTACACATTCACAGGACTTCACGCTTCACGAAAACGGATTCTGCTCTG
ACTGTGGCGGCT
ATCTTCCTCATAGCGCTGACGATTCTGTTTACACTGACGTGGCTAGTGAAACAACCAGCGGTGACTAC
GACCCAGGTAGG
CTTTAATACATTAGCTTTACTATTTATTACTCTTGAAGTTTGCTTATGTATTAACTCCTACAGGTAAC
CTGGGGGATACG

FIG. 12A

```
GACGGAGAGGACTCCAAGTCAGAAGCATCGGAAGTGGATTATTGTCCACCCAAGAAAAGGCGTGTGAT
TTCAGCAACTCC
ACCAAACAGTCCAGTAAGTGGTCCAAGCCTTTCTACCTTTTTAGATACTTGGCAATCACAACCTAGAG
ACGACGATGAGC
TCAGAATCTACGAAGAACAGGCATCGCAGTTCCAAAAGAACACCAAGTCCACTTCAGAAAGAGAGGAA
GCGCAACTGGGA
GAATCGCAAGAGCCGCAGCCGGAGCCCGATCCGACGGCATGGGGAGAAAAACTTGGAGTATGCTCATC
ACAACAACCAGG
ACAACCGCCAATCGTCCTATACTGCTTCGAAGACCTCAGACCAAGCGATGAAGACGAAGGAGAAAACA
TCGGGGGGGACT
AGAACAAATCCTTATACTGTATTCAGTCAACACAGGGCTAATCATTCAAATGCTCCTGGCTGGTGTGG
GTTTTACTGGCA
TTCAACTAGGCTTGCTAGAAATGGCACTAATAATATTTTTAATGAAATGAAACAAAAATTTCAAGAAC
TACAAATAGATG
GGAAAATCAGTTGGGATACTACTAGAGAACTATTGTTTACTCAGAAAAAAACATTAGATCAAGGCTAC
AGAAACATGTTG
TACCACTTTAGACACAGTCCTGATTGTCCTAGATGTGATTATTGGGATGATGTTTACCGTAAACACTT
AGCTAATGTCTC
TTCACAGGAATCAGAGGAGGTTACAGACGAAGAAATGCTTTCTGCTGTTGAAAGCATGGAAACAAATG
CCTCCAATTAAA
CGCCAACCTGGAGGGTGGGTGCTTCCTGGTTATAAATACCTTGGTCCATTTAATCCTCTTGAAAACGG
TGAACCAGTTAA
TAAAGCTGATCGTGCTGCTCAAGCTCATGATAAATCATATTCTGAACTAATAAAAAGTGGAAAAAATC
CTTACTTATATT
TCAATAAAGCTGATGAAAAATTCATTGACGATTTGAAAGACGATTGGTCTCTTGGTGGCATTATTGGC
TCAAGTTTTTTT
AAACTTAAACGCGCCGTGGCTCCTGCTCTAGGAAATAAAGAGCGAGCTCAAAAAAGACATTTCTACTT
TGCAAACTCAAA
TAAAGGTGCTAAAAAAACAAAAAACAACGAACCTAAGCCAGGCACTTCAAAAATGTCTGAAAATGAAA
TTCAAGACCAAC
AACCATCAGATTCTATGGATGGACAACGAGGGGCGGAGGAGGTGCAACTGGCAGTGTGGGAGGGGGG
AAAGGTTCTGGT
GTGGGTATATCCACAGGCGGATGGGTAGGAGGCAGCTATTTTACTGACTCATATGTTATAACAAAAAA
CACCAGACAATT
TCTAGTTAAAATACAAAACAACCATCAATACAAAACAGAATTAATATCGCCTTCCACATCTCAAGGAA
AATCACAAAGAT
GCGTCAGCACGCCTTGGTCTTACTTTAACTTTAATCAATACAGCAGTCATTTTTCACCACAAGACTGG
CAGCGATTAACA
AACGAATATAAAAGATTCAGACCCAAAGGCATGCATGTTAAAATATACAATTTACAAATAAAACAAAT
TCTTTCAAATGG
TGCTGACACTACATACAACAACGACCTCACAGCTGGTGTTCACATTTTTTGTGATGGCGAACACGCAT
ATCCAAATGCAA
CACATCCTTGGGATGAAGACGTTATGCCAGAGCTGCCATACCAAACATGGTATTTGTTTCAATATGGA
TATATTCCAGTT
ATACATGAACTTGCTGAAATGGAAGACTCAAATGCTGTAGAAAAAGCAATTTGCTTACAAATACCATT
TTTTATGCTTGA
AAACAGCGACCACGAAGTTTTAAGAACAGGTGAAAGCACAGAATTTACTTTCAACTTTGACTGTGAAT
GGATAAACAATG
AAAGAGCATACATTCCTCCAGGCTTAATGTTTAATCCACTAGTACCTACTAGAAGAGCACAGTACATA
AGAAGAAACAAC
```

FIG. 12A (continued)

```
AATCCTCAAACTGCTGAAAGCACATCCAGAATTGCTCCATATGCAAAACCTACAAGTTGGATGACTGG
ACCAGGTTTACT
CAGTGCACAAAGAGTAGGTCCAGCTACTTCAGACACAGGAGCCTGGATGGTTGCAGTTAAACCAGAAA
ACGCAAGCATTG
ACACAGGAATGTCTGGAATTGGAAGTGGATTTGATCCACCACAAGGATCACTAGCACCAACAAATCTA
GAATACAAAATC
CAATGGTACCAAACACCACAAGGAACAAACAACAATGGAAACATCATATCTAATCAACCACTATCTAT
GCTAAGAGATCA
AGCTTTATTTAGAGGAAATCAAACAACCTATAACCTATGTTCAGATGTATGGATGTTTCCAAATCAAA
TTTGGGACAGAT
ACCCAATAACCAGAGAAAATCCAATATGGTGTAAAAAACCCAGATCAGACAAACACACAACAATTGAT
CCTTTTGATGGA
TCCCTTGCAATGGATCATCCTCCAGGCACAATTTTTATTAAAATGGCAAAAATTCCAGTTCCTTCAAA
CAACAATGCAGA
CTCATACTTAAACATTTACTGCACAGGGCAAGTCAGCTGTGAAATTGTCTGGGAAGTTGAAAGATATG
CAACAAAGAACT
GGAGACCAGAAAGAAGACACACAACATTTGGTCTTGGAATTGGAGGAGCTGACAACTTAAATCCAACC
TACCATGTTGAC
AAAAACGGAACTTACATTCAACCAACAACATGGGACATGTGCTTTCCAGTTAAAACAAACATCAATAA
AGTGTTGTAACC
TTCTAAGCCTCTTTTTTGCTTATGCTTATAAGTTCCTCTCCAATGGACAAGTGGAAAGAAAAGGGTGA
CTGTAATCCCGA
GCTCATGAGTTCGAGGCTACAGTCCGATGGCAGTGGTGTTGCCGTCTCGAACCTAGCCGTTACACC
```

FIG. 12A (continued)

>HBoV3-NI385-NS1
MAFSAPVLRAFSQPTFTYVIKFPYNNWKEDEHLLWSLLAPGTESLMIQLKNCAPHPEDD
PIREDILCSLADLHYGAVFAKACYIATSTLMGQKQRTLFPRCDIVCQSEIGSDFLHCHIL
VGGAGLSKRNAKISRATLLGLVMAELTQRCKLLLAHRPFEPAEATIYHELKRIEREAWSG
HTGNWVQILQYKDKRGDLHAQPIDPLRFLKHYILPKNRLISPSSKPDVCTSPDNWFILAD
KTYSHTIINGLPLLERNRKAYLQELESEVIPGPSAMAFGGRGAWEQLPEVGEQRLITSNT
STAYKANKKEKLMLNLLDKCDELNLLVYEDLVSACPDLLLMLEGQPGGARLIEQVLGMHH
IKVCAKHTALSFLFHLHPDQLLTSSNKALKLLLIQGYNPLQVGHAICCVLNKQMGKQNTI
CFYGPASTGKTNFAKAIVQGVRLYGCVNHLNKGFVFNDCRQRLIIWWEECLMHQDWVEPA
KCILGGTECRIDVKHKDSVLLQQTPVIISTNHDIYSVVGGNTVSHVHAAPLKERVLQLNF
MKQLPQTFGEISPSEIAELLQWCFNEYDCTLAGFKQKWNLDKVPNSFPIGDLCPTHSQDF
TLHENGFCSDCGGYLPHSADDSVYTDVASETTSGDYDPGRL

>HBoV3-NI385-NS2
MAFSAPVLRAFSQPTFTYVIKFPYNNWKEDEHLLWSLLAPGTESLMIQLKNCAPHPEDD
PIREDILCSLADLHYGAVFAKACYIATSTLMGQKQRTLFPRCDIVCQSEIGSDFLHCHIL
VGGAGLSKRNAKISRATLLGLVMAELTQRCKLLLAHRPFEPAEATIYHELKRIEREAWSG
HTGNWVQILQYKDKRGDLHAQPIDPLRFLKHYILPKNRLISPSSKPDVCTSPDNWFILAD
KTYSHTIINGLPLLERNRKAYLQELESEVIPGPSAMAFGGRGAWEQLPEVGEQRLITSNT
STAYKANKKEKLMLNLLDKCDELNLLVYEDLVSACPDLLLMLEGQPGGARLIEQVLGMHH
IKVCAKHTALSFLFHLHPDQLLTSSNKALKLLLIQGYNPLQVGHAICCVLNKQMGKQNTI
CFYGPASTGKTNFAKAIVQGVRLYGCVNHLNKGFVFNDCRQRLIIWWEECLMHQDWVEPA
KCILGGTECRIDVKHKDSVLLQQTPVIISTNHDIYSVVGGNTVSHVHAAPLKERVLQLNF
MKQLPQTFGEISPSEIAELLQWCFNEYDCTLAGFKQKWNLDKVPNSFPIGDLCPTHSQDF
TLHENGFCSDCGGYLPHSADDSVYTDVASETTSGDYDPGNLGDTDGEDSKSEASEVDYCP
PKKRRVISATPPNSPVSGPSLSTFLDTWQSQPRDDDELRIYEEQASQFQKNTKSTSEREE
AQLGESQEPQPEPDPTAWGEKLGVCSSQQPGQPPIVLYCFEDLRPSDEDEGENIGGD

FIG. 12B

> NI-385-NP-1
>HBoV3-NI385-NP1
MS
SESTKNRHRSSKRTPSPLQKERKRNWENRKSRSRSPIRRHGEKNLEYAHHNNQDNRQSSY
TASKTSDQAMKTKEKTSGGTRTNPYTVFSQHRANHSNAPGWCGFYWHSTRLARNGTNNIF
NEMKQKFQELQIDGKISWDTTRELLFTQKKTLDQGYRNMLYHFRHSPDCPRCDYWDDVYR
KHLANVSSQESEEVTDEEMLSAVESMETNASN

FIG. 12C

>HBoV3-NI385-VP1
MPPIKRQPGGWVLPGYKYLGPFNPLENGEPVN
KADRAAQAHDKSYSELIKSGKNPYLYFNKADEKFIDDLKDDWSLGGIIGSSFFKLKRAVA
PALGNKERAQKRHFYFANSNKGAKKTKNNEPKPGTSKMSENEIQDQQPSDSMDGQRGGGG
GATGSVGGGKGSGVGISTGGWVGGSYFTDSYVITKNTRQFLVKIQNNHQYKTELISPSTS
QGKSQRCVSTPWSYFNFNQYSSHFSPQDWQRLTNEYKRFRPKGMHVKIYNLQIKQILSNG
ADTTYNNDLTAGVHIFCDGEHAYPNATHPWDEDVMPELPYQTWYLFQYGYIPVIHELAEM
EDSNAVEKAICLQIPFFMLENSDHEVLRTGESTEFTFNFDCEWINNERAYIPPGLMFNPL
VPTRRAQYIRRNNNPQTAESTSRIAPYAKPTSWMTGPGLLSAQRVGPATSDTGAWMVAVK
PENASIDTGMSGIGSGFDPPQGSLAPTNLEYKIQWYQTPQGTNNNGNIISNQPLSMLRDQ
ALFRGNQTTYNLCSDVWMFPNQIWDRYPITRENPIWCKKPRSDKHTTIDPFDGSLAMDHP
PGTIFIKMAKIPVPSNNNADSYLNIYCTGQVSCEIVWEVERYATKNWRPERRHTTFGLGI
GGADNLNPTYHVDKNGTYIQPTTWDMCFPVKTNINKVL

>HBoV3-NI385-VP2
MSENEIQDQQPSDSMDGQRGGGG
GATGSVGGGKGSGVGISTGGWVGGSYFTDSYVITKNTRQFLVKIQNNHQYKTELISPSTS
QGKSQRCVSTPWSYFNFNQYSSHFSPQDWQRLTNEYKRFRPKGMHVKIYNLQIKQILSNG
ADTTYNNDLTAGVHIFCDGEHAYPNATHPWDEDVMPELPYQTWYLFQYGYIPVIHELAEM
EDSNAVEKAICLQIPFFMLENSDHEVLRTGESTEFTFNFDCEWINNERAYIPPGLMFNPL
VPTRRAQYIRRNNNPQTAESTSRIAPYAKPTSWMTGPGLLSAQRVGPATSDTGAWMVAVK
PENASIDTGMSGIGSGFDPPQGSLAPTNLEYKIQWYQTPQGTNNNGNIISNQPLSMLRDQ
ALFRGNQTTYNLCSDVWMFPNQIWDRYPITRENPIWCKKPRSDKHTTIDPFDGSLAMDHP
PGTIFIKMAKIPVPSNNNADSYLNIYCTGQVSCEIVWEVERYATKNWRPERRHTTFGLGI
GGADNLNPTYHVDKNGTYIQPTTWDMCFPVKTNINKVL

FIG. 12D

>HBoV2A-PK2255
GACGTATGTCAACCAATCAGCATCGAGCATATATCCTATATAAGCCAATGCACTTCCGCATCTCGTCA
GACTGCATCCGG
TCTCCGGCGAGTGAACATCTCTGGGAAGAGCTCCACGCACGTGGTGAGTGACACTATGGCCTTTTCTG
CTCCTGTAATTA
GAGCTTTTTCTCAACCTGCTTTCACTTATGTTGTTAAATTTCCATATGATAACTGGAAAGAGGAAGAG
CACTTACTATGG
AGCTTACTTGCTCCTGGGACTGAACGTCTCATGATCCAACTAAGAAACTGCGCACCACATCCTGAAGA
TGATCCTGTCAG
GGAAGATATTTTATGCTCACTAGCAGACCAACACTATGCTGCTATTTTCACCAAAGCTTGCTACATGG
CTGTAACTTCAC
TTATGGGGCAGAAACAGAGAACACACTTTCCACGATGCGACATAATTTGCCAGGCTGAGATCGGCTCA
GAATATCTACAC
TGTCACATACTTGTTGGAGGAGCAGGTCTGAGCAAGAGAAATGCTAAAATTTCATGTGCTACGCTCCT
AGGCCTTGTGAT
GGCTGAATTAACACAACGCTGCAAACTACTTCTTGCACAGCGTCCATTTGAACCAGATGAAGCTAGAA
TATTTCATCTAC
TCAGACGCGTTGAACGCGAAGCATGGTCAGGGCACACTGGTAACTGGGTTCAAATTCTTCAATACAGA
GACAAGCGAGGT
GACCTTCATGCTCAACACATTGATCCTTTACGCTTTTTCAAACACTACCTGCTGCCAAAAAATCGGTT
GATCTCTCCTTC
CAGCAAGCCTGACGTCTGCACTACTCCAGATAACTGGTTTGTCCTAGCTGAAAAAACATACGCTCACA
CTATTGTTAATG
GGCTTCCGCTGCTAGAACATAACAGAAAGGCCTATCTACAAGAGTTAGAAAGTGAAGTCATCCCAGGG
CCTTCTACCATG
GCCTTTGGGGACGTGGTGCGTGGGAACATCTGCCTGAGGTAGGAGAACAACGCCTAATAACTTCTAA
TACTTCTACTGC
TTATAAAGCTAACAAAAAGAAAAATTAATGCTAAACTTACTTGATAAATGTGATGAACTTAACTTAC
TTGTGTATGAAG
ACTTAGTTAGTGCTTGTCCTGACCTTTTACTTATGCTTGAAGGTCAGCCAGGTGGTGCACGCCTAATT
GAACAGGTGCTC
GGCATGCATCATATTAAAGTGTGTGCTAATTACACAGCGTTATCTTTCCTATTTCATTTACATCCTGA
TCAATTATTAAC
TTCTAGCAATAAAGCACTAAAACTATTGTTGATTCAAGGGTACAACCCATTGCAAGTGGGCCACGCCA
TCTGTTGTGTCC
TTAACAAACAGATGGGCAAGCAGAACACAATTTGCTTTTATGGCCCTGCTTCAACAGGCAAAACAAAT
ATTGCAAAGGCC
ATAGTTCAAGGCGTTCGTCTGTATGGCTGTGTTAATCATTTAAACAAAGGGTTTGTCTTTAACGATTG
CAGACAACGCCT
TATAATCTGGTGGGAGGAGTGTTTAATGCACCAAGACTGGGTGGAACCTGCTAAATGCATTCTAGGCG
GAACTGAATGTA
GAATTGATGTTAAACATAAAGACAGTGTTCTTCTTCAACAAACACCAGTAATTATTTCCACTAACCAT
GACATCTACTCT
GTAGTTGGTGGCAATACTGTATCTCATGTTCATGCAGCGCCCTTAAAAGAGCGAATCCTTCAGCTAAA
TTTTATGAAACA
ACTGCCACAAACATTTGGAGAAATTTCTCCAGTTGAAATTGCAGAATTACTGCAATGGTGCTTTAATG
AGTACGACTGTA
CTCTTACTGGCTTTAAACAAAATGGAACTTAGATAAAGTTCCAAACTCATTTCCTCTTGGGGACCTT
TGTCCTACACAT
TCACAGGACTACGTGCTTCACGAAAACGGATTCTGCACTGACTGCGGCGGCTATATTCCTCATAGTGC
TGACGACTCTGT

FIG. 16A

```
GTACACTGACGTGGCTAGCGAGACATCAATCAGCAGCGACGACCCAGGTAGGCATTAATACATTAGCC
TTTTAATATACT
ACCTTCCAAGTGCTTATGTATTAACTCCTACAGGTGACTTGGGGGATACGGACGGAGAGAACTCCCAG
CCGGAGACATCG
AACGTGGATAATCGTCCATCCAAGAAGAGACGTGTGATTCCAGAAACTCCACCAAACAGTCCAGTAAG
TCGCCAAAGCCT
TTCTAGCTTTTTAGATACGTGGCAGTCACAACCTAGAGACGAAGATGAGCTCCGAATCTATGAAGCAC
AGGCATCGCGCA
TCAAAGAGAACACCGAGTCCACTCCGGAGAGAGAGAAGACACCAGTGGGAGAACCACAAGAAGAGTCG
CAGTCGGAGCCC
AATCCGACAGCATGGGAGAAAAGCTTGGAGTCTACTCCTCGCTACAACCAGGAGAGCCGCCAATCGT
CTTACACTGCTT
CGAAGACCTCAGACCAAGCGACGAAGACGAGGGAGAAAACATCGGGGGGGAATAGAACCAATCCTTAT
ACTGTGTTCAGT
CAACACAGGGCTAATCATCCAGATGCTCCTGGATGGTGTGGGTTTTACTGGCATTCTACTAGGCTTGC
TAGAGATGGCAC
TAATTGTATCTTTAATGAAATGAAACAAGAATTTCAAGAATTACAAATAAATGGGAAAATTACTTGGG
ACAATGTTAGAG
AACTATTGTTTAGCCAGAAAAAAAAGCTAGATCAAAAATACAGAAACATGCTGTATCATTTCAGACAT
AACACTGATTGT
CCTAGATGTGATTATTGGGATGATGTATACCGTAAACACTTAGCTCATGTCTCTTCACAGGAATCAGA
GGAGGTAACAGA
CGAAGAAATGCTTTCTGCTGTTGAAAGCATGGAAACAAATGCCTCCAATTAAACGCCAACCTGGAGGG
TGGGTGCTTCCT
GGTTATAAATACCTTGGTCCATTTAATCCTCTTGAAAACGGTGAACCAGTTAATAAAGCTGATCGTGC
TGCTCAAGCTCA
TGATAAATCATATTCTGAACTAATAAAAAGTGGAAAAAATCCTTACTTATATTTCAATAAAGCTGATG
AAAAATTCATTG
ACGATTTGAAAAACGACTGGTCTCTTGGTGGCATTATTGGCTCAAGTTTCTTTAAACTTAAGCGCGCC
GTGGCTCCTGCT
CTAGGAAATAAAGAGCGAGCTCAAAAAAGACATTTTTACTTTGCAAACTCAAATAAAGGTGCTAAAAA
ACCAAAAAATAA
CGAGCCTAAACCAGGCACATCAAAAATGTCTGAAAATGAAATCCAAGACCAACAACCATCTGGCTCCA
TGGAGGAGCGAG
GAGGCGGAGGAGGTGCGGTCGGTAGTGTGGGAGGGGGGAAAGGTTCTGGTGTGGGTATATCCACARGC
GGCTGGGTTGGA
GGCAGCTACTTTACTGACTCATATGTCATAACAAAGAACACTAGACAGTTCTTAGTTAAAATACAAAA
TGACCACAAATA
CAGAACAGAGAATATAATTCCAAGCAACGCAGGAGGAAAATTCCAGCGATGCGTAAGCACACCTTGGT
CATACTTTAACT
TCAATCAATACAGCAGTCACTTCTCACCACAAGACTGGCAGCGTTTAACAAATGAATATAAACGCTTT
AAGCCTAGAAAA
ATGCATGTAAAAATTTACAACTTACAAATAAAACAAATACTCTCAAATGGTGCTGACACTACATACAA
CAACGACCTAAC
AGCTGGTGTTCACATCTTTTGTGATGGTGAACACGCATATCCAAATGCAACACATCCATGGGATGAAG
ATGTCATGCCAG
AACTTCCATATGAAACATGGTATTTGTTTCAATATGGATACATTCCAGTTATTCATGAACTGGCTGAA
ATGGAAGACGCA
AATGCTGTAGAAAAAGCTATAGCACTACAAATACCTTTCTTCATGCTTGAAAACAGCGACCATGAAGT
GTTAAGAACAGG
```

FIG. 16A (continued)

```
AGAAAGCACAGAATTCACTTTTGACTTTGACTGTGAATGGATAAACAACGAAAGAGCATACATTCCTC
CTGGATTAATGT
TTAATCCAAAAGTTCCTACAAGAAGAGCTCAATACATCAGACAGCACGGAAACACAGCATCCAGCAAC
ACCAGAATTCAA
CCATATGCAAAACCTACAAGCTGGATGACAGGACCAGGTCTACTCAGCGCACAAAGAGTAGGACCAGC
TGGCTCAGACAC
TGCATCATGGATGGTTGTTGTCAATCCAGACGGAGCTGCAGTTAACTCAGGAATGGCAGGAGTTGGTT
CAGGATTTGATC
CTCCTTCAGGATCTCTAAGACCAACTGACTTAGAATACAAAATACAATGGTACCAAACTCCTGCAGGT
ACCAACAGTGAT
GGAAACATCATTTCAAATCCACCACTATCCATGCTCAGAGATCAAGCTCTCTACAGAGGAAATCAAAC
AACCTACAACCT
ATGCTCAGATGTGTGGATGTTCCCAAATCAAATTTGGGACAGATATCCAATAACCAGAGAAAATCCAA
TCTGGTGTAAAA
AACCAAGATCAGACAAAAACACAATAATTGATCCTTTCGATGGAACACTTGCAATGGATCATCCGCCA
GGAACAATCTTC
ATAAAAATGGCAAAAATTCCAGTTCCTTCAAACAACAACGCAGACTCATACCTAAACATCTACTGCAC
TGGACAAGTCAG
CTGCGAAATTGTCTGGGAAGTTGAAAGATACGCAACAAAGAACTGGAGACCAGAAAGAAGACACACCG
CACTTGGTCTTG
GAATTGGAGGAGAAGAAAACGTAAATCCAACTTATCATGTAGACAAAAATGGAAAATACATTCAGCCA
ACAACTTGGGAC
ATGTGCTATCCTATCAAAACAAACATCAATAAAGTGTTGTAATCTCTTAAGCCTGTTCATTGCTTATG
CTTATAAGTTCC
TCTCCAATGGACAAGAGGAAAGAAAAGGGTGACTGTAATCCCGAGCTCATAAGTTCGAGGCTACAGTC
CGATGGCAGTGG
TGTTGCCGTCTCGAACCTAGCCGTTACACCCTTGTGCATTGTGGGAGGAGCTGTTTTGCTTACGCAAT
CGCGAAATTTTA
TATATTTAATGTAG
```

FIG. 16A (continued)

```
>HBoV2A-PK2255-NS1
MAFSAPVIRAFSQPA
FTYVVKFPYDNWKEEEHLLWSLLAPGTERLMIQLRNCAPHPEDDPVREDILCSLADQHYA
AIFTKACYMAVTSLMGQKQRTHFPRCDIICQAEIGSEYLHCILVGGAGLSKRNAKISCA
TLLGLVMAELTQRCKLLLAQRPFEPDEARIFHLLRRVEREAWSGHTGNWVQILQYRDKRG
DLHAQHIDPLRFFKHYLLPKNRLISPSSKPDVCTTPDNWFVLAEKTYAHTIVNGLPLLEH
NRKAYLQELESEVIPGPSTMAFGGRGAWEHLPEVGEQRLITSNTSTAYKANKKEKLMLNL
LDKCDELNLLVYEDLVSACPDLLLMLEGQPGGARLIEQVLGMHHIKVCANYTALSFLFHL
HPDQLLTSSNKALKLLLIQGYNPLQVGHAICCVLNKQMGKQNTICFYGPASTGKTNIAKA
IVQGVRLYGCVNHLNKGFVFNDCRQRLIIWWEECLMHQDWVEPAKCILGGTECRIDVKHK
DSVLLQQTPVIISTNHDIYSVVGGNTVSHVHAAPLKERILQLNFMKQLPQTFGEISPVEI
AELLQWCFNEYDCTLTGFKQKWNLDKVPNSFPLGDLCPTHSQDYVLHENGFCTDCGGYIP
HSADDSVYTDVASETSISSDDPGRH
```

FIG. 16B

>HBoV2A-PK2255-NS2
MAFSAPVIRAFSQPA
FTYVVKFPYDNWKEEEHLLWSLLAPGTERLMIQLRNCAPHPEDDPVREDILCSLADQHYA
AIFTKACYMAVTSLMGQKQRTHFPRCDIICQAEIGSEYLHCILVGGAGLSKRNAKISCA
TLLGLVMAELTQRCKLLLAQRPFEPDEARIFHLLRRVEREAWSGHTGNWVQILQYRDKRG
DLHAQHIDPLRFFKHYLLPKNRLISPSSKPDVCTTPDNWFVLAEKTYAHTIVNGLPLLEH
NRKAYLQELESEVIPGPSTMAFGGRGAWEHLPEVGEQRLITSNTSTAYKANKKEKLMLNL
LDKCDELNLLVYEDLVSACPDLLLMLEGQPGGARLIEQVLGMHHIKVCANYTALSFLFHL
HPDQLLTSSNKALKLLLIQGYNPLQVGHAICCVLNKQMGKQNTICFYGPASTGKTNIAKA
IVQGVRLYGCVNHLNKGFVFNDCRQRLIIWWEECLMHQDWVEPAKCILGGTECRIDVKHK
DSVLLQQTPVIISTNHDIYSVVGGNTVSHVHAAPLKERILQLNFMKQLPQTFGEISPVEI
AELLQWCFNEYDCTLTGFKQKWNLDKVPNSFPLGDLCPTHSQDYVLHENGFCTDCGGYIP
HSADDSVYTDVASETSISSDDPGDLGDTDGENSQPETSNVDNRPSKKRRVIPETPPNSPV
SRQSLSSFLDTWQSQPRDEDELRIYEAQASRIKENTESTPEREKTPVGEPQEESQSEPNP
TAWGEKLGVYSSLQPGEPPIVLHCFEDLRPSDEDEGENIGGE

FIG. 16B (continued)

>HBoV2A-PK2255-NP1
MSSESMKHRHRASKRTPSP
LRRERRHQWENHKKSRSRSPIRQHGEKSLESTPRYNQESRQSSYTASKTSDQATKTREKT
SGGNRTNPYTVFSQHRANHPDAPGWCGFYWHSTRLARDGTNCIFNEMKQEFQELQINGKI
TWDNVRELLFSQKKKLDQKYRNMLYHFRHNTDCPRCDYWDDVYRKHLAHVSSQESEEVTD
EEMLSAVESMETNASN

FIG. 16C

>HBoV2A-PK2255-VP1
MPPIKRQPGGWVLPGYKYLGPFNPLENGEPVNKADRAAQAHDKSYSEL
IKSGKNPYLYFNKADEKFIDDLKNDWSLGGIIGSSFFKLKRAVAPALGNKERAQKRHFYF
ANSNKGAKKPKNNEPKPGTSKMSENEIQDQQPSGSMEERGGGGGAVGSVGGGKGSGVGIS
TXGWVGGSYFTDSYVITKNTRQFLVKIQNDHKYRTENIIPSNAGGKFQRCVSTPWSYFNF
NQYSSHFSPQDWQRLTNEYKRFKPRKMHVKIYNLQIKQILSNGADTTYNNDLTAGVHIFC
DGEHAYPNATHPWDEDVMPELPYETWYLFQYGYIPVIHELAEMEDANAVEKAIALQIPFF
MLENSDHEVLRTGESTEFTFDFDCEWINNERAYIPPGLMFNPKVPTRRAQYIRQHGNTAS
SNTRIQPYAKPTSWMTGPGLLSAQRVGPAGSDTASWMVVVNPDGAAVNSGMAGVGSGFDP
PSGSLRPTDLEYKIQWYQTPAGTNSDGNIISNPPLSMLRDQALYRGNQTTYNLCSDVWMF
PNQIWDRYPITRENPIWCKKPRSDKNTIIDPFDGTLAMDHPPGTIFIKMAKIPVPSNNNA
DSYLNIYCTGQVSCEIVWEVERYATKNWRPERRHTALGLGIGGEENVNPTYHVDKNGKYI
QPTTWDMCYPIKTNINKVL

>HBoV2A-PK2255-VP2
MSENEIQDQQPSGSMEERGGGGGAVGSVGGGKGSGVGIS
TXGWVGGSYFTDSYVITKNTRQFLVKIQNDHKYRTENIIPSNAGGKFQRCVSTPWSYFNF
NQYSSHFSPQDWQRLTNEYKRFKPRKMHVKIYNLQIKQILSNGADTTYNNDLTAGVHIFC
DGEHAYPNATHPWDEDVMPELPYETWYLFQYGYIPVIHELAEMEDANAVEKAIALQIPFF
MLENSDHEVLRTGESTEFTFDFDCEWINNERAYIPPGLMFNPKVPTRRAQYIRQHGNTAS
SNTRIQPYAKPTSWMTGPGLLSAQRVGPAGSDTASWMVVVNPDGAAVNSGMAGVGSGFDP
PSGSLRPTDLEYKIQWYQTPAGTNSDGNIISNPPLSMLRDQALYRGNQTTYNLCSDVWMF
PNQIWDRYPITRENPIWCKKPRSDKNTIIDPFDGTLAMDHPPGTIFIKMAKIPVPSNNNA
DSYLNIYCTGQVSCEIVWEVERYATKNWRPERRHTALGLGIGGEENVNPTYHVDKNGKYI
QPTTWDMCYPIKTNINKVL

FIG. 16D

>HBoV2A-UK648
GACGTATGTCAACCAATCAGCATCGAGCATATATCCTATATAAGCCGATGCACTTCCGCATCTCGTCA
GACTGCATCCGG
TCTCCGGCGAGTGAACATCTCTGGGAAGAGCTCCACGCACGTGGTGAGTGACACTATGGCCTTTTCTG
CTCCTGTAATTA
GAGCTTTTTCTCAACCTGCTTTCACTTATGTTGTTAAATTTCCATATGATAACTGGAAAGAGGAAGAA
CACTTACTATGG
AGCTTACTTGCTCCTGGGACTGAACGTCTCATGATCCAACTAAGAAACTGCGCACCACATCCTGAAGA
TGATCCTGTCAG
GGAAGATATTTTATGCTCACTAGCAGACCAACACTATGCTGCTATTTTCACCAAGGCTTGCTACATGG
CTGTAACTTCAC
TCATGGGGCAGAAACAGAGAACACACTTTCCACGATGCGACATAATATGCCAGGCTGAGATCGGCTCA
GAATATCTACAC
TGTCACATACTTGTTGGAGGAGCAGGTCTAAGCAAGAGAAATGCTAAAATTTCATGTGCTACGCTCCT
AGGCCTTGTGAT
GGCTGAATTAACACAACGCTGCAAACTACTTCTTGCACAGCGTCCATTTGAACCAGATGAAGCTAGAA
TATTCCATCTAC
TCAGACGCGTTGAACGCGAAGCATGGTCAGGGCACACTGGTAACTGGGTTCAAATTCTTCAATACAGA
GACAAGCGAGGT
GACCTTCATGCTCAACACATTGATCCTTTACGCTTTTTCAAACACTACCTGCTGCCAAAAAATCGATT
GATCTCTCCTTC
CAGCAAGCCTGACGTCTGCACTACTCCAGATAACTGGTTTGTCCTAGCTGATAAAACATACGCTCACA
CTATTGTTAATG
GGCTTCCGCTGCTAGAACATAACAGAAAGGCCTATCTACAAGAGTTAGAGAGTGAAGTCATCCCGGGG
CCTTCTACCATG
GCCTTTGGGGACGTGGTGCGTGGGAACATCTGCCTGAGGTAGGAGAACAACGCCTAATTACTTCTAA
TACTTCTACTGC
TTATAAAGCTAACAAAAAGAAAAACTAATGCTAAACTTACTTGATAAATGTGATGAACTTAACTTAC
TTGTATATGAAG
ACTTAGTTAGTGCTTGTCCTGACCTTTTACTTATGCTTGAAGGTCAGCCAGGTGGTGCACGCCTAATT
GAACAGGTGCTA
GGCATGCATCATATTAAAGTGTGTGCTAATTATACAGCTCTATCATTCCTATTTCATTTACATCCTAA
TCAATTATTAAC
TTCTAGCAATAAAGCACTAAAACTATTGTTGATTCAAGGATACAACCCATTGCAGGTAGGGCACGCCA
TCTGCTGTGTAC
TTAACAAACAGATGGGCAAGCAGAACACTATCTGCTTTTATGGTCCTGCTTCAACAGGCAAAACAAAT
ATTGCAAAGGCC
ATAGTCCAAGGCGTTCGCCTTTATGGCTGTGTTAATCATCTAAACAAAGGGTTTGTCTTTAACGATTG
CAGACAACGCCT
TATAATTTGGTGGGAGGAATGTTTAATGCATCAAGATTGGGTTGAACCTGCTAAATGCATTTTAGGTG
GAACCGAATGTA
GAATTGATGTTAAACACAAAGACAGTGTTCTTCTTCAACAAACACCAGTAATTATTTCCACTAACCAT
GACATCTACTCT
GTAGTTGGTGGCAATACTGTATCTCATGTTCATGCAGCGCCCTTAAAAGAGCGAATTCTTCAACTAAA
TTTTATGAAACA
ACTGCCACAAACATTTGGAGAGATTTCTCCAGTTGAAATTGCAGAGTTGCTGCAATGGTGCTTTAATG
AGTACGAATGTA
CTCTTACTGGCTTTAAACAAAAATGGAACTTAGATAAAGTTCCAAACTCATTTCCTCTTGGGGACCTT
TGTCCTACACAT
TCACAGGACTACGTGCTTCACGAAAACGGATTCTGCACTGACTGCGGCGGCTATATTCCTCATAGTGC
TGACGACTCTGT

FIG. 17A

GTATACTGACGTGGCTAGCGAGACATCAATCAGCAGCTGCGACCCAGGTAGGCATTAATACATTAGCC
TTTTAATATGCT
ACTTTCTAGATGCTTATGTATTAACTCCTACAGGTGACTTGGGGGATACGGACGGAGAGAACTCCCAG
CCGGAGACATCG
AACGTGGATAATCGTCCATCCAAGAAGAGACGTGTGATTCCAGAAACTCCACCAAACAGTCCAGTAAG
TCGCCAAAGCCT
TTCTAGCTTTTTAGATACGTGGCAGTCACAACCTAGAGACGAAGATGAGCTCCGAATCTATGAAGCAC
AGGCATCGCGCA
TCAAAGAGAACACCGAGTCCACTCCGGAGAGAGAGAAGACACCAGTGGGAGAACCACAAGAAGAGTCG
CAGTCGGAGCCC
GATCCGACAGCATGGGGAGAAAAGCTTGGAGTCTACTCCTCGCTACAACCAGGAGAGCCGCCAATCGT
CTTACACTGCTT
CGAAGACCTCAGACCAAGCGACGAAGACGAAGGAGAAAACATCGGGGGGGAATAGAACCAATCCTTAT
ACTGTGTTCAGT
CAACACAGGGCTAATCATCCAGATGCTCCTGGATGGTGTGGGTTTTACTGGCATTCTACTAGGCTTGC
TAGAGATGGCAC
TAATTGTATCTTTAATGAAATGAAACAAGAATTTCAAGAATTGCAAATAAATGGAAAAATTACCTGGG
ACAATGTTAGAG
AACTATTGTTTAGCCAGAAAAAAAAGCTAGATCAAAAATACAGAAACATGCTGTACCATTTCAGACAT
AATGCTGATTGT
CCTAGATGTGATTATTGGGATGATGTCTACCGTAAACACTTAGCTCATGTCTCTTCACAGGAATCAGA
GGAGGTAACAGA
CGAAGAAATGCTTTCTGCTGTTGAAAGCATGGAAACAAATGCCTCCAATTAAACGCCAACCTGGAGGG
TGGGTGCTTCCT
GGTTATAAATACCTTGGTCCATTTAATCCTCTTGAAAACGGTAAACCAGTTAATAAAGCTGATCGTGC
TGCTCAAGCTCA
TGATAAATCATATTCTGAATTAATAAAGAGTGGAAAAAATCCTTACTTGTATTTCAATAAAGCTGATG
AGAAATTCATTG
ACGATTTGAAAACGACTGGTCTCTTGGTGGCATTATTGGCTCAAGTTTCTTTAAACTTAAGCGCGCC
GTGGCTCCTGCT
CTAGGAAATAAAGAGCGAGCTCAAAAAAGACATTTTTACTTTGCAAACTCAAATAAAGGTGCTAAAAA
ACCAAAAAATAA
CGAGCCTAAACCAGGCACTTCAAAAATGTCTGAAAATGAAATCCAAGACCAACAACCATCTGACTCAA
TGGAAGAGCGAG
GAGGAGGAGGAGGTGCGACCGGTAGTGTGGGAGGGGGGAAAGGTTCTGGTGTGGGTATATCCACAGGT
GGCTGGGTAGGA
GGCAGCTACTTCACTGACTCATATGTCATAACAAAAAACACCAGACAATTTCTGGTAAAAATACAAAA
TGACCACAAATA
CAGAACTGAAAATATTATTCCAAGCAATGCTGGAGGAAAATCACAAAGATGCGTCAGCACACCGTGGT
CATATTTCAACT
TCAATCAATACAGCAGTCATTTTTCACCACAAGACTGGCAGCGCCTAACAAATGAATATAAGCGCTTT
AAACCTAGAAAA
ATGCATGTAAAAATTTACAATCTACAAATAAAACAAATACTTTCAAATGGTGCTGACACTACATACAA
CAACGACCTAAC
AGCTGGTGTTCACATCTTTTGTGATGGTGAACACGCATATCCAAATGCAACACATCCATGGGATGAAG
ACGTGATGCCAG
AACTTCCATATGAAACATGGTATCTGTTTCAATATGGATACATTCCAGTTATTCATGAACTTGCTGAA
ATGGAAGACGCA
AATGCTGTAGAAAAAGCTATAGCACTACAAATACCATTCTTCATGCTTGAAAACAGTGACCATGAAGT
TCTAAGAACTGG

```
AGAAAGCACAGAATTCACTTTTGATTTTGACTGTGAGTGGATCAACAACGAAAGAGCATACATTCCTC
CTGGATTAATGT
TTAATCCAAAAGTTCCTACGAGAAGAGCTCAATACATTAGACAGCACGGAAACACAGCATCAAGCAAC
ACCAGAATTCAA
CCATATGCAAAACCTACAAGCTGGATGACAGGACCAGGTCTACTCAGTGCACAAAGAGTAGGACCAGC
TGGCTCAGACAC
TGCATCATGGATGGTTGTTGTTAATCCAGACGGAACTGCCGTTAACTCAGGAATGGCAGGAGTTGGAT
CAGGATTTGATC
CTCCTTCAGGATCTCTAAGACCAACTGACTTAGAATACAAAATACAATGGTACCAAACTCCTGAAGGT
ACCAACAGTGAT
GGAAACATAATTTCAAATCCACCACTGTCCATGCTTAGAGATCAAGCTCTCTACAGAGGAAATCAAAC
AACCTATAACCT
ATGCTCAGATGTATGGATGTTCCCAAATCAAATTTGGGACAGATATCCAATAACCAGAGAAAACCCAA
TTTGGTGCAAAA
AGCCAAGATCAGATAAAAACACAATAATTGATCCTTTCGATGGAACACTCGCAATGGATCATCCTCCT
GGAACAATCTTC
ATAAAAATGGCAAAAATTCCAGTTCCTTCAAACAACAACGCAGACTCATACCTAAACATCTACTGCAC
AGGACAAGTCAG
CTGCGAAATTGTCTGGGAAGTTGAAAGATACGCAACAAAGAACTGGAGACCAGAGAGAAGACACACCG
CACTTGGTCTTG
GAATCGGAGGAGAAGAAAACATAAATCCAACTTACCATGTAGACAAAAATGGAAAATACATTCAGCCA
ACAACATGGGAC
ATGTGCTATCCTATCAAAACAAACATCAATAAAGTGTTGTAATCTCTTAAGCCTGTTCATTGCTTATG
CTTATAAGTTCC
TCTCCAATGGACAAGAGGAAAGAAAAGGGTGACTGTAATCCCGAGCTCATGAGTTCGAGGCTACAGTC
CGATGGCAGTGG
TGTTGCCGTCTCGAACCTAGCCGTTACACCCTTGTGCATTGTGGGAGGAGCTGTTTTGCTTACGCAAC
CGCGAAATTTTA
TATATTTAATGTAG
```

FIG. 17A (continued)

```
>HBoV2A-UK648-NS1
MAFSAPVIRAFSQPA
FTYVVKFPYDNWKEEEHLLWSLLAPGTERLMIQLRNCAPHPEDDPVREDILCSLADQHYA
AIFTKACYMAVTSLMGQKQRTHFPRCDIICQAEIGSEYLHCHILVGGAGLSKRNAKISCA
TLLGLVMAELTQRCKLLLAQRPFEPDEARIFHLLRRVEREAWSGHTGNWVQILQYRDKRG
DLHAQHIDPLRFFKHYLLPKNRLISPSSKPDVCTTPDNWFVLADKTYAHTIVNGLPLLEH
NRKAYLQELESEVIPGPSTMAFGGRGAWEHLPEVGEQRLITSNTSTAYKANKKEKLMLNL
LDKCDELNLLVYEDLVSACPDLLLMLEGQPGGARLIEQVLGMHHIKVCANYTALSFLFHL
HPNQLLTSSNKALKLLLIQGYNPLQVGHAICCVLNKQMGKQNTICFYGPASTGKTNIAKA
IVQGVRLYGCVNHLNKGFVFNDCRQRLIIWWEECLMHQDWVEPAKCILGGTECRIDVKHK
DSVLLQQTPVIISTNHDIYSVVGGNTVSHVHAAPLKERILQLNFMKQLPQTFGEISPVEI
AELLQWCFNEYECTLTGFKQWNLDKVPNSFPLGDLCPTHSQDYVLHENGFCTDCGGYIP
HSADDSVYTDVASETSISSCDPGRH
```

FIG. 17B

>HBoV2A-UK648-NS2
MAFSAPVIRAFSQPA
FTYVVKFPYDNWKEEEHLLWSLLAPGTERLMIQLRNCAPHPEDDPVREDILCSLADQHYA
AIFTKACYMAVTSLMGQKQRTHFPRCDIICQAEIGSEYLHCHILVGGAGLSKRNAKISCA
TLLGLVMAELTQRCKLLLAQRPFEPDEARIFHLLRRVEREAWSGHTGNWVQILQYRDKRG
DLHAQHIDPLRFFKHYLLPKNRLISPSSKPDVCTTPDNWFVLADKTYAHTIVNGLPLLEH
NRKAYLQELESEVIPGPSTMAFGGRGAWEHLPEVGEQRLITSNTSTAYKANKKEKLMLNL
LDKCDELNLLVYEDLVSACPDLLLMLEGQPGGARLIEQVLGMHHIKVCANYTALSFLFHL
HPNQLLTSSNKALKLLLIQGYNPLQVGHAICCVLNKQMGKQNTICFYGPASTGKTNIAKA
IVQGVRLYGCVNHLNKGFVFNDCRQRLIIWWEECLMHQDWVEPAKCILGGTECRIDVKHK
DSVLLQQTPVIISTNHDIYSVVGGNTVSHVHAAPLKERILQLNFMKQLPQTFGEISPVEI
AELLQWCFNEYECTLTGFKQKWNLDKVPNSFPLGDLCPTHSQDYVLHENGFCTDCGGYIP
HSADDSVYTDVASETSISSCDPGDLGDTDGENSQPETSNVDNRPSKKRRVIPETPPNSPV
SRQSLSSFLDTWQSQPRDEDELRIYEAQASRIKENTESTPEREKTPVGEPQEESQSEPDP
TAWGEKLGVYSSLQPGEPPIVLHCFEDLRPSDEDEGENIGGE

FIG. 17B (continued)

>HBoV2A-UK648-NP1
MSSESMKHRHRASKRTPSP
LRRERRHQWENHKKSRSRSPIRQHGEKSLESTPRYNQESRQSSYTASKTSDQATKTKEKT
SGGNRTNPYTVFSQHRANHPDAPGWCGFYWHSTRLARDGTNCIFNEMKQEFQELQINGKI
TWDNVRELLFSQKKKLDQKYRNMLYHFRHNADCPRCDYWDDVYRKHLAHVSSQESEEVTD
EEMLSAVESMETNASN

FIG. 17C

```
>HBoV2A-UK648-VP1
MPPIKRQPGGWVLPGYKYLGPFNPLENGKPVNKADRAAQAHDKSYSEL
IKSGKNPYLYFNKADEKFIDDLKNDWSLGGIIGSSFFKLKRAVAPALGNKERAQKRHFYF
ANSNKGAKKPKNNEPKPGTSKMSENEIQDQQPSDSMEERGGGGATGSVGGGKGSGVGIS
TGGWVGGSYFTDSYVITKNTRQFLVKIQNDHKYRTENIIPSNAGGKSQRCVSTPWSYFNF
NQYSSHFSPQDWQRLTNEYKRFKPRKMHVKIYNLQIKQILSNGADTTYNNDLTAGVHIFC
DGEHAYPNATHPWDEDVMPELPYETWYLFQYGYIPVIHELAEMEDANAVEKAIALQIPFF
MLENSDHEVLRTGESTEFTFDFDCEWINNERAYIPPGLMFNPKVPTRRAQYIRQHGNTAS
SNTRIQPYAKPTSWMTGPGLLSAQRVGPAGSDTASWMVVVNPDGTAVNSGMAGVGSGFDP
PSGSLRPTDLEYKIQWYQTPEGTNSDGNIISNPPLSMLRDQALYRGNQTTYNLCSDVWMF
PNQIWDRYPITRENPIWCKKPRSDKNTIIDPFDGTLAMDHPPGTIFIKMAKIPVPSNNNA
DSYLNIYCTGQVSCEIVWEVERYATKNWRPERRHTALGLGIGGEENINPTYHVDKNGKYI
QPTTWDMCYPIKTNINKVL

>HBoV2A-UK648-VP2
MSENEIQDQQPSDSMEERGGGGATGSVGGGKGSGVGIS
TGGWVGGSYFTDSYVITKNTRQFLVKIQNDHKYRTENIIPSNAGGKSQRCVSTPWSYFNF
NQYSSHFSPQDWQRLTNEYKRFKPRKMHVKIYNLQIKQILSNGADTTYNNDLTAGVHIFC
DGEHAYPNATHPWDEDVMPELPYETWYLFQYGYIPVIHELAEMEDANAVEKAIALQIPFF
MLENSDHEVLRTGESTEFTFDFDCEWINNERAYIPPGLMFNPKVPTRRAQYIRQHGNTAS
SNTRIQPYAKPTSWMTGPGLLSAQRVGPAGSDTASWMVVVNPDGTAVNSGMAGVGSGFDP
PSGSLRPTDLEYKIQWYQTPEGTNSDGNIISNPPLSMLRDQALYRGNQTTYNLCSDVWMF
PNQIWDRYPITRENPIWCKKPRSDKNTIIDPFDGTLAMDHPPGTIFIKMAKIPVPSNNNA
DSYLNIYCTGQVSCEIVWEVERYATKNWRPERRHTALGLGIGGEENINPTYHVDKNGKYI
QPTTWDMCYPIKTNINKVL
```

FIG. 17D

SEQUENCE LISTING

```
<160> NUMBER OF SEQ ID NOS: 65

<210> SEQ ID NO 1
<211> LENGTH: 5196
<212> TYPE: DNA
<213> ORGANISM: Bocavirus

<400> SEQUENCE: 1
ggagtggcta cgtatggggt gatcataaac acgcccagga agtgacgtat gtcaaccaat      60
cagcatcgag catatatcct atataagccg atgcactycc gcatctcgtc agactgcatc     120
cggtctccgg cgagtgaaca tctctgggaa gagctccacg cacgtggtga gtgacactat     180
ggccttttct gctcctgtaa ttagagcttt ttctcaacct gcttttactt atgttgttaa     240
atttccatat gaaaactgga aagaggaaga gcacttacta tggagcttac ttgctcctgg     300
gactgaacgt ctcatgattc aactaagaaa ctgcgcacca catcctgaag atgatcctgt     360
cagggaagat attttatgct cactagcaga tcaacactat ggtgctattt ttgctaaagc     420
ttgctacata gctacaacta cactaatggg gcagaaacag agaacacctt ttccacgctg     480
cgacattata tgccaatctg aaattggttc agaacatcta cattgtcaca tacttgttgg     540
aggagccggt ctcagcaaaa gaaatgctaa aatttcacgt gctacacttc tgggtcttgt     600
gatggctgaa ctaacacaac gctgcaaaca gcttcttgcg cttcgtccat ttgaaccagc     660
tgaggctaat attttcatc tcctcaagcg cattgaacgc gaagcatggt cagggcatac     720
tggtaactgg gttcaaattc ttcaatacaa agataagcga ggtgatcttc acgctcaacc     780
aattgatcct ttacgctttt taaagcatta catactacca aaaaatcgat tgatttctcc     840
ttccagcaaa cctgacgtct gcactactcc agataactgg ttcattctag ctgacaaaac     900
atacgctcac actattatta tgggcttcc gctgctagaa cataacagaa aagcctatct     960
acaagagtta gaaagtgaag tcatcccggg gccttctacc atggcctttg ggggacgtgg    1020
tgcgtgggaa caacttcctg aggtaggaga caacgcttta attacttcta atgcttctac    1080
tgcttataaa gctaacaaaa aagaaaaatt aatgctaaat ttacttgata aatgtgatga    1140
acttaattta cttgtttatg aagacttagt tagtgcttgt cctgacccttt tacttatgct    1200 tgaaggtcag ccaggtggtg cacgcctaat tgaacaggtc cttggcatgc atcatattaa    1260
ggtgtgtgct aaatacactg cattaacatt tttatttcat ttacatccgg atcaattatt    1320
aacttctaac aataaagctt taaaactact gttgattcaa gggtacaacc cacttcaagt    1380
agggcatgcc atctgttgtg tacttaacaa acagatgggc aagcagaaca ctatctgctt    1440
ttatggtcct gcttcaacag gcaaaacaaa cttttgcaaaa gcaatagttc aaggtgttcg    1500
cctttatggc tgtgttaatc atttaaacaa agggtttgtc tttaacgatt gcagacaacg    1560
ccttataatt tggtgggaag agtgtttaat gcaccaagat tgggtggaac ctgctaaatg    1620
cattttaggc ggaactgaat gtagaattga tgttaaacat aaagacagtg ttcttcttca    1680
```

```
acaaacacca gtaattattt ccactaacca tgacatctac tctgtagttg gtggcaatac    1740
tgtttctcat gttcatgcag caccattaaa agagcgagtc cttcagctaa atttcatgaa    1800
acaactgcca caaacatttg gagaaatttc tccagttgaa attgcagaac tattgcaatg    1860
gtgctttaat gagtacgaat gtactcttac tggctttaaa caaaaatgga acttagataa    1920
agttccaaac tcatttcctc ttggagacct ttgtcctaca cattcacagg actacacgct    1980
tcacgaaaac ggattctgca ctgactgtgg cggctatctt cctcatagtg ctgacgattt    2040
tgtctacact gacgtggcta gcgaaacaac aagcggagac tgcgacccag gtaggcttta    2100
atacatttgc ttaattaaat tatatatttg cactttgctt atgtattaac tcctacaggt    2160
aacctggggg atacgacgg agaggactcc aagtcagagg catcggaagt ggactttcgt    2220
ccatccaaga agaggcgtgt gatttcagca actccaccaa gcagtccagt aagtggtcca    2280
agcctttcta ccttttaga tacttggcag tcacaaccta gggacgaaga tgagctccga    2340
atctatgaag aacaagcatc gcaactccaa agaacacca agtccactcc agaaagagag    2400
gaggcgcaac tgggagagcc acaagagccg cagccggagc ccgatccgac ggcatgggga    2460
gaaaaacttg gagtatgctc atcacagcaa ccaggagaac cgccagtcgt cttatactgc    2520
tttgaagacc tcagaccaag cgacgaagac gaaggagaaa catcggggg ggaatagaac    2580 caatccttat actgtattca gtcaacacag ggctaatcat tcagatgctc ctggatggtg    2640
tgggttttac tggcattcta ctagacttgc tagagatggg actaattgta tctttaatga    2700
aatgaaacaa gaatttcaag aattacaaat aaatggaaaa attacttggg acaatgctag    2760
agaactattg tttagtcaga aaaaaaagct agatcaaaaa tacagaaaca tgctgtatca    2820
tttcagacac agtcctgatt gtcctagatg tgattattgg gataatgtat accgtagaca    2880
cttagctcat gtctcttcac aggaatcaga ggaggttaca gacgaagaaa tgctttctgc    2940
tgttgaaagc atggatacaa atgcctccaa ttaaacgcca gcctggaggg tgggtgcttc    3000
ctggttataa ataccttggt ccattcaatc ctcttgaaaa cggtgaacca gttaataaag    3060
ctgatcgtgc tgctcaagct catgataaat catattctga aataataaaa agtgaaaaa     3120 atccttactt gtatttcaat aaagctgatg aaaaattcat tgacgatttg aaaaacgact    3180
ggtctcttgg tggcattatt ggctcaagtt tctttaaact taagcgcgcc gtggctcctg    3240
ctctaggaaa taagagcga gctcaaaaaa gacattttta ctttgcaaac tcaaataaag    3300
gtgctaaaaa accaaaaaat aacgagccta accaggcac atcaaaaatg tctgaaaatg    3360
aaatccaaga ccaacaacca tctggctcca tggaggagcg aggaggcgga ggaggtgcgg    3420
tcggtagtgt gggaggggg aaaggttcta gtgtgggtat atccacaggc ggctgggttg    3480
gaggcagcta ctttactgac tcatatgtca taacaaagaa cactagacag ttcttagtta    3540
aaatacaaaa tgaccacaaa tacagaacag agaatataat tccaagcaac gcaggaggaa    3600
aatcccagcg atgcgtaagc acaccttggt catactttaa cttcaatcaa tacagcagtc    3660
acttctcacc acaagactgg cagcatttaa caaatgaata taaacgcttt aagcctagaa    3720
aaatgcatgt aaaaatttac aacttacaaa taaaacaaat actctcaaat ggtgctgaca    3780
ctacatacaa caacgaccta acagctggtg ttcacatctt ttgtgatggt gaacacgcat    3840
atccaaatgc aacacatcca tgggatgaag atgtcatgcc agaacttcca tatgaaacat    3900
ggtatttgtt tcaatatgga tacattccag ttattcatga actggctgaa atggaagacg    3960
caaatgctgt agaaaagct atagcactac aaataccctt tttcatgctt gaaaacagcg    4020
accatgaagt gttaagaaca ggagaaagca cagaattcac ttttgacttt gactgtgaat    4080
```

```
ggataaacaa cgaaagagca tacattcctc ctggattaat gtttaatcca aaagttccta    4140
caagaagagc tcaatacatc agacagcacg gaaacacagc atccagcaac accagaattc    4200
aaccatatgc aaaacctaca agctggatga caggaccagg tctactcagc gcacaaagag    4260
taggaccagc tggctcagac actgcatcat ggatggttgt tgtcaatcca gacggagctg    4320
cagttaactc aggaatggca ggagttggtt caggatttga tcctccttca ggatctctaa    4380
gaccaactga cttagaatac aaaatacaat ggtaccaaac tcctgcaggt accaacagtg    4440
atggaaacat catttcaaat ccaccactat ccatgctcag agatcaagct ctctacagag    4500
gaaatcaaac aacctacaac ctatgctcag atgtgtggat gttcccaaat caaatttggg    4560
acagatatcc aataaccaga gaaaatccaa tctggtgtaa aaaaccaaga tcagacaaaa    4620
acacaataat tgatcctttc gatggaacac ttgcaatgga tcatccgcca ggaacaatct    4680
tcataaaaat ggcaaaaatt ccagttcctt caaacaacaa cgcagactca tacctaaaca    4740
tctactgcac tggacaagtc agctgcgaaa ttgtctggga agttgaaaga tacgcaacaa    4800
agaactggag accagaaaga agacacaccg cacttggtct tggaattgga ggagaagaaa    4860
acgtaaatcc aacttatcat gtagacaaaa atggaaaata cattcaacca acaacttggg    4920
acatgtgcta tcctatcaaa acaaacatca ataaagtgtt gtaatctctt aagcctgttc    4980
attgcttatg cttataagtt cctctccaat ggacaagagg aaagaaaagg gtgactgtaa    5040
tcccgagctc atgagttcga ggctacagtc cgatggcagt ggtgttgccg tctcgaacct    5100
agccggtaca cccttgtgca ttgtgggagg agctgttttg cttacgcaat cgcgaaattt    5160
tatatattta atgtagtgtt gtactgcgtc aggcat                              5196
```

<210> SEQ ID NO 2
<211> LENGTH: 640
<212> TYPE: PRT
<213> ORGANISM: Bocavirus

<400> SEQUENCE: 2

```
Met Ala Phe Ser Ala Pro Val Ile Arg Ala Phe Ser Gln Pro Ala Phe
1               5                   10                  15

Thr Tyr Val Val Lys Phe Pro Tyr Glu Asn Trp Lys Glu Glu Glu His
            20                  25                  30

Leu Leu Trp Ser Leu Leu Ala Pro Gly Thr Glu Arg Leu Met Ile Gln
        35                  40                  45

Leu Arg Asn Cys Ala Pro His Pro Glu Asp Asp Pro Val Arg Glu Asp
    50                  55                  60

Ile Leu Cys Ser Leu Ala Asp Gln His Tyr Gly Ala Ile Phe Ala Lys
65                  70                  75                  80

Ala Cys Tyr Ile Ala Thr Thr Thr Leu Met Gly Gln Lys Gln Arg Thr
                85                  90                  95

Pro Phe Pro Arg Cys Asp Ile Ile Cys Gln Ser Glu Ile Gly Ser Glu
            100                 105                 110

His Leu His Cys His Ile Leu Val Gly Gly Ala Gly Leu Ser Lys Arg
        115                 120                 125

Asn Ala Lys Ile Ser Arg Ala Thr Leu Leu Gly Leu Val Met Ala Glu
    130                 135                 140

Leu Thr Gln Arg Cys Lys Gln Leu Leu Ala Leu Arg Pro Phe Glu Pro
145                 150                 155                 160

Ala Glu Ala Asn Ile Phe His Leu Leu Lys Arg Ile Glu Arg Glu Ala
                165                 170                 175
```

```
Trp Ser Gly His Thr Gly Asn Trp Val Gln Ile Leu Gln Tyr Lys Asp
            180                 185                 190

Lys Arg Gly Asp Leu His Ala Gln Pro Ile Asp Pro Leu Arg Phe Leu
        195                 200                 205

Lys His Tyr Ile Leu Pro Lys Asn Arg Leu Ile Ser Pro Ser Ser Lys
    210                 215                 220

Pro Asp Val Cys Thr Thr Pro Asp Asn Trp Phe Ile Leu Ala Asp Lys
225                 230                 235                 240

Thr Tyr Ala His Thr Ile Ile Asn Gly Leu Pro Leu Leu Glu His Asn
                245                 250                 255

Arg Lys Ala Tyr Leu Gln Glu Leu Glu Ser Glu Val Ile Pro Gly Pro
            260                 265                 270

Ser Thr Met Ala Phe Gly Gly Arg Gly Ala Trp Glu Gln Leu Pro Glu
        275                 280                 285

Val Gly Glu Gln Arg Leu Ile Thr Ser Asn Ala Ser Thr Ala Tyr Lys
    290                 295                 300

Ala Asn Lys Lys Glu Lys Leu Met Leu Asn Leu Leu Asp Lys Cys Asp
305                 310                 315                 320

Glu Leu Asn Leu Leu Val Tyr Glu Asp Leu Val Ser Ala Cys Pro Asp
                325                 330                 335

Leu Leu Leu Met Leu Glu Gly Gln Pro Gly Gly Ala Arg Leu Ile Glu
            340                 345                 350

Gln Val Leu Gly Met His His Ile Lys Val Cys Ala Lys Tyr Thr Ala
        355                 360                 365

Leu Thr Phe Leu Phe His Leu His Pro Asp Gln Leu Leu Thr Ser Asn
    370                 375                 380

Asn Lys Ala Leu Lys Leu Leu Ile Gln Gly Tyr Asn Pro Leu Gln
385                 390                 395                 400

Val Gly His Ala Ile Cys Cys Val Leu Asn Lys Gln Met Gly Lys Gln
                405                 410                 415

Asn Thr Ile Cys Phe Tyr Gly Pro Ala Ser Thr Gly Lys Thr Asn Phe
            420                 425                 430

Ala Lys Ala Ile Val Gln Gly Val Arg Leu Tyr Gly Cys Val Asn His
        435                 440                 445

Leu Asn Lys Gly Phe Val Phe Asn Asp Cys Arg Gln Arg Leu Ile Ile
    450                 455                 460

Trp Trp Glu Glu Cys Leu Met His Gln Asp Trp Val Glu Pro Ala Lys
465                 470                 475                 480

Cys Ile Leu Gly Gly Thr Glu Cys Arg Ile Asp Val Lys His Lys Asp
                485                 490                 495

Ser Val Leu Leu Gln Gln Thr Pro Val Ile Ile Ser Thr Asn His Asp
            500                 505                 510

Ile Tyr Ser Val Val Gly Gly Asn Thr Val Ser His Val His Ala Ala
        515                 520                 525

Pro Leu Lys Glu Arg Val Leu Gln Leu Asn Phe Met Lys Gln Leu Pro
    530                 535                 540

Gln Thr Phe Gly Glu Ile Ser Pro Val Glu Ile Ala Glu Leu Leu Gln
545                 550                 555                 560

Trp Cys Phe Asn Glu Tyr Glu Cys Thr Leu Thr Gly Phe Lys Gln Lys
                565                 570                 575

Trp Asn Leu Asp Lys Val Pro Asn Ser Phe Pro Leu Gly Asp Leu Cys
            580                 585                 590

Pro Thr His Ser Gln Asp Tyr Thr Leu His Glu Asn Gly Phe Cys Thr
        595                 600                 605
```

```
Asp Cys Gly Gly Tyr Leu Pro His Ser Ala Asp Asp Phe Val Tyr Thr
        610                 615                 620
Asp Val Ala Ser Glu Thr Thr Ser Gly Asp Cys Asp Pro Gly Arg Leu
625                 630                 635                 640

<210> SEQ ID NO 3
<211> LENGTH: 214
<212> TYPE: PRT
<213> ORGANISM: Bocavirus

<400> SEQUENCE: 3

Met Ser Ser Glu Ser Met Lys Asn Lys His Arg Asn Ser Lys Arg Thr
  1               5                  10                  15
Pro Ser Pro Leu Gln Lys Glu Arg Arg Arg Asn Trp Glu Ser His Lys
             20                  25                  30
Ser Arg Ser Arg Ser Pro Ile Arg Arg His Gly Glu Lys Asn Leu Glu
         35                  40                  45
Tyr Ala His His Ser Asn Gln Glu Asn Arg Gln Ser Ser Tyr Thr Ala
     50                  55                  60
Leu Lys Thr Ser Asp Gln Ala Thr Lys Thr Lys Glu Lys Thr Ser Gly
 65                  70                  75                  80
Gly Asn Arg Thr Asn Pro Tyr Thr Val Phe Ser Gln His Arg Ala Asn
                 85                  90                  95
His Ser Asp Ala Pro Gly Trp Cys Gly Phe Tyr Trp His Ser Thr Arg
            100                 105                 110
Leu Ala Arg Asp Gly Thr Asn Cys Ile Phe Asn Glu Met Lys Gln Glu
        115                 120                 125
Phe Gln Glu Leu Gln Ile Asn Gly Lys Ile Thr Trp Asp Asn Ala Arg
    130                 135                 140
Glu Leu Leu Phe Ser Gln Lys Lys Leu Asp Gln Lys Tyr Arg Asn
145                 150                 155                 160
Met Leu Tyr His Phe Arg His Ser Pro Asp Cys Pro Arg Cys Asp Tyr
                165                 170                 175
Trp Asp Asn Val Tyr Arg Arg His Leu Ala His Val Ser Ser Gln Glu
            180                 185                 190
Ser Glu Glu Val Thr Asp Glu Glu Met Leu Ser Ala Val Glu Ser Met
        195                 200                 205
Asp Thr Asn Ala Ser Asn
        210

<210> SEQ ID NO 4
<211> LENGTH: 667
<212> TYPE: PRT
<213> ORGANISM: Bocavirus

<400> SEQUENCE: 4

Met Pro Pro Ile Lys Arg Gln Pro Gly Gly Trp Val Leu Pro Gly Tyr
  1               5                  10                  15
Lys Tyr Leu Gly Pro Phe Asn Pro Leu Glu Asn Gly Glu Pro Val Asn
             20                  25                  30
Lys Ala Asp Arg Ala Ala Gln Ala His Asp Lys Ser Tyr Ser Glu Ile
         35                  40                  45
Ile Lys Ser Gly Lys Asn Pro Tyr Leu Tyr Phe Asn Lys Ala Asp Glu
     50                  55                  60
Lys Phe Ile Asp Asp Leu Lys Asn Asp Trp Ser Leu Gly Gly Ile Ile
 65                  70                  75                  80
```

-continued

```
Gly Ser Ser Phe Phe Lys Leu Lys Arg Ala Val Ala Pro Ala Leu Gly
             85                  90                  95

Asn Lys Glu Arg Ala Gln Lys Arg His Phe Tyr Phe Ala Asn Ser Asn
            100                 105                 110

Lys Gly Ala Lys Lys Pro Lys Asn Asn Glu Pro Lys Pro Gly Thr Ser
        115                 120                 125

Lys Met Ser Glu Asn Glu Ile Gln Asp Gln Gln Pro Ser Gly Ser Met
    130                 135                 140

Glu Arg Gly Gly Gly Gly Ala Val Gly Ser Val Gly Gly
145                 150                 155                 160

Lys Gly Ser Ser Val Gly Ile Ser Thr Gly Gly Trp Val Gly Gly Ser
                165                 170                 175

Tyr Phe Thr Asp Ser Tyr Val Ile Thr Lys Asn Thr Arg Gln Phe Leu
            180                 185                 190

Val Lys Ile Gln Asn Asp His Lys Tyr Arg Thr Glu Asn Ile Ile Pro
        195                 200                 205

Ser Asn Ala Gly Gly Lys Ser Gln Arg Cys Val Ser Thr Pro Trp Ser
    210                 215                 220

Tyr Phe Asn Phe Asn Gln Tyr Ser Ser His Phe Ser Pro Gln Asp Trp
225                 230                 235                 240

Gln His Leu Thr Asn Glu Tyr Lys Arg Phe Lys Pro Arg Lys Met His
                245                 250                 255

Val Lys Ile Tyr Asn Leu Gln Ile Lys Gln Ile Leu Ser Asn Gly Ala
            260                 265                 270

Asp Thr Thr Tyr Asn Asn Asp Leu Thr Ala Gly Val His Ile Phe Cys
        275                 280                 285

Asp Gly Glu His Ala Tyr Pro Asn Ala Thr His Pro Trp Asp Glu Asp
    290                 295                 300

Val Met Pro Glu Leu Pro Tyr Glu Thr Trp Tyr Leu Phe Gln Tyr Gly
305                 310                 315                 320

Tyr Ile Pro Val Ile His Glu Leu Ala Glu Met Glu Asp Ala Asn Ala
                325                 330                 335

Val Glu Lys Ala Ile Ala Leu Gln Ile Pro Phe Phe Met Leu Glu Asn
            340                 345                 350

Ser Asp His Glu Val Leu Arg Thr Gly Glu Ser Thr Glu Phe Thr Phe
        355                 360                 365

Asp Phe Asp Cys Glu Trp Ile Asn Asn Glu Arg Ala Tyr Ile Pro Pro
    370                 375                 380

Gly Leu Met Phe Asn Pro Lys Val Pro Thr Arg Arg Ala Gln Tyr Ile
385                 390                 395                 400

Arg Gln His Gly Asn Thr Ala Ser Ser Asn Thr Arg Ile Gln Pro Tyr
                405                 410                 415

Ala Lys Pro Thr Ser Trp Met Thr Gly Pro Gly Leu Leu Ser Ala Gln
            420                 425                 430

Arg Val Gly Pro Ala Gly Ser Asp Thr Ala Ser Trp Met Val Val
        435                 440                 445

Asn Pro Asp Gly Ala Ala Val Asn Ser Gly Met Ala Gly Val Gly Ser
    450                 455                 460

Gly Phe Asp Pro Pro Ser Gly Ser Leu Arg Pro Thr Asp Leu Glu Tyr
465                 470                 475                 480

Lys Ile Gln Trp Tyr Gln Thr Pro Ala Gly Thr Asn Ser Asp Gly Asn
                485                 490                 495

Ile Ile Ser Asn Pro Pro Leu Ser Met Leu Arg Asp Gln Ala Leu Tyr
            500                 505                 510
```

```
Arg Gly Asn Gln Thr Thr Tyr Asn Leu Cys Ser Asp Val Trp Met Phe
            515                 520                 525

Pro Asn Gln Ile Trp Asp Arg Tyr Pro Ile Thr Arg Glu Asn Pro Ile
            530                 535                 540

Trp Cys Lys Lys Pro Arg Ser Asp Lys Asn Thr Ile Ile Asp Pro Phe
545                 550                 555                 560

Asp Gly Thr Leu Ala Met Asp His Pro Gly Thr Ile Phe Ile Lys
            565                 570                 575

Met Ala Lys Ile Pro Val Pro Ser Asn Asn Asn Ala Asp Ser Tyr Leu
            580                 585                 590

Asn Ile Tyr Cys Thr Gly Gln Val Ser Cys Glu Ile Val Trp Glu Val
            595                 600                 605

Glu Arg Tyr Ala Thr Lys Asn Trp Arg Pro Glu Arg Arg His Thr Ala
            610                 615                 620

Leu Gly Leu Gly Ile Gly Gly Glu Asn Val Asn Pro Thr Tyr His
625                 630                 635                 640

Val Asp Lys Asn Gly Lys Tyr Ile Gln Pro Thr Thr Trp Asp Met Cys
            645                 650                 655

Tyr Pro Ile Lys Thr Asn Ile Asn Lys Val Leu
            660                 665

<210> SEQ ID NO 5
<211> LENGTH: 4972
<212> TYPE: DNA
<213> ORGANISM: Bocavirus

<400> SEQUENCE: 5
gtggtgagtc acattatggc tttcaatcca cctgttatta gagcattctc ttcacctgct      60
tttacttatg tcttcaaatt tccatatcca tcatggaaag aaaaagaatg gcttcttcat     120
gcacttctgg ctcatggtac cgagcaagcc atgatccagc tgagaaactg tgttcctcat     180
ccggatgaag atataatccg tgatgactta ctactttctc tagaagatcg ccattttggg     240
gcaattctct gcaaggctgt ctatatggct actactactt ttatgtcaca gaaacaaaga     300
aatatgtttc ctcgctgtga cataatagtc aatctgagc ttggggagac aaacctacac     360
tgccatatta tagttggggg agaaggctta agcaagagaa atgcaaaaac atcatgtcct     420
caactatatg gactgatact aggggaatta atccaacgct gcaaaactct tctggctacg     480 cgtcctttg aaccggaaga ggcagaaatt tatcatgctt taaaacgagc tgagcgagaa     540
gcttggggtg gagttactag cggcaaccta caaattctcc aatacagaga tcgcagagga     600
gaccttcacg cacaacaagt ggatgctctt cgcttcttca aaaactacct attgcctaaa     660
aatagatgca ttcatcttta cagcagacct gatgtctgta cttctccaga aaactggttt     720
gttttagctg aaaaaactta ctgtcacact cttgttaacg ggctgccgct tccagaacat     780
tacagaaaac actaccacgc aaccctagat aacgaagttc taccagggcc tcagacaatg     840
gcctttgggg gacgtggtcc gtgggaacat cttcctgagg taggagatca acgtttagct     900
gcttcttctg ttagtacaac atataaacca aacaaaaaag aaaaacttat gcttaactta     960
ctagataaat gcagcgaatt aaatctttta gtttatgaag acttagtagc taactgtcct    1020
gaacttttgc ttatgcttga aggtcaacca ggtggggcac gcttaataga acaagtccta    1080
ggcatgcacc atattaatgt tgctctaac tttactgctc ttagttatct ctttcacctt    1140
tacccctggc aacccttatc ttcagataac aaggctttgc agctgttgtt gatacaaggt    1200
tacaacccat taatggttgg tcacgccttg tgctgtgtac tcaacaagca atttggcaaa    1260
```

```
caaaacactg tttgctttta tggaccagct tctactggta aaacaaacat ggcaaaggcc    1320
atagtccaag gcattagact atatggctgt gttaatcatt taaacaaagg gtttgtcttt    1380
aatgattgca gacaacgcct agttgtttgg tgggaggagt gcttaatgca ccaggattgg    1440
gtggaaccag caaagtgtat cttgggtgga actgagtgta gaattgacgt caaacacaga    1500
gatagtgtat tattgacaca aactccagta attatttcca ctaaccacga tatctacgcg    1560
gttgttggtg gtaattctgt ttctcatgtt catgcggctc cattaaaaga aagagtgatt    1620
cagctaaatt ttatgaaaca acttcctcaa acatttggag agatcactcc agaagaaatt    1680
gcagctctac tgcaatggtg tttcaatgag tacgaatgta ctctgacagg ctttaaaaca    1740
aaatggagcc tagataaaat tccaaactca tttcctcttg gggtcctttg tcctactcat    1800
tcacaggact tcatactcca cgaaaacgga tactgcactg attgtggtgg ttaccttgct    1860
catagcgctg acgattctgt gtacactgat cgtgcaagcg acactagcaa agaagccatc    1920
gacgcaggta agtttacgtt ctccaggcac tttatatata tcctatacac aacactaaaa    1980
catatgttta attacaggtg acttggggga tacggacgga gaggactccg agtcagaagc    2040
atcggaagtg ggtgttcgtc catccaagaa gcgacgcata actattcctg caactccacc    2100
aaattctcct ggcagctctg tgagtacttc tgccttcttt gataattggt gcgcacaacc    2160
gcgagacgaa gatgagctca gggaatacga agacaagca tcgcgcctac aaaagaaaag    2220
ggagtccagg gagagacgag aagaaacgcc catggcaacc tcgtcacagg agtcggagtc    2280
ggagcccaat ccgacgcagt ggggagacaa gctcggggtc ataccgtcag gaacaccaga    2340
tcagccacct atcgtcttgc actgcttcga agatctcaga cccagtgacg aagacgaagg    2400
agaatacatc gggaaagaga gactctagaa ctaatcccata cactgtattc agccagcata    2460
aagcctcaca tcctgatgct ccaggatggt gtgggttcta ttggcattct actagaattg    2520
ctagaaatgg tactaatgca atctttaatg aaatgaaaca gcagttccaa caactgcagc    2580
tagacaacaa aattggctgg gataatgcta gagaattatt gtttagtcag aaaaaatcac    2640
tagatcaaca atacagaaat atgttctggc actttagaaa tgcttctgat tgtgaacgtt    2700
gtaattactg ggacaatgta taccgtatgc acttagctca tgtttcctct cagacagaat    2760
cagaagaaat aactgacgag gaaatgcttt ctgctgctga agtatggaa acagatgcct    2820 ccaattaaaa ggcaacctgg agggtgggtg cttcctggtt acaaatacct tggtccattt    2880
aatcctcttg ataacggtga accagttaat aaagctgatc gtgctgctca atctcatgat    2940
aaatcatatt ctgaattaat aaaaagtgga aaaaatcctt acttatattt caataaagct    3000
gatgaaaaat tcattgacga tttgaaaaac gactggtctc ttggtggcat tattggctca    3060 agtttctta aacttaagcg cgccgtggct cctgctctag gaaataaaga gcgagctcaa    3120
aaaagacact tttatttccc aaactcaaat aaaggtgcta aaaatcaaa aacaacgaa    3180 cctaaaccaa acacctcaaa aatgtctgaa aatgaaattc aagatcaaca gccatcagaa    3240
cctaatgatg gccaacgagg agggggagga ggtgcgaccg gcagtgtggg aggggggaaa    3300
ggttctggtg tgggtatatc cacaggtgga tgggtaggag gcagctactt tactgactcc    3360
tatgtcataa caaaaaacac cagacaattt ctggttaaaa tccaaaacaa ccatcaatat    3420
aaaactgaaa atataattcc ttccaatgga ggaggaaaat cacaaagatg tgtcagcaca    3480
ccatggtcat actttaactt taatcaatac agcagtcatt tctcaccaca ggactggcag    3540
cgcctaacaa atgaatacaa aagattcaga cctaaaggta tgcatgttaa aatctacaat    3600
ttacaaataa aacagatttt atcaaatggt gctgatgtta catacaacaa cgacctaaca    3660
```

```
gcaggagtac acatctttg tgatggcgaa catgcatatc caaacgctac acatccatgg   3720
gacgaagatg taatgccaga acttccttac caaacatggt atctgtttca atatggatac   3780
ataccacca ttcatgaact tgcagaaatg aagactcca atgcagtaga aaaagcaatt    3840
gctttacaga taccattctt catgcttgaa acagcgacc atgaagttct aagaactgga    3900
gaaagtgcag aatttaactt caactttgac tgtgaatgga ttaacaatga aagagcattc   3960
attcctccag gactgatgtt taatccattg gtaccaacaa aagagctca atacatacga    4020
agaaatggaa acactcaagc aagtacatca cgaattcaac cctatgctaa acctacaagc   4080
tggatgactg ggccaggttt actcagtgca caacgagtag gtccagctgc ttctgacaca   4140
gctgcatgga tggttggtgt agatccagaa ggcgcaaaca tcaactcagg aagagcagga   4200
gttagcagtg gatttgatcc tccagctgga tcactcagac ctacagatct agaatacaaa   4260
gtacaatggt accaaactcc agctggaaca acaacgatg aaacatcat ttcaaatcca    4320
cctttatcaa tgcttagaga tcaaactctc tacagaggaa accaaacaac ctacaactta   4380
tgctcagatg tatggatgtt tccaaatcaa atttgggaca gatacccagt aacaagagaa   4440
aatcctattt ggtgcaaaca accaagatca gacaaacaca caacaattga tccttttgac   4500
ggatcaatag ccatggatca tccaccaggc acaattttca tcaaaatggc aaaaattcca   4560
gttccttcaa acaacaacgc agactcatac ttaaacatct actgcactgg acaagtcagc   4620
tgcgaaattg tctgggaagt cgaaagatat gcaacaaaga actggagacc agaaagaaga   4680
cacacagcac tcggccttgg aattggaggg gcagatgaaa tcaacccaac ataccatgtt   4740
gacaaaaacg gagcatacat tcaacctaca acatgggaca tgtgctttcc agttaaaaca   4800
aacattaata aagtgttgta atctcttaag cctctttatt gcttacgctt gtaagttcct   4860
ctccaatgga caagtggaaa gaaaagggtg actgtaatcc cgagctcatg agttcgaggc   4920
tacagtccga tggcagtggt gttgccgtct cgaacctagc cgttacaccc tt           4972
```

<210> SEQ ID NO 6
<211> LENGTH: 661
<212> TYPE: PRT
<213> ORGANISM: Bocavirus

<400> SEQUENCE: 6

```
Met Ala Phe Asn Pro Pro Val Ile Arg Ala Phe Ser Ser Pro Ala Phe
1               5                   10                  15

Thr Tyr Val Phe Lys Phe Pro Tyr Pro Ser Trp Lys Glu Lys Glu Trp
            20                  25                  30

Leu Leu His Ala Leu Leu Ala His Gly Thr Glu Gln Ala Met Ile Gln
        35                  40                  45

Leu Arg Asn Cys Val Pro His Pro Asp Glu Asp Ile Ile Arg Asp Asp
    50                  55                  60

Leu Leu Leu Ser Leu Glu Asp Arg His Phe Gly Ala Ile Leu Cys Lys
65                  70                  75                  80

Ala Val Tyr Met Ala Thr Thr Thr Phe Met Ser Gln Lys Gln Arg Asn
                85                  90                  95

Met Phe Pro Arg Cys Asp Ile Ile Val Gln Ser Glu Leu Gly Glu Thr
            100                 105                 110

Asn Leu His Cys His Ile Ile Val Gly Gly Glu Gly Leu Ser Lys Arg
        115                 120                 125

Asn Ala Lys Thr Ser Cys Pro Gln Leu Tyr Gly Leu Ile Leu Gly Glu
    130                 135                 140
```

-continued

```
Leu Ile Gln Arg Cys Lys Thr Leu Leu Ala Thr Arg Pro Phe Glu Pro
145                 150                 155                 160

Glu Glu Ala Glu Ile Tyr His Ala Leu Lys Arg Ala Glu Arg Glu Ala
                165                 170                 175

Trp Gly Gly Val Thr Ser Gly Asn Leu Gln Ile Leu Gln Tyr Arg Asp
            180                 185                 190

Arg Arg Gly Asp Leu His Ala Gln Gln Val Asp Ala Leu Arg Phe Phe
        195                 200                 205

Lys Asn Tyr Leu Leu Pro Lys Asn Arg Cys Ile Thr Ser Tyr Ser Arg
210                 215                 220

Pro Asp Val Cys Thr Ser Pro Glu Asn Trp Phe Val Leu Ala Glu Lys
225                 230                 235                 240

Thr Tyr Cys His Thr Leu Val Asn Gly Leu Pro Leu Pro Glu His Tyr
                245                 250                 255

Arg Lys His Tyr His Ala Thr Leu Asp Asn Glu Val Leu Pro Gly Pro
            260                 265                 270

Gln Thr Met Ala Phe Gly Gly Arg Gly Pro Trp Glu His Leu Pro Glu
        275                 280                 285

Val Gly Asp Gln Arg Leu Ala Ala Ser Ser Val Ser Thr Thr Tyr Lys
290                 295                 300

Pro Asn Lys Lys Glu Lys Leu Met Leu Asn Leu Leu Asp Lys Cys Ser
305                 310                 315                 320

Glu Leu Asn Leu Leu Val Tyr Glu Asp Leu Val Ala Asn Cys Pro Glu
                325                 330                 335

Leu Leu Leu Met Leu Glu Gly Gln Pro Gly Gly Ala Arg Leu Ile Glu
            340                 345                 350

Gln Val Leu Gly Met His His Ile Asn Val Cys Ser Asn Phe Thr Ala
        355                 360                 365

Leu Ser Tyr Leu Phe His Leu Tyr Pro Gly Thr Thr Leu Ser Ser Asp
370                 375                 380

Asn Lys Ala Leu Gln Leu Leu Ile Gln Gly Tyr Asn Pro Leu Met
385                 390                 395                 400

Val Gly His Ala Leu Cys Cys Val Leu Asn Lys Gln Phe Gly Lys Gln
                405                 410                 415

Asn Thr Val Cys Phe Tyr Gly Pro Ala Ser Thr Gly Lys Thr Asn Met
            420                 425                 430

Ala Lys Ala Ile Val Gln Gly Ile Arg Leu Tyr Gly Cys Val Asn His
        435                 440                 445

Leu Asn Lys Gly Phe Val Phe Asn Asp Cys Arg Gln Arg Leu Val Val
450                 455                 460

Trp Trp Glu Glu Cys Leu Met His Gln Asp Trp Val Glu Pro Ala Lys
465                 470                 475                 480

Cys Ile Leu Gly Gly Thr Glu Cys Arg Ile Asp Val Lys His Arg Asp
                485                 490                 495

Ser Val Leu Leu Thr Gln Thr Pro Val Ile Ile Ser Thr Asn His Asp
            500                 505                 510

Ile Tyr Ala Val Val Gly Gly Asn Ser Val Ser His Val His Ala Ala
        515                 520                 525

Pro Leu Lys Glu Arg Val Ile Gln Leu Asn Phe Met Lys Gln Leu Pro
530                 535                 540

Gln Thr Phe Gly Glu Ile Thr Pro Glu Glu Ile Ala Ala Leu Leu Gln
545                 550                 555                 560

Trp Cys Phe Asn Glu Tyr Glu Cys Thr Leu Thr Gly Phe Lys Thr Lys
                565                 570                 575
```

```
Trp Ser Leu Asp Lys Ile Pro Asn Ser Phe Pro Leu Gly Val Leu Cys
            580                 585                 590

Pro Thr His Ser Gln Asp Phe Ile Leu His Glu Asn Gly Tyr Cys Thr
            595                 600                 605

Asp Cys Gly Gly Tyr Leu Ala His Ser Ala Asp Asp Ser Val Tyr Thr
    610                 615                 620

Asp Arg Ala Ser Asp Thr Ser Lys Glu Ala Ile Asp Ala Gly Lys Phe
625                 630                 635                 640

Thr Phe Ser Arg His Phe Ile Tyr Ile Leu Tyr Thr Thr Leu Lys His
                645                 650                 655

Met Phe Asn Tyr Arg
            660
```

<210> SEQ ID NO 7
<211> LENGTH: 218
<212> TYPE: PRT
<213> ORGANISM: Bocavirus

<400> SEQUENCE: 7

```
Met Ser Ser Gly Asn Thr Lys Asp Lys His Arg Ala Tyr Lys Arg Lys
1               5                   10                  15

Gly Ser Pro Gly Arg Asp Glu Lys Lys Arg Pro Trp Gln Pro Arg His
            20                  25                  30

Arg Ser Arg Ser Arg Ser Pro Ile Arg Arg Ser Gly Glu Thr Ser Ser
        35                  40                  45

Gly Ser Tyr Arg Gln Glu His Gln Ile Ser His Leu Ser Ser Cys Thr
    50                  55                  60

Ala Ser Lys Ile Ser Asp Pro Val Thr Lys Thr Lys Glu Asn Thr Ser
65                  70                  75                  80

Gly Lys Arg Asp Ser Arg Thr Asn Pro Tyr Thr Val Phe Ser Gln His
                85                  90                  95

Lys Ala Ser His Pro Asp Ala Pro Gly Trp Cys Gly Phe Tyr Trp His
            100                 105                 110

Ser Thr Arg Ile Ala Arg Asn Gly Thr Asn Ala Ile Phe Asn Glu Met
        115                 120                 125

Lys Gln Gln Phe Gln Gln Leu Gln Leu Asp Asn Lys Ile Gly Trp Asp
    130                 135                 140

Asn Ala Arg Glu Leu Leu Phe Ser Gln Lys Lys Ser Leu Asp Gln Gln
145                 150                 155                 160

Tyr Arg Asn Met Phe Trp His Phe Arg Asn Ala Ser Asp Cys Glu Arg
                165                 170                 175

Cys Asn Tyr Trp Asp Asn Val Tyr Arg Met His Leu Ala His Val Ser
            180                 185                 190

Ser Gln Thr Glu Ser Glu Glu Ile Thr Asp Glu Glu Met Leu Ser Ala
        195                 200                 205

Ala Glu Ser Met Glu Thr Asp Ala Ser Asn
    210                 215
```

<210> SEQ ID NO 8
<211> LENGTH: 668
<212> TYPE: PRT
<213> ORGANISM: Bocavirus

<400> SEQUENCE: 8

```
Met Pro Pro Ile Lys Arg Gln Pro Gly Gly Trp Val Leu Pro Gly Tyr
1               5                   10                  15
```

```
Lys Tyr Leu Gly Pro Phe Asn Pro Leu Asp Asn Gly Glu Pro Val Asn
             20                  25                  30
Lys Ala Asp Arg Ala Ala Gln Ser His Asp Lys Ser Tyr Ser Glu Leu
         35                  40                  45
Ile Lys Ser Gly Lys Asn Pro Tyr Leu Tyr Phe Asn Lys Ala Asp Glu
 50                  55                  60
Lys Phe Ile Asp Asp Leu Lys Asn Asp Trp Ser Leu Gly Gly Ile Ile
 65                  70                  75                  80
Gly Ser Ser Phe Phe Lys Leu Lys Arg Ala Val Ala Pro Ala Leu Gly
                 85                  90                  95
Asn Lys Glu Arg Ala Gln Lys Arg His Phe Tyr Phe Pro Asn Ser Asn
            100                 105                 110
Lys Gly Ala Lys Lys Ser Lys Asn Asn Glu Pro Lys Pro Asn Thr Ser
        115                 120                 125
Lys Met Ser Glu Asn Glu Ile Gln Asp Gln Gln Pro Ser Glu Pro Asn
130                 135                 140
Asp Gly Gln Arg Gly Gly Gly Gly Ala Thr Gly Ser Val Gly Gly
145                 150                 155                 160
Gly Lys Gly Ser Gly Val Gly Ile Ser Thr Gly Gly Trp Val Gly Gly
                165                 170                 175
Ser Tyr Phe Thr Asp Ser Tyr Val Ile Thr Lys Asn Thr Arg Gln Phe
            180                 185                 190
Leu Val Lys Ile Gln Asn Asn His Gln Tyr Lys Thr Glu Asn Ile Ile
        195                 200                 205
Pro Ser Asn Gly Gly Lys Ser Gln Arg Cys Val Ser Thr Pro Trp
210                 215                 220
Ser Tyr Phe Asn Phe Asn Gln Tyr Ser Ser His Phe Ser Pro Gln Asp
225                 230                 235                 240
Trp Gln Arg Leu Thr Asn Glu Tyr Lys Arg Phe Arg Pro Lys Gly Met
                245                 250                 255
His Val Lys Ile Tyr Asn Leu Gln Ile Lys Gln Ile Leu Ser Asn Gly
            260                 265                 270
Ala Asp Val Thr Tyr Asn Asn Asp Leu Thr Ala Gly Val His Ile Phe
        275                 280                 285
Cys Asp Gly Glu His Ala Tyr Pro Asn Ala Thr His Pro Trp Asp Glu
290                 295                 300
Asp Val Met Pro Glu Leu Pro Tyr Gln Thr Trp Tyr Leu Phe Gln Tyr
305                 310                 315                 320
Gly Tyr Ile Pro Thr Ile His Glu Leu Ala Glu Met Glu Asp Ser Asn
                325                 330                 335
Ala Val Glu Lys Ala Ile Ala Leu Gln Ile Pro Phe Phe Met Leu Glu
            340                 345                 350
Asn Ser Asp His Glu Val Leu Arg Thr Gly Glu Ser Ala Glu Phe Asn
        355                 360                 365
Phe Asn Phe Asp Cys Glu Trp Ile Asn Asn Glu Arg Ala Phe Ile Pro
370                 375                 380
Pro Gly Leu Met Phe Asn Pro Leu Val Pro Thr Arg Arg Ala Gln Tyr
385                 390                 395                 400
Ile Arg Arg Asn Gly Asn Thr Gln Ala Ser Thr Arg Ile Gln Pro
                405                 410                 415
Tyr Ala Lys Pro Thr Ser Trp Met Thr Gly Pro Gly Leu Leu Ser Ala
            420                 425                 430
Gln Arg Val Gly Pro Ala Ala Ser Asp Thr Ala Ala Trp Met Val Gly
        435                 440                 445
```

| Val | Asp | Pro | Glu | Gly | Ala | Asn | Ile | Asn | Ser | Gly | Arg | Ala | Gly | Val | Ser |
| | 450 | | | | 455 | | | | | 460 | | | | | |

Ser Gly Phe Asp Pro Pro Ala Gly Ser Leu Arg Pro Thr Asp Leu Glu
465                 470                     475                 480

Tyr Lys Val Gln Trp Tyr Gln Thr Pro Ala Gly Thr Asn Asn Asp Gly
                485                     490                     495

Asn Ile Ile Ser Asn Pro Pro Leu Ser Met Leu Arg Asp Gln Thr Leu
            500                     505                     510

Tyr Arg Gly Asn Gln Thr Thr Tyr Asn Leu Cys Ser Asp Val Trp Met
                515                     520                 525

Phe Pro Asn Gln Ile Trp Asp Arg Tyr Pro Val Thr Arg Glu Asn Pro
            530                     535                 540

Ile Trp Cys Lys Gln Pro Arg Ser Asp Lys His Thr Ile Asp Pro
545                 550                     555                 560

Phe Asp Gly Ser Ile Ala Met Asp His Pro Pro Gly Thr Ile Phe Ile
                565                     570                 575

Lys Met Ala Lys Ile Pro Val Pro Ser Asn Asn Asn Ala Asp Ser Tyr
            580                     585                 590

Leu Asn Ile Tyr Cys Thr Gly Gln Val Ser Cys Glu Ile Val Trp Glu
                595                     600                 605

Val Glu Arg Tyr Ala Thr Lys Asn Trp Arg Pro Glu Arg Arg His Thr
610                 615                         620

Ala Leu Gly Leu Gly Ile Gly Gly Ala Asp Glu Ile Asn Pro Thr Tyr
625                 630                     635                 640

His Val Asp Lys Asn Gly Ala Tyr Ile Gln Pro Thr Thr Trp Asp Met
                645                     650                 655

Cys Phe Pro Val Lys Thr Asn Ile Asn Lys Val Leu
            660                     665

<210> SEQ ID NO 9
<211> LENGTH: 4966
<212> TYPE: DNA
<213> ORGANISM: Bocavirus

<400> SEQUENCE: 9

```
tggtgagtga cactatggcc ttttctgctc ctgtaattag agcttttttct caacctgctt      60
tcacttatgt tgttaaattt ccatatgata actggaaaga ggaagaacac ttactatgga     120
gcttacttgc tcctgggact gaacgtctca tgatccaact aagaaactgc gcaccacatc     180
ctgaagatga tcctgtcagg gaagatattt tatgctcact agcagaccaa cactatgctg     240
ctattttcac caaggcttgc tacatggctg taacttcact catggggcag aaacagagaa     300
cacactttcc acgatgcgac ataatatgcc aggctgagat cggctcagaa tatctacact     360
gtcacatact tgttgagga gcaggtctga gcaagagaaa tgctaaaatt tcatgtgcta     420
cgctcttagg ccttgtgatg gctgaattaa cacaacgctg caaactactt cttacacagc     480
gtccatttga accagatgaa gctagaatat tccatctact cagacgcgtt gaacgcgaag     540
catggtcagg gcacactggt aactgggttc aaattcttca atacagagac aagcgaggtg     600
accttcatgc tcaacacatt gatcctttac gcttttttcaa acactacctg ctgccaaaaa     660
atcgattgat ctctccttcc agcaagcctg acgtctgcac tactccagat aactggtttg     720
tcctagctga taaaacatac gctcacacta ttgttaatgg gcttccgctg ctagaacata     780
acagaaaggc ctatctacaa gagttagaga gtgaagtcat cccggggcct tctaccatgg     840
cctttggggg acgtggtgcg tgggaacatc tgcctgaggt aggagaacaa cgcctaatta     900
```

```
cttctaatac ttctactgct tataaagcta acaaaaaaga aaattaatg ctaaacttac      960 ttgataaatg tgatgaactt aacttacttg tgtatgaaga cttagttagt gcttgtcctg     1020 acctttact tatgcttgaa ggtcaaccag gtggtgcacg cctaattgaa caggtgcttg     1080
gcatgcatca tattaaagta tgtgctaatt acacagcatt atctttctta tttcatttac     1140
atcctaatca attattaact tctagcaata aagcactaaa actattgttg attcaagggt     1200
acaacccatt acaggtaggg cacgccatct gctgtgtact taacaaacag atgggcaagc     1260
agaacactat ctgcttttat ggtcctgctt caacaggtaa aacaaatatt gcaaaggcca     1320
tagtccaagg cgttcgcctt tatggctgtg ttaatcatct aaacaagggg tttgtcttta     1380
acgattgcag acaacgcctt ataatttggt gggaggaatg tttaatgcat caagattggg     1440
ttgaacctgc taaatgcatt ttaggtggaa ctgaatgtag aattgatgtt aaacacaaag     1500
acagtgttct tcttcaacaa acaccagtaa ttatttccac taaccatgac atctactctg     1560
tagttggtgg caatactgta tctcatgttc atgcagcgcc cttaaaagag cgaattcttc     1620
aactaaattt tatgaaacaa ctgccacaaa catttggaga gatttctcca gttgaaattg     1680
cagagttgct gcaatggtgc tttaatgagt acgaatgtac tcttactggc tttaaacaaa     1740
aatggaactt agataaagtt ccaaactcat ttcctcttgg ggacctttgt cctacacatt     1800
cacaggacta cgtgcttcac gaaaacggat tctgcactga ctgcggcggc tatattcctc     1860
atagtgctga cgactctgtg tatactgacg tggctagcga cacatcaatc agcagctgcg     1920
acccaggtag gcattaatac attagccttt taatatacta cttctagat gcttatgtat      1980 taactcctac aggtgacttg ggggatacgg acggagagaa ctcccagccg gagacatcga     2040
acgtggataa tcgtccatcc aagaagcgac gtgtgattcc agaaactcca ccaaacagtc     2100
cagtaagtcg ccaaagcctt tctagctttt tagatacgtg gcagtcacaa cctagagacg     2160
aagatgagct ccgaatctat gaagcacagg catcgcgcat caaagagaac accgagtcca     2220
ctccggagag agagaagaca ccagtgggag aaccacaaga agagtcgcag gcggagcccg     2280
atccgacagc atggggagaa aagcttggag tctactcctc gctgcaacca ggagagccgc     2340
caatcgtctt acactgcttc gaagacctca gaccaagcga cgaagacgaa ggagaaaaca     2400
tcggggggga atagaaccaa tccttatact gtgttcagtc aacacagggc taatcatcca     2460
gatgctcctg gatggtgtgg gttttactgg cattctacta ggcttgctag agatggcact     2520
aattgtatct ttaatgaaat gaacaagaa tttcaagaat tgcaaataaa tgggaaaatt     2580
acctgggaca atgttagaga actattgttt agccagaaaa aaaagctaga tcaaaaatac     2640
agaaacatgc tgtaccattt cagacataat gctgattgtc ctagatgtga ttattgggat     2700
gatgtctacc gtaaacactt agctcatgtc tcttcacagg aatcagagga ggtaacagac     2760
gaagaaatgc tttctgctgt tgaaagcatg gaaacaaatg cctccaatta acgccaacc     2820 tggagggtgg gtgcttcctg gttataaata ccttggtcca tttaatcctc ttgagaacgg     2880
tgaaccagtt aataaagctg atcgtgctgc tcaagctcat gataaatcat attctgagtt     2940
aataaagagt ggaaaaaatc cttacttgta tttcaataaa gctgatgaga aattcattga     3000
cgatttgaaa aacgactggt ctcttggtgg cattattggc tcaagtttct ttaaacttaa     3060
gcgcgccgtg gctcctgctc taggaaataa agagcgagct caaaaaagac attttactt     3120 tgcaaactca aataaggtg ctaaaaaacc aaaaaataac gagcctaaac caggcacttc     3180
aaaaatgtct gaaaatgaaa tccaagacca acaccatct ggctcgatgg acgaacagcg     3240
aggaggcgga gggggcgccg ttggcagtgt gggaggggg aaaggttctg gtgtgggtat     3300
```

```
atccacaggt ggctgggtag gaggcagcta tttcactgac tcatatgtca taacaaaaaa    3360
caccagacaa tttctggtaa aaatacaaaa tgaccacaaa tacagaactg aaaatattat    3420
tccaagcaat gctggaggaa aatcacaaag gtgcgtcagc acaccatggt catatttcaa    3480
cttcaatcaa tacagcagtc attttcacc acaagactgg caacgcctaa caaatgaata    3540
taaacgcttt aaacctagaa aaatgcatgt aaaaatttac aatctacaaa taaaacaaat    3600
actttcaaat ggtgctgaca ctacatacaa caacgaccta acagctggtg ttcacatatt    3660
ttgtgatggt gaacacgcat atccaaatgc aacacatcca tgggatgaag acgtcatgcc    3720
agaacttcca tatgaaacat ggtatctgtt tcaatatgga tacattccag ttattcatga    3780
acttgctgaa atggaagacg caaatgctgt agaaaaagct atagcactac aaataccatt    3840
cttcatgctt gaaacagtg accatgaagt tctaagaact ggagaaagca cagaattcac    3900
ttttgatttt gactgtgagt ggatcaacaa cgaaagagca tacattcctc ctggattaat    3960
gtttaatcca aaagttccta cgagaagagc tcaatacatt agacagcacg aaacacagc    4020 atcaagcaac accagaattc aaccatatgc aaaacctaca agctggatga caggaccagg    4080
tctactcagt gcacaaagag taggaccagc tggctcagac actgcatcat ggatggttgt    4140
tgttaatcca gacggaactg ccgttaactc aggaatggca ggagttggat caggatttga    4200
tcctccttca ggatctctaa gaccaactga cttagaatac aaaatacaat ggtaccaaac    4260
tcctgaaggt accaacagtg atggaaacat aatttcaaat ccaccactgt ccatgcttag    4320
agatcaagct ctctcagag gaaatcaaac aacctataac ctatgctcag atgtatggat    4380
gttcccaaat caatttggg acagatatcc aataaccaga gaaatccaa tctggtgcaa    4440 aaaaccaaga tcagataaaa gcacagtaat tgatcctttc gatggaacac tcgcaatgga    4500
tcatcctcct ggaacaatct tcataaaaat ggcaaaaatt ccagttcctt caaacaacaa    4560
cgcagactca tacctaaaca tctactgcac aggacaagtc agctgcgaaa ttgtctggga    4620
agttgaaaga tacgcaacaa agaactggag accagagaga agacacaccg cacttggtct    4680
tggaatcgga ggagaagaaa acataaatcc aacttaccat gtagacaaaa atggaaaata    4740
cattcagcca acaacatggg acatgtgcta tcctatcaaa acaaacatca ataaagtgtt    4800
gtaatctctt aagcctattc attgcttatg cttataagtt cctctccaat ggacaagagg    4860
aaagaaaagg gtgactgtaa tcccgagctc atgagttcga ggctacagtc cgatggcagt    4920
ggtgttgccg tctcgaacct agccgttaca cccttgtgca ttgtgg              4966
```

<210> SEQ ID NO 10
<211> LENGTH: 640
<212> TYPE: PRT
<213> ORGANISM: Bocavirus

<400> SEQUENCE: 10

```
Met Ala Phe Ser Ala Pro Val Ile Arg Ala Phe Ser Gln Pro Ala Phe
1               5                   10                  15

Thr Tyr Val Val Lys Phe Pro Tyr Asp Asn Trp Lys Glu Glu Glu His
            20                  25                  30

Leu Leu Trp Ser Leu Leu Ala Pro Gly Thr Glu Arg Leu Met Ile Gln
        35                  40                  45

Leu Arg Asn Cys Ala Pro His Pro Glu Asp Asp Pro Val Arg Glu Asp
    50                  55                  60

Ile Leu Cys Ser Leu Ala Asp Gln His Tyr Ala Ala Ile Phe Thr Lys
65                  70                  75                  80
```

```
Ala Cys Tyr Met Ala Val Thr Ser Leu Met Gly Gln Lys Gln Arg Thr
                85                  90                  95

His Phe Pro Arg Cys Asp Ile Ile Cys Gln Ala Glu Ile Gly Ser Glu
            100                 105                 110

Tyr Leu His Cys His Ile Leu Val Gly Gly Ala Gly Leu Ser Lys Arg
        115                 120                 125

Asn Ala Lys Ile Ser Cys Ala Thr Leu Leu Gly Leu Val Met Ala Glu
    130                 135                 140

Leu Thr Gln Arg Cys Lys Leu Leu Thr Gln Arg Pro Phe Glu Pro
145                 150                 155                 160

Asp Glu Ala Arg Ile Phe His Leu Leu Arg Arg Val Glu Arg Glu Ala
                165                 170                 175

Trp Ser Gly His Thr Gly Asn Trp Val Gln Ile Leu Gln Tyr Arg Asp
            180                 185                 190

Lys Arg Gly Asp Leu His Ala Gln His Ile Asp Pro Leu Arg Phe Phe
        195                 200                 205

Lys His Tyr Leu Leu Pro Lys Asn Arg Leu Ile Ser Pro Ser Ser Lys
    210                 215                 220

Pro Asp Val Cys Thr Thr Pro Asp Asn Trp Phe Val Leu Ala Asp Lys
225                 230                 235                 240

Thr Tyr Ala His Thr Ile Val Asn Gly Leu Pro Leu Leu Glu His Asn
                245                 250                 255

Arg Lys Ala Tyr Leu Gln Glu Leu Glu Ser Glu Val Ile Pro Gly Pro
            260                 265                 270

Ser Thr Met Ala Phe Gly Gly Arg Gly Ala Trp Glu His Leu Pro Glu
        275                 280                 285

Val Gly Glu Gln Arg Leu Ile Thr Ser Asn Thr Ser Thr Ala Tyr Lys
    290                 295                 300

Ala Asn Lys Lys Glu Lys Leu Met Leu Asn Leu Leu Asp Lys Cys Asp
305                 310                 315                 320

Glu Leu Asn Leu Leu Val Tyr Glu Asp Leu Val Ser Ala Cys Pro Asp
                325                 330                 335

Leu Leu Leu Met Leu Glu Gly Gln Pro Gly Gly Ala Arg Leu Ile Glu
            340                 345                 350

Gln Val Leu Gly Met His His Ile Lys Val Cys Ala Asn Tyr Thr Ala
        355                 360                 365

Leu Ser Phe Leu Phe His Leu His Pro Asn Gln Leu Leu Thr Ser Ser
    370                 375                 380

Asn Lys Ala Leu Lys Leu Leu Ile Gln Gly Tyr Asn Pro Leu Gln
385                 390                 395                 400

Val Gly His Ala Ile Cys Cys Val Leu Asn Lys Gln Met Gly Lys Gln
                405                 410                 415

Asn Thr Ile Cys Phe Tyr Gly Pro Ala Ser Thr Gly Lys Thr Asn Ile
            420                 425                 430

Ala Lys Ala Ile Val Gln Gly Val Arg Leu Tyr Gly Cys Val Asn His
        435                 440                 445

Leu Asn Lys Gly Phe Val Phe Asn Asp Cys Arg Gln Arg Leu Ile Ile
    450                 455                 460

Trp Trp Glu Glu Cys Leu Met His Gln Asp Trp Val Glu Pro Ala Lys
465                 470                 475                 480

Cys Ile Leu Gly Gly Thr Glu Cys Arg Ile Asp Val Lys His Lys Asp
                485                 490                 495

Ser Val Leu Leu Gln Gln Thr Pro Val Ile Ile Ser Thr Asn His Asp
            500                 505                 510
```

Ile Tyr Ser Val Val Gly Gly Asn Thr Val Ser His Val His Ala Ala
            515                 520                 525

Pro Leu Lys Glu Arg Ile Leu Gln Leu Asn Phe Met Lys Gln Leu Pro
        530                 535                 540

Gln Thr Phe Gly Glu Ile Ser Pro Val Glu Ile Ala Glu Leu Leu Gln
545                 550                 555                 560

Trp Cys Phe Asn Glu Tyr Glu Cys Thr Leu Thr Gly Phe Lys Gln Lys
                565                 570                 575

Trp Asn Leu Asp Lys Val Pro Asn Ser Phe Pro Leu Gly Asp Leu Cys
            580                 585                 590

Pro Thr His Ser Gln Asp Tyr Val Leu His Glu Asn Gly Phe Cys Thr
        595                 600                 605

Asp Cys Gly Gly Tyr Ile Pro His Ser Ala Asp Ser Val Tyr Thr
    610                 615                 620

Asp Val Ala Ser Glu Thr Ser Ile Ser Ser Cys Asp Pro Gly Arg His
625                 630                 635                 640

<210> SEQ ID NO 11
<211> LENGTH: 215
<212> TYPE: PRT
<213> ORGANISM: Bocavirus

<400> SEQUENCE: 11

Met Ser Ser Glu Ser Met Lys His Arg His Ala Ser Lys Arg Thr
1               5                   10                  15

Pro Ser Pro Leu Arg Arg Glu Arg Arg His Gln Trp Glu Asn His Lys
            20                  25                  30

Lys Ser Arg Arg Arg Ser Pro Ile Arg Gln His Gly Glu Lys Ser Leu
        35                  40                  45

Glu Ser Thr Pro Arg Cys Asn Gln Glu Ser Arg Gln Ser Ser Tyr Thr
    50                  55                  60

Ala Ser Lys Thr Ser Asp Gln Ala Thr Lys Thr Lys Glu Lys Thr Ser
65                  70                  75                  80

Gly Gly Asn Arg Thr Asn Pro Tyr Thr Val Phe Ser Gln His Arg Ala
                85                  90                  95

Asn His Pro Asp Ala Pro Gly Trp Cys Gly Phe Tyr Trp His Ser Thr
            100                 105                 110

Arg Leu Ala Arg Asp Gly Thr Asn Cys Ile Phe Asn Glu Met Lys Gln
        115                 120                 125

Glu Phe Gln Glu Leu Gln Ile Asn Gly Lys Ile Thr Trp Asp Asn Val
    130                 135                 140

Arg Glu Leu Leu Phe Ser Gln Lys Lys Leu Asp Gln Lys Tyr Arg
145                 150                 155                 160

Asn Met Leu Tyr His Phe Arg His Asn Ala Asp Cys Pro Arg Cys Asp
                165                 170                 175

Tyr Trp Asp Asp Val Tyr Arg Lys His Leu Ala His Val Ser Ser Gln
            180                 185                 190

Glu Ser Glu Glu Val Thr Asp Glu Glu Met Leu Ser Ala Val Glu Ser
        195                 200                 205

Met Glu Thr Asn Ala Ser Asn
    210                 215

<210> SEQ ID NO 12
<211> LENGTH: 668
<212> TYPE: PRT
<213> ORGANISM: Bocavirus

<400> SEQUENCE: 12

```
Met Pro Pro Ile Lys Arg Gln Pro Gly Gly Trp Val Leu Pro Gly Tyr
1               5                   10                  15

Lys Tyr Leu Gly Pro Phe Asn Pro Leu Glu Asn Gly Glu Pro Val Asn
            20                  25                  30

Lys Ala Asp Arg Ala Ala Gln Ala His Asp Lys Ser Tyr Ser Glu Leu
        35                  40                  45

Ile Lys Ser Gly Lys Asn Pro Tyr Leu Tyr Phe Asn Lys Ala Asp Glu
    50                  55                  60

Lys Phe Ile Asp Asp Leu Lys Asn Asp Trp Ser Leu Gly Gly Ile Ile
65                  70                  75                  80

Gly Ser Ser Phe Phe Lys Leu Lys Arg Ala Val Ala Pro Ala Leu Gly
                85                  90                  95

Asn Lys Glu Arg Ala Gln Lys Arg His Phe Tyr Phe Ala Asn Ser Asn
            100                 105                 110

Lys Gly Ala Lys Lys Pro Lys Asn Asn Glu Pro Lys Pro Gly Thr Ser
        115                 120                 125

Lys Met Ser Glu Asn Glu Ile Gln Asp Gln Pro Ser Gly Ser Met
130                 135                 140

Asp Glu Gln Arg Gly Gly Gly Gly Ala Val Gly Ser Val Gly Gly
145                 150                 155                 160

Gly Lys Gly Ser Gly Val Gly Ile Ser Thr Gly Gly Trp Val Gly Gly
                165                 170                 175

Ser Tyr Phe Thr Asp Ser Tyr Val Ile Thr Lys Asn Thr Arg Gln Phe
            180                 185                 190

Leu Val Lys Ile Gln Asn Asp His Lys Tyr Arg Thr Glu Asn Ile Ile
        195                 200                 205

Pro Ser Asn Ala Gly Gly Lys Ser Gln Arg Cys Val Ser Thr Pro Trp
    210                 215                 220

Ser Tyr Phe Asn Phe Asn Gln Tyr Ser Ser His Phe Ser Pro Gln Asp
225                 230                 235                 240

Trp Gln Arg Leu Thr Asn Glu Tyr Lys Arg Phe Lys Pro Arg Lys Met
                245                 250                 255

His Val Lys Ile Tyr Asn Leu Gln Ile Lys Gln Ile Leu Ser Asn Gly
            260                 265                 270

Ala Asp Thr Thr Tyr Asn Asn Asp Leu Thr Ala Gly Val His Ile Phe
        275                 280                 285

Cys Asp Gly Glu His Ala Tyr Pro Asn Ala Thr His Pro Trp Asp Glu
    290                 295                 300

Asp Val Met Pro Glu Leu Pro Tyr Glu Thr Trp Tyr Leu Phe Gln Tyr
305                 310                 315                 320

Gly Tyr Ile Pro Val Ile His Glu Leu Ala Glu Met Glu Asp Ala Asn
                325                 330                 335

Ala Val Glu Lys Ala Ile Ala Leu Gln Ile Pro Phe Phe Met Leu Glu
            340                 345                 350

Asn Ser Asp His Glu Val Leu Arg Thr Gly Ser Thr Glu Phe Thr
        355                 360                 365

Phe Asp Phe Asp Cys Glu Trp Ile Asn Asn Glu Arg Ala Tyr Ile Pro
    370                 375                 380

Pro Gly Leu Met Phe Asn Pro Lys Val Pro Thr Arg Arg Ala Gln Tyr
385                 390                 395                 400

Ile Arg Gln His Gly Asn Thr Ala Ser Ser Asn Thr Arg Ile Gln Pro
                405                 410                 415
```

Tyr Ala Lys Pro Thr Ser Trp Met Thr Gly Pro Gly Leu Leu Ser Ala
          420                 425                 430

Gln Arg Val Gly Pro Ala Gly Ser Asp Thr Ala Ser Trp Met Val Val
          435                 440                 445

Val Asn Pro Asp Gly Thr Ala Val Asn Ser Gly Met Ala Gly Val Gly
450                 455                 460

Ser Gly Phe Asp Pro Pro Ser Gly Ser Leu Arg Pro Thr Asp Leu Glu
465                 470                 475                 480

Tyr Lys Ile Gln Trp Tyr Gln Thr Pro Glu Gly Thr Asn Ser Asp Gly
                    485                 490                 495

Asn Ile Ile Ser Asn Pro Pro Leu Ser Met Leu Arg Asp Gln Ala Leu
              500                 505                 510

Tyr Arg Gly Asn Gln Thr Thr Tyr Asn Leu Cys Ser Asp Val Trp Met
          515                 520                 525

Phe Pro Asn Gln Ile Trp Asp Arg Tyr Pro Ile Thr Arg Glu Asn Pro
      530                 535                 540

Ile Trp Cys Lys Lys Pro Arg Ser Asp Lys Ser Thr Val Ile Asp Pro
545                 550                 555                 560

Phe Asp Gly Thr Leu Ala Met Asp His Pro Pro Gly Thr Ile Phe Ile
                    565                 570                 575

Lys Met Ala Lys Ile Pro Val Pro Ser Asn Asn Asn Ala Asp Ser Tyr
              580                 585                 590

Leu Asn Ile Tyr Cys Thr Gly Gln Val Ser Cys Glu Ile Val Trp Glu
          595                 600                 605

Val Glu Arg Tyr Ala Thr Lys Asn Trp Arg Pro Glu Arg Arg His Thr
      610                 615                 620

Ala Leu Gly Leu Gly Ile Gly Gly Glu Glu Asn Ile Asn Pro Thr Tyr
625                 630                 635                 640

His Val Asp Lys Asn Gly Lys Tyr Ile Gln Pro Thr Thr Trp Asp Met
                    645                 650                 655

Cys Tyr Pro Ile Lys Thr Asn Ile Asn Lys Val Leu
              660                 665

<210> SEQ ID NO 13
<211> LENGTH: 4958
<212> TYPE: DNA
<213> ORGANISM: Bocavirus

<400> SEQUENCE: 13
cgcacgtggt gagtgacact atggcctttt ctgctcctgt aattagagct ttttctcaac     60
ctgctttcac ttatgttgtt aaatttccat atgataactg gaaagaggaa gagcacttac    120
tatggagctt acttgctcct gggactgaac gtctcatgat ccaactaaga aactgcgcac    180
cacatcctga agatgatcct gtcagggaag atattttatg ctcactagca gaccaacact    240
atgctgctat tttcaccaaa gcttgctaca tggctgtaac ttcactcatg gggcagaaac    300
agagaacaca ctttccacga tgcgacataa tttgccaggc tgagatcggc tcagaatatc    360
tacactgtca catacttgtt ggaggagcag gtctgagcaa gagaaatgct aaaatttcat    420
gtgctacgct cctaggcctt gtgatggctg aattaacaca acgctgcaaa ctacttcttg    480
cacagcgtcc atttgaacca gatgaagcta gaatatttca tctactcaga cgcgttgaac    540
gcgaagcatg gtcagggcac actggtaact gggttcaaat tcttcaatac agagacaagc    600
gaggtgacct tcatgctcaa cacattgatc ctttacgctt tttcaaacac tacctgctgc    660
caaaaaatcg gttgatctct ccttccagca agcctgacgt ctgcactact ccagataact    720

```
ggtttgtcct agctgaaaaa acatacgctc acactattgt taatgggctt ccgctgctag    780
aacataacag aaaggcctat ctacaagagt tagaaagtga agtcatccca gggccttcta    840
ccatggcctt tggggacgt ggtgcgtggg aacatctgcc tgaggtagga gaacaacgcc    900
taataacttc taatacttct actgcttata aagctaacaa aaaagaaaaa ttaatgctaa    960
acttacttga taaatgtgat gaacttaact tacttgtgta tgaagactta gttagtgctt   1020
gtcctgacct tttacttatg cttgaaggtc agccaggtgg tgcacgccta attgaacagg   1080
tgcttggcat gcatcatatt aaagtgtgtg ctaattacac agcgttatct ttcttgtttc   1140
atctacatcc tgatcaatta ttaacttcta gcaataaagc actaaaacta ttgttgattc   1200
aagggtacaa cccattgcaa gtaggccacg ccatctgttg tgttcttaac aaacagatgg   1260
gcaagcagaa cacaatttgc ttttatggcc ctgcttcaac aggcaaaaca aatattgcaa   1320
aggccatagt tcaaggcgtt cgtctgtatg gctgtgttaa tcatttaaac aaagggtttg   1380
tctttaacga ttgcagacaa cgcctcataa tctggtggga ggagtgttta atgcaccaag   1440
actgggtgga acctgctaaa tgcattctag gtggaactga atgtagaatt gatgttaaac   1500
ataaggacag tgttcttctt caacaaacac cagtaattat ttccactaac catgacatct   1560
actctgtagt tggtggcaat actgtatctc atgttcatgc agcgcccta aaagagcgaa    1620 tccttcagct aaatttttatg aaacaactgc cacaaacatt tggagaaatt tctccagttg   1680
agattgcaga attactgcaa tggtgcttta atgagtacga ctgtactctt actggcttta   1740
aacaaaaatg gaacttagat aaagttccaa actcatttcc tcttggggac ctttgtccta   1800
cacattcaca ggactacgtg cttcacgaaa acggattctg cactgactgc ggcggctata   1860
ttcctcatag tgctgacgac tctgtgtaca ctgacgtggc tagcgaaaca tcaatcagca   1920
gcgacgaccc aggtaggcat taatacatta gccttttaat atactacctt ccaagtgctt   1980
atgtattaac tcctacaggt gacttgggggg atacggacgg agagaactcc cagccggaga   2040
catcgaacgt ggataatcgt ccatccaaga agagacgtgt gattccagaa actccaccaa   2100
acagtccagt aagtcgccaa agcctttcta gcttttttaga tacgtggcag tcacaaccta   2160
gagacgaaga tgagctccga atctatgaag cacaggcatc gcgcatcaaa gagaacgccg   2220
agtccactcc ggagagagag aagacaccag tgggagaacc acaagaagag tcgcagtcgg   2280
agcccgatcc gacagcatgg ggagaaaagc ttggagtcta ctcctcgcta caaccaggag   2340
agccgccaat cgtcttacac tgcttcgaag acctcagacc aagcgacgaa gacgaaggag   2400
agaacatcgg gggggaatag aaccaatcct tatactgtgt tcagtcaaca cagggctaat   2460
catccagatg ctcctggatg gtgtgggttt tactggcatt ctactcggct tgctagagat   2520
ggcactaatt gtatctttaa tgaaatgaaa caagaatttc aagaactaca aataaatgga   2580
aaaattactt gggataatgt tagagaattg ctgtttagcc agaaaaagaa actagatcag   2640
aaatatagaa atatgctgta tcatttcaga cataacactg attgtcctag atgtgattat   2700
tgggatgatg tataccgtaa acacttagct catgtctctt cacaggaatc agaggaggta   2760
acagacgaag aaatgcttc tgctgttgaa agcatggaaa caaatgcctc caattaaacg   2820
ccaacctgga gggtgggtgc ttcctggtta taaataccctt ggtccattta atcctcttga   2880
aaacggtgaa ccagttaata aagctgatcg tgctgctcaa gctcatgata aatcatattc   2940
tgaattaata aagagtggaa aaaccccta cttatatttt aataaagctg atgaaaaatt   3000
cattgacgat ttgaaaaacg actggtctgt tggtggcatt attggctcaa gtttctttaa   3060
acttaagcgc gccgtggctc ctgctctagg aaataaagag cgagctcaaa aaagacattt   3120
```

-continued

```
ttactttgca aactcaaata aaggtgctaa aagatcaaaa aacagcgaac ctaagccaag    3180
cacttcaaaa atgtctgaaa atgaaattca agaccaacaa ccatcagact ctatggatgg    3240
acaacgaggg ggcggaggag gtgcgactgg cagtgtggga gggggaaag gttctggtgt     3300
gggtatatcc acaggcggat gggtaggagg cagctacttt actgactcat atgtcataac    3360
aaaaaacacc agacaatttc tagtaaagat acaaaatgac cacaaataca gaacagaaaa    3420
tattattcca agcaatgctg gaggaaaatc acaaagatgc gtcagcacac cgtggtcata    3480
ttttaacttc aatcaataca gcagtcactt ttcaccacaa gactggcagc gcctaacaaa    3540
tgaatacaag cgctttaaac ctagaaaaat gcatgtaaaa atttacaacc tacaaataaa    3600
acaaatactg tcaaatggtg ctgacactac atacaacaac gacctaacag ctggtgttca    3660
catcttctgt gatggtgagc atgcgtatcc aaacgccaca cacccatggg acgaagatgt    3720
aatgccagaa cttccatatg agacatggta tctgtttcaa tatggataca ttccagttat    3780
tcatgaactt gctgaaatgg aagatgcaaa tgctgtagaa aaagctatag cactacaaat    3840
accattcttc atgcttgaaa acagtgacca tgaagttcta agaactggag aaagcacaga    3900
attcactttt gactttgact gtgaatggat caataacgaa agagcataca ttcctcctgg    3960
attaatgttt aatccaaagg ttcctacaag aagagctcaa tacataagac aacacggaag    4020
cacagcatca agcaacacca gaattccacc atatgcaaaa cctacaagct ggatgacagg    4080
accaggtcta ctcagcgcac agagagtagg accagctgct tcagactcag cagcatggat    4140
ggttgttgta atccagacg gagctgctat taactcagga atggcaggaa ttggtacagg    4200
ctttgatcct cctggtggat ctttaagacc aactgattta gaatataaaa tacaatggta    4260
ccaaactcct gcaggtacaa acagcgatgg aaacatcatt tcaaatccat cattatccat    4320
gcttagagat caagctctct acagaggaaa ccagacaaca tataacctat gttcagacgt    4380
atggatgttc ccaaatcaaa tttgggacag atatccaata accagagaaa atccaatctg    4440
gtgtaaaaaa ccaagatcag acaaaagcac aataattgat ccattcgatg gatcaattgc    4500
aatggatcat cctccaggaa caattttcat aaaaatggca aaaattccag ttccttcaaa    4560
caacaatgca gactcatact taaacatcta ctgcactgga caagtcagct gcgaaattgt    4620
ctgggaagtt gaaagatatg caacaaagaa ctggagacca gaaagaagac acacggcact    4680
tggccttggg attggaggag aagagaatgt aaatccaact taccatgttg acaaaaatgg    4740
aaaatacatt cagccaacaa catgggacat gtgctatcct atcaaaacaa acatcaataa    4800
agtgttgtaa ccttgtaagc ctcttttttg cttatgcttg taagttcctc tccaatggac    4860
aagtggaaag aaaagggtga ctgtaatccc gagctcataa gttcgaggct acagtccgat    4920
ggcagtggtg ttgccgtctc gaacctagcc gttacacc                          4958
```

<210> SEQ ID NO 14
<211> LENGTH: 640
<212> TYPE: PRT
<213> ORGANISM: Bocavirus

<400> SEQUENCE: 14

```
Met Ala Phe Ser Ala Pro Val Ile Arg Ala Phe Ser Gln Pro Ala Phe
1               5                   10                  15

Thr Tyr Val Val Lys Phe Pro Tyr Asp Asn Trp Lys Glu Glu Glu His
                20                  25                  30

Leu Leu Trp Ser Leu Leu Ala Pro Gly Thr Glu Arg Leu Met Ile Gln
        35                  40                  45
```

```
Leu Arg Asn Cys Ala Pro His Pro Glu Asp Asp Pro Val Arg Glu Asp
 50                  55                  60

Ile Leu Cys Ser Leu Ala Asp Gln His Tyr Ala Ala Ile Phe Thr Lys
 65                  70                  75                  80

Ala Cys Tyr Met Ala Val Thr Ser Leu Met Gly Gln Lys Gln Arg Thr
                     85                  90                  95

His Phe Pro Arg Cys Asp Ile Ile Cys Gln Ala Glu Ile Gly Ser Glu
                100                 105                 110

Tyr Leu His Cys His Ile Leu Val Gly Gly Ala Gly Leu Ser Lys Arg
                115                 120                 125

Asn Ala Lys Ile Ser Cys Ala Thr Leu Leu Gly Leu Val Met Ala Glu
130                 135                 140

Leu Thr Gln Arg Cys Lys Leu Leu Leu Ala Gln Arg Pro Phe Glu Pro
145                 150                 155                 160

Asp Glu Ala Arg Ile Phe His Leu Leu Arg Arg Val Glu Arg Glu Ala
                165                 170                 175

Trp Ser Gly His Thr Gly Asn Trp Val Gln Ile Leu Gln Tyr Arg Asp
                180                 185                 190

Lys Arg Gly Asp Leu His Ala Gln His Ile Asp Pro Leu Arg Phe Phe
                195                 200                 205

Lys His Tyr Leu Leu Pro Lys Asn Arg Leu Ile Ser Pro Ser Ser Lys
210                 215                 220

Pro Asp Val Cys Thr Thr Pro Asp Asn Trp Phe Val Leu Ala Glu Lys
225                 230                 235                 240

Thr Tyr Ala His Thr Ile Val Asn Gly Leu Pro Leu Leu Glu His Asn
                245                 250                 255

Arg Lys Ala Tyr Leu Gln Glu Leu Glu Ser Glu Val Ile Pro Gly Pro
                260                 265                 270

Ser Thr Met Ala Phe Gly Gly Arg Gly Ala Trp Glu His Leu Pro Glu
                275                 280                 285

Val Gly Glu Gln Arg Leu Ile Thr Ser Asn Thr Ser Thr Ala Tyr Lys
290                 295                 300

Ala Asn Lys Lys Glu Lys Leu Met Leu Asn Leu Leu Asp Lys Cys Asp
305                 310                 315                 320

Glu Leu Asn Leu Leu Val Tyr Glu Asp Leu Val Ser Ala Cys Pro Asp
                325                 330                 335

Leu Leu Leu Met Leu Glu Gly Gln Pro Gly Gly Ala Arg Leu Ile Glu
                340                 345                 350

Gln Val Leu Gly Met His His Ile Lys Val Cys Ala Asn Tyr Thr Ala
                355                 360                 365

Leu Ser Phe Leu Phe His Leu His Pro Asp Gln Leu Leu Thr Ser Ser
                370                 375                 380

Asn Lys Ala Leu Lys Leu Leu Ile Gln Gly Tyr Asn Pro Leu Gln
385                 390                 395                 400

Val Gly His Ala Ile Cys Cys Val Leu Asn Lys Gln Met Gly Lys Gln
                405                 410                 415

Asn Thr Ile Cys Phe Tyr Gly Pro Ala Ser Thr Gly Lys Thr Asn Ile
                420                 425                 430

Ala Lys Ala Ile Val Gln Gly Val Arg Leu Tyr Gly Cys Val Asn His
                435                 440                 445

Leu Asn Lys Gly Phe Val Phe Asn Asp Cys Arg Gln Arg Leu Ile Ile
450                 455                 460

Trp Trp Glu Glu Cys Leu Met His Gln Asp Trp Val Glu Pro Ala Lys
465                 470                 475                 480
```

```
Cys Ile Leu Gly Gly Thr Glu Cys Arg Ile Asp Val Lys His Lys Asp
                485                 490                 495

Ser Val Leu Leu Gln Gln Thr Pro Val Ile Ser Thr Asn His Asp
            500                 505                 510

Ile Tyr Ser Val Val Gly Asn Thr Val Ser His Val His Ala Ala
            515                 520                 525

Pro Leu Lys Glu Arg Ile Leu Gln Leu Asn Phe Met Lys Gln Leu Pro
        530                 535                 540

Gln Thr Phe Gly Glu Ile Ser Pro Val Glu Ile Ala Glu Leu Leu Gln
545                 550                 555                 560

Trp Cys Phe Asn Glu Tyr Asp Cys Thr Leu Thr Gly Phe Lys Gln Lys
                565                 570                 575

Trp Asn Leu Asp Lys Val Pro Asn Ser Phe Pro Leu Gly Asp Leu Cys
                580                 585                 590

Pro Thr His Ser Gln Asp Tyr Val Leu His Glu Asn Gly Phe Cys Thr
                595                 600                 605

Asp Cys Gly Gly Tyr Ile Pro His Ser Ala Asp Asp Ser Val Tyr Thr
            610                 615                 620

Asp Val Ala Ser Glu Thr Ser Ile Ser Ser Asp Pro Gly Arg His
625                 630                 635                 640

<210> SEQ ID NO 15
<211> LENGTH: 215
<212> TYPE: PRT
<213> ORGANISM: Bocavirus

<400> SEQUENCE: 15

Met Ser Ser Glu Ser Met Lys His Arg His Arg Ala Ser Lys Arg Thr
1               5                   10                  15

Pro Ser Pro Leu Arg Arg Glu Arg Arg His Gln Trp Glu Asn His Lys
            20                  25                  30

Lys Ser Arg Ser Arg Ser Pro Ile Arg Gln His Gly Glu Lys Ser Leu
        35                  40                  45

Glu Ser Thr Pro Arg Tyr Asn Gln Glu Ser Arg Gln Ser Ser Tyr Thr
    50                  55                  60

Ala Ser Lys Thr Ser Asp Gln Ala Thr Lys Thr Lys Glu Arg Thr Ser
65                  70                  75                  80

Gly Gly Asn Arg Thr Asn Pro Tyr Thr Val Phe Ser Gln His Arg Ala
                85                  90                  95

Asn His Pro Asp Ala Pro Gly Trp Cys Gly Phe Tyr Trp His Ser Thr
            100                 105                 110

Arg Leu Ala Arg Asp Gly Thr Asn Cys Ile Phe Asn Glu Met Lys Gln
        115                 120                 125

Glu Phe Gln Glu Leu Gln Ile Asn Gly Lys Ile Thr Trp Asp Asn Val
    130                 135                 140

Arg Glu Leu Leu Phe Ser Gln Lys Lys Lys Leu Asp Gln Lys Tyr Arg
145                 150                 155                 160

Asn Met Leu Tyr His Phe Arg His Asn Thr Asp Cys Pro Arg Cys Asp
                165                 170                 175

Tyr Trp Asp Asp Val Tyr Arg Lys His Leu Ala His Val Ser Ser Gln
            180                 185                 190

Glu Ser Glu Glu Val Thr Asp Glu Glu Met Leu Ser Ala Val Glu Ser
        195                 200                 205

Met Glu Thr Asn Ala Ser Asn
        210                 215
```

<210> SEQ ID NO 16
<211> LENGTH: 668
<212> TYPE: PRT
<213> ORGANISM: Bocavirus

<400> SEQUENCE: 16

Met Pro Pro Ile Lys Arg Gln Pro Gly Gly Trp Val Leu Pro Gly Tyr
1               5                   10                  15

Lys Tyr Leu Gly Pro Phe Asn Pro Leu Glu Asn Gly Glu Pro Val Asn
            20                  25                  30

Lys Ala Asp Arg Ala Ala Gln Ala His Asp Lys Ser Tyr Ser Glu Leu
        35                  40                  45

Ile Lys Ser Gly Lys Asn Pro Tyr Leu Tyr Phe Asn Lys Ala Asp Glu
    50                  55                  60

Lys Phe Ile Asp Asp Leu Lys Asn Asp Trp Ser Val Gly Gly Ile Ile
65                  70                  75                  80

Gly Ser Ser Phe Phe Lys Leu Lys Arg Ala Val Ala Pro Ala Leu Gly
                85                  90                  95

Asn Lys Glu Arg Ala Gln Lys Arg His Phe Tyr Phe Ala Asn Ser Asn
            100                 105                 110

Lys Gly Ala Lys Arg Ser Lys Asn Ser Glu Pro Lys Pro Ser Thr Ser
        115                 120                 125

Lys Met Ser Glu Asn Glu Ile Gln Asp Gln Gln Pro Ser Asp Ser Met
    130                 135                 140

Asp Gly Gln Arg Gly Gly Gly Gly Ala Thr Gly Ser Val Gly Gly
145                 150                 155                 160

Gly Lys Gly Ser Gly Val Gly Ile Ser Thr Gly Gly Trp Val Gly Gly
                165                 170                 175

Ser Tyr Phe Thr Asp Ser Tyr Val Ile Thr Lys Asn Thr Arg Gln Phe
            180                 185                 190

Leu Val Lys Ile Gln Asn Asp His Lys Tyr Arg Thr Glu Asn Ile Ile
        195                 200                 205

Pro Ser Asn Ala Gly Gly Lys Ser Gln Arg Cys Val Ser Thr Pro Trp
    210                 215                 220

Ser Tyr Phe Asn Phe Asn Gln Tyr Ser Ser His Phe Ser Pro Gln Asp
225                 230                 235                 240

Trp Gln Arg Leu Thr Asn Glu Tyr Lys Arg Phe Lys Pro Arg Lys Met
                245                 250                 255

His Val Lys Ile Tyr Asn Leu Gln Ile Lys Gln Ile Leu Ser Asn Gly
            260                 265                 270

Ala Asp Thr Thr Tyr Asn Asn Asp Leu Thr Ala Gly Val His Ile Phe
        275                 280                 285

Cys Asp Gly Glu His Ala Tyr Pro Asn Ala Thr His Pro Trp Asp Glu
    290                 295                 300

Asp Val Met Pro Glu Leu Pro Tyr Glu Thr Trp Tyr Leu Phe Gln Tyr
305                 310                 315                 320

Gly Tyr Ile Pro Val Ile His Glu Leu Ala Glu Met Glu Asp Ala Asn
                325                 330                 335

Ala Val Glu Lys Ala Ile Ala Leu Gln Ile Pro Phe Phe Met Leu Glu
            340                 345                 350

Asn Ser Asp His Glu Val Leu Arg Thr Gly Glu Ser Thr Glu Phe Thr
        355                 360                 365

Phe Asp Phe Asp Cys Glu Trp Ile Asn Asn Glu Arg Ala Tyr Ile Pro
    370                 375                 380

```
Pro Gly Leu Met Phe Asn Pro Lys Val Pro Thr Arg Arg Ala Gln Tyr
385                 390                 395                 400

Ile Arg Gln His Gly Ser Thr Ala Ser Ser Asn Thr Arg Ile Pro Pro
            405                 410                 415

Tyr Ala Lys Pro Thr Ser Trp Met Thr Gly Pro Gly Leu Leu Ser Ala
        420                 425                 430

Gln Arg Val Gly Pro Ala Ala Ser Asp Ser Ala Ala Trp Met Val Val
    435                 440                 445

Val Asn Pro Asp Gly Ala Ala Ile Asn Ser Gly Met Ala Gly Ile Gly
450                 455                 460

Thr Gly Phe Asp Pro Pro Gly Gly Ser Leu Arg Pro Thr Asp Leu Glu
465                 470                 475                 480

Tyr Lys Ile Gln Trp Tyr Gln Thr Pro Ala Gly Thr Asn Ser Asp Gly
                485                 490                 495

Asn Ile Ile Ser Asn Pro Ser Leu Ser Met Leu Arg Asp Gln Ala Leu
            500                 505                 510

Tyr Arg Gly Asn Gln Thr Thr Tyr Asn Leu Cys Ser Asp Val Trp Met
        515                 520                 525

Phe Pro Asn Gln Ile Trp Asp Arg Tyr Pro Ile Thr Arg Glu Asn Pro
    530                 535                 540

Ile Trp Cys Lys Lys Pro Arg Ser Asp Lys Ser Thr Ile Ile Asp Pro
545                 550                 555                 560

Phe Asp Gly Ser Ile Ala Met Asp His Pro Pro Gly Thr Ile Phe Ile
                565                 570                 575

Lys Met Ala Lys Ile Pro Val Pro Ser Asn Asn Asn Ala Asp Ser Tyr
            580                 585                 590

Leu Asn Ile Tyr Cys Thr Gly Gln Val Ser Cys Glu Ile Val Trp Glu
        595                 600                 605

Val Glu Arg Tyr Ala Thr Lys Asn Trp Arg Pro Glu Arg Arg His Thr
    610                 615                 620

Ala Leu Gly Leu Gly Ile Gly Gly Glu Glu Asn Val Asn Pro Thr Tyr
625                 630                 635                 640

His Val Asp Lys Asn Gly Lys Tyr Ile Gln Pro Thr Thr Trp Asp Met
                645                 650                 655

Cys Tyr Pro Ile Lys Thr Asn Ile Asn Lys Val Leu
                660                 665

<210> SEQ ID NO 17
<211> LENGTH: 4948
<212> TYPE: DNA
<213> ORGANISM: Bocavirus

<400> SEQUENCE: 17
gtgacactat ggcctttct gctcctgtaa ttagagcttt ttctcaacct gctttcactt      60
atgttgttaa atttccatat gataactgga aagaggaaga gcacttacta tggagcttac     120
ttgctcctgg gactgaacgt ctcatgatcc aactaagaaa ctgcgcacca catcctgaag     180
atgatcctgt cagggaagat attttatgct cactagcaga ccaacactat gctgctattt     240
tcaccaaagc ttgctacatg gctgtaactt cactcatggg gcagaaacag agaacacact     300
ttccacgatg cgacataatt tgccaggctg agatcggctc agaatatcta cactgtcaca     360
tacttgttgg aggagcaggt ctgagcaaga gaatgctaa aatttcatgt gctacgctcc      420
taggccttgt gatggctgaa ttaacacaac gctgcaaact acttcttgca cagcgtccat     480
ttgaaccaga tgaagctaga atatttcatc tactcagacg cgttgaacgc gaagcatggt     540
```

```
cagggcacac tggtaactgg gttcaaattc ttcaatacag agacaagcga ggtgaccttc    600
atgctcaaca cattgatcct ttacgctttt tcaaacacta cctgctgcca aaaatcggt     660 tgatctctcc ttccagcaag cctgacgtct gcactactcc agataactgg tttgtcctag    720
ctgaaaaaac atacgctcac actattgtta atgggcttcc gctgctagaa cataacagaa    780
aggcctatct acaagagtta gaaagtgaag tcatcccagg gccttctacc atggcctttg    840
ggggacgtgg tgcgtgggaa catctgcctg aggtaggaga acaacgccta ataacttcta    900
atacttctac tgcttataaa gctaacaaaa agaaaaatt aatgctaaac ttacttgata     960
aatgtgatga acttaactta cttgtgtatg aagacttagt tagtgcttgt cctgaccttt   1020
tacttatgct tgaaggtcag ccaggtggtg cacgcctaat tgaacaggtg cttggcatgc   1080
atcatattaa agtgtgtgct aattacacag cgttatcttt cttatttcat ctacatcctg   1140
atcaattatt aacttctagc aataaagcac taaaactatt gttgattcaa gggtacaacc   1200
cattgcaagt aggccacgcc atctgttgtg tccttaacaa acagatgggc aaacagaaca   1260
caatttgctt ttatggccct gcttcaacag gcaaaacaaa tattgcaaag gccatagttc   1320
aaggcgttcg tctgtatggc tgtgttaatc atttaaacaa agggtttgtc tttaacgatt   1380
gcagacaacg cctcataatc tggtgggagg agtgtttaat gcaccaagac tgggtagaac   1440
ctgctaaatg cattctaggt ggaactgaat gtagaattga tgttaaacat aaggacagtg   1500
ttcttcttca acaaacacca gtaattattt ccactaacca tgacatctac tctgtagttg   1560
gtggcaatac tgtatctcat gttcatgcag cgcccttaaa agagcgaatc cttcagctaa   1620
attttatgaa acaactgcca caaacatttg gagaaatttc tccagttgaa attgcagaat   1680
tactgcaatg tgtctttaat gagtacgact gtactcttac tggctttaaa caaaatgga    1740 acttagataa agttccaaac tcatttcctc ttggggacct tgtcctaca cattcacagg    1800 actacgtgct tcacgaaaac ggattctgca ctgactgcgg cggctatatt cctcatagtg   1860
ctgacgactc tgtgtacact gacgtggcta gcgagacatc aatcagcagc gacgacccag   1920
gtaggcatta atacattagc ctttaatat actaccttcc aagtgcttat gtattaactc     1980
ctacaggtga cttgggggat acggacggag agaactccca gccggagaca tcgaacgtgg   2040
ataatcgtcc atccaagaag agacgtgtga ttccagaaac tccaccaaac agtccagtaa   2100
gtcgccaaag cctttctagc tttttagata cgtggcagtc acaacctaga gacgaagatg   2160
agctccgaat ctatgaagca caggcatcgc gcatcaaaga gaacgccgag tccactccgg   2220
agagagagaa gacaccagtg ggagaaccac aagaagagtc gcagtcggag cccgatccga   2280
cagcatgggg agaaaagctt ggagtctact cctcgctaca accaggagag ccgccaatcg   2340
tcttacactg cttcgaagac ctcagaccaa gcgacgaaga cgaaggagag aacatcgggg   2400
gggaatagaa ccaatcctta tactgtgttc agtcaacaca gggctaatca tccagatgct   2460
cctggatggt gcgggtttta ctggcattct actcggcttg ctagagatgg cactaattgt   2520
atctttaatg aaatgaaaca agaatttcaa gaactacaaa taaatggaaa aattacttgg   2580
gataatgtta gagaattgct gtttagccag aaaaagaaac tagatcagaa atatagaaat   2640
atgctgtatc atttcagaca taacactgat tgtcctagat gtgattattg ggatgatgta   2700
taccgtaaac acttagctca tgtctcttca caggaatcag aggaggtaac agacgaagaa   2760
atgctttctg ctgttgaaag catggaaaca aatgcctcca attaaacgcc aacctggagg   2820
gtgggtgctt cctggttata aatacctggg tccatttaat cctcttgaaa acggtgaacc   2880
agttaataaa gctgatcgtg ctgctcaagc tcatgataaa tcatattctg aattaataaa   2940
```

```
gagtggaaaaa aacccttact tatattttaa taaagctgat gaaaaattca ttgacgattt    3000
gaaaaacgac tggtctgttg gtggcattat tggctcaagt ttctttaaac ttaagcgcgc    3060
cgtggctcct gctctaggaa ataaagagcg agctcaaaaa agacattttt actttgcaaa    3120
ctcaaataaa ggtgctaaaa aatcaaaaaa cagcgaacct aagccaggca cttcaaaaat    3180
gtctgaaaat gaaattcaag accaacaacc atcagactct atggatggac aacgaggggg    3240
cggaggaggt gcggctggca gtgtgggagg ggggaaaggt tctggtgtgg gtatatccac    3300
aggcggatgg gtaggaggca gctactttac tgactcatat gtcataacaa aaaacaccag    3360
acaatttcta gtaaaaatac aaaatgacca caaatacaga acagaaaata ttattccaag    3420
caatgctgga ggaaaatcac aaagatgcgt cagcacaccg tggtcatatt ttaacttcaa    3480
tcaatacagc agtcactttt caccacaaga ctggcagcgc ctaacaaatg aatacaagcg    3540
ctttaagcct agaaaaatgc atgtaaaaat ttacaaccta caaataaaac aaatactgtc    3600
aaatggtgct gacactacat acaacaacga cctaacagct ggtgttcaca tcttctgtga    3660
tggtgagcat gcgtatccaa acgccacaca cccatgggac gaagatgtaa tgccagaact    3720
tccatatgag acatggtatc tgtttcaata tggatacatt ccagttattc atgaacttgc    3780
tgaaatggaa gatgcaaatg ctgtagaaaa agctatagca ctacaaatac cattcttcat    3840
gcttgaaaac agtgaccatg aagttctaag aactggagaa agcacagaat tcacttttga    3900
ctttgactgt gaatggatca caacgaaag agcatacatt cctcctggat taatgtttaa    3960
tccaaaggtt cctacaagaa gagctcaata cataagacaa cacggaagca cagcatcaag    4020
caacaccaga attccaccat atgcaaaacc tacaagctgg atgacaggac caggtctact    4080
cagcgcacag agagtaggac cagctgcttc agactcagca gcatggatgg ttgttgtaaa    4140
tccagacgga gctgctatta actcaggaat ggcaggaatt ggtacaggct tgatcctcc    4200 tggtggatct ttaagaccaa ctgatttaga atataaaata caatggtacc aaactcctgc    4260
aggtacaaac agcgatggaa acatcatttc aaatccatca ttatccatgc ttagagatca    4320
agctctctac agaggaaacc agacaacata taacctatgt tcagacgtat ggatgttccc    4380
aaatcaaatt tgggacagat atccaataac aagagaaaat ccaatctggt gtaaaaaacc    4440
aagatcagac aaaagcacaa taattgatcc attcgatgga tcaattgcaa tggatcatcc    4500
tccaggaaca attttcataa aaatggcaaa aattccagtt ccttcaaaca acaatgcaga    4560
ctcatactta aacatatact gcactggaca agtcagctgc gaaattgtct gggaagttga    4620
aagatatgca acaaagaact ggagaccaga agaagacac acggcacttg gccttgggat    4680
tggaggagaa gaaaatgtaa atccaactta ccatgttgac aaaaatggta atacattca    4740 gccaacaact tgggacatgt gctatcctat caaaacaaac atcaataaag tgttgtaatc    4800
tcttaagcct gttcattgct tatgcttata agttcctctc caatggacaa gaggaaagaa    4860
aagggtgact gtaatcccga gctcatgagt tcgaggctac agtccgatgg cagtggtgtt    4920
gccgtctcga acctagccgt tacaccct                                       4948
```

<210> SEQ ID NO 18
<211> LENGTH: 640
<212> TYPE: PRT
<213> ORGANISM: Bocavirus

<400> SEQUENCE: 18

Met Ala Phe Ser Ala Pro Val Ile Arg Ala Phe Ser Gln Pro Ala Phe
1               5                   10                  15

```
Thr Tyr Val Val Lys Phe Pro Tyr Asp Asn Trp Lys Glu Glu His
        20                  25                  30

Leu Leu Trp Ser Leu Leu Ala Pro Gly Thr Glu Arg Leu Met Ile Gln
            35                  40                  45

Leu Arg Asn Cys Ala Pro His Pro Glu Asp Pro Val Arg Glu Asp
50                  55                  60

Ile Leu Cys Ser Leu Ala Asp Gln His Tyr Ala Ala Ile Phe Thr Lys
65                  70                  75                  80

Ala Cys Tyr Met Ala Val Thr Ser Leu Met Gly Gln Lys Gln Arg Thr
                85                  90                  95

His Phe Pro Arg Cys Asp Ile Ile Cys Gln Ala Glu Ile Gly Ser Glu
            100                 105                 110

Tyr Leu His Cys His Ile Leu Val Gly Gly Ala Gly Leu Ser Lys Arg
            115                 120                 125

Asn Ala Lys Ile Ser Cys Ala Thr Leu Leu Gly Leu Val Met Ala Glu
            130                 135                 140

Leu Thr Gln Arg Cys Lys Leu Leu Ala Gln Arg Pro Phe Glu Pro
145                 150                 155                 160

Asp Glu Ala Arg Ile Phe His Leu Leu Arg Arg Val Glu Arg Glu Ala
                165                 170                 175

Trp Ser Gly His Thr Gly Asn Trp Val Gln Ile Leu Gln Tyr Arg Asp
            180                 185                 190

Lys Arg Gly Asp Leu His Ala Gln His Ile Asp Pro Leu Arg Phe Phe
            195                 200                 205

Lys His Tyr Leu Leu Pro Lys Asn Arg Leu Ile Ser Pro Ser Ser Lys
            210                 215                 220

Pro Asp Val Cys Thr Thr Pro Asp Asn Trp Phe Val Leu Ala Glu Lys
225                 230                 235                 240

Thr Tyr Ala His Thr Ile Val Asn Gly Leu Pro Leu Leu Glu His Asn
                245                 250                 255

Arg Lys Ala Tyr Leu Gln Glu Leu Glu Ser Glu Val Ile Pro Gly Pro
            260                 265                 270

Ser Thr Met Ala Phe Gly Gly Arg Gly Ala Trp Glu His Leu Pro Glu
            275                 280                 285

Val Gly Glu Gln Arg Leu Ile Thr Ser Asn Thr Ser Thr Ala Tyr Lys
            290                 295                 300

Ala Asn Lys Lys Glu Lys Leu Met Leu Asn Leu Leu Asp Lys Cys Asp
305                 310                 315                 320

Glu Leu Asn Leu Leu Val Tyr Glu Asp Leu Val Ser Ala Cys Pro Asp
                325                 330                 335

Leu Leu Leu Met Leu Glu Gly Gln Pro Gly Gly Ala Arg Leu Ile Glu
            340                 345                 350

Gln Val Leu Gly Met His His Ile Lys Val Cys Ala Asn Tyr Thr Ala
            355                 360                 365

Leu Ser Phe Leu Phe His Leu His Pro Asp Gln Leu Leu Thr Ser Ser
            370                 375                 380

Asn Lys Ala Leu Lys Leu Leu Ile Gln Gly Tyr Asn Pro Leu Gln
385                 390                 395                 400

Val Gly His Ala Ile Cys Cys Val Leu Asn Lys Gln Met Gly Lys Gln
                405                 410                 415

Asn Thr Ile Cys Phe Tyr Gly Pro Ala Ser Thr Gly Lys Thr Asn Ile
            420                 425                 430

Ala Lys Ala Ile Val Gln Gly Val Arg Leu Tyr Gly Cys Val Asn His
            435                 440                 445
```

```
Leu Asn Lys Gly Phe Val Phe Asn Asp Cys Arg Gln Arg Leu Ile Ile
    450                 455                 460

Trp Trp Glu Glu Cys Leu Met His Gln Asp Trp Val Glu Pro Ala Lys
465                 470                 475                 480

Cys Ile Leu Gly Gly Thr Glu Cys Arg Ile Asp Val Lys His Lys Asp
                485                 490                 495

Ser Val Leu Leu Gln Gln Thr Pro Val Ile Ile Ser Thr Asn His Asp
            500                 505                 510

Ile Tyr Ser Val Val Gly Gly Asn Thr Val Ser His Val His Ala Ala
        515                 520                 525

Pro Leu Lys Glu Arg Ile Leu Gln Leu Asn Phe Met Lys Gln Leu Pro
    530                 535                 540

Gln Thr Phe Gly Glu Ile Ser Pro Val Glu Ile Ala Glu Leu Leu Gln
545                 550                 555                 560

Trp Cys Phe Asn Glu Tyr Asp Cys Thr Leu Thr Gly Phe Lys Gln Lys
                565                 570                 575

Trp Asn Leu Asp Lys Val Pro Asn Ser Phe Pro Leu Gly Asp Leu Cys
            580                 585                 590

Pro Thr His Ser Gln Asp Tyr Val Leu His Glu Asn Gly Phe Cys Thr
        595                 600                 605

Asp Cys Gly Gly Tyr Ile Pro His Ser Ala Asp Ser Val Tyr Thr
    610                 615                 620

Asp Val Ala Ser Glu Thr Ser Ile Ser Ser Asp Pro Gly Arg His
625                 630                 635                 640

<210> SEQ ID NO 19
<211> LENGTH: 215
<212> TYPE: PRT
<213> ORGANISM: Bocavirus

<400> SEQUENCE: 19

Met Ser Ser Glu Ser Met Lys His Arg His Arg Ala Ser Lys Arg Thr
1               5                   10                  15

Pro Ser Pro Leu Arg Arg Glu Arg Arg His Gln Trp Glu Asn His Lys
            20                  25                  30

Lys Ser Arg Ser Arg Ser Pro Ile Arg Gln His Gly Glu Lys Ser Leu
        35                  40                  45

Glu Ser Thr Pro Arg Tyr Asn Gln Glu Ser Arg Gln Ser Ser Tyr Thr
    50                  55                  60

Ala Ser Lys Thr Ser Asp Gln Ala Thr Lys Thr Lys Glu Arg Thr Ser
65                  70                  75                  80

Gly Gly Asn Arg Thr Asn Pro Tyr Thr Val Phe Ser Gln His Arg Ala
                85                  90                  95

Asn His Pro Asp Ala Pro Gly Trp Cys Gly Phe Tyr Trp His Ser Thr
            100                 105                 110

Arg Leu Ala Arg Asp Gly Thr Asn Cys Ile Phe Asn Glu Met Lys Gln
        115                 120                 125

Glu Phe Gln Glu Leu Gln Ile Asn Gly Lys Ile Thr Trp Asp Asn Val
    130                 135                 140

Arg Glu Leu Leu Phe Ser Gln Lys Lys Leu Asp Gln Lys Tyr Arg
145                 150                 155                 160

Asn Met Leu Tyr His Phe Arg His Asn Thr Asp Cys Pro Arg Cys Asp
                165                 170                 175

Tyr Trp Asp Asp Val Tyr Arg Lys His Leu Ala His Val Ser Ser Gln
            180                 185                 190
```

```
Glu Ser Glu Glu Val Thr Asp Glu Glu Met Leu Ser Ala Val Glu Ser
        195                 200                 205

Met Glu Thr Asn Ala Ser Asn
    210             215

<210> SEQ ID NO 20
<211> LENGTH: 668
<212> TYPE: PRT
<213> ORGANISM: Bocavirus

<400> SEQUENCE: 20

Met Pro Pro Ile Lys Arg Gln Pro Gly Gly Trp Val Leu Pro Gly Tyr
1               5                  10                  15

Lys Tyr Leu Gly Pro Phe Asn Pro Leu Glu Asn Gly Glu Pro Val Asn
            20                  25                  30

Lys Ala Asp Arg Ala Ala Gln Ala His Asp Lys Ser Tyr Ser Glu Leu
        35                  40                  45

Ile Lys Ser Gly Lys Asn Pro Tyr Leu Tyr Phe Asn Lys Ala Asp Glu
    50                  55                  60

Lys Phe Ile Asp Asp Leu Lys Asn Asp Trp Ser Val Gly Gly Ile Ile
65                  70                  75                  80

Gly Ser Ser Phe Phe Lys Leu Lys Arg Ala Val Ala Pro Ala Leu Gly
                85                  90                  95

Asn Lys Glu Arg Ala Gln Lys Arg His Phe Tyr Phe Ala Asn Ser Asn
            100                 105                 110

Lys Gly Ala Lys Lys Ser Lys Asn Ser Glu Pro Lys Pro Gly Thr Ser
        115                 120                 125

Lys Met Ser Glu Asn Glu Ile Gln Asp Gln Gln Pro Ser Asp Ser Met
    130                 135                 140

Asp Gly Gln Arg Gly Gly Gly Gly Ala Ala Gly Ser Val Gly Gly Gly
145                 150                 155                 160

Gly Lys Gly Ser Gly Val Gly Ile Ser Thr Gly Gly Trp Val Gly Gly
                165                 170                 175

Ser Tyr Phe Thr Asp Ser Tyr Val Ile Thr Lys Asn Thr Arg Gln Phe
            180                 185                 190

Leu Val Lys Ile Gln Asn Asp His Lys Tyr Arg Thr Glu Asn Ile Ile
        195                 200                 205

Pro Ser Asn Ala Gly Gly Lys Ser Gln Arg Cys Val Ser Thr Pro Trp
    210                 215                 220

Ser Tyr Phe Asn Phe Asn Gln Tyr Ser Ser His Phe Ser Pro Gln Asp
225                 230                 235                 240

Trp Gln Arg Leu Thr Asn Glu Tyr Lys Arg Phe Lys Pro Arg Lys Met
                245                 250                 255

His Val Lys Ile Tyr Asn Leu Gln Ile Lys Gln Ile Leu Ser Asn Gly
            260                 265                 270

Ala Asp Thr Thr Tyr Asn Asn Asp Leu Thr Ala Gly Val His Ile Phe
        275                 280                 285

Cys Asp Gly Glu His Ala Tyr Pro Asn Ala Thr His Pro Trp Asp Glu
    290                 295                 300

Asp Val Met Pro Glu Leu Pro Tyr Glu Thr Trp Tyr Leu Phe Gln Tyr
305                 310                 315                 320

Gly Tyr Ile Pro Val Ile His Glu Leu Ala Glu Met Glu Asp Ala Asn
                325                 330                 335

Ala Val Glu Lys Ala Ile Ala Leu Gln Ile Pro Phe Phe Met Leu Glu
            340                 345                 350
```

```
Asn Ser Asp His Glu Val Leu Arg Thr Gly Glu Ser Thr Glu Phe Thr
            355                 360                 365

Phe Asp Phe Asp Cys Glu Trp Ile Asn Asn Glu Arg Ala Tyr Ile Pro
    370                 375                 380

Pro Gly Leu Met Phe Asn Pro Lys Val Pro Thr Arg Arg Ala Gln Tyr
385                 390                 395                 400

Ile Arg Gln His Gly Ser Thr Ala Ser Ser Asn Thr Arg Ile Pro Pro
                405                 410                 415

Tyr Ala Lys Pro Thr Ser Trp Met Thr Gly Pro Gly Leu Leu Ser Ala
            420                 425                 430

Gln Arg Val Gly Pro Ala Ala Ser Asp Ser Ala Ala Trp Met Val Val
    435                 440                 445

Val Asn Pro Asp Gly Ala Ala Ile Asn Ser Gly Met Ala Gly Ile Gly
450                 455                 460

Thr Gly Phe Asp Pro Pro Gly Gly Ser Leu Arg Pro Thr Asp Leu Glu
465                 470                 475                 480

Tyr Lys Ile Gln Trp Tyr Gln Thr Pro Ala Gly Thr Asn Ser Asp Gly
                485                 490                 495

Asn Ile Ile Ser Asn Pro Ser Leu Ser Met Leu Arg Asp Gln Ala Leu
            500                 505                 510

Tyr Arg Gly Asn Gln Thr Thr Tyr Asn Leu Cys Ser Asp Val Trp Met
    515                 520                 525

Phe Pro Asn Gln Ile Trp Asp Arg Tyr Pro Ile Thr Arg Glu Asn Pro
530                 535                 540

Ile Trp Cys Lys Lys Pro Arg Ser Asp Lys Ser Thr Ile Ile Asp Pro
545                 550                 555                 560

Phe Asp Gly Ser Ile Ala Met Asp His Pro Pro Gly Thr Ile Phe Ile
                565                 570                 575

Lys Met Ala Lys Ile Pro Val Pro Ser Asn Asn Asn Ala Asp Ser Tyr
            580                 585                 590

Leu Asn Ile Tyr Cys Thr Gly Gln Val Ser Cys Glu Ile Val Trp Glu
    595                 600                 605

Val Glu Arg Tyr Ala Thr Lys Asn Trp Arg Pro Glu Arg Arg His Thr
610                 615                 620

Ala Leu Gly Leu Gly Ile Gly Gly Glu Glu Asn Val Asn Pro Thr Tyr
625                 630                 635                 640

His Val Asp Lys Asn Gly Lys Tyr Ile Gln Pro Thr Thr Trp Asp Met
                645                 650                 655

Cys Tyr Pro Ile Lys Thr Asn Ile Asn Lys Val Leu
            660                 665

<210> SEQ ID NO 21
<211> LENGTH: 4948
<212> TYPE: DNA
<213> ORGANISM: Bocavirus

<400> SEQUENCE: 21
tccacctgtt attagagcat tctcttcccc tgcttttact tatgtcttca aatttccata      60
tcgatcatgg aaagaaaaag aatggcttct tcatgcgctt ctagctcatg gtaccgagca     120
agccatgatc cagctgagaa actgtgttcc tcatccggat gaagatataa tccgtgatga     180
cttactgctt tctctagaag atcgccattt tggggcaatt ctctgcaaag ctgtttatat     240
ggctactact actttcatgt cacagaaaca aagaaatatg tttcctcgct gtgacataat     300
agtccagtct gagcttgggg agacaaacct acactgccat attatagttg ggggagaagg     360
```

```
cttaagcaag agaaatgcaa aaacatcatg tcctcaacta tatggactga tactagggga       420
attaatccaa cgctgcaaaa ctcttctggc tacgcgtcct ttcgaaccgg aagaggcaga       480
aatttatcat gctttaaaac gagctgagcg agaagcttgg ggtggagtta ctagcggcaa       540
cctacaaatt ctccaataca gagatcgcag aggagacctt cacgcacaac aagtggatgc       600
tcttcgcttc ttcaaaaact acctattgcc taaaaataga tgcattacat cttacagcag       660
acctgatgtc tgtacttctc cagaaaactg gtttgtttta gctgaaaaaa cttactgtca       720
cactcttgtt aacgggctgc cgcttccaga acattacaga aaacactacc acgcaaccct       780
agataacgaa gttctaccgg ggcctcagac aatggccttt gggggacgtg gtccgtggga       840
acatcttcct gaggtaggag atcaacgttt agctgcctct tctgttagta caacatataa       900
accaaacaaa aagaaaaac ttatgcttaa cttactagat aaatgcagcg aattaaacct       960
tttagtttat gaagacttag tagctaactg tcctgaactt ttgcttatgc ttgaaggtca      1020
accaggtgga gcacgcctaa tagaacaagt cctaggcatg caccatatta atgtttgctc      1080
taactttact gctcttagtt atctctttca cctttaccct agcacaactt tatcttcaga      1140
taacaaggct ttgcagctgt tgttgataca aggttacaac ccattaatgg ttggtcacgc      1200
cttgtgctgt gtactcaaca agcagtttgg caaacagaac actgtttgct tttatggacc      1260
agcttctact ggtaaaacaa acatggcaaa ggccatagtc caaggcattc gactatatgg      1320
ctgtgttaat catttaaaca aagggtttgt ctttaatgat tgcagacaac gcctagttgt      1380
ttggtgggag gagtgcttaa tgcaccagga ttgggtggaa ccagcaaagt gtatcttggg      1440
tggaactgag tgtagaattg acgtcaaaca cagagatagt gtattattga cacaaactcc      1500
agtaattatt tccactaacc acgatatcta cgcggttgtt ggtggtaatt ctgtttctca      1560
tgttcatgcg gctccattaa agaaagagt gattcagcta aattttatga acaacttcc       1620 tcaaaccttt ggagagatca ctccagaaga aattgcagct ctactgcaat ggtgtttcaa      1680
tgagtacgag tgtactctga caggctttaa acaaaatgg agcctagata agattccaaa       1740
ctcatttcct cttggggtcc tttgtcctac tcattcacag gacttcatac tccacgaaaa      1800
cggatactgc actgattgtg gtggttacct tgctcatagc gctgacgatt ctgtgtacac      1860
tgatcgtgca agcgacacta gcaaagaagc catcgacgca ggtaagttta cattctccag      1920
acacttcata tatcctac acaccacact aaaacatatg tttaattaca ggtgacttgg       1980
gggatacgga cggagaggac tccgagtctg aagcatcgga agtgggtgtt cgtccatcca      2040
agaagcgacg cataactatt cctgcaactc caccaaattc tcctggcagc tctgtgagta      2100
cttctgcctt ctttgataat tggtgcgcac aaccgcgaga cgaagatgag ctcagggaat      2160
acaaaagaca agcatcgcgc ctacaaaaga aaagggagtc cagggagaga cgagaggaaa      2220
cgcccatggc aacctcgtca caggagtcgg agcggagcc caatccgacg cagtgggaag      2280
acaagctcgg ggtcataccg tcaggaacac cagatcagcc acctatcgtc ttgcactgct      2340
tcgaagatct cagacccagt gacgaagacg aaggagaata catcgggaa gagagactct       2400 agaactaatc catatactgt attcagccag cataaagctt caaatcctga tgctccaggg      2460
tggtgtgggt tttattggca ctctactaga attgctagaa atggtactaa tgcaatcttt      2520
aatgaaatga acagcagtt tcaacaactg caactagaca acaagattgg ctgggataat       2580
gctagagaac tattgtttag ccagaaaaaa tcactagatc aacaatacag aaatatgttt      2640
tggcacttta gaaatgctcc tgattgtgaa cgctgtaatt actgggataa tgtgtaccgt      2700
atgcacttag ctcatgtttc ctctcaggca gaatcagaag aaataactga cgaggaaatg      2760
```

```
ctttctgctg ctgaaagtat ggaaacagat gcctccaatt aaaaggcaac ctggagggtg    2820
ggtacttcct ggttacaaat accttggtcc atttaatcct cttgataacg gtgaaccagt    2880
taataaagct gatcgtgctg ctcaagctca tgataaatca tattctgaat taataaaaaa    2940
gtggaaaaaa atccttactt gtattttcaa taaagctgat gaaaaattca ttgacgattt    3000
gaaaaacgac tggtctcttg gtggcattat tggctcaaat ttctttaaac ttaagcgcgc    3060
cgtggctcct gctctaggaa ataaagagcg agctcaaaaa agacattttt attttgcaaa    3120
ctcaaataaa ggtgctaaaa aatcaaaaaa caacgaacct aaaccaagca cctcaaaaat    3180
gtctgaaaat gaaattcaag accaacagcc atcagaacct aatgatggcc agcgaggagg    3240
gggcggaggt acaaccggca gtgtgggagg ggggaaaggt tctggtgtgg gtatatccac    3300
aggtggatgg gtaggaggca gctactttac tgactcatat gtcataacaa aaaacaccag    3360
acaatttctg gttaaaatcc aaaacaacca tcaatataaa actgaaaata taattccttc    3420
taatggagga ggaaaatcac aaagatgtgt cagcacacca tggtcatact ttaacttaa    3480 tcaatacagc agccatttct caccacaaga ctggcagcgc ctaacaaatg aatacaaaag    3540
attcagacct aaaggtatgc atgttaaaat ctacaattta cagataaaac aaattttatc    3600
aaatggtgct gatgttacat acaacaacga cctaacagca ggagtacaca tcttttgtga    3660
tggcgaacat gcatatccaa acgctacaca tccatgggac gaagatgtga tgccagagct    3720
tccttaccaa acatggtatc tatttcaata tggatacata cctacaattc atgaacttgc    3780
agaaatggaa gactccaatg cagtagaaaa agcaattgct ttacaaatac cattcttcat    3840
gcttgaaaac agcgaccatg aagttctaag aactggagaa agtgcagaat caactttaa    3900 ctttgattgt gaatggatta acaatgaaag agcattcatt cctccaggac tgatgttcaa    3960
tccattggta ccaacaagaa gagctcaata cataagaaga aatggaaaca ctcaagcaag    4020
taccacaaga atccaacctt actcaaaacc aacaagttgg atgactggac caggtctact    4080
cagtgcgcaa cgagtaggtc cagctgcttc agacacagct gcatggatgg ttggaataga    4140
tctagacggt gcaaacgtaa actcaggaag agcaggagtc agcacaggct ttgatcctcc    4200
agcaggttca cttagaccta cagatctaga atacaaaata caatggtacc agactccagc    4260
tggaacaaac aatgatggaa acatcatatc aaatccacct ctttcaatgc tcagagatca    4320
aactctatac aaaggaaacc aaacaaccta caacttatgc tcagatgtat ggatgttccc    4380
aaatcaaatt tgggacagat acccaataac cagagaaaat cctatttggt gcaaacaacc    4440
aagatcagac aaacacactg tcattgatcc gttcgatgga tctcttgcaa tggatcatcc    4500
tccaggaaca attttatca aaatggcaaa aattccagtt ccttcaagca caacgcaga    4560 ctcatactta aacatctact gcactggaca agtcagctgc gaaattgtct gggaagtcga    4620
aagatatgca acaagaact ggagaccaga aagaagacac acggcactcg gccttggaat    4680
tggaggagca gatgaaatca acccaacata ccatgttgac aaaaacggag cctacattca    4740
accaacatca tggacatgt gctttccagt taaaacaaac atcaataaag tgttgtaatc    4800
tcttaagcct ctttattgct cacgcttgta agttcctctc caatggacaa gtggaaagaa    4860
aagggtgact gtaatcccga gctcatgagt tcgaggctac agtccgatgg cagtggtgtt    4920
gccgtctcga acctagccgt taaaccct                                        4948
```

<210> SEQ ID NO 22
<211> LENGTH: 657
<212> TYPE: PRT
<213> ORGANISM: Bocavirus

<400> SEQUENCE: 22

```
Pro Pro Val Ile Arg Ala Phe Ser Ser Pro Ala Phe Thr Tyr Val Phe
1               5                   10                  15

Lys Phe Pro Tyr Arg Ser Trp Lys Glu Lys Glu Trp Leu Leu His Ala
            20                  25                  30

Leu Leu Ala His Gly Thr Glu Gln Ala Met Ile Gln Leu Arg Asn Cys
        35                  40                  45

Val Pro His Pro Asp Glu Asp Ile Ile Arg Asp Asp Leu Leu Leu Ser
    50                  55                  60

Leu Glu Asp Arg His Phe Gly Ala Ile Leu Cys Lys Ala Val Tyr Met
65                  70                  75                  80

Ala Thr Thr Thr Phe Met Ser Gln Lys Gln Arg Asn Met Phe Pro Arg
                85                  90                  95

Cys Asp Ile Ile Val Gln Ser Glu Leu Gly Glu Thr Asn Leu His Cys
            100                 105                 110

His Ile Ile Val Gly Gly Glu Gly Leu Ser Lys Arg Asn Ala Lys Thr
        115                 120                 125

Ser Cys Pro Gln Leu Tyr Gly Leu Ile Leu Gly Glu Leu Ile Gln Arg
    130                 135                 140

Cys Lys Thr Leu Leu Ala Thr Arg Pro Phe Glu Pro Glu Glu Ala Glu
145                 150                 155                 160

Ile Tyr His Ala Leu Lys Arg Ala Glu Arg Glu Ala Trp Gly Gly Val
                165                 170                 175

Thr Ser Gly Asn Leu Gln Ile Leu Gln Tyr Arg Asp Arg Arg Gly Asp
            180                 185                 190

Leu His Ala Gln Gln Val Asp Ala Leu Arg Phe Phe Lys Asn Tyr Leu
        195                 200                 205

Leu Pro Lys Asn Arg Cys Ile Thr Ser Tyr Ser Arg Pro Asp Val Cys
    210                 215                 220

Thr Ser Pro Glu Asn Trp Phe Val Leu Ala Glu Lys Thr Tyr Cys His
225                 230                 235                 240

Thr Leu Val Asn Gly Leu Pro Leu Pro Glu His Tyr Arg Lys His Tyr
                245                 250                 255

His Ala Thr Leu Asp Asn Glu Val Leu Pro Gly Pro Gln Thr Met Ala
            260                 265                 270

Phe Gly Gly Arg Gly Pro Trp Glu His Leu Pro Glu Val Gly Asp Gln
        275                 280                 285

Arg Leu Ala Ala Ser Ser Val Ser Thr Thr Tyr Lys Pro Asn Lys Lys
    290                 295                 300

Glu Lys Leu Met Leu Asn Leu Leu Asp Lys Cys Ser Glu Leu Asn Leu
305                 310                 315                 320

Leu Val Tyr Glu Asp Leu Val Ala Asn Cys Pro Glu Leu Leu Leu Met
                325                 330                 335

Leu Glu Gly Gln Pro Gly Gly Ala Arg Leu Ile Glu Gln Val Leu Gly
            340                 345                 350

Met His His Ile Asn Val Cys Ser Asn Phe Thr Ala Leu Ser Tyr Leu
        355                 360                 365

Phe His Leu Tyr Pro Ser Thr Thr Leu Ser Ser Asp Asn Lys Ala Leu
    370                 375                 380

Gln Leu Leu Leu Ile Gln Gly Tyr Asn Pro Leu Met Val Gly His Ala
385                 390                 395                 400

Leu Cys Cys Val Leu Asn Lys Gln Phe Gly Lys Gln Asn Thr Val Cys
                405                 410                 415
```

```
Phe Tyr Gly Pro Ala Ser Thr Gly Lys Thr Asn Met Ala Lys Ala Ile
            420                 425                 430

Val Gln Gly Ile Arg Leu Tyr Gly Cys Val Asn His Leu Asn Lys Gly
            435                 440                 445

Phe Val Phe Asn Asp Cys Arg Gln Arg Leu Val Val Trp Trp Glu Glu
            450                 455                 460

Cys Leu Met His Gln Asp Trp Val Glu Pro Lys Cys Ile Leu Gly
465                 470                 475                 480

Gly Thr Glu Cys Arg Ile Asp Val Lys His Arg Asp Ser Val Leu Leu
            485                 490                 495

Thr Gln Thr Pro Val Ile Ile Ser Thr Asn His Asp Ile Tyr Ala Val
            500                 505                 510

Val Gly Gly Asn Ser Val Ser His Val His Ala Ala Pro Leu Lys Glu
            515                 520                 525

Arg Val Ile Gln Leu Asn Phe Met Lys Gln Leu Pro Gln Thr Phe Gly
            530                 535                 540

Glu Ile Thr Pro Glu Glu Ile Ala Ala Leu Leu Gln Trp Cys Phe Asn
545                 550                 555                 560

Glu Tyr Glu Cys Thr Leu Thr Gly Phe Lys Thr Lys Trp Ser Leu Asp
            565                 570                 575

Lys Ile Pro Asn Ser Phe Pro Leu Gly Val Leu Cys Pro Thr His Ser
            580                 585                 590

Gln Asp Phe Ile Leu His Glu Asn Gly Tyr Cys Thr Asp Cys Gly Gly
            595                 600                 605

Tyr Leu Ala His Ser Ala Asp Asp Ser Val Tyr Thr Asp Arg Ala Ser
            610                 615                 620

Asp Thr Ser Lys Glu Ala Ile Asp Ala Gly Lys Phe Thr Phe Ser Arg
625                 630                 635                 640

His Phe Ile Tyr Ile Leu His Thr Thr Leu Lys His Met Phe Asn Tyr
            645                 650                 655

Arg

<210> SEQ ID NO 23
<211> LENGTH: 218
<212> TYPE: PRT
<213> ORGANISM: Bocavirus

<400> SEQUENCE: 23

Met Ser Ser Gly Asn Thr Lys Asp Lys His Arg Ala Tyr Lys Arg Lys
1               5                   10                  15

Gly Ser Pro Gly Arg Asp Glu Arg Lys Arg Pro Trp Gln Pro Arg His
            20                  25                  30

Arg Ser Arg Ser Arg Ser Pro Ile Arg Arg Ser Gly Lys Thr Ser Ser
            35                  40                  45

Gly Ser Tyr Arg Gln Glu His Gln Ile Ser His Leu Ser Ser Cys Thr
            50                  55                  60

Ala Ser Lys Ile Ser Asp Pro Val Thr Lys Thr Lys Glu Asn Thr Ser
65                  70                  75                  80

Gly Lys Arg Asp Ser Arg Thr Asn Pro Tyr Thr Val Phe Ser Gln His
            85                  90                  95

Lys Ala Ser Asn Pro Asp Ala Pro Gly Trp Cys Gly Phe Tyr Trp His
            100                 105                 110

Ser Thr Arg Ile Ala Arg Asn Gly Thr Asn Ala Ile Phe Asn Glu Met
            115                 120                 125
```

```
Lys Gln Gln Phe Gln Gln Leu Gln Leu Asp Asn Lys Ile Gly Trp Asp
    130                 135                 140
Asn Ala Arg Glu Leu Leu Phe Ser Gln Lys Lys Ser Leu Asp Gln Gln
145                 150                 155                 160
Tyr Arg Asn Met Phe Trp His Phe Arg Asn Ala Pro Asp Cys Glu Arg
                165                 170                 175
Cys Asn Tyr Trp Asp Asn Val Tyr Arg Met His Leu Ala His Val Ser
            180                 185                 190
Ser Gln Ala Glu Ser Glu Ile Thr Asp Glu Met Leu Ser Ala
        195                 200                 205
Ala Glu Ser Met Glu Thr Asp Ala Ser Asn
    210                 215
```

<210> SEQ ID NO 24
<211> LENGTH: 669
<212> TYPE: PRT
<213> ORGANISM: Bocavirus

<400> SEQUENCE: 24

```
Met Pro Pro Ile Lys Arg Gln Pro Gly Gly Trp Val Leu Pro Gly Tyr
1               5                   10                  15
Lys Tyr Leu Gly Pro Phe Asn Pro Leu Asp Asn Gly Glu Pro Val Asn
            20                  25                  30
Lys Ala Asp Arg Ala Ala Gln Ala His Asp Lys Ser Tyr Ser Glu Leu
        35                  40                  45
Ile Lys Lys Trp Lys Lys Ile Leu Thr Cys Ile Phe Asn Lys Ala Asp
    50                  55                  60
Glu Lys Phe Ile Asp Asp Leu Lys Asn Asp Trp Ser Leu Gly Gly Ile
65                  70                  75                  80
Ile Gly Ser Asn Phe Phe Lys Leu Lys Arg Ala Val Ala Pro Ala Leu
                85                  90                  95
Gly Asn Lys Glu Arg Ala Gln Lys Arg His Phe Tyr Phe Ala Asn Ser
            100                 105                 110
Asn Lys Gly Ala Lys Lys Ser Lys Asn Asn Glu Pro Lys Pro Ser Thr
        115                 120                 125
Ser Lys Met Ser Glu Asn Glu Ile Gln Asp Gln Gln Pro Ser Glu Pro
    130                 135                 140
Asn Asp Gly Gln Arg Gly Gly Gly Gly Thr Gly Ser Val Gly
145                 150                 155                 160
Gly Gly Lys Gly Ser Gly Val Gly Ile Ser Thr Gly Gly Trp Val Gly
                165                 170                 175
Gly Ser Tyr Phe Thr Asp Ser Tyr Val Ile Thr Lys Asn Thr Arg Gln
            180                 185                 190
Phe Leu Val Lys Ile Gln Asn Asn His Gln Tyr Lys Thr Glu Asn Ile
        195                 200                 205
Ile Pro Ser Asn Gly Gly Gly Lys Ser Gln Arg Cys Val Ser Thr Pro
    210                 215                 220
Trp Ser Tyr Phe Asn Phe Asn Gln Tyr Ser Ser His Phe Ser Pro Gln
225                 230                 235                 240
Asp Trp Gln Arg Leu Thr Asn Glu Tyr Lys Arg Phe Arg Pro Lys Gly
                245                 250                 255
Met His Val Lys Ile Tyr Asn Leu Gln Ile Lys Gln Ile Leu Ser Asn
            260                 265                 270
Gly Ala Asp Val Thr Tyr Asn Asn Asp Leu Thr Ala Gly Val His Ile
        275                 280                 285
```

| | | | | | | | | | | | | |
|---|---|---|---|---|---|---|---|---|---|---|---|---|
| Phe | Cys | Asp | Gly | Glu | His | Ala | Tyr | Pro | Asn | Ala | Thr | His | Pro | Trp | Asp |
| 290 | | | | | 295 | | | | | 300 | | | | | |

Phe Cys Asp Gly Glu His Ala Tyr Pro Asn Ala Thr His Pro Trp Asp
290 295 300

Glu Asp Val Met Pro Glu Leu Pro Tyr Gln Thr Trp Tyr Leu Phe Gln
305 310 315 320

Tyr Gly Tyr Ile Pro Thr Ile His Glu Leu Ala Glu Met Glu Asp Ser
325 330 335

Asn Ala Val Glu Lys Ala Ile Ala Leu Gln Ile Pro Phe Phe Met Leu
340 345 350

Glu Asn Ser Asp His Glu Val Leu Arg Thr Gly Ser Ala Glu Phe
355 360 365

Asn Phe Asn Phe Asp Cys Glu Trp Ile Asn Asn Glu Arg Ala Phe Ile
370 375 380

Pro Pro Gly Leu Met Phe Asn Pro Leu Val Pro Thr Arg Arg Ala Gln
385 390 395 400

Tyr Ile Arg Arg Asn Gly Asn Thr Gln Ala Ser Thr Arg Ile Gln
405 410 415

Pro Tyr Ser Lys Pro Thr Ser Trp Met Thr Gly Pro Gly Leu Leu Ser
420 425 430

Ala Gln Arg Val Gly Pro Ala Ala Ser Asp Thr Ala Ala Trp Met Val
435 440 445

Gly Ile Asp Leu Asp Gly Ala Asn Val Asn Ser Gly Arg Ala Gly Val
450 455 460

Ser Thr Gly Phe Asp Pro Pro Ala Gly Ser Leu Arg Pro Thr Asp Leu
465 470 475 480

Glu Tyr Lys Ile Gln Trp Tyr Gln Thr Pro Ala Gly Thr Asn Asn Asp
485 490 495

Gly Asn Ile Ile Ser Asn Pro Pro Leu Ser Met Leu Arg Asp Gln Thr
500 505 510

Leu Tyr Lys Gly Asn Gln Thr Thr Tyr Asn Leu Cys Ser Asp Val Trp
515 520 525

Met Phe Pro Asn Gln Ile Trp Asp Arg Tyr Pro Ile Thr Arg Glu Asn
530 535 540

Pro Ile Trp Cys Lys Gln Pro Arg Ser Asp Lys His Thr Val Ile Asp
545 550 555 560

Pro Phe Asp Gly Ser Leu Ala Met Asp His Pro Pro Gly Thr Ile Phe
565 570 575

Ile Lys Met Ala Lys Ile Pro Val Pro Ser Ser Asn Asn Ala Asp Ser
580 585 590

Tyr Leu Asn Ile Tyr Cys Thr Gly Gln Val Ser Cys Glu Ile Val Trp
595 600 605

Glu Val Glu Arg Tyr Ala Thr Lys Asn Trp Arg Pro Glu Arg Arg His
610 615 620

Thr Ala Leu Gly Leu Gly Ile Gly Gly Ala Asp Glu Ile Asn Pro Thr
625 630 635 640

Tyr His Val Asp Lys Asn Gly Ala Tyr Ile Gln Pro Thr Ser Trp Asp
645 650 655

Met Cys Phe Pro Val Lys Thr Asn Ile Asn Lys Val Leu
660 665

<210> SEQ ID NO 25
<211> LENGTH: 4946
<212> TYPE: DNA
<213> ORGANISM: Bocavirus

<400> SEQUENCE: 25

```
actatggcct tttctgctcc tgtacttaga gcttttctc aacctacttt tacctatgtt      60
attaaatttc catataataa ctggaaagaa gatgaacact tactatggag cttacttgct     120
cctgggactg aaagtctcat gattcaacta aaaaactgcg caccacatcc tgaagatgat     180
cctatcaggg aagatatttt atgctcacta gcagatctac actatggtgc tgttttttgcc   240 aaagcttgct acatagctac atctacacta atggggcaga acaaagaac actctttcca    300 cgctgcgaca ttgtttgcca gtctgaaatt ggctcagact ttctcactg tcacatactt     360 gttggaggag ccggtcttag caagagaaat gctaaaattt cacgcgctac acttttgggt    420
cttgtgatgg ctgaactaac acaacgctgc aagctacttc ttgcacatcg tccatttgaa    480
ccagctgaag ctactatcta tcatgaactt aaacgcattg aacgcgaagc atggtcaggg    540
catactggta actgggttca gattcttcaa tacaaagata aacgaggtga tcttcacgct    600
caaccaattg atcccttacg ctttctaaaa cattacattc taccaaaaaa tcgattgatt    660
tctccttcca gcaaacctga cgtctgcact tctccagata actggtttat tctagctgac    720
aaaacatact ctcacactat tattaatggg cttccgctgc tagaacgtaa cagaaaagcc    780
tatctacaag agttagaaag tgaagtcatc ccggggcctt ctgccatggc ctttggggga    840
cgtggtgcgt gggaacaact tcctgaggta ggagaacaac gcctaattac ttctaatact    900
tctactgctt ataagctaa caaaaaagaa aaattaatgt taaatttact tgataaatgt     960
gatgaactta atttgcttgt atatgaagac ttagttagtg cttgtcctga ccttttacta   1020
atgcttgaag gacaaccggg tggagcacga ctaattgaac aggtgcttgg catgcaccat   1080
attaaagtat gtgctaaaca tactgcctta tcttttttat ttcacttaca tcctgatcaa   1140
ttattaactt ctagcaataa agcactaaaa ctactattga ttcaaggata caacccatta   1200
caagtagggc atgccatctg ttgtgtactt aacaaacaga tgggcaagca gaacactatt   1260
tgcttttatg gccctgcttc aacaggcaaa acaaactttg caaaagctat agttcagggc   1320
gttcgccttt atgctgtgt taatcattta acaaggggt tgttttttaa cgattgcaga    1380
caacgcctta taatttggtg ggaagaatgt ttaatgcatc aagattgggt agaacctgct   1440 aaatgtatt taggcggaac tgaatgtaga attgatgtta aacataaaga tagtgttctc    1500
cttcaacaaa caccagtaat catttccact aaccatgaca tctactctgt agttggtggc   1560
aatactgttt ctcatgttca tgcagcacca ttaaaagaac gagttcttca gctaaatttt   1620
atgaaacaac taccacaaac atttggagaa atctctccaa gtgaaattgc agaactttg    1680 caatggtgct ttaatgagta cgactgtact cttgctggct ttaaacaaa atggaactta    1740 gacaaagttc caaactcatt tcctattgga gacctttgtc ctacacattc acaggacttc   1800
acgcttcacg aaaacggatt ctgctctgac tgtggcggct atcttcctca tagcgctgac   1860
gattctgttt acactgacgt ggctagtgaa acaaccagcg gtgactacga cccaggtagg   1920
ctttaataca ttagctttac tatttattac tcttgaagtt tgcttatgta ttaactccta   1980 caggtaaacct gggggatacg gacggagagg actccaagtc agaagcatcg gaagtggatt   2040
attgtccacc caagaaaagg cgtgtgattt cagcaactcc accaaacagt ccagtaagtg   2100
gtccaagcct ttctaccttt ttagatactt ggcaatcaca acctagagac gacgatgagc   2160
tcagaatcta cgaagaacag gcatcgcagt tccaaaagaa caccagtcc acttcagaaa    2220 gagaggaagc gcaactggga gaatcgcaag agccgcagcc ggagcccgat ccgacggcat   2280
ggggagaaaa acttggagta tgctcatcac aacaaccagg acaaccgcca atcgtcctat   2340
actgcttcga agacctcaga ccaagcgatg aagacgaagg agaaaacatc ggggggact    2400
```

```
agaacaaatc cttatactgt attcagtcaa cacagggcta atcattcaaa tgctcctggc   2460
tggtgtgggt tttactggca ttcaactagg cttgctagaa atggcactaa taatatttt    2520 aatgaaatga aacaaaaatt tcaagaacta caaatagatg ggaaaatcag ttgggatact   2580
actagagaac tattgtttac tcagaaaaaa acattagatc aaggctacag aaacatgttg   2640 taccactta gacacagtcc tgattgtcct agatgtgatt attgggatga tgtttaccgt    2700
aaacacttag ctaatgtctc ttcacaggaa tcagaggagg ttacagacga agaaatgctt   2760
tctgctgttg aaagcatgga aacaaatgcc tccaattaaa cgccaacctg agggtgggt    2820 gcttcctggt tataaatacc ttggtccatt taatcctctt gaaaacggtg aaccagttaa   2880
taaagctgat cgtgctgctc aagctcatga taaatcatat tctgaactaa taaaaagtgg   2940
aaaaaatcct tacttatatt tcaataaagc tgatgaaaaa ttcattgacg atttgaaaga   3000
cgattggtct cttggtggca ttattggctc aagttttttt aaacttaaac gcgccgtggc   3060
tcctgctcta ggaaataaag agcgagctca aaaaagacat ttctactttg caaactcaaa   3120
taaaggtgct aaaaaaacaa aaaacaacga acctaagcca ggcacttcaa aaatgtctga   3180
aaatgaaatt caagaccaac aaccatcaga ttctatggat ggacaacgag ggggcggagg   3240
aggtgcaact ggcagtgtgg gagggggggaa aggttctggt gtgggtatat ccacaggcgg   3300
atgggtagga ggcagctatt ttactgactc atatgttata acaaaaaaca ccagacaatt   3360
tctagttaaa atacaaaaca accatcaata caaaacagaa ttaatatcgc cttccacatc   3420
tcaaggaaaa tcacaaagat gcgtcagcac gccttggtct tactttaact ttaatcaata   3480
cagcagtcat ttttcaccac aagactggca gcgattaaca aacgaatata aaagattcag   3540
acccaaaggc atgcatgtta aaatatacaa tttacaaata aaacaaattc tttcaaatgg   3600
tgctgacact acatacaaca acgacctcac agctggtgtt cacatttttt gtgatggcga   3660
acacgcatat ccaaatgcaa cacatccttg ggatgaagac gttatgccag agctgccata   3720
ccaaacatgg tatttgtttc aatatggata tattccagtt atacatgaac ttgctgaaat   3780
ggaagactca aatgctgtag aaaaagcaat ttgcttacaa ataccatttt ttatgcttga   3840
aaacagcgac cacgaagttt taagaacagg tgaaagcaca gaatttactt tcaactttga   3900
ctgtgaatgg ataaacaatg aaagagcata cattcctcca ggcttaatgt ttaatccact   3960
agtacctact agaagagcac agtacataag aagaaacaac aatcctcaaa ctgctgaaag   4020
cacatccaga attgctccat atgcaaaacc tacaagttgg atgactggac caggtttact   4080
cagtgcacaa agagtaggtc cagctacttc agacacagga gcctggatgg ttgcagttaa   4140
accagaaaac gcaagcattg acacaggaat gtctggaatt ggaagtggat ttgatccacc   4200
acaaggatca ctagccaccaa caaatctaga atacaaaatc caatggtacc aaacaccaca   4260
aggaacaaac aacaatggaa acatcatatc taatcaacca ctatctatgc taagagatca   4320
agctttattt agaggaaatc aaacaaccta aacctatgt tcagatgtat ggatgtttcc    4380
aaatcaaatt tgggacagat acccaataac cagagaaaat ccaatatggt gtaaaaaacc   4440
cagatcagac aaacacacaa caattgatcc ttttgatgga tcccttgcaa tggatcatcc   4500
tccaggcaca atttttatta aaatggcaaa aattccagtt ccttcaaaca acaatgcaga   4560
ctcatactta aacatttact gcacagggca agtcagctgt gaaattgtct gggaagttga   4620
aagatatgca acaaagaact ggagaccaga aagaagacac acaacatttg gtcttggaat   4680
tggaggagct gacaacttaa atccaaccta ccatgttgac aaaaacggaa cttacattca   4740
accaacaaca tgggacatgt gctttccagt taaaacaaac atcaataaag tgttgtaacc   4800
```

-continued

```
ttctaagcct cttttttgct tatgcttata agttcctctc caatggacaa gtggaaagaa    4860
aagggtgact gtaatcccga gctcatgagt tcgaggctac agtccgatgg cagtggtgtt    4920
gccgtctcga acctagccgt tacacc                                         4946
```

<210> SEQ ID NO 26
<211> LENGTH: 640
<212> TYPE: PRT
<213> ORGANISM: Bocavirus

<400> SEQUENCE: 26

```
Met Ala Phe Ser Ala Pro Val Leu Arg Ala Phe Ser Gln Pro Thr Phe
1               5                   10                  15

Thr Tyr Val Ile Lys Phe Pro Tyr Asn Asn Trp Lys Glu Asp Glu His
                20                  25                  30

Leu Leu Trp Ser Leu Leu Ala Pro Gly Thr Glu Ser Leu Met Ile Gln
            35                  40                  45

Leu Lys Asn Cys Ala Pro His Pro Glu Asp Asp Pro Ile Arg Glu Asp
50                  55                  60

Ile Leu Cys Ser Leu Ala Asp Leu His Tyr Gly Ala Val Phe Ala Lys
65                  70                  75                  80

Ala Cys Tyr Ile Ala Thr Ser Thr Leu Met Gly Gln Lys Gln Arg Thr
                85                  90                  95

Leu Phe Pro Arg Cys Asp Ile Val Cys Gln Ser Glu Ile Gly Ser Asp
            100                 105                 110

Phe Leu His Cys His Ile Leu Val Gly Gly Ala Gly Leu Ser Lys Arg
        115                 120                 125

Asn Ala Lys Ile Ser Arg Ala Thr Leu Leu Gly Leu Val Met Ala Glu
130                 135                 140

Leu Thr Gln Arg Cys Lys Leu Leu Leu Ala His Arg Pro Phe Glu Pro
145                 150                 155                 160

Ala Glu Ala Thr Ile Tyr His Glu Leu Lys Arg Ile Glu Arg Glu Ala
                165                 170                 175

Trp Ser Gly His Thr Gly Asn Trp Val Gln Ile Leu Gln Tyr Lys Asp
            180                 185                 190

Lys Arg Gly Asp Leu His Ala Gln Pro Ile Asp Pro Leu Arg Phe Leu
        195                 200                 205

Lys His Tyr Ile Leu Pro Lys Asn Arg Leu Ile Ser Pro Ser Ser Lys
210                 215                 220

Pro Asp Val Cys Thr Ser Pro Asp Asn Trp Phe Ile Leu Ala Asp Lys
225                 230                 235                 240

Thr Tyr Ser His Thr Ile Ile Asn Gly Leu Pro Leu Leu Glu Arg Asn
                245                 250                 255

Arg Lys Ala Tyr Leu Gln Glu Leu Glu Ser Glu Val Ile Pro Gly Pro
            260                 265                 270

Ser Ala Met Ala Phe Gly Gly Arg Gly Ala Trp Glu Gln Leu Pro Glu
        275                 280                 285

Val Gly Glu Gln Arg Leu Ile Thr Ser Asn Thr Ser Thr Ala Tyr Lys
290                 295                 300

Ala Asn Lys Lys Glu Lys Leu Met Leu Asn Leu Leu Asp Lys Cys Asp
305                 310                 315                 320

Glu Leu Asn Leu Leu Val Tyr Glu Asp Leu Val Ser Ala Cys Pro Asp
                325                 330                 335

Leu Leu Leu Met Leu Glu Gly Gln Pro Gly Gly Ala Arg Leu Ile Glu
            340                 345                 350
```

```
Gln Val Leu Gly Met His His Ile Lys Val Cys Ala Lys His Thr Ala
            355                 360                 365

Leu Ser Phe Leu Phe His Leu His Pro Asp Gln Leu Thr Ser Ser
    370                 375                 380

Asn Lys Ala Leu Lys Leu Leu Ile Gln Gly Tyr Asn Pro Leu Gln
385                 390                 395                 400

Val Gly His Ala Ile Cys Cys Val Leu Asn Lys Gln Met Gly Lys Gln
                405                 410                 415

Asn Thr Ile Cys Phe Tyr Gly Pro Ala Ser Thr Gly Lys Thr Asn Phe
                420                 425                 430

Ala Lys Ala Ile Val Gln Gly Val Arg Leu Tyr Gly Cys Val Asn His
                435                 440                 445

Leu Asn Lys Gly Phe Val Phe Asn Asp Cys Arg Gln Arg Leu Ile Ile
    450                 455                 460

Trp Trp Glu Glu Cys Leu Met His Gln Asp Trp Val Glu Pro Ala Lys
465                 470                 475                 480

Cys Ile Leu Gly Gly Thr Glu Cys Arg Ile Asp Val Lys His Lys Asp
                485                 490                 495

Ser Val Leu Leu Gln Gln Thr Pro Val Ile Ile Ser Thr Asn His Asp
            500                 505                 510

Ile Tyr Ser Val Val Gly Gly Asn Thr Val Ser His Val His Ala Ala
        515                 520                 525

Pro Leu Lys Glu Arg Val Leu Gln Leu Asn Phe Met Lys Gln Leu Pro
    530                 535                 540

Gln Thr Phe Gly Glu Ile Ser Pro Ser Glu Ile Ala Glu Leu Leu Gln
545                 550                 555                 560

Trp Cys Phe Asn Glu Tyr Asp Cys Thr Leu Ala Gly Phe Lys Gln Lys
                565                 570                 575

Trp Asn Leu Asp Lys Val Pro Asn Ser Phe Pro Ile Gly Asp Leu Cys
                580                 585                 590

Pro Thr His Ser Gln Asp Phe Thr Leu His Glu Asn Gly Phe Cys Ser
            595                 600                 605

Asp Cys Gly Gly Tyr Leu Pro His Ser Ala Asp Ser Val Tyr Thr
610                 615                 620

Asp Val Ala Ser Glu Thr Thr Ser Gly Asp Tyr Asp Pro Gly Arg Leu
625                 630                 635                 640

<210> SEQ ID NO 27
<211> LENGTH: 214
<212> TYPE: PRT
<213> ORGANISM: Bocavirus

<400> SEQUENCE: 27

Met Ser Ser Glu Ser Thr Lys Asn Arg His Arg Ser Ser Lys Arg Thr
1               5                   10                  15

Pro Ser Pro Leu Gln Lys Glu Arg Lys Arg Asn Trp Glu Asn Arg Lys
                20                  25                  30

Ser Arg Ser Arg Ser Pro Ile Arg Arg His Gly Glu Lys Asn Leu Glu
            35                  40                  45

Tyr Ala His His Asn Asn Gln Asp Asn Arg Gln Ser Ser Tyr Thr Ala
        50                  55                  60

Ser Lys Thr Ser Asp Gln Ala Met Lys Thr Lys Glu Lys Thr Ser Gly
65                  70                  75                  80

Gly Thr Arg Thr Asn Pro Tyr Thr Val Phe Ser Gln His Arg Ala Asn
                85                  90                  95
```

```
His Ser Asn Ala Pro Gly Trp Cys Gly Phe Tyr Trp His Ser Thr Arg
            100                 105                 110
Leu Ala Arg Asn Gly Thr Asn Asn Ile Phe Asn Glu Met Lys Gln Lys
            115                 120                 125
Phe Gln Glu Leu Gln Ile Asp Gly Lys Ile Ser Trp Asp Thr Thr Arg
            130                 135                 140
Glu Leu Leu Phe Thr Gln Lys Lys Thr Leu Asp Gln Gly Tyr Arg Asn
145                 150                 155                 160
Met Leu Tyr His Phe Arg His Ser Pro Asp Cys Pro Arg Cys Asp Tyr
                165                 170                 175
Trp Asp Asp Val Tyr Arg Lys His Leu Ala Asn Val Ser Ser Gln Glu
                180                 185                 190
Ser Glu Glu Val Thr Asp Glu Glu Met Leu Ser Ala Val Glu Ser Met
            195                 200                 205
Glu Thr Asn Ala Ser Asn
            210

<210> SEQ ID NO 28
<211> LENGTH: 670
<212> TYPE: PRT
<213> ORGANISM: Bocavirus

<400> SEQUENCE: 28

Met Pro Pro Ile Lys Arg Gln Pro Gly Gly Trp Val Leu Pro Gly Tyr
1               5                   10                  15
Lys Tyr Leu Gly Pro Phe Asn Pro Leu Glu Asn Gly Glu Pro Val Asn
            20                  25                  30
Lys Ala Asp Arg Ala Ala Gln Ala His Asp Lys Ser Tyr Ser Glu Leu
        35                  40                  45
Ile Lys Ser Gly Lys Asn Pro Tyr Leu Tyr Phe Asn Lys Ala Asp Glu
    50                  55                  60
Lys Phe Ile Asp Asp Leu Lys Asp Asp Trp Ser Leu Gly Gly Ile Ile
65                  70                  75                  80
Gly Ser Ser Phe Phe Lys Leu Lys Arg Ala Val Ala Pro Ala Leu Gly
                85                  90                  95
Asn Lys Glu Arg Ala Gln Lys Arg His Phe Tyr Phe Ala Asn Ser Asn
            100                 105                 110
Lys Gly Ala Lys Lys Thr Lys Asn Asn Glu Pro Lys Pro Gly Thr Ser
            115                 120                 125
Lys Met Ser Glu Asn Glu Ile Gln Asp Gln Pro Ser Asp Ser Met
            130                 135                 140
Asp Gly Gln Arg Gly Gly Gly Gly Ala Thr Gly Ser Val Gly Gly
145                 150                 155                 160
Gly Lys Gly Ser Gly Val Gly Ile Ser Thr Gly Gly Trp Val Gly Gly
                165                 170                 175
Ser Tyr Phe Thr Asp Ser Tyr Val Ile Thr Lys Asn Thr Arg Gln Phe
                180                 185                 190
Leu Val Lys Ile Gln Asn Asn His Gln Tyr Lys Thr Glu Leu Ile Ser
            195                 200                 205
Pro Ser Thr Ser Gln Gly Lys Ser Gln Arg Cys Val Ser Thr Pro Trp
        210                 215                 220
Ser Tyr Phe Asn Phe Asn Gln Tyr Ser Ser His Phe Ser Pro Gln Asp
225                 230                 235                 240
Trp Gln Arg Leu Thr Asn Glu Tyr Lys Arg Phe Arg Pro Lys Gly Met
                245                 250                 255
```

His Val Lys Ile Tyr Asn Leu Gln Ile Lys Gln Ile Leu Ser Asn Gly
            260                 265                 270

Ala Asp Thr Thr Tyr Asn Asn Asp Leu Thr Ala Gly Val His Ile Phe
            275                 280                 285

Cys Asp Gly Glu His Ala Tyr Pro Asn Ala Thr His Pro Trp Asp Glu
290                 295                 300

Asp Val Met Pro Glu Leu Pro Tyr Gln Thr Trp Tyr Leu Phe Gln Tyr
305                 310                 315                 320

Gly Tyr Ile Pro Val Ile His Glu Leu Ala Glu Met Glu Asp Ser Asn
                325                 330                 335

Ala Val Glu Lys Ala Ile Cys Leu Gln Ile Pro Phe Phe Met Leu Glu
            340                 345                 350

Asn Ser Asp His Glu Val Leu Arg Thr Gly Glu Ser Thr Glu Phe Thr
            355                 360                 365

Phe Asn Phe Asp Cys Glu Trp Ile Asn Asn Glu Arg Ala Tyr Ile Pro
370                 375                 380

Pro Gly Leu Met Phe Asn Pro Leu Val Pro Thr Arg Arg Ala Gln Tyr
385                 390                 395                 400

Ile Arg Arg Asn Asn Pro Gln Thr Ala Glu Ser Thr Ser Arg Ile
                405                 410                 415

Ala Pro Tyr Ala Lys Pro Thr Ser Trp Met Thr Gly Pro Gly Leu Leu
            420                 425                 430

Ser Ala Gln Arg Val Gly Pro Ala Thr Ser Asp Thr Gly Ala Trp Met
            435                 440                 445

Val Ala Val Lys Pro Glu Asn Ala Ser Ile Asp Thr Gly Met Ser Gly
450                 455                 460

Ile Gly Ser Gly Phe Asp Pro Pro Gln Gly Ser Leu Ala Pro Thr Asn
465                 470                 475                 480

Leu Glu Tyr Lys Ile Gln Trp Tyr Gln Thr Pro Gln Gly Thr Asn Asn
                485                 490                 495

Asn Gly Asn Ile Ile Ser Asn Gln Pro Leu Ser Met Leu Arg Asp Gln
            500                 505                 510

Ala Leu Phe Arg Gly Asn Gln Thr Thr Tyr Asn Leu Cys Ser Asp Val
            515                 520                 525

Trp Met Phe Pro Asn Gln Ile Trp Asp Arg Tyr Pro Ile Thr Arg Glu
530                 535                 540

Asn Pro Ile Trp Cys Lys Lys Pro Arg Ser Asp Lys His Thr Thr Ile
545                 550                 555                 560

Asp Pro Phe Asp Gly Ser Leu Ala Met Asp His Pro Pro Gly Thr Ile
                565                 570                 575

Phe Ile Lys Met Ala Lys Ile Pro Val Pro Ser Asn Asn Asn Ala Asp
            580                 585                 590

Ser Tyr Leu Asn Ile Tyr Cys Thr Gly Gln Val Ser Cys Glu Ile Val
            595                 600                 605

Trp Glu Val Glu Arg Tyr Ala Thr Lys Asn Trp Arg Pro Glu Arg Arg
610                 615                 620

His Thr Thr Phe Gly Leu Gly Ile Gly Gly Ala Asp Asn Leu Asn Pro
625                 630                 635                 640

Thr Tyr His Val Asp Lys Asn Gly Thr Tyr Ile Gln Pro Thr Thr Trp
                645                 650                 655

Asp Met Cys Phe Pro Val Lys Thr Asn Ile Asn Lys Val Leu
            660                 665                 670

<210> SEQ ID NO 29

<211> LENGTH: 776
<212> TYPE: PRT
<213> ORGANISM: Bocavirus

<400> SEQUENCE: 29

```
Met Ala Phe Ser Ala Pro Val Ile Arg Ala Phe Ser Gln Pro Ala Phe
1               5                   10                  15

Thr Tyr Val Val Lys Phe Pro Tyr Glu Asn Trp Lys Glu Glu Glu His
            20                  25                  30

Leu Leu Trp Ser Leu Leu Ala Pro Gly Thr Glu Arg Leu Met Ile Gln
        35                  40                  45

Leu Arg Asn Cys Ala Pro His Pro Glu Asp Asp Pro Val Arg Glu Asp
    50                  55                  60

Ile Leu Cys Ser Leu Ala Asp Gln His Tyr Gly Ala Ile Phe Ala Lys
65                  70                  75                  80

Ala Cys Tyr Ile Ala Thr Thr Thr Leu Met Gly Gln Lys Gln Arg Thr
                85                  90                  95

Pro Phe Pro Arg Cys Asp Ile Ile Cys Gln Ser Glu Ile Gly Ser Glu
            100                 105                 110

His Leu His Cys His Ile Leu Val Gly Gly Ala Gly Leu Ser Lys Arg
        115                 120                 125

Asn Ala Lys Ile Ser Arg Ala Thr Leu Leu Gly Leu Val Met Ala Glu
    130                 135                 140

Leu Thr Gln Arg Cys Lys Gln Leu Leu Ala Leu Arg Pro Phe Glu Pro
145                 150                 155                 160

Ala Glu Ala Asn Ile Phe His Leu Leu Lys Arg Ile Glu Arg Glu Ala
                165                 170                 175

Trp Ser Gly His Thr Gly Asn Trp Val Gln Ile Leu Gln Tyr Lys Asp
            180                 185                 190

Lys Arg Gly Asp Leu His Ala Gln Pro Ile Asp Pro Leu Arg Phe Leu
        195                 200                 205

Lys His Tyr Ile Leu Pro Lys Asn Arg Leu Ile Ser Pro Ser Ser Lys
    210                 215                 220

Pro Asp Val Cys Thr Thr Pro Asp Asn Trp Phe Ile Leu Ala Asp Lys
225                 230                 235                 240

Thr Tyr Ala His Thr Ile Ile Asn Gly Leu Pro Leu Leu Glu His Asn
                245                 250                 255

Arg Lys Ala Tyr Leu Gln Glu Leu Glu Ser Glu Val Ile Pro Gly Pro
            260                 265                 270

Ser Thr Met Ala Phe Gly Gly Arg Gly Ala Trp Glu Gln Leu Pro Glu
        275                 280                 285

Val Gly Glu Gln Arg Leu Ile Thr Ser Asn Ala Ser Thr Ala Tyr Lys
    290                 295                 300

Ala Asn Lys Lys Glu Lys Leu Met Leu Asn Leu Leu Asp Lys Cys Asp
305                 310                 315                 320

Glu Leu Asn Leu Leu Val Tyr Glu Asp Leu Val Ser Ala Cys Pro Asp
                325                 330                 335

Leu Leu Leu Met Leu Glu Gly Gln Pro Gly Gly Ala Arg Leu Ile Glu
            340                 345                 350

Gln Val Leu Gly Met His His Ile Lys Val Cys Ala Lys Tyr Thr Ala
        355                 360                 365

Leu Thr Phe Leu Phe His Leu His Pro Asp Gln Leu Leu Thr Ser Asn
    370                 375                 380

Asn Lys Ala Leu Lys Leu Leu Leu Ile Gln Gly Tyr Asn Pro Leu Gln
385                 390                 395                 400
```

```
Val Gly His Ala Ile Cys Cys Val Leu Asn Lys Gln Met Gly Lys Gln
            405                 410                 415

Asn Thr Ile Cys Phe Tyr Gly Pro Ala Ser Thr Gly Lys Thr Asn Phe
            420                 425                 430

Ala Lys Ala Ile Val Gln Gly Val Arg Leu Tyr Gly Cys Val Asn His
            435                 440                 445

Leu Asn Lys Gly Phe Val Phe Asn Asp Cys Arg Gln Arg Leu Ile Ile
            450                 455                 460

Trp Trp Glu Glu Cys Leu Met His Gln Asp Trp Val Glu Pro Ala Lys
465                 470                 475                 480

Cys Ile Leu Gly Gly Thr Glu Cys Arg Ile Asp Val Lys His Lys Asp
                485                 490                 495

Ser Val Leu Leu Gln Gln Thr Pro Val Ile Ile Ser Thr Asn His Asp
            500                 505                 510

Ile Tyr Ser Val Val Gly Gly Asn Thr Val Ser His Val His Ala Ala
            515                 520                 525

Pro Leu Lys Glu Arg Val Leu Gln Leu Asn Phe Met Lys Gln Leu Pro
            530                 535                 540

Gln Thr Phe Gly Glu Ile Ser Pro Val Glu Ile Ala Glu Leu Leu Gln
545                 550                 555                 560

Trp Cys Phe Asn Glu Tyr Glu Cys Thr Leu Thr Gly Phe Lys Gln Lys
                565                 570                 575

Trp Asn Leu Asp Lys Val Pro Asn Ser Phe Pro Leu Gly Asp Leu Cys
            580                 585                 590

Pro Thr His Ser Gln Asp Tyr Thr Leu His Glu Asn Gly Phe Cys Thr
            595                 600                 605

Asp Cys Gly Gly Tyr Leu Pro His Ser Ala Asp Phe Val Tyr Thr
            610                 615                 620

Asp Val Ala Ser Glu Thr Thr Ser Gly Asp Cys Asp Pro Gly Asn Leu
625                 630                 635                 640

Gly Asp Thr Asp Gly Glu Asp Ser Lys Ser Glu Ala Ser Glu Val Asp
                645                 650                 655

Phe Arg Pro Ser Lys Lys Arg Arg Val Ile Ser Ala Thr Pro Pro Ser
            660                 665                 670

Ser Pro Val Ser Gly Pro Ser Leu Ser Thr Phe Leu Asp Thr Trp Gln
            675                 680                 685

Ser Gln Pro Arg Asp Glu Asp Glu Leu Arg Ile Tyr Glu Glu Gln Ala
            690                 695                 700

Ser Gln Leu Gln Lys Asn Thr Lys Ser Thr Pro Glu Arg Glu Glu Ala
705                 710                 715                 720

Gln Leu Gly Glu Pro Gln Glu Pro Gln Pro Glu Pro Asp Pro Thr Ala
                725                 730                 735

Trp Gly Glu Lys Leu Gly Val Cys Ser Ser Gln Gln Pro Gly Glu Pro
            740                 745                 750

Pro Val Val Leu Tyr Cys Phe Glu Asp Leu Arg Pro Ser Asp Glu Asp
            755                 760                 765

Glu Gly Glu Asn Ile Gly Gly Glu
    770                 775

<210> SEQ ID NO 30
<211> LENGTH: 538
<212> TYPE: PRT
<213> ORGANISM: Bocavirus

<400> SEQUENCE: 30
```

```
Met Ser Glu Asn Glu Ile Gln Asp Gln Gln Pro Ser Gly Ser Met Glu
1               5                   10                  15

Glu Arg Gly Gly Gly Gly Ala Val Gly Ser Val Gly Gly Gly Lys
            20                  25                  30

Gly Ser Ser Val Gly Ile Ser Thr Gly Gly Trp Val Gly Ser Tyr
        35                  40                  45

Phe Thr Asp Ser Tyr Val Ile Thr Lys Asn Thr Arg Gln Phe Leu Val
    50                  55                  60

Lys Ile Gln Asn Asp His Lys Tyr Arg Thr Glu Asn Ile Ile Pro Ser
65                  70                  75                  80

Asn Ala Gly Gly Lys Ser Gln Arg Cys Val Ser Thr Pro Trp Ser Tyr
                85                  90                  95

Phe Asn Phe Asn Gln Tyr Ser Ser His Phe Ser Pro Asp Trp Gln
                100                 105                 110

His Leu Thr Asn Glu Tyr Lys Arg Phe Lys Pro Arg Lys Met His Val
        115                 120                 125

Lys Ile Tyr Asn Leu Gln Ile Lys Gln Ile Leu Ser Asn Gly Ala Asp
        130                 135                 140

Thr Thr Tyr Asn Asn Asp Leu Thr Ala Gly Val His Ile Phe Cys Asp
145                 150                 155                 160

Gly Glu His Ala Tyr Pro Asn Ala Thr His Pro Trp Asp Glu Asp Val
                165                 170                 175

Met Pro Glu Leu Pro Tyr Glu Thr Trp Tyr Leu Phe Gln Tyr Gly Tyr
            180                 185                 190

Ile Pro Val Ile His Glu Leu Ala Glu Met Glu Asp Ala Asn Ala Val
            195                 200                 205

Glu Lys Ala Ile Ala Leu Gln Ile Pro Phe Phe Met Leu Glu Asn Ser
    210                 215                 220

Asp His Glu Val Leu Arg Thr Gly Glu Ser Thr Glu Phe Thr Phe Asp
225                 230                 235                 240

Phe Asp Cys Glu Trp Ile Asn Asn Glu Arg Ala Tyr Ile Pro Pro Gly
            245                 250                 255

Leu Met Phe Asn Pro Lys Val Pro Thr Arg Arg Ala Gln Tyr Ile Arg
            260                 265                 270

Gln His Gly Asn Thr Ala Ser Ser Asn Thr Arg Ile Gln Pro Tyr Ala
    275                 280                 285

Lys Pro Thr Ser Trp Met Thr Gly Pro Gly Leu Leu Ser Ala Gln Arg
    290                 295                 300

Val Gly Pro Ala Gly Ser Asp Thr Ala Ser Trp Met Val Val Val Asn
305                 310                 315                 320

Pro Asp Gly Ala Ala Val Asn Ser Gly Met Ala Gly Val Gly Ser Gly
                325                 330                 335

Phe Asp Pro Pro Ser Gly Ser Leu Arg Pro Thr Asp Leu Glu Tyr Lys
            340                 345                 350

Ile Gln Trp Tyr Gln Thr Pro Ala Gly Thr Asn Ser Asp Gly Asn Ile
        355                 360                 365

Ile Ser Asn Pro Pro Leu Ser Met Leu Arg Asp Gln Ala Leu Tyr Arg
        370                 375                 380

Gly Asn Gln Thr Thr Tyr Asn Leu Cys Ser Asp Val Trp Met Phe Pro
385                 390                 395                 400

Asn Gln Ile Trp Asp Arg Tyr Pro Ile Thr Arg Glu Asn Pro Ile Trp
                405                 410                 415

Cys Lys Lys Pro Arg Ser Asp Lys Asn Thr Ile Ile Asp Pro Phe Asp
```

-continued

```
                420             425             430
Gly Thr Leu Ala Met Asp His Pro Pro Gly Thr Ile Phe Ile Lys Met
            435                 440                 445
Ala Lys Ile Pro Val Pro Ser Asn Asn Asn Ala Asp Ser Tyr Leu Asn
        450                 455                 460
Ile Tyr Cys Thr Gly Gln Val Ser Cys Glu Ile Val Trp Glu Val Glu
465                 470                 475                 480
Arg Tyr Ala Thr Lys Asn Trp Arg Pro Glu Arg His Thr Ala Leu
                485                 490                 495
Gly Leu Gly Ile Gly Gly Glu Glu Asn Val Asn Pro Thr Tyr His Val
            500                 505                 510
Asp Lys Asn Gly Lys Tyr Ile Gln Pro Thr Thr Trp Asp Met Cys Tyr
        515                 520                 525
Pro Ile Lys Thr Asn Ile Asn Lys Val Leu
        530                 535

<210> SEQ ID NO 31
<211> LENGTH: 780
<212> TYPE: PRT
<213> ORGANISM: Bocavirus

<400> SEQUENCE: 31

Met Ala Phe Asn Pro Pro Val Ile Arg Ala Phe Ser Ser Pro Ala Phe
1               5                   10                  15
Thr Tyr Val Phe Lys Phe Pro Tyr Pro Ser Trp Lys Glu Lys Glu Trp
            20                  25                  30
Leu Leu His Ala Leu Leu Ala His Gly Thr Glu Gln Ala Met Ile Gln
        35                  40                  45
Leu Arg Asn Cys Val Pro His Pro Asp Glu Asp Ile Ile Arg Asp Asp
    50                  55                  60
Leu Leu Leu Ser Leu Glu Asp Arg His Phe Gly Ala Ile Leu Cys Lys
65                  70                  75                  80
Ala Val Tyr Met Ala Thr Thr Thr Phe Met Ser Gln Lys Gln Arg Asn
                85                  90                  95
Met Phe Pro Arg Cys Asp Ile Ile Val Gln Ser Glu Leu Gly Glu Thr
            100                 105                 110
Asn Leu His Cys His Ile Ile Val Gly Gly Glu Gly Leu Ser Lys Arg
        115                 120                 125
Asn Ala Lys Thr Ser Cys Pro Gln Leu Tyr Gly Leu Ile Leu Gly Glu
    130                 135                 140
Leu Ile Gln Arg Cys Lys Thr Leu Leu Ala Thr Arg Pro Phe Glu Pro
145                 150                 155                 160
Glu Glu Ala Glu Ile Tyr His Ala Leu Lys Arg Ala Glu Arg Glu Ala
                165                 170                 175
Trp Gly Gly Val Thr Ser Gly Asn Leu Gln Ile Leu Gln Tyr Arg Asp
            180                 185                 190
Arg Arg Gly Asp Leu His Ala Gln Gln Val Asp Ala Leu Arg Phe Phe
        195                 200                 205
Lys Asn Tyr Leu Leu Pro Lys Asn Arg Cys Ile Thr Ser Tyr Ser Arg
    210                 215                 220
Pro Asp Val Cys Thr Ser Pro Glu Asn Trp Phe Val Leu Ala Glu Lys
225                 230                 235                 240
Thr Tyr Cys His Thr Leu Val Asn Gly Leu Pro Leu Pro Glu His Tyr
                245                 250                 255
Arg Lys His Tyr His Ala Thr Leu Asp Asn Glu Val Leu Pro Gly Pro
```

```
              260                 265                 270
Gln Thr Met Ala Phe Gly Gly Arg Gly Pro Trp Glu His Leu Pro Glu
        275                 280                 285

Val Gly Asp Gln Arg Leu Ala Ala Ser Ser Val Ser Thr Thr Tyr Lys
        290                 295                 300

Pro Asn Lys Lys Glu Lys Leu Met Leu Asn Leu Leu Asp Lys Cys Ser
305                 310                 315                 320

Glu Leu Asn Leu Leu Val Tyr Glu Asp Leu Val Ala Asn Cys Pro Glu
                325                 330                 335

Leu Leu Leu Met Leu Glu Gly Gln Pro Gly Gly Ala Arg Leu Ile Glu
            340                 345                 350

Gln Val Leu Gly Met His His Ile Asn Val Cys Ser Asn Phe Thr Ala
            355                 360                 365

Leu Ser Tyr Leu Phe His Leu Tyr Pro Gly Thr Thr Leu Ser Ser Asp
        370                 375                 380

Asn Lys Ala Leu Gln Leu Leu Ile Gln Gly Tyr Asn Pro Leu Met
385                 390                 395                 400

Val Gly His Ala Leu Cys Cys Val Leu Asn Lys Gln Phe Gly Lys Gln
                405                 410                 415

Asn Thr Val Cys Phe Tyr Gly Pro Ala Ser Thr Gly Lys Thr Asn Met
                420                 425                 430

Ala Lys Ala Ile Val Gln Gly Ile Arg Leu Tyr Gly Cys Val Asn His
            435                 440                 445

Leu Asn Lys Gly Phe Val Phe Asn Asp Cys Arg Gln Arg Leu Val Val
        450                 455                 460

Trp Trp Glu Glu Cys Leu Met His Gln Asp Trp Val Glu Pro Ala Lys
465                 470                 475                 480

Cys Ile Leu Gly Gly Thr Glu Cys Arg Ile Asp Val Lys His Arg Asp
                485                 490                 495

Ser Val Leu Leu Thr Gln Thr Pro Val Ile Ile Ser Thr Asn His Asp
            500                 505                 510

Ile Tyr Ala Val Val Gly Gly Asn Ser Val Ser His Val His Ala Ala
            515                 520                 525

Pro Leu Lys Glu Arg Val Ile Gln Leu Asn Phe Met Lys Gln Leu Pro
        530                 535                 540

Gln Thr Phe Gly Glu Ile Thr Pro Glu Glu Ile Ala Ala Leu Leu Gln
545                 550                 555                 560

Trp Cys Phe Asn Glu Tyr Glu Cys Thr Leu Thr Gly Phe Lys Thr Lys
                565                 570                 575

Trp Ser Leu Asp Lys Ile Pro Asn Ser Phe Pro Leu Gly Val Leu Cys
            580                 585                 590

Pro Thr His Ser Gln Asp Phe Ile Leu His Glu Asn Gly Tyr Cys Thr
        595                 600                 605

Asp Cys Gly Gly Tyr Leu Ala His Ser Ala Asp Ser Val Tyr Thr
        610                 615                 620

Asp Arg Ala Ser Asp Thr Ser Lys Glu Ala Ile Asp Ala Gly Asp Leu
625                 630                 635                 640

Gly Asp Thr Asp Gly Glu Asp Ser Glu Ser Glu Ala Ser Glu Val Gly
                645                 650                 655

Val Arg Pro Ser Lys Lys Arg Arg Ile Thr Ile Pro Ala Thr Pro Pro
            660                 665                 670

Asn Ser Pro Gly Ser Ser Val Ser Thr Ser Ala Phe Phe Asp Asn Trp
        675                 680                 685
```

```
Cys Ala Gln Pro Arg Asp Glu Asp Glu Leu Arg Glu Tyr Glu Arg Gln
690                 695                 700

Ala Ser Arg Leu Gln Lys Lys Arg Glu Ser Arg Glu Arg Glu
705                 710                 715                 720

Thr Pro Met Ala Thr Ser Ser Gln Glu Ser Glu Ser Glu Pro Asn Pro
                    725                 730                 735

Thr Gln Trp Gly Asp Lys Leu Gly Val Ile Pro Ser Gly Thr Pro Asp
            740                 745                 750

Gln Pro Pro Ile Val Leu His Cys Phe Glu Asp Leu Arg Pro Ser Asp
                755                 760                 765

Glu Asp Glu Gly Glu Tyr Ile Gly Lys Glu Arg Leu
770                 775                 780

<210> SEQ ID NO 32
<211> LENGTH: 539
<212> TYPE: PRT
<213> ORGANISM: Bocavirus

<400> SEQUENCE: 32

Met Ser Glu Asn Glu Ile Gln Asp Gln Gln Pro Ser Glu Pro Asn Asp
1               5                   10                  15

Gly Gln Arg Gly Gly Gly Gly Ala Thr Gly Ser Val Gly Gly Gly
                20                  25                  30

Lys Gly Ser Gly Val Gly Ile Ser Thr Gly Gly Trp Val Gly Gly Ser
                35                  40                  45

Tyr Phe Thr Asp Ser Tyr Val Ile Thr Lys Asn Thr Arg Gln Phe Leu
            50                  55                  60

Val Lys Ile Gln Asn Asn His Gln Tyr Lys Thr Glu Asn Ile Ile Pro
65              70                  75                  80

Ser Asn Gly Gly Gly Lys Ser Gln Arg Cys Val Ser Thr Pro Trp Ser
                85                  90                  95

Tyr Phe Asn Phe Asn Gln Tyr Ser Ser His Phe Ser Pro Gln Asp Trp
                100                 105                 110

Gln Arg Leu Thr Asn Glu Tyr Lys Arg Phe Arg Pro Lys Gly Met His
            115                 120                 125

Val Lys Ile Tyr Asn Leu Gln Ile Lys Gln Ile Leu Ser Asn Gly Ala
130                 135                 140

Asp Val Thr Tyr Asn Asn Asp Leu Thr Ala Gly Val His Ile Phe Cys
145                 150                 155                 160

Asp Gly Glu His Ala Tyr Pro Asn Ala Thr His Pro Trp Asp Glu Asp
                165                 170                 175

Val Met Pro Glu Leu Pro Tyr Gln Thr Trp Tyr Leu Phe Gln Tyr Gly
            180                 185                 190

Tyr Ile Pro Thr Ile His Glu Leu Ala Glu Met Glu Asp Ser Asn Ala
        195                 200                 205

Val Glu Lys Ala Ile Ala Leu Gln Ile Pro Phe Phe Met Leu Glu Asn
210                 215                 220

Ser Asp His Glu Val Leu Arg Thr Gly Glu Ser Ala Glu Phe Asn Phe
225                 230                 235                 240

Asn Phe Asp Cys Glu Trp Ile Asn Asn Glu Arg Ala Phe Ile Pro Pro
                245                 250                 255

Gly Leu Met Phe Asn Pro Leu Val Pro Thr Arg Arg Ala Gln Tyr Ile
            260                 265                 270

Arg Arg Asn Gly Asn Thr Gln Ala Ser Thr Ser Arg Ile Gln Pro Tyr
        275                 280                 285
```

```
Ala Lys Pro Thr Ser Trp Met Thr Gly Pro Gly Leu Leu Ser Ala Gln
    290                 295                 300

Arg Val Gly Pro Ala Ala Ser Asp Thr Ala Ala Trp Met Val Gly Val
305                 310                 315                 320

Asp Pro Glu Gly Ala Asn Ile Asn Ser Gly Arg Ala Gly Val Ser Ser
                325                 330                 335

Gly Phe Asp Pro Pro Ala Gly Ser Leu Arg Pro Thr Asp Leu Glu Tyr
            340                 345                 350

Lys Val Gln Trp Tyr Gln Thr Pro Ala Gly Thr Asn Asn Asp Gly Asn
        355                 360                 365

Ile Ile Ser Asn Pro Pro Leu Ser Met Leu Arg Asp Gln Thr Leu Tyr
    370                 375                 380

Arg Gly Asn Gln Thr Thr Tyr Asn Leu Cys Ser Asp Val Trp Met Phe
385                 390                 395                 400

Pro Asn Gln Ile Trp Asp Arg Tyr Pro Val Thr Arg Glu Asn Pro Ile
                405                 410                 415

Trp Cys Lys Gln Pro Arg Ser Asp Lys His Thr Thr Ile Asp Pro Phe
            420                 425                 430

Asp Gly Ser Ile Ala Met Asp His Pro Pro Gly Thr Ile Phe Ile Lys
        435                 440                 445

Met Ala Lys Ile Pro Val Pro Ser Asn Asn Ala Asp Ser Tyr Leu
    450                 455                 460

Asn Ile Tyr Cys Thr Gly Gln Val Ser Cys Glu Ile Val Trp Glu Val
465                 470                 475                 480

Glu Arg Tyr Ala Thr Lys Asn Trp Arg Pro Gly Arg Arg His Thr Ala
                485                 490                 495

Leu Gly Leu Gly Ile Gly Gly Ala Asp Glu Ile Asn Pro Thr Tyr His
            500                 505                 510

Val Asp Lys Asn Gly Ala Tyr Ile Gln Pro Thr Thr Trp Asp Met Cys
        515                 520                 525

Phe Pro Val Lys Thr Asn Ile Asn Lys Val Leu
    530                 535

<210> SEQ ID NO 33
<211> LENGTH: 777
<212> TYPE: PRT
<213> ORGANISM: Bocavirus

<400> SEQUENCE: 33

Met Ala Phe Ser Ala Pro Val Ile Arg Ala Phe Ser Gln Pro Ala Phe
1               5                   10                  15

Thr Tyr Val Val Lys Phe Pro Tyr Asp Asn Trp Lys Glu Glu His
            20                  25                  30

Leu Leu Trp Ser Leu Leu Ala Pro Gly Thr Glu Arg Leu Met Ile Gln
        35                  40                  45

Leu Arg Asn Cys Ala Pro His Pro Glu Asp Pro Val Arg Glu Asp
    50                  55                  60

Ile Leu Cys Ser Leu Ala Asp Gln His Tyr Ala Ala Ile Phe Thr Lys
65                  70                  75                  80

Ala Cys Tyr Met Ala Val Thr Ser Leu Met Gly Gln Lys Gln Arg Thr
                85                  90                  95

His Phe Pro Arg Cys Asp Ile Ile Cys Gln Ala Glu Ile Gly Ser Glu
            100                 105                 110

Tyr Leu His Cys His Ile Leu Val Gly Gly Ala Gly Leu Ser Lys Arg
        115                 120                 125
```

-continued

```
Asn Ala Lys Ile Ser Cys Ala Thr Leu Leu Gly Leu Val Met Ala Glu
130                 135                 140

Leu Thr Gln Arg Cys Lys Leu Leu Leu Thr Gln Arg Pro Phe Glu Pro
145                 150                 155                 160

Asp Glu Ala Arg Ile Phe His Leu Leu Arg Arg Val Glu Arg Glu Ala
                    165                 170                 175

Trp Ser Gly His Thr Gly Asn Trp Val Gln Ile Leu Gln Tyr Arg Asp
                    180                 185                 190

Lys Arg Gly Asp Leu His Ala Gln His Ile Asp Pro Leu Arg Phe Phe
                195                 200                 205

Lys His Tyr Leu Leu Pro Lys Asn Arg Leu Ile Ser Pro Ser Ser Lys
210                 215                 220

Pro Asp Val Cys Thr Thr Pro Asp Asn Trp Phe Val Leu Ala Asp Lys
225                 230                 235                 240

Thr Tyr Ala His Thr Ile Val Asn Gly Leu Pro Leu Leu Glu His Asn
                    245                 250                 255

Arg Lys Ala Tyr Leu Gln Glu Leu Glu Ser Glu Val Ile Pro Gly Pro
                260                 265                 270

Ser Thr Met Ala Phe Gly Gly Arg Gly Ala Trp Glu His Leu Pro Glu
            275                 280                 285

Val Gly Glu Gln Arg Leu Ile Thr Ser Asn Thr Ser Thr Ala Tyr Lys
        290                 295                 300

Ala Asn Lys Lys Glu Lys Leu Met Leu Asn Leu Leu Asp Lys Cys Asp
305                 310                 315                 320

Glu Leu Asn Leu Leu Val Tyr Glu Asp Leu Val Ser Ala Cys Pro Asp
                    325                 330                 335

Leu Leu Leu Met Leu Glu Gly Gln Pro Gly Gly Ala Arg Leu Ile Glu
                340                 345                 350

Gln Val Leu Gly Met His His Ile Lys Val Cys Ala Asn Tyr Thr Ala
                355                 360                 365

Leu Ser Phe Leu Phe His Leu His Pro Asn Gln Leu Leu Thr Ser Ser
            370                 375                 380

Asn Lys Ala Leu Lys Leu Leu Ile Gln Gly Tyr Asn Pro Leu Gln
385                 390                 395                 400

Val Gly His Ala Ile Cys Cys Val Leu Asn Lys Gln Met Gly Lys Gln
                    405                 410                 415

Asn Thr Ile Cys Phe Tyr Gly Pro Ala Ser Thr Gly Lys Thr Asn Ile
                420                 425                 430

Ala Lys Ala Ile Val Gln Gly Val Arg Leu Tyr Gly Cys Val Asn His
                435                 440                 445

Leu Asn Lys Gly Phe Val Phe Asn Asp Cys Arg Gln Arg Leu Ile Ile
450                 455                 460

Trp Trp Glu Glu Cys Leu Met His Gln Asp Trp Val Glu Pro Ala Lys
465                 470                 475                 480

Cys Ile Leu Gly Gly Thr Glu Cys Arg Ile Asp Val Lys His Lys Asp
                485                 490                 495

Ser Val Leu Leu Gln Thr Pro Val Ile Ile Ser Thr Asn His Asp
            500                 505                 510

Ile Tyr Ser Val Val Gly Gly Asn Thr Val Ser His Val His Ala Ala
            515                 520                 525

Pro Leu Lys Glu Arg Ile Leu Gln Leu Asn Phe Met Lys Gln Leu Pro
            530                 535                 540

Gln Thr Phe Gly Glu Ile Ser Pro Val Glu Ile Ala Glu Leu Leu Gln
545                 550                 555                 560
```

```
Trp Cys Phe Asn Glu Tyr Glu Cys Thr Leu Thr Gly Phe Lys Gln Lys
                565                 570                 575

Trp Asn Leu Asp Lys Val Pro Asn Ser Phe Pro Leu Gly Asp Leu Cys
            580                 585                 590

Pro Thr His Ser Gln Asp Tyr Val Leu His Glu Asn Gly Phe Cys Thr
        595                 600                 605

Asp Cys Gly Gly Tyr Ile Pro His Ser Ala Asp Asp Ser Val Tyr Thr
    610                 615                 620

Asp Val Ala Ser Glu Thr Ser Ile Ser Ser Cys Asp Pro Gly Asp Leu
625                 630                 635                 640

Gly Asp Thr Asp Gly Glu Asn Ser Gln Pro Glu Thr Ser Asn Val Asp
                645                 650                 655

Asn Arg Pro Ser Lys Lys Arg Val Ile Pro Glu Thr Pro Pro Asn
            660                 665                 670

Ser Pro Val Ser Arg Gln Ser Leu Ser Ser Phe Leu Asp Thr Trp Gln
        675                 680                 685

Ser Gln Pro Arg Asp Glu Asp Glu Leu Arg Ile Tyr Glu Ala Gln Ala
    690                 695                 700

Ser Arg Ile Lys Glu Asn Thr Glu Ser Thr Pro Glu Arg Glu Lys Thr
705                 710                 715                 720

Pro Val Gly Glu Pro Gln Glu Glu Ser Gln Ala Glu Pro Asp Pro Thr
                725                 730                 735

Ala Trp Gly Glu Lys Leu Gly Val Tyr Ser Ser Leu Gln Pro Gly Glu
            740                 745                 750

Pro Pro Ile Val Leu His Cys Phe Glu Asp Leu Arg Pro Ser Asp Glu
        755                 760                 765

Asp Glu Gly Glu Asn Ile Gly Gly Glu
    770                 775

<210> SEQ ID NO 34
<211> LENGTH: 539
<212> TYPE: PRT
<213> ORGANISM: Bocavirus

<400> SEQUENCE: 34

Met Ser Glu Asn Glu Ile Gln Asp Gln Pro Ser Gly Ser Met Asp
1               5                   10                  15

Glu Gln Arg Gly Gly Gly Gly Ala Val Gly Ser Val Gly Gly Gly
                20                  25                  30

Lys Gly Ser Gly Val Gly Ile Ser Thr Gly Gly Trp Val Gly Gly Ser
            35                  40                  45

Tyr Phe Thr Asp Ser Tyr Val Ile Thr Lys Asn Thr Arg Gln Phe Leu
    50                  55                  60

Val Lys Ile Gln Asn Asp His Lys Tyr Arg Thr Glu Asn Ile Ile Pro
65                  70                  75                  80

Ser Asn Ala Gly Gly Lys Ser Gln Arg Cys Val Ser Thr Pro Trp Ser
                85                  90                  95

Tyr Phe Asn Phe Asn Gln Tyr Ser Ser His Phe Ser Pro Gln Asp Trp
            100                 105                 110

Gln Arg Leu Thr Asn Glu Tyr Lys Arg Phe Lys Pro Arg Lys Met His
        115                 120                 125

Val Lys Ile Tyr Asn Leu Gln Ile Lys Gln Ile Leu Ser Asn Gly Ala
    130                 135                 140

Asp Thr Thr Tyr Asn Asn Asp Leu Thr Ala Gly Val His Ile Phe Cys
145                 150                 155                 160
```

Asp Gly Glu His Ala Tyr Pro Asn Ala Thr His Pro Trp Asp Glu Asp
            165                 170                 175

Val Met Pro Glu Leu Pro Tyr Glu Thr Trp Tyr Leu Phe Gln Tyr Gly
            180                 185                 190

Tyr Ile Pro Val Ile His Glu Leu Ala Glu Met Glu Asp Ala Asn Ala
            195                 200                 205

Val Glu Lys Ala Ile Ala Leu Gln Ile Pro Phe Phe Met Leu Glu Asn
            210                 215                 220

Ser Asp His Glu Val Leu Arg Thr Gly Glu Ser Thr Glu Phe Thr Phe
225                 230                 235                 240

Asp Phe Asp Cys Glu Trp Ile Asn Asn Glu Arg Ala Tyr Ile Pro Pro
            245                 250                 255

Gly Leu Met Phe Asn Pro Lys Val Pro Thr Arg Arg Ala Gln Tyr Ile
            260                 265                 270

Arg Gln His Gly Asn Thr Ala Ser Ser Asn Thr Arg Ile Gln Pro Tyr
            275                 280                 285

Ala Lys Pro Thr Ser Trp Met Thr Gly Pro Gly Leu Leu Ser Ala Gln
            290                 295                 300

Arg Val Gly Pro Ala Gly Ser Asp Thr Ala Ser Trp Met Val Val Val
305                 310                 315                 320

Asn Pro Asp Gly Thr Ala Val Asn Ser Gly Met Ala Gly Val Gly Ser
            325                 330                 335

Gly Phe Asp Pro Pro Ser Gly Ser Leu Arg Pro Thr Asp Leu Glu Tyr
            340                 345                 350

Lys Ile Gln Trp Tyr Gln Thr Pro Glu Gly Thr Asn Ser Asp Gly Asn
            355                 360                 365

Ile Ile Ser Asn Pro Pro Leu Ser Met Leu Arg Asp Gln Ala Leu Tyr
            370                 375                 380

Arg Gly Asn Gln Thr Thr Tyr Asn Leu Cys Ser Asp Val Trp Met Phe
385                 390                 395                 400

Pro Asn Gln Ile Trp Asp Arg Tyr Pro Ile Thr Arg Glu Asn Pro Ile
            405                 410                 415

Trp Cys Lys Lys Pro Arg Ser Asp Lys Ser Thr Val Ile Asp Pro Phe
            420                 425                 430

Asp Gly Thr Leu Ala Met Asp His Pro Pro Gly Thr Ile Phe Ile Lys
            435                 440                 445

Met Ala Lys Ile Pro Val Pro Ser Asn Asn Ala Asp Ser Tyr Leu
450                 455                 460

Asn Ile Tyr Cys Thr Gly Gln Val Ser Cys Glu Ile Val Trp Glu Val
465                 470                 475                 480

Glu Arg Tyr Ala Thr Lys Asn Trp Arg Pro Glu Arg Arg His Thr Ala
            485                 490                 495

Leu Gly Leu Gly Ile Gly Gly Glu Asn Ile Asn Pro Thr Tyr His
            500                 505                 510

Val Asp Lys Asn Gly Lys Tyr Ile Gln Pro Thr Thr Trp Asp Met Cys
            515                 520                 525

Tyr Pro Ile Lys Thr Asn Ile Asn Lys Val Leu
            530                 535

<210> SEQ ID NO 35
<211> LENGTH: 777
<212> TYPE: PRT
<213> ORGANISM: Bocavirus

<400> SEQUENCE: 35

```
Met Ala Phe Ser Ala Pro Val Ile Arg Ala Phe Ser Gln Pro Ala Phe
1               5                   10                  15

Thr Tyr Val Val Lys Phe Pro Tyr Asp Asn Trp Lys Glu Glu Glu His
                20                  25                  30

Leu Leu Trp Ser Leu Leu Ala Pro Gly Thr Glu Arg Leu Met Ile Gln
            35                  40                  45

Leu Arg Asn Cys Ala Pro His Pro Glu Asp Asp Pro Val Arg Glu Asp
        50                  55                  60

Ile Leu Cys Ser Leu Ala Asp Gln His Tyr Ala Ala Ile Phe Thr Lys
65                  70                  75                  80

Ala Cys Tyr Met Ala Val Thr Ser Leu Met Gly Gln Lys Gln Arg Thr
                85                  90                  95

His Phe Pro Arg Cys Asp Ile Ile Cys Gln Ala Glu Ile Gly Ser Glu
                100                 105                 110

Tyr Leu His Cys His Ile Leu Val Gly Gly Ala Gly Leu Ser Lys Arg
            115                 120                 125

Asn Ala Lys Ile Ser Cys Ala Thr Leu Leu Gly Leu Val Met Ala Glu
        130                 135                 140

Leu Thr Gln Arg Cys Lys Leu Leu Leu Ala Gln Arg Pro Phe Glu Pro
145                 150                 155                 160

Asp Glu Ala Arg Ile Phe His Leu Leu Arg Arg Val Glu Arg Glu Ala
                165                 170                 175

Trp Ser Gly His Thr Gly Asn Trp Val Gln Ile Leu Gln Tyr Arg Asp
            180                 185                 190

Lys Arg Gly Asp Leu His Ala Gln His Ile Asp Pro Leu Arg Phe Phe
        195                 200                 205

Lys His Tyr Leu Leu Pro Lys Asn Arg Leu Ile Ser Pro Ser Ser Lys
            210                 215                 220

Pro Asp Val Cys Thr Thr Pro Asp Asn Trp Phe Val Leu Ala Glu Lys
225                 230                 235                 240

Thr Tyr Ala His Thr Ile Val Asn Gly Leu Pro Leu Leu Glu His Asn
                245                 250                 255

Arg Lys Ala Tyr Leu Gln Glu Leu Glu Ser Glu Val Ile Pro Gly Pro
            260                 265                 270

Ser Thr Met Ala Phe Gly Gly Arg Gly Ala Trp Glu His Leu Pro Glu
        275                 280                 285

Val Gly Glu Gln Arg Leu Ile Thr Ser Asn Thr Ser Thr Ala Tyr Lys
            290                 295                 300

Ala Asn Lys Lys Glu Lys Leu Met Leu Asn Leu Leu Asp Lys Cys Asp
305                 310                 315                 320

Glu Leu Asn Leu Leu Val Tyr Glu Asp Leu Val Ser Ala Cys Pro Asp
                325                 330                 335

Leu Leu Leu Met Leu Glu Gly Gln Pro Gly Gly Ala Arg Leu Ile Glu
            340                 345                 350

Gln Val Leu Gly Met His His Ile Lys Val Cys Ala Asn Tyr Thr Ala
        355                 360                 365

Leu Ser Phe Leu Phe His Leu His Pro Asp Gln Leu Leu Thr Ser Ser
    370                 375                 380

Asn Lys Ala Leu Lys Leu Leu Ile Gln Gly Tyr Asn Pro Leu Gln
385                 390                 395                 400

Val Gly His Ala Ile Cys Cys Val Leu Asn Lys Gln Met Gly Lys Gln
                405                 410                 415

Asn Thr Ile Cys Phe Tyr Gly Pro Ala Ser Thr Gly Lys Thr Asn Ile
```

```
                420               425               430
Ala Lys Ala Ile Val Gln Gly Val Arg Leu Tyr Gly Cys Val Asn His
        435               440               445
Leu Asn Lys Gly Phe Val Phe Asn Asp Cys Arg Gln Arg Leu Ile Ile
    450               455               460
Trp Trp Glu Glu Cys Leu Met His Gln Asp Trp Val Glu Pro Ala Lys
465               470               475               480
Cys Ile Leu Gly Gly Thr Glu Cys Arg Ile Asp Val Lys His Lys Asp
            485               490               495
Ser Val Leu Leu Gln Gln Thr Pro Val Ile Ile Ser Thr Asn His Asp
        500               505               510
Ile Tyr Ser Val Val Gly Gly Asn Thr Val Ser His Val His Ala Ala
            515               520               525
Pro Leu Lys Glu Arg Ile Leu Gln Leu Asn Phe Met Lys Gln Leu Pro
        530               535               540
Gln Thr Phe Gly Glu Ile Ser Pro Val Glu Ile Ala Glu Leu Leu Gln
545               550               555               560
Trp Cys Phe Asn Glu Tyr Asp Cys Thr Leu Thr Gly Phe Lys Gln Lys
            565               570               575
Trp Asn Leu Asp Lys Val Pro Asn Ser Phe Pro Leu Gly Asp Leu Cys
        580               585               590
Pro Thr His Ser Gln Asp Tyr Val Leu His Glu Asn Gly Phe Cys Thr
        595               600               605
Asp Cys Gly Gly Tyr Ile Pro His Ser Ala Asp Asp Ser Val Tyr Thr
    610               615               620
Asp Val Ala Ser Glu Thr Ser Ile Ser Ser Asp Pro Gly Asp Leu
625               630               635               640
Gly Asp Thr Asp Gly Glu Asn Ser Gln Pro Glu Thr Ser Asn Val Asp
            645               650               655
Asn Arg Pro Ser Lys Lys Arg Arg Val Ile Pro Glu Thr Pro Pro Asn
            660               665               670
Ser Pro Val Ser Arg Gln Ser Leu Ser Ser Phe Leu Asp Thr Trp Gln
        675               680               685
Ser Gln Pro Arg Asp Glu Asp Glu Leu Arg Ile Tyr Glu Ala Gln Ala
        690               695               700
Ser Arg Ile Lys Glu Asn Ala Glu Ser Thr Pro Glu Arg Glu Lys Thr
705               710               715               720
Pro Val Gly Glu Pro Gln Glu Glu Ser Gln Ser Glu Pro Asp Pro Thr
            725               730               735
Ala Trp Gly Glu Lys Leu Gly Val Tyr Ser Ser Leu Gln Pro Gly Glu
            740               745               750
Pro Pro Ile Val Leu His Cys Phe Glu Asp Leu Arg Pro Ser Asp Glu
        755               760               765
Asp Glu Gly Glu Asn Ile Gly Gly Glu
        770               775

<210> SEQ ID NO 36
<211> LENGTH: 539
<212> TYPE: PRT
<213> ORGANISM: Bocavirus

<400> SEQUENCE: 36

Met Ser Glu Asn Glu Ile Gln Asp Gln Gln Pro Ser Asp Ser Met Asp
1               5                   10                  15

Gly Gln Arg Gly Gly Gly Gly Gly Ala Thr Gly Ser Val Gly Gly Gly
```

-continued

```
                20                  25                  30
Lys Gly Ser Gly Val Gly Ile Ser Thr Gly Trp Val Gly Gly Ser
             35                  40                  45

Tyr Phe Thr Asp Ser Tyr Val Ile Thr Lys Asn Thr Arg Gln Phe Leu
 50                  55                  60

Val Lys Ile Gln Asn Asp His Lys Tyr Arg Thr Glu Asn Ile Ile Pro
 65                  70                  75                  80

Ser Asn Ala Gly Gly Lys Ser Gln Arg Cys Val Ser Thr Pro Trp Ser
                 85                  90                  95

Tyr Phe Asn Phe Asn Gln Tyr Ser Ser His Phe Ser Pro Gln Asp Trp
            100                 105                 110

Gln Arg Leu Thr Asn Glu Tyr Lys Arg Phe Lys Pro Arg Lys Met His
            115                 120                 125

Val Lys Ile Tyr Asn Leu Gln Ile Lys Gln Ile Leu Ser Asn Gly Ala
            130                 135                 140

Asp Thr Thr Tyr Asn Asn Asp Leu Thr Ala Gly Val His Ile Phe Cys
145                 150                 155                 160

Asp Gly Glu His Ala Tyr Pro Asn Ala Thr His Pro Trp Asp Glu Asp
                165                 170                 175

Val Met Pro Glu Leu Pro Tyr Glu Thr Trp Tyr Leu Phe Gln Tyr Gly
            180                 185                 190

Tyr Ile Pro Val Ile His Glu Leu Ala Glu Met Glu Asp Ala Asn Ala
            195                 200                 205

Val Glu Lys Ala Ile Ala Leu Gln Ile Pro Phe Phe Met Leu Glu Asn
            210                 215                 220

Ser Asp His Glu Val Leu Arg Thr Gly Glu Ser Thr Glu Phe Thr Phe
225                 230                 235                 240

Asp Phe Asp Cys Glu Trp Ile Asn Asn Glu Arg Ala Tyr Ile Pro Pro
                245                 250                 255

Gly Leu Met Phe Asn Pro Lys Val Pro Thr Arg Arg Ala Gln Tyr Ile
            260                 265                 270

Arg Gln His Gly Ser Thr Ala Ser Ser Asn Thr Arg Ile Pro Pro Tyr
            275                 280                 285

Ala Lys Pro Thr Ser Trp Met Thr Gly Pro Gly Leu Leu Ser Ala Gln
            290                 295                 300

Arg Val Gly Pro Ala Ala Ser Asp Ser Ala Ala Trp Met Val Val Val
305                 310                 315                 320

Asn Pro Asp Gly Ala Ala Ile Asn Ser Gly Met Ala Gly Ile Gly Thr
                325                 330                 335

Gly Phe Asp Pro Pro Gly Gly Ser Leu Arg Pro Thr Asp Leu Glu Tyr
            340                 345                 350

Lys Ile Gln Trp Tyr Gln Thr Pro Ala Gly Thr Asn Ser Asp Gly Asn
            355                 360                 365

Ile Ile Ser Asn Pro Ser Leu Ser Met Leu Arg Asp Gln Ala Leu Tyr
            370                 375                 380

Arg Gly Asn Gln Thr Thr Tyr Asn Leu Cys Ser Asp Val Trp Met Phe
385                 390                 395                 400

Pro Asn Gln Ile Trp Asp Arg Tyr Pro Ile Thr Arg Glu Asn Pro Ile
                405                 410                 415

Trp Cys Lys Lys Pro Arg Ser Asp Lys Ser Thr Ile Ile Asp Pro Phe
            420                 425                 430

Asp Gly Ser Ile Ala Met Asp His Pro Pro Gly Thr Ile Phe Ile Lys
            435                 440                 445
```

Met Ala Lys Ile Pro Val Pro Ser Asn Asn Ala Asp Ser Tyr Leu
            450             455                 460

Asn Ile Tyr Cys Thr Gly Gln Val Ser Cys Glu Ile Val Trp Glu Val
465             470                 475                 480

Glu Arg Tyr Ala Thr Lys Asn Trp Arg Pro Glu Arg Arg His Thr Ala
                485                 490                 495

Leu Gly Leu Gly Ile Gly Gly Glu Asn Val Asn Pro Thr Tyr His
            500                 505                 510

Val Asp Lys Asn Gly Lys Tyr Ile Gln Pro Thr Thr Trp Asp Met Cys
            515                 520                 525

Tyr Pro Ile Lys Thr Asn Ile Asn Lys Val Leu
            530                 535

<210> SEQ ID NO 37
<211> LENGTH: 777
<212> TYPE: PRT
<213> ORGANISM: Bocavirus

<400> SEQUENCE: 37

Met Ala Phe Ser Ala Pro Val Ile Arg Ala Phe Ser Gln Pro Ala Phe
1               5                   10                  15

Thr Tyr Val Val Lys Phe Pro Tyr Asp Asn Trp Lys Glu Glu His
            20                  25                  30

Leu Leu Trp Ser Leu Leu Ala Pro Gly Thr Glu Arg Leu Met Ile Gln
            35                  40                  45

Leu Arg Asn Cys Ala Pro His Pro Glu Asp Pro Val Arg Glu Asp
        50                  55                  60

Ile Leu Cys Ser Leu Ala Asp Gln His Tyr Ala Ala Ile Phe Thr Lys
65                  70                  75                  80

Ala Cys Tyr Met Ala Val Thr Ser Leu Met Gly Lys Gln Arg Thr
                85                  90                  95

His Phe Pro Arg Cys Asp Ile Ile Cys Gln Ala Glu Ile Gly Ser Glu
            100                 105                 110

Tyr Leu His Cys His Ile Leu Val Gly Gly Ala Gly Leu Ser Lys Arg
            115                 120                 125

Asn Ala Lys Ile Ser Cys Ala Thr Leu Leu Gly Leu Val Met Ala Glu
        130                 135                 140

Leu Thr Gln Arg Cys Lys Leu Leu Leu Ala Gln Arg Pro Phe Glu Pro
145                 150                 155                 160

Asp Glu Ala Arg Ile Phe His Leu Leu Arg Arg Val Glu Arg Glu Ala
                165                 170                 175

Trp Ser Gly His Thr Gly Asn Trp Val Gln Ile Leu Gln Tyr Arg Asp
            180                 185                 190

Lys Arg Gly Asp Leu His Ala Gln His Ile Asp Pro Leu Arg Phe Phe
        195                 200                 205

Lys His Tyr Leu Leu Pro Lys Asn Arg Leu Ile Ser Pro Ser Ser Lys
            210                 215                 220

Pro Asp Val Cys Thr Thr Pro Asp Asn Trp Phe Val Leu Ala Glu Lys
225                 230                 235                 240

Thr Tyr Ala His Thr Ile Val Asn Gly Leu Pro Leu Leu Glu His Asn
                245                 250                 255

Arg Lys Ala Tyr Leu Gln Glu Leu Glu Ser Glu Val Ile Pro Gly Pro
            260                 265                 270

Ser Thr Met Ala Phe Gly Gly Arg Gly Ala Trp Glu His Leu Pro Glu
            275                 280                 285

```
Val Gly Glu Gln Arg Leu Ile Thr Ser Asn Thr Ser Thr Ala Tyr Lys
        290                 295                 300

Ala Asn Lys Lys Glu Lys Leu Met Leu Asn Leu Leu Asp Lys Cys Asp
305                 310                 315                 320

Glu Leu Asn Leu Leu Val Tyr Glu Asp Leu Val Ser Ala Cys Pro Asp
                    325                 330                 335

Leu Leu Leu Met Leu Glu Gly Gln Pro Gly Gly Ala Arg Leu Ile Glu
                340                 345                 350

Gln Val Leu Gly Met His His Ile Lys Val Cys Ala Asn Tyr Thr Ala
            355                 360                 365

Leu Ser Phe Leu Phe His Leu His Pro Asp Gln Leu Leu Thr Ser Ser
        370                 375                 380

Asn Lys Ala Leu Lys Leu Leu Ile Gln Gly Tyr Asn Pro Leu Gln
385                 390                 395                 400

Val Gly His Ala Ile Cys Cys Val Leu Asn Lys Gln Met Gly Lys Gln
                    405                 410                 415

Asn Thr Ile Cys Phe Tyr Gly Pro Ala Ser Thr Gly Lys Thr Asn Ile
                420                 425                 430

Ala Lys Ala Ile Val Gln Gly Val Arg Leu Tyr Gly Cys Val Asn His
            435                 440                 445

Leu Asn Lys Gly Phe Val Phe Asn Asp Cys Arg Gln Arg Leu Ile Ile
        450                 455                 460

Trp Trp Glu Glu Cys Leu Met His Gln Asp Trp Val Glu Pro Ala Lys
465                 470                 475                 480

Cys Ile Leu Gly Gly Thr Glu Cys Arg Ile Asp Val Lys His Lys Asp
                    485                 490                 495

Ser Val Leu Leu Gln Gln Thr Pro Val Ile Ile Ser Thr Asn His Asp
                500                 505                 510

Ile Tyr Ser Val Val Gly Gly Asn Thr Val Ser His Val His Ala Ala
            515                 520                 525

Pro Leu Lys Glu Arg Ile Leu Gln Leu Asn Phe Met Lys Gln Leu Pro
        530                 535                 540

Gln Thr Phe Gly Glu Ile Ser Pro Val Glu Ile Ala Glu Leu Leu Gln
545                 550                 555                 560

Trp Cys Phe Asn Glu Tyr Asp Cys Thr Leu Thr Gly Phe Lys Gln Lys
                    565                 570                 575

Trp Asn Leu Asp Lys Val Pro Asn Ser Phe Pro Leu Gly Asp Leu Cys
                580                 585                 590

Pro Thr His Ser Gln Asp Tyr Val Leu His Glu Asn Gly Phe Cys Thr
            595                 600                 605

Asp Cys Gly Gly Tyr Ile Pro His Ser Ala Asp Ser Val Tyr Thr
        610                 615                 620

Asp Val Ala Ser Glu Thr Ser Ile Ser Ser Asp Pro Gly Asp Leu
625                 630                 635                 640

Gly Asp Thr Asp Gly Glu Asn Ser Gln Pro Glu Thr Ser Asn Val Asp
                    645                 650                 655

Asn Arg Pro Ser Lys Lys Arg Val Ile Pro Glu Thr Pro Pro Asn
                660                 665                 670

Ser Pro Val Ser Arg Gln Ser Leu Ser Ser Phe Leu Asp Thr Trp Gln
            675                 680                 685

Ser Gln Pro Arg Asp Glu Asp Glu Leu Arg Ile Tyr Glu Ala Gln Ala
        690                 695                 700

Ser Arg Ile Lys Glu Asn Ala Glu Ser Thr Pro Glu Arg Glu Lys Thr
705                 710                 715                 720
```

```
Pro Val Gly Glu Pro Gln Glu Ser Gln Ser Glu Pro Asp Pro Thr
            725                 730                 735
Ala Trp Gly Glu Lys Leu Gly Val Tyr Ser Ser Leu Gln Pro Gly Glu
        740                 745                 750
Pro Pro Ile Val Leu His Cys Phe Glu Asp Leu Arg Pro Ser Asp Glu
            755                 760                 765
Asp Glu Gly Glu Asn Ile Gly Gly Glu
            770                 775

<210> SEQ ID NO 38
<211> LENGTH: 539
<212> TYPE: PRT
<213> ORGANISM: Bocavirus

<400> SEQUENCE: 38

Met Ser Glu Asn Glu Ile Gln Asp Gln Gln Pro Ser Asp Ser Met Asp
1               5                   10                  15
Gly Gln Arg Gly Gly Gly Gly Ala Gly Ser Val Gly Gly Gly
            20                  25                  30
Lys Gly Ser Gly Val Gly Ile Ser Thr Gly Gly Trp Val Gly Gly Ser
        35                  40                  45
Tyr Phe Thr Asp Ser Tyr Val Ile Thr Lys Asn Thr Arg Gln Phe Leu
    50                  55                  60
Val Lys Ile Gln Asn Asp His Lys Tyr Arg Thr Glu Asn Ile Ile Pro
65                  70                  75                  80
Ser Asn Ala Gly Gly Lys Ser Gln Arg Cys Val Ser Thr Pro Trp Ser
                85                  90                  95
Tyr Phe Asn Phe Asn Gln Tyr Ser Ser His Phe Ser Pro Gln Asp Trp
            100                 105                 110
Gln Arg Leu Thr Asn Glu Tyr Lys Arg Phe Lys Pro Arg Lys Met His
        115                 120                 125
Val Lys Ile Tyr Asn Leu Gln Ile Lys Gln Ile Leu Ser Asn Gly Ala
    130                 135                 140
Asp Thr Thr Tyr Asn Asn Asp Leu Thr Ala Gly Val His Ile Phe Cys
145                 150                 155                 160
Asp Gly Glu His Ala Tyr Pro Asn Ala Thr His Pro Trp Asp Glu Asp
                165                 170                 175
Val Met Pro Glu Leu Pro Tyr Glu Thr Trp Tyr Leu Phe Gln Tyr Gly
            180                 185                 190
Tyr Ile Pro Val Ile His Glu Leu Ala Glu Met Glu Asp Ala Asn Ala
        195                 200                 205
Val Glu Lys Ala Ile Ala Leu Gln Ile Pro Phe Phe Met Leu Glu Asn
    210                 215                 220
Ser Asp His Glu Val Leu Arg Thr Gly Glu Ser Thr Glu Phe Thr Phe
225                 230                 235                 240
Asp Phe Asp Cys Glu Trp Ile Asn Asn Glu Arg Ala Tyr Ile Pro Pro
                245                 250                 255
Gly Leu Met Phe Asn Pro Lys Val Pro Thr Arg Arg Ala Gln Tyr Ile
            260                 265                 270
Arg Gln His Gly Ser Thr Ala Ser Ser Asn Thr Arg Ile Pro Pro Tyr
        275                 280                 285
Ala Lys Pro Thr Ser Trp Met Thr Gly Pro Gly Leu Leu Ser Ala Gln
    290                 295                 300
Arg Val Gly Pro Ala Ala Ser Asp Ser Ala Ala Trp Met Val Val Val
305                 310                 315                 320
```

```
Asn Pro Asp Gly Ala Ala Ile Asn Ser Gly Met Ala Gly Ile Gly Thr
            325                 330                 335

Gly Phe Asp Pro Pro Gly Gly Ser Leu Arg Pro Thr Asp Leu Glu Tyr
        340                 345                 350

Lys Ile Gln Trp Tyr Gln Thr Pro Ala Gly Thr Asn Ser Asp Gly Asn
            355                 360                 365

Ile Ile Ser Asn Pro Ser Leu Ser Met Leu Arg Asp Gln Ala Leu Tyr
    370                 375                 380

Arg Gly Asn Gln Thr Thr Tyr Asn Leu Cys Ser Asp Val Trp Met Phe
385                 390                 395                 400

Pro Asn Gln Ile Trp Asp Arg Tyr Pro Ile Thr Arg Glu Asn Pro Ile
                405                 410                 415

Trp Cys Lys Lys Pro Arg Ser Asp Lys Ser Thr Ile Ile Asp Pro Phe
                420                 425                 430

Asp Gly Ser Ile Ala Met Asp His Pro Pro Gly Thr Ile Phe Ile Lys
            435                 440                 445

Met Ala Lys Ile Pro Val Pro Ser Asn Asn Asn Ala Asp Ser Tyr Leu
    450                 455                 460

Asn Ile Tyr Cys Thr Gly Gln Val Ser Cys Glu Ile Val Trp Glu Val
465                 470                 475                 480

Glu Arg Tyr Ala Thr Lys Asn Trp Arg Pro Glu Arg Arg His Thr Ala
                485                 490                 495

Leu Gly Leu Gly Ile Gly Gly Glu Glu Asn Val Asn Pro Thr Tyr His
            500                 505                 510

Val Asp Lys Asn Gly Lys Tyr Ile Gln Pro Thr Thr Trp Asp Met Cys
    515                 520                 525

Tyr Pro Ile Lys Thr Asn Ile Asn Lys Val Leu
    530                 535

<210> SEQ ID NO 39
<211> LENGTH: 776
<212> TYPE: PRT
<213> ORGANISM: Bocavirus

<400> SEQUENCE: 39

Pro Pro Val Ile Arg Ala Phe Ser Ser Pro Ala Phe Thr Tyr Val Phe
1               5                   10                  15

Lys Phe Pro Tyr Arg Ser Trp Lys Glu Lys Glu Trp Leu Leu His Ala
            20                  25                  30

Leu Leu Ala His Gly Thr Glu Gln Ala Met Ile Gln Leu Arg Asn Cys
        35                  40                  45

Val Pro His Pro Asp Glu Asp Ile Ile Arg Asp Asp Leu Leu Leu Ser
    50                  55                  60

Leu Glu Asp Arg His Phe Gly Ala Ile Leu Cys Lys Ala Val Tyr Met
65                  70                  75                  80

Ala Thr Thr Thr Phe Met Ser Gln Lys Gln Arg Asn Met Phe Pro Arg
                85                  90                  95

Cys Asp Ile Ile Val Gln Ser Glu Leu Gly Glu Thr Asn Leu His Cys
            100                 105                 110

His Ile Ile Val Gly Gly Glu Gly Leu Ser Lys Arg Asn Ala Lys Thr
        115                 120                 125

Ser Cys Pro Gln Leu Tyr Gly Leu Ile Leu Gly Glu Leu Ile Gln Arg
    130                 135                 140

Cys Lys Thr Leu Leu Ala Thr Arg Pro Phe Glu Pro Glu Glu Ala Glu
145                 150                 155                 160
```

-continued

```
Ile Tyr His Ala Leu Lys Arg Ala Glu Arg Glu Ala Trp Gly Gly Val
            165                 170                 175

Thr Ser Gly Asn Leu Gln Ile Leu Gln Tyr Arg Asp Arg Arg Gly Asp
            180                 185                 190

Leu His Ala Gln Gln Val Asp Ala Leu Arg Phe Phe Lys Asn Tyr Leu
            195                 200                 205

Leu Pro Lys Asn Arg Cys Ile Thr Ser Tyr Ser Arg Pro Asp Val Cys
            210                 215                 220

Thr Ser Pro Glu Asn Trp Phe Val Leu Ala Glu Lys Thr Tyr Cys His
225                 230                 235                 240

Thr Leu Val Asn Gly Leu Pro Leu Pro Glu His Tyr Arg Lys His Tyr
                    245                 250                 255

His Ala Thr Leu Asp Asn Glu Val Leu Pro Gly Pro Gln Thr Met Ala
                    260                 265                 270

Phe Gly Gly Arg Gly Pro Trp Glu His Leu Pro Glu Val Gly Asp Gln
                    275                 280                 285

Arg Leu Ala Ala Ser Ser Val Ser Thr Thr Tyr Lys Pro Asn Lys Lys
            290                 295                 300

Glu Lys Leu Met Leu Asn Leu Leu Asp Lys Cys Ser Glu Leu Asn Leu
305                 310                 315                 320

Leu Val Tyr Glu Asp Leu Val Ala Asn Cys Pro Glu Leu Leu Leu Met
                    325                 330                 335

Leu Glu Gly Gln Pro Gly Gly Ala Arg Leu Ile Glu Gln Val Leu Gly
                    340                 345                 350

Met His His Ile Asn Val Cys Ser Asn Phe Thr Ala Leu Ser Tyr Leu
            355                 360                 365

Phe His Leu Tyr Pro Ser Thr Thr Leu Ser Ser Asp Asn Lys Ala Leu
            370                 375                 380

Gln Leu Leu Leu Ile Gln Gly Tyr Asn Pro Leu Met Val Gly His Ala
385                 390                 395                 400

Leu Cys Cys Val Leu Asn Lys Gln Phe Gly Lys Gln Asn Thr Val Cys
                    405                 410                 415

Phe Tyr Gly Pro Ala Ser Thr Gly Lys Thr Asn Met Ala Lys Ala Ile
                    420                 425                 430

Val Gln Gly Ile Arg Leu Tyr Gly Cys Val Asn His Leu Asn Lys Gly
            435                 440                 445

Phe Val Phe Asn Asp Cys Arg Gln Arg Leu Val Val Trp Trp Glu Glu
            450                 455                 460

Cys Leu Met His Gln Asp Trp Val Glu Pro Ala Lys Cys Ile Leu Gly
465                 470                 475                 480

Gly Thr Glu Cys Arg Ile Asp Val Lys His Arg Asp Ser Val Leu Leu
                    485                 490                 495

Thr Gln Thr Pro Val Ile Ile Ser Thr Asn His Asp Ile Tyr Ala Val
                    500                 505                 510

Val Gly Gly Asn Ser Val Ser His Val His Ala Ala Pro Leu Lys Glu
            515                 520                 525

Arg Val Ile Gln Leu Asn Phe Met Lys Gln Leu Pro Gln Thr Phe Gly
            530                 535                 540

Glu Ile Thr Pro Glu Glu Ile Ala Ala Leu Leu Gln Trp Cys Phe Asn
545                 550                 555                 560

Glu Tyr Glu Cys Thr Leu Thr Gly Phe Lys Thr Lys Trp Ser Leu Asp
                    565                 570                 575

Lys Ile Pro Asn Ser Phe Pro Leu Gly Val Leu Cys Pro Thr His Ser
```

```
                    580             585             590
Gln Asp Phe Ile Leu His Glu Asn Gly Tyr Cys Thr Asp Cys Gly Gly
            595                 600                 605

Tyr Leu Ala His Ser Ala Asp Ser Val Tyr Thr Asp Arg Ala Ser
            610                 615                 620

Asp Thr Ser Lys Glu Ala Ile Asp Ala Gly Asp Leu Gly Asp Thr Asp
625                 630                 635                 640

Gly Glu Asp Ser Glu Ser Glu Ala Ser Glu Val Gly Val Arg Pro Ser
                    645                 650                 655

Lys Lys Arg Arg Ile Thr Ile Pro Ala Thr Pro Pro Asn Ser Pro Gly
                    660                 665                 670

Ser Ser Val Ser Thr Ser Ala Phe Phe Asp Asn Trp Cys Ala Gln Pro
                    675                 680                 685

Arg Asp Glu Asp Glu Leu Arg Glu Tyr Lys Arg Gln Ala Ser Arg Leu
            690                 695                 700

Gln Lys Lys Arg Glu Ser Arg Glu Arg Glu Glu Thr Pro Met Ala
705                 710                 715                 720

Thr Ser Ser Gln Glu Ser Glu Pro Glu Pro Asn Pro Thr Gln Trp Glu
                    725                 730                 735

Asp Lys Leu Gly Val Ile Pro Ser Gly Thr Pro Asp Gln Pro Pro Ile
                    740                 745                 750

Val Leu His Cys Phe Glu Asp Leu Arg Pro Ser Asp Glu Asp Glu Gly
                    755                 760                 765

Glu Tyr Ile Gly Glu Glu Arg Leu
            770                 775

<210> SEQ ID NO 40
<211> LENGTH: 539
<212> TYPE: PRT
<213> ORGANISM: Bocavirus

<400> SEQUENCE: 40

Met Ser Glu Asn Glu Ile Gln Asp Gln Gln Pro Ser Glu Pro Asn Asp
1               5                   10                  15

Gly Gln Arg Gly Gly Gly Gly Thr Thr Gly Ser Val Gly Gly
            20                  25                  30

Lys Gly Ser Gly Val Gly Ile Ser Thr Gly Gly Trp Val Gly Gly Ser
            35                  40                  45

Tyr Phe Thr Asp Ser Tyr Val Ile Thr Lys Asn Thr Arg Gln Phe Leu
            50                  55                  60

Val Lys Ile Gln Asn Asn His Gln Tyr Lys Thr Glu Asn Ile Ile Pro
65                  70                  75                  80

Ser Asn Gly Gly Gly Lys Ser Gln Arg Cys Val Ser Thr Pro Trp Ser
                    85                  90                  95

Tyr Phe Asn Phe Asn Gln Tyr Ser Ser His Phe Ser Pro Gln Asp Trp
            100                 105                 110

Gln Arg Leu Thr Asn Glu Tyr Lys Arg Phe Arg Pro Lys Gly Met His
            115                 120                 125

Val Lys Ile Tyr Asn Leu Gln Ile Lys Gln Ile Leu Ser Asn Gly Ala
            130                 135                 140

Asp Val Thr Tyr Asn Asn Asp Leu Thr Ala Gly Val His Ile Phe Cys
145                 150                 155                 160

Asp Gly Glu His Ala Tyr Pro Asn Ala Thr His Pro Trp Asp Glu Asp
                    165                 170                 175

Val Met Pro Glu Leu Pro Tyr Gln Thr Trp Tyr Leu Phe Gln Tyr Gly
```

```
            180                 185                 190
Tyr Ile Pro Thr Ile His Glu Leu Ala Glu Met Glu Asp Ser Asn Ala
        195                 200                 205

Val Glu Lys Ala Ile Ala Leu Gln Ile Pro Phe Phe Met Leu Glu Asn
    210                 215                 220

Ser Asp His Glu Val Leu Arg Thr Gly Glu Ser Ala Glu Phe Asn Phe
225                 230                 235                 240

Asn Phe Asp Cys Glu Trp Ile Asn Asn Glu Arg Ala Phe Ile Pro Pro
                245                 250                 255

Gly Leu Met Phe Asn Pro Leu Val Pro Thr Arg Arg Ala Gln Tyr Ile
            260                 265                 270

Arg Arg Asn Gly Asn Thr Gln Ala Ser Thr Thr Arg Ile Gln Pro Tyr
        275                 280                 285

Ser Lys Pro Thr Ser Trp Met Thr Gly Pro Gly Leu Leu Ser Ala Gln
    290                 295                 300

Arg Val Gly Pro Ala Ala Ser Asp Thr Ala Ala Trp Met Val Gly Ile
305                 310                 315                 320

Asp Leu Asp Gly Ala Asn Val Asn Ser Gly Arg Ala Gly Val Ser Thr
                325                 330                 335

Gly Phe Asp Pro Pro Ala Gly Ser Leu Arg Pro Thr Asp Leu Glu Tyr
            340                 345                 350

Lys Ile Gln Trp Tyr Gln Thr Pro Ala Gly Thr Asn Asn Asp Gly Asn
        355                 360                 365

Ile Ile Ser Asn Pro Pro Leu Ser Met Leu Arg Asp Gln Thr Leu Tyr
    370                 375                 380

Lys Gly Asn Gln Thr Thr Tyr Asn Leu Cys Ser Asp Val Trp Met Phe
385                 390                 395                 400

Pro Asn Gln Ile Trp Asp Arg Tyr Pro Ile Thr Arg Glu Asn Pro Ile
                405                 410                 415

Trp Cys Lys Gln Pro Arg Ser Asp Lys His Thr Val Ile Asp Pro Phe
            420                 425                 430

Asp Gly Ser Leu Ala Met Asp His Pro Pro Gly Thr Ile Phe Ile Lys
        435                 440                 445

Met Ala Lys Ile Pro Val Pro Ser Ser Asn Asn Ala Asp Ser Tyr Leu
    450                 455                 460

Asn Ile Tyr Cys Thr Gly Gln Val Ser Cys Glu Ile Val Trp Glu Val
465                 470                 475                 480

Glu Arg Tyr Ala Thr Lys Asn Trp Arg Pro Glu Arg Arg His Thr Ala
                485                 490                 495

Leu Gly Leu Gly Ile Gly Gly Ala Asp Glu Ile Asn Pro Thr Tyr His
            500                 505                 510

Val Asp Lys Asn Gly Ala Tyr Ile Gln Pro Thr Ser Trp Asp Met Cys
        515                 520                 525

Phe Pro Val Lys Thr Asn Ile Asn Lys Val Leu
    530                 535

<210> SEQ ID NO 41
<211> LENGTH: 776
<212> TYPE: PRT
<213> ORGANISM: Bocavirus

<400> SEQUENCE: 41

Met Ala Phe Ser Ala Pro Val Leu Arg Ala Phe Ser Gln Pro Thr Phe
1               5                   10                  15

Thr Tyr Val Ile Lys Phe Pro Tyr Asn Asn Trp Lys Glu Asp Glu His
```

```
                    20                  25                  30
Leu Leu Trp Ser Leu Leu Ala Pro Gly Thr Glu Ser Leu Met Ile Gln
            35                  40                  45
Leu Lys Asn Cys Ala Pro His Pro Glu Asp Pro Ile Arg Glu Asp
        50                  55                  60
Ile Leu Cys Ser Leu Ala Asp Leu His Tyr Gly Ala Val Phe Ala Lys
65                  70                  75                  80
Ala Cys Tyr Ile Ala Thr Ser Thr Leu Met Gly Gln Lys Gln Arg Thr
                    85                  90                  95
Leu Phe Pro Arg Cys Asp Ile Val Cys Gln Ser Glu Ile Gly Ser Asp
                100                 105                 110
Phe Leu His Cys His Ile Leu Val Gly Gly Ala Gly Leu Ser Lys Arg
                115                 120                 125
Asn Ala Lys Ile Ser Arg Ala Thr Leu Leu Gly Leu Val Met Ala Glu
            130                 135                 140
Leu Thr Gln Arg Cys Lys Leu Leu Leu Ala His Arg Pro Phe Glu Pro
145                 150                 155                 160
Ala Glu Ala Thr Ile Tyr His Glu Leu Lys Arg Ile Glu Arg Glu Ala
                    165                 170                 175
Trp Ser Gly His Thr Gly Asn Trp Val Gln Ile Leu Gln Tyr Lys Asp
                180                 185                 190
Lys Arg Gly Asp Leu His Ala Gln Pro Ile Asp Pro Leu Arg Phe Leu
                195                 200                 205
Lys His Tyr Ile Leu Pro Lys Asn Arg Leu Ile Ser Pro Ser Ser Lys
            210                 215                 220
Pro Asp Val Cys Thr Ser Pro Asp Asn Trp Phe Ile Leu Ala Asp Lys
225                 230                 235                 240
Thr Tyr Ser His Thr Ile Ile Asn Gly Leu Pro Leu Leu Glu Arg Asn
                    245                 250                 255
Arg Lys Ala Tyr Leu Gln Glu Leu Glu Ser Glu Val Ile Pro Gly Pro
                260                 265                 270
Ser Ala Met Ala Phe Gly Gly Arg Gly Ala Trp Glu Gln Leu Pro Glu
            275                 280                 285
Val Gly Glu Gln Arg Leu Ile Thr Ser Asn Thr Ser Thr Ala Tyr Lys
        290                 295                 300
Ala Asn Lys Lys Glu Lys Leu Met Leu Asn Leu Leu Asp Lys Cys Asp
305                 310                 315                 320
Glu Leu Asn Leu Leu Val Tyr Glu Asp Leu Val Ser Ala Cys Pro Asp
                    325                 330                 335
Leu Leu Leu Met Leu Glu Gly Gln Pro Gly Gly Ala Arg Leu Ile Glu
                340                 345                 350
Gln Val Leu Gly Met His His Ile Lys Val Cys Ala Lys His Thr Ala
            355                 360                 365
Leu Ser Phe Leu Phe His Leu His Pro Asp Gln Leu Leu Thr Ser Ser
        370                 375                 380
Asn Lys Ala Leu Lys Leu Leu Ile Gln Gly Tyr Asn Pro Leu Gln
385                 390                 395                 400
Val Gly His Ala Ile Cys Cys Val Leu Asn Lys Gln Met Gly Lys Gln
                    405                 410                 415
Asn Thr Ile Cys Phe Tyr Gly Pro Ala Ser Thr Gly Lys Thr Asn Phe
                420                 425                 430
Ala Lys Ala Ile Val Gln Gly Val Arg Leu Tyr Gly Cys Val Asn His
            435                 440                 445
```

```
Leu Asn Lys Gly Phe Val Phe Asn Asp Cys Arg Gln Arg Leu Ile Ile
    450                 455                 460

Trp Trp Glu Glu Cys Leu Met His Gln Asp Trp Val Glu Pro Ala Lys
465                 470                 475                 480

Cys Ile Leu Gly Thr Glu Cys Arg Ile Asp Val Lys His Lys Asp
                485                 490                 495

Ser Val Leu Leu Gln Gln Thr Pro Val Ile Ser Thr Asn His Asp
                500                 505                 510

Ile Tyr Ser Val Val Gly Gly Asn Thr Val Ser His Val His Ala Ala
        515                 520                 525

Pro Leu Lys Glu Arg Val Leu Gln Leu Asn Phe Met Lys Gln Leu Pro
    530                 535                 540

Gln Thr Phe Gly Glu Ile Ser Pro Ser Glu Ile Ala Glu Leu Leu Gln
545                 550                 555                 560

Trp Cys Phe Asn Glu Tyr Asp Cys Thr Leu Ala Gly Phe Lys Gln Lys
                565                 570                 575

Trp Asn Leu Asp Lys Val Pro Asn Ser Phe Pro Ile Gly Asp Leu Cys
                580                 585                 590

Pro Thr His Ser Gln Asp Phe Thr Leu His Glu Asn Gly Phe Cys Ser
            595                 600                 605

Asp Cys Gly Gly Tyr Leu Pro His Ser Ala Asp Ser Val Tyr Thr
        610                 615                 620

Asp Val Ala Ser Glu Thr Thr Ser Gly Asp Tyr Asp Pro Gly Asn Leu
625                 630                 635                 640

Gly Asp Thr Asp Gly Glu Asp Ser Lys Ser Glu Ala Ser Glu Val Asp
                645                 650                 655

Tyr Cys Pro Pro Lys Lys Arg Arg Val Ile Ser Ala Thr Pro Pro Asn
                660                 665                 670

Ser Pro Val Ser Gly Pro Ser Leu Ser Thr Phe Leu Asp Thr Trp Gln
            675                 680                 685

Ser Gln Pro Arg Asp Asp Asp Glu Leu Arg Ile Tyr Glu Glu Gln Ala
        690                 695                 700

Ser Gln Phe Gln Lys Asn Thr Lys Ser Thr Ser Glu Arg Glu Glu Ala
705                 710                 715                 720

Gln Leu Gly Glu Ser Gln Glu Pro Gln Pro Glu Pro Asp Pro Thr Ala
                725                 730                 735

Trp Gly Glu Lys Leu Gly Val Cys Ser Ser Gln Gln Pro Gly Gln Pro
                740                 745                 750

Pro Ile Val Leu Tyr Cys Phe Glu Asp Leu Arg Pro Ser Asp Glu Asp
            755                 760                 765

Glu Gly Glu Asn Ile Gly Gly Asp
    770                 775

<210> SEQ ID NO 42
<211> LENGTH: 541
<212> TYPE: PRT
<213> ORGANISM: Bocavirus

<400> SEQUENCE: 42

Met Ser Glu Asn Glu Ile Gln Asp Gln Gln Pro Ser Asp Ser Met Asp
1               5                   10                  15

Gly Gln Arg Gly Gly Gly Gly Ala Thr Gly Ser Val Gly Gly
                20                  25                  30

Lys Gly Ser Gly Val Gly Ile Ser Thr Gly Gly Trp Val Gly Gly Ser
            35                  40                  45
```

Tyr Phe Thr Asp Ser Tyr Val Ile Thr Lys Asn Thr Arg Gln Phe Leu
 50                  55                  60

Val Lys Ile Gln Asn Asn His Gln Tyr Lys Thr Glu Leu Ile Ser Pro
 65                  70                  75                  80

Ser Thr Ser Gln Gly Lys Ser Gln Arg Cys Val Ser Thr Pro Trp Ser
                 85                  90                  95

Tyr Phe Asn Phe Asn Gln Tyr Ser Ser His Phe Ser Pro Gln Asp Trp
            100                 105                 110

Gln Arg Leu Thr Asn Glu Tyr Lys Arg Phe Arg Pro Lys Gly Met His
        115                 120                 125

Val Lys Ile Tyr Asn Leu Gln Ile Lys Gln Ile Leu Ser Asn Gly Ala
130                 135                 140

Asp Thr Thr Tyr Asn Asn Asp Leu Thr Ala Gly Val His Ile Phe Cys
145                 150                 155                 160

Asp Gly Glu His Ala Tyr Pro Asn Ala Thr His Pro Trp Asp Glu Asp
                165                 170                 175

Val Met Pro Glu Leu Pro Tyr Gln Thr Trp Tyr Leu Phe Gln Tyr Gly
            180                 185                 190

Tyr Ile Pro Val Ile His Glu Leu Ala Glu Met Glu Asp Ser Asn Ala
        195                 200                 205

Val Glu Lys Ala Ile Cys Leu Gln Ile Pro Phe Phe Met Leu Glu Asn
210                 215                 220

Ser Asp His Glu Val Leu Arg Thr Gly Glu Ser Thr Glu Phe Thr Phe
225                 230                 235                 240

Asn Phe Asp Cys Glu Trp Ile Asn Asn Glu Arg Ala Tyr Ile Pro Pro
                245                 250                 255

Gly Leu Met Phe Asn Pro Leu Val Pro Thr Arg Arg Ala Gln Tyr Ile
            260                 265                 270

Arg Arg Asn Asn Asn Pro Gln Thr Ala Glu Ser Thr Ser Arg Ile Ala
        275                 280                 285

Pro Tyr Ala Lys Pro Thr Ser Trp Met Thr Gly Pro Gly Leu Leu Ser
290                 295                 300

Ala Gln Arg Val Gly Pro Ala Thr Ser Asp Thr Gly Ala Trp Met Val
305                 310                 315                 320

Ala Val Lys Pro Glu Asn Ala Ser Ile Asp Thr Gly Met Ser Gly Ile
                325                 330                 335

Gly Ser Gly Phe Asp Pro Pro Gln Gly Ser Leu Ala Pro Thr Asn Leu
            340                 345                 350

Glu Tyr Lys Ile Gln Trp Tyr Gln Thr Pro Gln Gly Thr Asn Asn Asn
        355                 360                 365

Gly Asn Ile Ile Ser Asn Gln Pro Leu Ser Met Leu Arg Asp Gln Ala
370                 375                 380

Leu Phe Arg Gly Asn Gln Thr Thr Tyr Asn Leu Cys Ser Asp Val Trp
385                 390                 395                 400

Met Phe Pro Asn Gln Ile Trp Asp Arg Tyr Pro Ile Thr Arg Glu Asn
                405                 410                 415

Pro Ile Trp Cys Lys Lys Pro Arg Ser Asp Lys His Thr Thr Ile Asp
            420                 425                 430

Pro Phe Asp Gly Ser Leu Ala Met Asp His Pro Pro Gly Thr Ile Phe
        435                 440                 445

Ile Lys Met Ala Lys Ile Pro Val Pro Ser Asn Asn Asn Ala Asp Ser
450                 455                 460

Tyr Leu Asn Ile Tyr Cys Thr Gly Gln Val Ser Cys Glu Ile Val Trp
465                 470                 475                 480

```
Glu Val Glu Arg Tyr Ala Thr Lys Asn Trp Arg Pro Glu Arg Arg His
                485                 490                 495
Thr Thr Phe Gly Leu Gly Ile Gly Gly Ala Asp Asn Leu Asn Pro Thr
            500                 505                 510
Tyr His Val Asp Lys Asn Gly Thr Tyr Ile Gln Pro Thr Thr Trp Asp
        515                 520                 525
Met Cys Phe Pro Val Lys Thr Asn Ile Asn Lys Val Leu
    530                 535                 540

<210> SEQ ID NO 43
<211> LENGTH: 5134
<212> TYPE: DNA
<213> ORGANISM: Bocavirus

<400> SEQUENCE: 43
gacgtatgtc aaccaatcag catcgagcat atatcctata taagccaatg cacttccgca      60
tctcgtcaga ctgcatccgg tctccggcga gtgaacatct ctgggaagag ctccacgcac     120
gtggtgagtg acactatggc cttttctgct cctgtaatta gcttttttc tcaacctgct     180
ttcacttatg ttgttaaatt tccatatgat aactggaaag aggaagagca cttactatgg     240
agcttacttg ctcctgggac tgaacgtctc atgatccaac taagaaactg cgcaccacat     300
cctgaagatg atcctgtcag ggaagatatt ttatgctcac tagcagacca acactatgct     360
gctattttca ccaaagcttg ctacatggct gtaacttcac ttatggggca gaaacagaga     420
acacactttc cacgatgcga cataaatttgc aggctgaga tcggctcaga atatctacac     480
tgtcacatac ttgttggagg agcaggtctg agcaagagaa atgctaaaat tcatgtgct      540
acgctcctag gccttgtgat ggctgaatta acacaacgct gcaaactact tcttgcacag     600
cgtccatttg aaccagatga agctagaata tttcatctac tcagacgcgt tgaacgcgaa     660
gcatggtcag ggcacactgg taactgggtt caaattcttc aatacagaga caagcgaggt     720
gaccttcatg ctcaacacat tgatccttta cgctttttca aacactacct gctgccaaaa     780
aatcggttga tctctccttc cagcaagcct gacgtctgca ctactccaga taactggttt     840
gtcctagctg aaaaaacata cgctcacact attgttaatg gcttccgct gctagaacat     900
aacagaaagg cctatctaca agagttagaa agtgaagtca tcccagggcc ttctaccatg     960
gcctttgggg gacgtggtgc gtgggaacat ctgcctgagg taggagaaca acgcctaata    1020
acttctaata cttctactgc ttataaagct aacaaaaaag aaaaattaat gctaaactta    1080
cttgataaat gtgatgaact taacttactt gtgtatgaag acttagttag tgcttgtcct    1140
gacctttac ttatgcttga aggtcagcca ggtggtgcac gcctaattga acaggtgctc    1200
ggcatgcatc atattaaagt gtgtgctaat tacacagcgt tatctttcct atttcattta    1260
catcctgatc aattattaac ttctagcaat aaagcactaa actattgtt gattcaaggg    1320
tacaacccat tgcaagtggg ccacgccatc tgttgtgtcc ttaacaaaca gatgggcaag    1380
cagaacacaa tttgctttta tggccctgct tcaacaggca aaacaaatat tgcaaaggcc    1440
atagttcaag gcgttcgtct gtatggctgt gttaatcatt taaacaaagg gtttgtcttt    1500
aacgattgca gacaacgcct tataatctgg tgggaggagt gtttaatgca ccaagactgg    1560
gtggaacctg ctaaatgcat tctaggcgga actgaatgta gaattgatgt taaacataaa    1620
gacagtgttc ttcttcaaca aacaccagta attatttcca ctaaccatga catctactct    1680
gtagttggtg gcaatactgt atctcatgtt catgcagcgc ccttaaaaga gcgaatcctt    1740
cagctaaatt ttatgaaaca actgccacaa acatttggag aaatttctcc agttgaaatt    1800
```

```
gcagaattac tgcaatggtg ctttaatgag tacgactgta ctcttactgg ctttaaacaa   1860
aaatggaact tagataaagt tccaaactca tttcctcttg gggacctttg tcctacacat   1920
tcacaggact acgtgcttca cgaaaacgga ttctgcactg actgcggcgg ctatattcct   1980
catagtgctg acgactctgt gtacactgac gtggctagcg agacatcaat cagcagcgac   2040
gacccaggta ggcattaata cattagcctt ttaatatact accttccaag tgcttatgta   2100
ttaactccta caggtgactt gggggatacg gacggagaga actcccagcc ggagacatcg   2160
aacgtggata tcgtccatc caagaagaga cgtgtgattc cagaaactcc accaaacagt    2220
ccagtaagtc gccaaagcct ttctagcttt ttagatacgt ggcagtcaca acctagagac   2280
gaagatgagc tccgaatcta tgaagcacag gcatcgcgca tcaaagagaa caccgagtcc   2340
actccggaga gagagaagac accagtggga gaaccacaag aagagtcgca gtcggagccc   2400
aatccgacag catggggaga aaagcttgga gtctactcct cgctacaacc aggagagccg   2460
ccaatcgtct tacactgctt cgaagacctc agaccaagcg acgaagacga gggagaaaac   2520 atcgggggggg aatagaacca atccttatac tgtgttcagt caacacaggg ctaatcatcc   2580
agatgctcct ggatggtgtg ggttttactg gcattctact aggcttgcta gagatggcac   2640
taattgtatc tttaatgaaa tgaaacaaga atttcaagaa ttacaaataa atgggaaaat   2700
tacttgggac aatgttagag aactattgtt tagccagaaa aaaagctag atcaaaaata    2760 cagaaacatg ctgtatcatt tcagacataa cactgattgt cctagatgtg attattggga   2820
tgatgtatac cgtaaacact agctcatgt ctcttcacag gaatcagagg aggtaacaga    2880
cgaagaaatg ctttctgctg ttgaaagcat ggaaacaaat gcctccaatt aaacgccaac   2940
ctggagggtg ggtgcttcct ggttataaat accttggtcc atttaatcct cttgaaaacg   3000
gtgaaccagt taataaagct gatcgtgctg ctcaagctca tgataaatca tattctgaac   3060
taataaaaag tggaaaaaat ccttacttat atttcaataa agctgatgaa aaattcattg   3120
acgatttgaa aaacgactgg tctcttggtg gcattattgg ctcaagtttc tttaaactta   3180
agcgcgccgt ggctcctgct ctaggaaata aagagcgagc tcaaaaaaga catttttact   3240
ttgcaaactc aaataaaggt gctaaaaaac caaaaaataa cgagcctaaa ccaggcacat   3300
caaaaatgtc tgaaaatgaa atccaagacc aacaaccatc tggctccatg gaggagcgag   3360
gaggcggagg aggtgcggtc ggtagtgtgg gagggggaa aggttctggt gtgggtatat    3420
ccacargcgg ctgggttgga ggcagctact ttactgactc atatgtcata acaaagaaca   3480
ctagacagtt cttagttaaa atacaaaatg accacaaata cagaacagag aatataattc   3540
caagcaacgc aggaggaaaa ttccagcgat gcgtaagcac accttggtca tactttaact   3600
tcaatcaata cagcagtcac ttctcaccac aagactggca gcgtttaaca aatgaatata   3660
aacgctttaa gcctagaaaa atgcatgtaa aaatttacaa cttacaaata aaacaaatac   3720
tctcaaatgg tgctgacact acatacaaca acgacctaac agctggtgtt cacatctttt   3780
gtgatggtga acacgcatat ccaaatgcaa cacatccatg ggatgaagat gtcatgccag   3840
aacttccata tgaaacatgg tatttgtttc aatatggata cattccagtt attcatgaac   3900
tggctgaaat ggaagacgca aatgctgtag aaaaagctat agcactacaa atacctttct   3960
tcatgcttga aaacagcgac catgaagtgt taagaacagg agaaagcaca gaattcactt   4020
ttgactttga ctgtgaatgg ataaacaacg aaagagcata cattcctcct ggattaatgt   4080
ttaatccaaa agttcctaca agaagagctc aatacatcag acagcacgga aacacagcat   4140
ccagcaacac cagaattcaa ccatatgcaa aacctacaag ctggatgaca ggaccaggtc   4200
```

```
tactcagcgc acaaagagta ggaccagctg gctcagacac tgcatcatgg atggttgttg      4260
tcaatccaga cggagctgca gttaactcag gaatggcagg agttggttca ggatttgatc      4320
ctccttcagg atctctaaga ccaactgact tagaatacaa aatacaatgg taccaaactc      4380
ctgcaggtac caacagtgat ggaaacatca tttcaaatcc accactatcc atgctcagag      4440
atcaagctct ctacagagga aatcaaacaa cctacaacct atgctcagat gtgtggatgt      4500
tcccaaatca aatttgggac agatatccaa taaccagaga aaatccaatc tggtgtaaaa      4560
aaccaagatc agacaaaaac acaataattg atcctttcga tggaacactt gcaatggatc      4620
atccgccagg aacaatcttc ataaaaatgg caaaaattcc agttccttca aacaacaacg      4680
cagactcata cctaaacatc tactgcactg gacaagtcag ctgcgaaatt gtctgggaag      4740
ttgaaagata cgcaacaaag aactggagac cagaagaag acacaccgca cttggtcttg      4800
gaattggagg agaagaaaac gtaaatccaa cttatcatgt agacaaaaat ggaaaataca      4860
ttcagccaac aacttgggac atgtgctatc ctatcaaaac aaacatcaat aaagtgttgt      4920
aatctcttaa gcctgttcat tgcttatgct tataagttcc tctccaatgg acaagaggaa      4980
agaaaagggt gactgtaatc ccgagctcat aagttcgagg ctacagtccg atggcagtgg      5040
tgttgccgtc tcgaacctag ccgttacacc cttgtgcatt gtgggaggag ctgttttgct      5100
tacgcaatcg cgaaatttta tatatttaat gtag                                  5134
```

<210> SEQ ID NO 44
<211> LENGTH: 640
<212> TYPE: PRT
<213> ORGANISM: Bocavirus

<400> SEQUENCE: 44

```
Met Ala Phe Ser Ala Pro Val Ile Arg Ala Phe Ser Gln Pro Ala Phe
1               5                   10                  15

Thr Tyr Val Val Lys Phe Pro Tyr Asp Asn Trp Lys Glu Glu His
            20                  25                  30

Leu Leu Trp Ser Leu Leu Ala Pro Gly Thr Glu Arg Leu Met Ile Gln
        35                  40                  45

Leu Arg Asn Cys Ala Pro His Pro Glu Asp Asp Pro Val Arg Glu Asp
    50                  55                  60

Ile Leu Cys Ser Leu Ala Asp Gln His Tyr Ala Ile Phe Thr Lys
65                  70                  75                  80

Ala Cys Tyr Met Ala Val Thr Ser Leu Met Gly Gln Lys Gln Arg Thr
                85                  90                  95

His Phe Pro Arg Cys Asp Ile Ile Cys Gln Ala Glu Ile Gly Ser Glu
            100                 105                 110

Tyr Leu His Cys His Ile Leu Val Gly Gly Ala Gly Leu Ser Lys Arg
        115                 120                 125

Asn Ala Lys Ile Ser Cys Ala Thr Leu Leu Gly Leu Val Met Ala Glu
    130                 135                 140

Leu Thr Gln Arg Cys Lys Leu Leu Leu Ala Gln Arg Pro Phe Glu Pro
145                 150                 155                 160

Asp Glu Ala Arg Ile Phe His Leu Leu Arg Arg Val Glu Arg Glu Ala
                165                 170                 175

Trp Ser Gly His Thr Gly Asn Trp Val Gln Ile Leu Gln Tyr Arg Asp
            180                 185                 190

Lys Arg Gly Asp Leu His Ala Gln His Ile Asp Pro Leu Arg Phe Phe
        195                 200                 205
```

-continued

```
Lys His Tyr Leu Leu Pro Lys Asn Arg Leu Ile Ser Pro Ser Ser Lys
    210                 215                 220
Pro Asp Val Cys Thr Thr Pro Asp Asn Trp Phe Val Leu Ala Glu Lys
225                 230                 235                 240
Thr Tyr Ala His Thr Ile Val Asn Gly Leu Pro Leu Leu Glu His Asn
                245                 250                 255
Arg Lys Ala Tyr Leu Gln Glu Leu Glu Ser Glu Val Ile Pro Gly Pro
            260                 265                 270
Ser Thr Met Ala Phe Gly Gly Arg Gly Ala Trp Glu His Leu Pro Glu
        275                 280                 285
Val Gly Glu Gln Arg Leu Ile Thr Ser Asn Thr Ser Thr Ala Tyr Lys
    290                 295                 300
Ala Asn Lys Lys Glu Lys Leu Met Leu Asn Leu Leu Asp Lys Cys Asp
305                 310                 315                 320
Glu Leu Asn Leu Leu Val Tyr Glu Asp Leu Val Ser Ala Cys Pro Asp
                325                 330                 335
Leu Leu Leu Met Leu Glu Gly Gln Pro Gly Gly Ala Arg Leu Ile Glu
            340                 345                 350
Gln Val Leu Gly Met His His Ile Lys Val Cys Ala Asn Tyr Thr Ala
        355                 360                 365
Leu Ser Phe Leu Phe His Leu His Pro Asp Gln Leu Leu Thr Ser Ser
    370                 375                 380
Asn Lys Ala Leu Lys Leu Leu Ile Gln Gly Tyr Asn Pro Leu Gln
385                 390                 395                 400
Val Gly His Ala Ile Cys Cys Val Leu Asn Lys Gln Met Gly Lys Gln
                405                 410                 415
Asn Thr Ile Cys Phe Tyr Gly Pro Ala Ser Thr Gly Lys Thr Asn Ile
            420                 425                 430
Ala Lys Ala Ile Val Gln Gly Val Arg Leu Tyr Gly Cys Val Asn His
        435                 440                 445
Leu Asn Lys Gly Phe Val Phe Asn Asp Cys Arg Gln Arg Leu Ile Ile
    450                 455                 460
Trp Trp Glu Glu Cys Leu Met His Gln Asp Trp Val Glu Pro Ala Lys
465                 470                 475                 480
Cys Ile Leu Gly Gly Thr Glu Cys Arg Ile Asp Val Lys His Lys Asp
                485                 490                 495
Ser Val Leu Leu Gln Gln Thr Pro Val Ile Ile Ser Thr Asn His Asp
            500                 505                 510
Ile Tyr Ser Val Val Gly Gly Asn Thr Val Ser His Val His Ala Ala
        515                 520                 525
Pro Leu Lys Glu Arg Ile Leu Gln Leu Asn Phe Met Lys Gln Leu Pro
    530                 535                 540
Gln Thr Phe Gly Glu Ile Ser Pro Val Glu Ile Ala Glu Leu Leu Gln
545                 550                 555                 560
Trp Cys Phe Asn Glu Tyr Asp Cys Thr Leu Thr Gly Phe Lys Gln Lys
                565                 570                 575
Trp Asn Leu Asp Lys Val Pro Asn Ser Phe Pro Leu Gly Asp Leu Cys
            580                 585                 590
Pro Thr His Ser Gln Asp Tyr Val Leu His Glu Asn Gly Phe Cys Thr
        595                 600                 605
Asp Cys Gly Gly Tyr Ile Pro His Ser Ala Asp Ser Val Tyr Thr
610                 615                 620
Asp Val Ala Ser Glu Thr Ser Ile Ser Ser Asp Asp Pro Gly Arg His
625                 630                 635                 640
```

-continued

```
<210> SEQ ID NO 45
<211> LENGTH: 777
<212> TYPE: PRT
<213> ORGANISM: Bocavirus

<400> SEQUENCE: 45

Met Ala Phe Ser Ala Pro Val Ile Arg Ala Phe Ser Gln Pro Ala Phe
1               5                   10                  15

Thr Tyr Val Val Lys Phe Pro Tyr Asp Asn Trp Lys Glu Glu Glu His
                20                  25                  30

Leu Leu Trp Ser Leu Leu Ala Pro Gly Thr Glu Arg Leu Met Ile Gln
            35                  40                  45

Leu Arg Asn Cys Ala Pro His Pro Glu Asp Asp Pro Val Arg Glu Asp
    50                  55                  60

Ile Leu Cys Ser Leu Ala Asp Gln His Tyr Ala Ala Ile Phe Thr Lys
65                  70                  75                  80

Ala Cys Tyr Met Ala Val Thr Ser Leu Met Gly Gln Lys Gln Arg Thr
                85                  90                  95

His Phe Pro Arg Cys Asp Ile Ile Cys Gln Ala Glu Ile Gly Ser Glu
            100                 105                 110

Tyr Leu His Cys His Ile Leu Val Gly Gly Ala Gly Leu Ser Lys Arg
        115                 120                 125

Asn Ala Lys Ile Ser Cys Ala Thr Leu Leu Gly Leu Val Met Ala Glu
    130                 135                 140

Leu Thr Gln Arg Cys Lys Leu Leu Leu Ala Gln Arg Pro Phe Glu Pro
145                 150                 155                 160

Asp Glu Ala Arg Ile Phe His Leu Leu Arg Arg Val Glu Arg Glu Ala
                165                 170                 175

Trp Ser Gly His Thr Gly Asn Trp Val Gln Ile Leu Gln Tyr Arg Asp
            180                 185                 190

Lys Arg Gly Asp Leu His Ala Gln His Ile Asp Pro Leu Arg Phe Phe
    195                 200                 205

Lys His Tyr Leu Leu Pro Lys Asn Arg Leu Ile Ser Pro Ser Ser Lys
210                 215                 220

Pro Asp Val Cys Thr Thr Pro Asp Asn Trp Phe Val Leu Ala Glu Lys
225                 230                 235                 240

Thr Tyr Ala His Thr Ile Val Asn Gly Leu Pro Leu Leu Glu His Asn
                245                 250                 255

Arg Lys Ala Tyr Leu Gln Glu Leu Glu Ser Glu Val Ile Pro Gly Pro
            260                 265                 270

Ser Thr Met Ala Phe Gly Gly Arg Gly Ala Trp Glu His Leu Pro Glu
    275                 280                 285

Val Gly Glu Gln Arg Leu Ile Thr Ser Asn Thr Ser Thr Ala Tyr Lys
290                 295                 300

Ala Asn Lys Lys Glu Lys Leu Met Leu Asn Leu Leu Asp Lys Cys Asp
305                 310                 315                 320

Glu Leu Asn Leu Leu Val Tyr Glu Asp Leu Val Ser Ala Cys Pro Asp
                325                 330                 335

Leu Leu Leu Met Leu Glu Gly Gln Pro Gly Gly Ala Arg Leu Ile Glu
            340                 345                 350

Gln Val Leu Gly Met His His Ile Lys Val Cys Ala Asn Tyr Thr Ala
    355                 360                 365

Leu Ser Phe Leu Phe His Leu His Pro Asp Gln Leu Leu Thr Ser Ser
370                 375                 380
```

```
Asn Lys Ala Leu Lys Leu Leu Ile Gln Gly Tyr Asn Pro Leu Gln
385                 390                 395                 400

Val Gly His Ala Ile Cys Cys Val Leu Asn Lys Gln Met Gly Lys Gln
                405                 410                 415

Asn Thr Ile Cys Phe Tyr Gly Pro Ala Ser Thr Gly Lys Thr Asn Ile
                420                 425                 430

Ala Lys Ala Ile Val Gln Gly Val Arg Leu Tyr Gly Cys Val Asn His
                435                 440                 445

Leu Asn Lys Gly Phe Val Phe Asn Asp Cys Arg Gln Arg Leu Ile Ile
            450                 455                 460

Trp Trp Glu Glu Cys Leu Met His Gln Asp Trp Val Glu Pro Ala Lys
465                 470                 475                 480

Cys Ile Leu Gly Gly Thr Glu Cys Arg Ile Asp Val Lys His Lys Asp
                485                 490                 495

Ser Val Leu Leu Gln Gln Thr Pro Val Ile Ser Thr Asn His Asp
            500                 505                 510

Ile Tyr Ser Val Val Gly Gly Asn Thr Val Ser His Val His Ala Ala
                515                 520                 525

Pro Leu Lys Glu Arg Ile Leu Gln Leu Asn Phe Met Lys Gln Leu Pro
            530                 535                 540

Gln Thr Phe Gly Glu Ile Ser Pro Val Glu Ile Ala Glu Leu Leu Gln
545                 550                 555                 560

Trp Cys Phe Asn Glu Tyr Asp Cys Thr Leu Thr Gly Phe Lys Gln Lys
                565                 570                 575

Trp Asn Leu Asp Lys Val Pro Asn Ser Phe Pro Leu Gly Asp Leu Cys
                580                 585                 590

Pro Thr His Ser Gln Asp Tyr Val Leu His Glu Asn Gly Phe Cys Thr
            595                 600                 605

Asp Cys Gly Gly Tyr Ile Pro His Ser Ala Asp Asp Ser Val Tyr Thr
610                 615                 620

Asp Val Ala Ser Glu Thr Ser Ile Ser Ser Asp Pro Gly Asp Leu
625                 630                 635                 640

Gly Asp Thr Asp Gly Glu Asn Ser Gln Pro Glu Thr Ser Asn Val Asp
                645                 650                 655

Asn Arg Pro Ser Lys Lys Arg Val Ile Pro Glu Thr Pro Asn
            660                 665                 670

Ser Pro Val Ser Arg Gln Ser Leu Ser Ser Phe Leu Asp Thr Trp Gln
            675                 680                 685

Ser Gln Pro Arg Asp Glu Asp Glu Leu Arg Ile Tyr Glu Ala Gln Ala
            690                 695                 700

Ser Arg Ile Lys Glu Asn Thr Glu Ser Thr Pro Glu Arg Glu Lys Thr
705                 710                 715                 720

Pro Val Gly Glu Pro Gln Glu Glu Ser Gln Ser Glu Pro Asn Pro Thr
                725                 730                 735

Ala Trp Gly Glu Lys Leu Gly Val Tyr Ser Ser Leu Gln Pro Gly Glu
                740                 745                 750

Pro Pro Ile Val Leu His Cys Phe Glu Asp Leu Arg Pro Ser Asp Glu
            755                 760                 765

Asp Glu Gly Glu Asn Ile Gly Gly Glu
            770                 775

<210> SEQ ID NO 46
<211> LENGTH: 215
<212> TYPE: PRT
```

<213> ORGANISM: Bocavirus

<400> SEQUENCE: 46

Met Ser Ser Glu Ser Met Lys His Arg His Arg Ala Ser Lys Arg Thr
1 5 10 15

Pro Ser Pro Leu Arg Arg Glu Arg Arg His Gln Trp Glu Asn His Lys
20 25 30

Lys Ser Arg Ser Arg Ser Pro Ile Arg Gln His Gly Glu Lys Ser Leu
35 40 45

Glu Ser Thr Pro Arg Tyr Asn Gln Glu Ser Arg Gln Ser Ser Tyr Thr
50 55 60

Ala Ser Lys Thr Ser Asp Gln Ala Thr Lys Thr Arg Glu Lys Thr Ser
65 70 75 80

Gly Gly Asn Arg Thr Asn Pro Tyr Thr Val Phe Ser Gln His Arg Ala
85 90 95

Asn His Pro Asp Ala Pro Gly Trp Cys Gly Phe Tyr Trp His Ser Thr
100 105 110

Arg Leu Ala Arg Asp Gly Thr Asn Cys Ile Phe Asn Glu Met Lys Gln
115 120 125

Glu Phe Gln Glu Leu Gln Ile Asn Gly Lys Ile Thr Trp Asp Asn Val
130 135 140

Arg Glu Leu Leu Phe Ser Gln Lys Lys Lys Leu Asp Gln Lys Tyr Arg
145 150 155 160

Asn Met Leu Tyr His Phe Arg His Asn Thr Asp Cys Pro Arg Cys Asp
165 170 175

Tyr Trp Asp Asp Val Tyr Arg Lys His Leu Ala His Val Ser Ser Gln
180 185 190

Glu Ser Glu Glu Val Thr Asp Glu Glu Met Leu Ser Ala Val Glu Ser
195 200 205

Met Glu Thr Asn Ala Ser Asn
210 215

<210> SEQ ID NO 47
<211> LENGTH: 667
<212> TYPE: PRT
<213> ORGANISM: Bocavirus
<220> FEATURE:
<221> NAME/KEY: misc_feature
<222> LOCATION: (170)..(170)
<223> OTHER INFORMATION: Xaa can be any naturally occurring amino acid

<400> SEQUENCE: 47

Met Pro Pro Ile Lys Arg Gln Pro Gly Gly Trp Val Leu Pro Gly Tyr
1 5 10 15

Lys Tyr Leu Gly Pro Phe Asn Pro Leu Glu Asn Gly Glu Pro Val Asn
20 25 30

Lys Ala Asp Arg Ala Ala Gln Ala His Asp Lys Ser Tyr Ser Glu Leu
35 40 45

Ile Lys Ser Gly Lys Asn Pro Tyr Leu Tyr Phe Asn Lys Ala Asp Glu
50 55 60

Lys Phe Ile Asp Asp Leu Lys Asn Asp Trp Ser Leu Gly Gly Ile Ile
65 70 75 80

Gly Ser Ser Phe Phe Lys Leu Lys Arg Ala Val Ala Pro Ala Leu Gly
85 90 95

Asn Lys Glu Arg Ala Gln Lys Arg His Phe Tyr Phe Ala Asn Ser Asn
100 105 110

Lys Gly Ala Lys Lys Pro Lys Asn Asn Glu Pro Lys Pro Gly Thr Ser

```
                   115                 120                 125
Lys Met Ser Glu Asn Glu Ile Gln Asp Gln Gln Pro Ser Gly Ser Met
130                 135                 140

Glu Glu Arg Gly Gly Gly Gly Ala Val Gly Ser Val Gly Gly
145                 150                 155                 160

Lys Gly Ser Gly Val Gly Ile Ser Thr Xaa Gly Trp Val Gly Ser
                165                 170                 175

Tyr Phe Thr Asp Ser Tyr Val Ile Thr Lys Asn Thr Arg Gln Phe Leu
                180                 185                 190

Val Lys Ile Gln Asn Asp His Lys Tyr Arg Thr Glu Asn Ile Ile Pro
                195                 200                 205

Ser Asn Ala Gly Gly Lys Phe Gln Arg Cys Val Ser Thr Pro Trp Ser
210                 215                 220

Tyr Phe Asn Phe Asn Gln Tyr Ser Ser His Phe Ser Pro Gln Asp Trp
225                 230                 235                 240

Gln Arg Leu Thr Asn Glu Tyr Lys Arg Phe Lys Pro Arg Lys Met His
                245                 250                 255

Val Lys Ile Tyr Asn Leu Gln Ile Lys Gln Ile Leu Ser Asn Gly Ala
                260                 265                 270

Asp Thr Thr Tyr Asn Asn Asp Leu Thr Ala Gly Val His Ile Phe Cys
                275                 280                 285

Asp Gly Glu His Ala Tyr Pro Asn Ala Thr His Pro Trp Asp Glu Asp
290                 295                 300

Val Met Pro Glu Leu Pro Tyr Glu Thr Trp Tyr Leu Phe Gln Tyr Gly
305                 310                 315                 320

Tyr Ile Pro Val Ile His Glu Leu Ala Glu Met Glu Asp Ala Asn Ala
                325                 330                 335

Val Glu Lys Ala Ile Ala Leu Gln Ile Pro Phe Phe Met Leu Glu Asn
                340                 345                 350

Ser Asp His Glu Val Leu Arg Thr Gly Glu Ser Thr Glu Phe Thr Phe
                355                 360                 365

Asp Phe Asp Cys Glu Trp Ile Asn Asn Glu Arg Ala Tyr Ile Pro Pro
                370                 375                 380

Gly Leu Met Phe Asn Pro Lys Val Pro Thr Arg Arg Ala Gln Tyr Ile
385                 390                 395                 400

Arg Gln His Gly Asn Thr Ala Ser Ser Asn Thr Arg Ile Gln Pro Tyr
                405                 410                 415

Ala Lys Pro Thr Ser Trp Met Thr Gly Pro Gly Leu Leu Ser Ala Gln
                420                 425                 430

Arg Val Gly Pro Ala Gly Ser Asp Thr Ala Ser Trp Met Val Val
                435                 440                 445

Asn Pro Asp Gly Ala Ala Val Asn Ser Gly Met Ala Gly Val Gly Ser
450                 455                 460

Gly Phe Asp Pro Pro Ser Gly Ser Leu Arg Pro Thr Asp Leu Glu Tyr
465                 470                 475                 480

Lys Ile Gln Trp Tyr Gln Thr Pro Ala Gly Thr Asn Ser Asp Gly Asn
                485                 490                 495

Ile Ile Ser Asn Pro Pro Leu Ser Met Leu Arg Asp Gln Ala Leu Tyr
                500                 505                 510

Arg Gly Asn Gln Thr Thr Tyr Asn Leu Cys Ser Asp Val Trp Met Phe
                515                 520                 525

Pro Asn Gln Ile Trp Asp Arg Tyr Pro Ile Thr Arg Glu Asn Pro Ile
530                 535                 540
```

```
Trp Cys Lys Lys Pro Arg Ser Asp Lys Asn Thr Ile Ile Asp Pro Phe
545                 550                 555                 560

Asp Gly Thr Leu Ala Met Asp His Pro Pro Gly Thr Ile Phe Ile Lys
            565                 570                 575

Met Ala Lys Ile Pro Val Pro Ser Asn Asn Asn Ala Asp Ser Tyr Leu
            580                 585                 590

Asn Ile Tyr Cys Thr Gly Gln Val Ser Cys Glu Ile Val Trp Glu Val
        595                 600                 605

Glu Arg Tyr Ala Thr Lys Asn Trp Arg Pro Glu Arg Arg His Thr Ala
610                 615                 620

Leu Gly Leu Gly Ile Gly Gly Glu Glu Asn Val Asn Pro Thr Tyr His
625                 630                 635                 640

Val Asp Lys Asn Gly Lys Tyr Ile Gln Pro Thr Thr Trp Asp Met Cys
                645                 650                 655

Tyr Pro Ile Lys Thr Asn Ile Asn Lys Val Leu
                660                 665

<210> SEQ ID NO 48
<211> LENGTH: 538
<212> TYPE: PRT
<213> ORGANISM: Bocavirus
<220> FEATURE:
<221> NAME/KEY: misc_feature
<222> LOCATION: (41)..(41)
<223> OTHER INFORMATION: Xaa can be any naturally occurring amino acid

<400> SEQUENCE: 48

Met Ser Glu Asn Glu Ile Gln Asp Gln Gln Pro Ser Gly Ser Met Glu
1               5                   10                  15

Glu Arg Gly Gly Gly Gly Gly Ala Val Gly Ser Val Gly Gly Gly Lys
            20                  25                  30

Gly Ser Gly Val Gly Ile Ser Thr Xaa Gly Trp Val Gly Gly Ser Tyr
        35                  40                  45

Phe Thr Asp Ser Tyr Val Ile Thr Lys Asn Thr Arg Gln Phe Leu Val
    50                  55                  60

Lys Ile Gln Asn Asp His Lys Tyr Arg Thr Glu Asn Ile Ile Pro Ser
65                  70                  75                  80

Asn Ala Gly Gly Lys Phe Gln Arg Cys Val Ser Thr Pro Trp Ser Tyr
                85                  90                  95

Phe Asn Phe Asn Gln Tyr Ser Ser His Phe Ser Pro Gln Asp Trp Gln
            100                 105                 110

Arg Leu Thr Asn Glu Tyr Lys Arg Phe Lys Pro Arg Lys Met His Val
        115                 120                 125

Lys Ile Tyr Asn Leu Gln Ile Lys Gln Ile Leu Ser Asn Gly Ala Asp
130                 135                 140

Thr Thr Tyr Asn Asn Asp Leu Thr Ala Gly Val His Ile Phe Cys Asp
145                 150                 155                 160

Gly Glu His Ala Tyr Pro Asn Ala Thr His Pro Trp Asp Glu Asp Val
                165                 170                 175

Met Pro Glu Leu Pro Tyr Glu Thr Trp Tyr Leu Phe Gln Tyr Gly Tyr
            180                 185                 190

Ile Pro Val Ile His Glu Leu Ala Glu Met Glu Asp Ala Asn Ala Val
        195                 200                 205

Glu Lys Ala Ile Ala Leu Gln Ile Pro Phe Phe Met Leu Glu Asn Ser
210                 215                 220

Asp His Glu Val Leu Arg Thr Gly Glu Ser Thr Glu Phe Thr Phe Asp
225                 230                 235                 240
```

Phe Asp Cys Glu Trp Ile Asn Asn Glu Arg Ala Tyr Ile Pro Pro Gly
            245                 250                 255

Leu Met Phe Asn Pro Lys Val Pro Thr Arg Arg Ala Gln Tyr Ile Arg
        260                 265                 270

Gln His Gly Asn Thr Ala Ser Ser Asn Thr Arg Ile Gln Pro Tyr Ala
            275                 280                 285

Lys Pro Thr Ser Trp Met Thr Gly Pro Gly Leu Leu Ser Ala Gln Arg
        290                 295                 300

Val Gly Pro Ala Gly Ser Asp Thr Ala Ser Trp Met Val Val Val Asn
305                 310                 315                 320

Pro Asp Gly Ala Ala Val Asn Ser Gly Met Ala Gly Val Gly Ser Gly
                325                 330                 335

Phe Asp Pro Pro Ser Gly Ser Leu Arg Pro Thr Asp Leu Glu Tyr Lys
            340                 345                 350

Ile Gln Trp Tyr Gln Thr Pro Ala Gly Thr Asn Ser Asp Gly Asn Ile
            355                 360                 365

Ile Ser Asn Pro Pro Leu Ser Met Leu Arg Asp Gln Ala Leu Tyr Arg
        370                 375                 380

Gly Asn Gln Thr Thr Tyr Asn Leu Cys Ser Asp Val Trp Met Phe Pro
385                 390                 395                 400

Asn Gln Ile Trp Asp Arg Tyr Pro Ile Thr Arg Glu Asn Pro Ile Trp
                405                 410                 415

Cys Lys Lys Pro Arg Ser Asp Lys Asn Thr Ile Ile Asp Pro Phe Asp
            420                 425                 430

Gly Thr Leu Ala Met Asp His Pro Pro Gly Thr Ile Phe Ile Lys Met
        435                 440                 445

Ala Lys Ile Pro Val Pro Ser Asn Asn Ala Asp Ser Tyr Leu Asn
        450                 455                 460

Ile Tyr Cys Thr Gly Gln Val Ser Cys Glu Ile Val Trp Glu Val Glu
465                 470                 475                 480

Arg Tyr Ala Thr Lys Asn Trp Arg Pro Glu Arg Arg His Thr Ala Leu
                485                 490                 495

Gly Leu Gly Ile Gly Gly Glu Glu Asn Val Asn Pro Thr Tyr His Val
            500                 505                 510

Asp Lys Asn Gly Lys Tyr Ile Gln Pro Thr Thr Trp Asp Met Cys Tyr
        515                 520                 525

Pro Ile Lys Thr Asn Ile Asn Lys Val Leu
        530                 535

<210> SEQ ID NO 49
<211> LENGTH: 5134
<212> TYPE: DNA
<213> ORGANISM: Bocavirus

<400> SEQUENCE: 49
gacgtatgtc aaccaatcag catcgagcat atatcctata taagccgatg cacttccgca      60
tctcgtcaga ctgcatccgg tctccggcga gtgaacatct ctgggaagag ctccacgcac     120
gtggtgagtg acactatggc cttttctgct cctgtaatta gagcttttc tcaacctgct     180 ttcacttatg ttgttaaatt tccatatgat aactggaaag aggaagaaca cttactatgg     240
agcttacttg ctcctgggac tgaacgtctc atgatccaac taagaaactg cgcaccacat     300
cctgaagatg atcctgtcag ggaagatatt ttatgctcac tagcagacca acactatgct     360
gctattttca ccaaggcttg ctacatggct gtaacttcac tcatggggca gaaacagaga     420

```
acacactttc cacgatgcga cataatatgc caggctgaga tcggctcaga atatctacac     480
tgtcacatac ttgttggagg agcaggtcta agcaagagaa atgctaaaat ttcatgtgct     540
acgctcctag gccttgtgat ggctgaatta acacaacgct gcaaactact tcttgcacag     600
cgtccatttg aaccagatga agctagaata ttccatctac tcagacgcgt tgaacgcgaa     660
gcatggtcag ggcacactgg taactgggtt caaattcttc aatacagaga caagcgaggt     720
gaccttcatg ctcaacacat tgatccttta cgcttttca aacactacct gctgccaaaa     780
aatcgattga tctctccttc cagcaagcct gacgtctgca ctactccaga taactggttt     840
gtcctagctg ataaaacata cgctcacact attgttaatg gcttccgct gctagaacat      900 aacagaaagg cctatctaca agagttagag agtgaagtca tcccgggcc ttctaccatg       960 gcctttgggg gacgtggtgc gtgggaacat ctgcctgagg taggagaaca acgcctaatt    1020
acttctaata cttctactgc ttataaagct aacaaaaaag aaaaactaat gctaaactta    1080
cttgataaat gtgatgaact taacttactt gtatatgaag acttagttag tgcttgtcct    1140
gaccttttac ttatgcttga aggtcagcca ggtggtgcac gcctaattga acaggtgcta    1200
ggcatgcatc atattaaagt gtgtgctaat tatacagctc tatcattcct atttcattta    1260
catcctaatc aattattaac ttctagcaat aaagcactaa aactattgtt gattcaagga    1320
tacaacccat tgcaggtagg gcacgccatc tgctgtgtac ttaacaaaca gatgggcaag    1380
cagaacacta tctgctttta tggtcctgct tcaacaggca aaacaaatat tgcaaaggcc    1440
atagtccaag gcgttcgcct ttatggctgt gttaatcatc taaacaaagg gtttgtcttt    1500
aacgattgca gacaacgcct tataatttgg tgggaggaat gtttaatgca tcaagattgg    1560
gttgaacctg ctaaatgcat tttaggtgga accgaatgta gaattgatgt taaacacaaa    1620
gacagtgttc ttcttcaaca aacaccagta attatttcca ctaaccatga catctactct    1680
gtagttggtg gcaatactgt atctcatgtt catgcagcgc ccttaaaaga gcgaattctt    1740
caactaaatt ttatgaaaca actgccacaa acatttggag agatttctcc agttgaaatt    1800
gcagagttgc tgcaatggtg ctttaatgag tacgaatgta ctcttactgg ctttaaacaa    1860
aaatggaact tagataaagt tccaaactca tttcctcttg ggacctttg tcctacacat    1920 tcacaggact acgtgcttca cgaaaacgga ttctgcactg actgcggcgg ctatattcct    1980
catagtgctg acgactctgt gtatactgac gtggctagcg agacatcaat cagcagctgc    2040
gacccaggta ggcattaata cattagcctt ttaatatgct actttctaga tgcttatgta    2100
ttaactccta caggtgactt gggggatacg gacggagaga actcccagcc ggagacatcg    2160
aacgtggata atcgtccatc caagaagaga cgtgtgattc cagaaactcc accaaacagt    2220
ccagtaagtc gccaaagcct ttctagcttt ttagatacgt ggcagtcaca acctagagac    2280
gaagatgagc tccgaatcta tgaagcacag gcatcgcgca tcaaagagaa caccgagtcc    2340
actccggaga gagagaagac accagtggga gaaccacaag aagagtcgca gtcggagccc    2400
gatccgacag catggggaga aaagcttgga gtctactcct cgctacaacc aggagagccg    2460
ccaatcgtct tacactgctt cgaagacctc agaccaagcg acgaagacga aggagaaaac    2520
atcggggggg aatagaacca atccttatac tgtgttcagt caacacaggg ctaatcatcc    2580
agatgctcct ggatggtgtg ggttttactg gcattctact aggcttgcta gagatggcac    2640
taattgtatc tttaatgaaa tgaaacaaga atttcaagaa ttgcaaataa atggaaaaat    2700
tacctgggac aatgttagag aactattgtt tagccagaaa aaaagctag atcaaaaata     2760 cagaaacatg ctgtaccatt tcagacataa tgctgattgt cctagatgtg attattggga    2820
```

```
tgatgtctac cgtaaacact tagctcatgt ctcttcacag gaatcagagg aggtaacaga    2880
cgaagaaatg ctttctgctg ttgaaagcat ggaaacaaat gcctccaatt aaacgccaac    2940
ctggagggtg ggtgcttcct ggttataaat accttggtcc atttaatcct cttgaaaacg    3000 gtaaccagt  taataaagct gatcgtgctg ctcaagctca tgataaatca tattctgaat    3060
taataaagag tggaaaaaat ccttacttgt atttcaataa agctgatgag aaattcattg    3120
acgatttgaa aaacgactgg tctcttggtg gcattattgg ctcaagtttc tttaaactta    3180
agcgcgccgt ggctcctgct ctaggaaata aagagcgagc tcaaaaaaga cattttttact   3240 ttgcaaactc aaataaaggt gctaaaaaac caaaaaataa cgagcctaaa ccaggcactt    3300
caaaaatgtc tgaaaatgaa atccaagacc aacaaccatc tgactcaatg aagagcgag    3360 gaggaggagg aggtgcgacc ggtagtgtgg gaggggggaa aggttctggt gtgggtatat   3420
ccacaggtgg ctgggtagga ggcagctact tcactgactc atatgtcata caaaaaaaca    3480
ccagacaatt tctggtaaaa atacaaaatg accacaaata cagaactgaa aatattattc    3540
caagcaatgc tggaggaaaa tcacaaagat gcgtcagcac accgtggtca tatttcaact    3600
tcaatcaata cagcagtcat ttttcaccac aagactggca gcgcctaaca aatgaatata    3660
agcgctttaa acctagaaaa atgcatgtaa aaatttacaa tctacaaata aaacaaatac    3720
tttcaaatgg tgctgacact acatacaaca acgacctaac agctggtgtt cacatcttttt   3780 gtgatggtga acacgcatat ccaaatgcaa cacatccatg ggatgaagac gtgatgccag    3840
aacttccata tgaaacatgg tatctgtttc aatatggata cattccagtt attcatgaac    3900
ttgctgaaat ggaagacgca aatgctgtag aaaaagctat agcactacaa ataccattct    3960
tcatgcttga aaacagtgac catgaagttc taagaactgg agaaagcaca gaattcactt    4020
ttgattttga ctgtgagtgg atcaacaacg aaagagcata cattcctcct ggattaatgt    4080
ttaatccaaa agttcctacg agaagagctc aatacattag acagcacgga aacacagcat    4140
caagcaacac cagaattcaa ccatatgcaa aacctacaag ctggatgaca ggaccaggtc    4200
tactcagtgc acaaagagta ggaccagctg gctcagacac tgcatcatgg atggttgttg    4260
ttaatccaga cggaactgcc gttaactcag gaatggcagg agttggatca ggatttgatc    4320
ctccttcagg atctctaaga ccaactgact agaatacaa aatacaatgg taccaaactc    4380
ctgaaggtac caacagtgat ggaaacataa tttcaaatcc accactgtcc atgcttagag    4440
atcaagctct ctacagagga aatcaaacaa cctataacct atgctcagat gtatggatgt    4500
tcccaaatca aatttgggac agatatccaa taaccagaga aaacccaatt tggtgcaaaa    4560
agccaagatc agataaaaac acaataattg atcctttcga tggaacactc gcaatggatc    4620
atcctcctgg aacaatcttc ataaaaatgg caaaaattcc agttccttca aacaacaacg    4680
cagactcata cctaaacatc tactgcacag acaagtcag ctgcgaaatt gtctgggaag    4740
ttgaaagata cgcaacaaag aactgggaca cagagaaag acacaccgca cttggtcttg    4800
gaatcggagg agaagaaaac ataaatccaa cttaccatgt agacaaaaat ggaaaataca    4860
ttcagccaac aacatgggac atgtgctatc ctatcaaaac aaacatcaat aaagtgttgt    4920
aatctcttaa gcctgttcat tgcttatgct tataagttcc tctccaatgg acaagaggaa    4980
agaaaagggt gactgtaatc ccgagctcat gagttcgagg ctacagtccg atggcagtgg    5040
tgttgccgtc tcgaacctag ccgttacacc cttgtgcatt gtgggaggag ctgttttgct    5100
tacgcaaccg cgaaatttta tatatttaat gtag                                5134
```

<210> SEQ ID NO 50

<211> LENGTH: 640
<212> TYPE: PRT
<213> ORGANISM: Bocavirus

<400> SEQUENCE: 50

```
Met Ala Phe Ser Ala Pro Val Ile Arg Ala Phe Ser Gln Pro Ala Phe
1               5                   10                  15

Thr Tyr Val Val Lys Phe Pro Tyr Asp Asn Trp Lys Glu Glu Glu His
            20                  25                  30

Leu Leu Trp Ser Leu Leu Ala Pro Gly Thr Glu Arg Leu Met Ile Gln
        35                  40                  45

Leu Arg Asn Cys Ala Pro His Pro Glu Asp Pro Val Arg Glu Asp
50                  55                  60

Ile Leu Cys Ser Leu Ala Asp Gln His Tyr Ala Ala Ile Phe Thr Lys
65                  70                  75                  80

Ala Cys Tyr Met Ala Val Thr Ser Leu Met Gly Gln Lys Gln Arg Thr
                85                  90                  95

His Phe Pro Arg Cys Asp Ile Ile Cys Gln Ala Glu Ile Gly Ser Glu
            100                 105                 110

Tyr Leu His Cys His Ile Leu Val Gly Gly Ala Gly Leu Ser Lys Arg
        115                 120                 125

Asn Ala Lys Ile Ser Cys Ala Thr Leu Leu Gly Leu Val Met Ala Glu
130                 135                 140

Leu Thr Gln Arg Cys Lys Leu Leu Ala Gln Arg Pro Phe Glu Pro
145                 150                 155                 160

Asp Glu Ala Arg Ile Phe His Leu Leu Arg Arg Val Glu Arg Glu Ala
                165                 170                 175

Trp Ser Gly His Thr Gly Asn Trp Val Gln Ile Leu Gln Tyr Arg Asp
            180                 185                 190

Lys Arg Gly Asp Leu His Ala Gln His Ile Asp Pro Leu Arg Phe Phe
        195                 200                 205

Lys His Tyr Leu Leu Pro Lys Asn Arg Leu Ile Ser Pro Ser Ser Lys
210                 215                 220

Pro Asp Val Cys Thr Thr Pro Asp Asn Trp Phe Val Leu Ala Asp Lys
225                 230                 235                 240

Thr Tyr Ala His Thr Ile Val Asn Gly Leu Pro Leu Leu Glu His Asn
                245                 250                 255

Arg Lys Ala Tyr Leu Gln Glu Leu Glu Ser Glu Val Ile Pro Gly Pro
            260                 265                 270

Ser Thr Met Ala Phe Gly Gly Arg Gly Ala Trp Glu His Leu Pro Glu
        275                 280                 285

Val Gly Glu Gln Arg Leu Ile Thr Ser Asn Thr Ser Thr Ala Tyr Lys
290                 295                 300

Ala Asn Lys Lys Glu Lys Leu Met Leu Asn Leu Leu Asp Lys Cys Asp
305                 310                 315                 320

Glu Leu Asn Leu Leu Val Tyr Glu Asp Leu Val Ser Ala Cys Pro Asp
                325                 330                 335

Leu Leu Leu Met Leu Glu Gly Gln Pro Gly Gly Ala Arg Leu Ile Glu
            340                 345                 350

Gln Val Leu Gly Met His His Ile Lys Val Cys Ala Asn Tyr Thr Ala
        355                 360                 365

Leu Ser Phe Leu Phe His Leu His Pro Asn Gln Leu Leu Thr Ser Ser
370                 375                 380

Asn Lys Ala Leu Lys Leu Leu Leu Ile Gln Gly Tyr Asn Pro Leu Gln
385                 390                 395                 400
```

```
Val Gly His Ala Ile Cys Cys Val Leu Asn Lys Gln Met Gly Lys Gln
                405                 410                 415

Asn Thr Ile Cys Phe Tyr Gly Pro Ala Ser Thr Gly Lys Thr Asn Ile
            420                 425                 430

Ala Lys Ala Ile Val Gln Gly Val Arg Leu Tyr Gly Cys Val Asn His
        435                 440                 445

Leu Asn Lys Gly Phe Val Phe Asn Asp Cys Arg Gln Arg Leu Ile Ile
    450                 455                 460

Trp Trp Glu Glu Cys Leu Met His Gln Asp Trp Val Glu Pro Ala Lys
465                 470                 475                 480

Cys Ile Leu Gly Gly Thr Glu Cys Arg Ile Asp Val Lys His Lys Asp
                485                 490                 495

Ser Val Leu Leu Gln Gln Thr Pro Val Ile Ile Ser Thr Asn His Asp
            500                 505                 510

Ile Tyr Ser Val Val Gly Gly Asn Thr Val Ser His Val His Ala Ala
        515                 520                 525

Pro Leu Lys Glu Arg Ile Leu Gln Leu Asn Phe Met Lys Gln Leu Pro
    530                 535                 540

Gln Thr Phe Gly Glu Ile Ser Pro Val Glu Ile Ala Glu Leu Leu Gln
545                 550                 555                 560

Trp Cys Phe Asn Glu Tyr Glu Cys Thr Leu Thr Gly Phe Lys Gln Lys
                565                 570                 575

Trp Asn Leu Asp Lys Val Pro Asn Ser Phe Pro Leu Gly Asp Leu Cys
            580                 585                 590

Pro Thr His Ser Gln Asp Tyr Val Leu His Glu Asn Gly Phe Cys Thr
        595                 600                 605

Asp Cys Gly Gly Tyr Ile Pro His Ser Ala Asp Ser Val Tyr Thr
    610                 615                 620

Asp Val Ala Ser Glu Thr Ser Ile Ser Ser Cys Asp Pro Gly Arg His
625                 630                 635                 640

<210> SEQ ID NO 51
<211> LENGTH: 777
<212> TYPE: PRT
<213> ORGANISM: Bocavirus

<400> SEQUENCE: 51

Met Ala Phe Ser Ala Pro Val Ile Arg Ala Phe Ser Gln Pro Ala Phe
1               5                   10                  15

Thr Tyr Val Val Lys Phe Pro Tyr Asp Asn Trp Lys Glu Glu His
                20                  25                  30

Leu Leu Trp Ser Leu Leu Ala Pro Gly Thr Glu Arg Leu Met Ile Gln
            35                  40                  45

Leu Arg Asn Cys Ala Pro His Pro Glu Asp Asp Pro Val Arg Glu Asp
        50                  55                  60

Ile Leu Cys Ser Leu Ala Asp Gln His Tyr Ala Ala Ile Phe Thr Lys
65                  70                  75                  80

Ala Cys Tyr Met Ala Val Thr Ser Leu Met Gly Gln Lys Gln Arg Thr
                85                  90                  95

His Phe Pro Arg Cys Asp Ile Ile Cys Gln Ala Glu Ile Gly Ser Glu
            100                 105                 110

Tyr Leu His Cys His Ile Leu Val Gly Gly Ala Gly Leu Ser Lys Arg
        115                 120                 125

Asn Ala Lys Ile Ser Cys Ala Thr Leu Leu Gly Leu Val Met Ala Glu
    130                 135                 140
```

```
Leu Thr Gln Arg Cys Lys Leu Leu Ala Gln Arg Pro Phe Glu Pro
145                 150                 155                 160

Asp Glu Ala Arg Ile Phe His Leu Leu Arg Arg Val Glu Arg Glu Ala
                165                 170                 175

Trp Ser Gly His Thr Gly Asn Trp Val Gln Ile Leu Gln Tyr Arg Asp
            180                 185                 190

Lys Arg Gly Asp Leu His Ala Gln His Ile Asp Pro Leu Arg Phe Phe
                195                 200                 205

Lys His Tyr Leu Leu Pro Lys Asn Arg Leu Ile Ser Pro Ser Ser Lys
210                 215                 220

Pro Asp Val Cys Thr Thr Pro Asp Asn Trp Phe Val Leu Ala Asp Lys
225                 230                 235                 240

Thr Tyr Ala His Thr Ile Val Asn Gly Leu Pro Leu Leu Glu His Asn
                245                 250                 255

Arg Lys Ala Tyr Leu Gln Glu Leu Glu Ser Glu Val Ile Pro Gly Pro
                260                 265                 270

Ser Thr Met Ala Phe Gly Gly Arg Gly Ala Trp Glu His Leu Pro Glu
            275                 280                 285

Val Gly Glu Gln Arg Leu Ile Thr Ser Asn Thr Ser Thr Ala Tyr Lys
290                 295                 300

Ala Asn Lys Lys Glu Lys Leu Met Leu Asn Leu Leu Asp Lys Cys Asp
305                 310                 315                 320

Glu Leu Asn Leu Leu Val Tyr Glu Asp Leu Val Ser Ala Cys Pro Asp
                325                 330                 335

Leu Leu Leu Met Leu Glu Gly Gln Pro Gly Gly Ala Arg Leu Ile Glu
                340                 345                 350

Gln Val Leu Gly Met His His Ile Lys Val Cys Ala Asn Tyr Thr Ala
            355                 360                 365

Leu Ser Phe Leu Phe His Leu His Pro Asn Gln Leu Leu Thr Ser Ser
            370                 375                 380

Asn Lys Ala Leu Lys Leu Leu Ile Gln Gly Tyr Asn Pro Leu Gln
385                 390                 395                 400

Val Gly His Ala Ile Cys Cys Val Leu Asn Lys Met Gly Lys Gln
                405                 410                 415

Asn Thr Ile Cys Phe Tyr Gly Pro Ala Ser Thr Gly Lys Thr Asn Ile
            420                 425                 430

Ala Lys Ala Ile Val Gln Gly Val Arg Leu Tyr Gly Cys Val Asn His
            435                 440                 445

Leu Asn Lys Gly Phe Val Phe Asn Asp Cys Arg Gln Arg Leu Ile Ile
    450                 455                 460

Trp Trp Glu Glu Cys Leu Met His Gln Asp Trp Val Glu Pro Ala Lys
465                 470                 475                 480

Cys Ile Leu Gly Gly Thr Glu Cys Arg Ile Asp Val Lys His Lys Asp
                485                 490                 495

Ser Val Leu Leu Gln Gln Thr Pro Val Ile Ser Thr Asn His Asp
                500                 505                 510

Ile Tyr Ser Val Val Gly Gly Asn Thr Val Ser His Val His Ala Ala
            515                 520                 525

Pro Leu Lys Glu Arg Ile Leu Gln Leu Asn Phe Met Lys Gln Leu Pro
530                 535                 540

Gln Thr Phe Gly Glu Ile Ser Pro Val Glu Ile Ala Glu Leu Leu Gln
545                 550                 555                 560

Trp Cys Phe Asn Glu Tyr Glu Cys Thr Leu Thr Gly Phe Lys Gln Lys
```

```
                    565                 570                 575
Trp Asn Leu Asp Lys Val Pro Asn Ser Phe Pro Leu Gly Asp Leu Cys
            580                 585                 590

Pro Thr His Ser Gln Asp Tyr Val Leu His Glu Asn Gly Phe Cys Thr
        595                 600                 605

Asp Cys Gly Gly Tyr Ile Pro His Ser Ala Asp Asp Ser Val Tyr Thr
    610                 615                 620

Asp Val Ala Ser Glu Thr Ser Ile Ser Ser Cys Asp Pro Gly Asp Leu
625                 630                 635                 640

Gly Asp Thr Asp Gly Glu Asn Ser Gln Pro Glu Thr Ser Asn Val Asp
                645                 650                 655

Asn Arg Pro Ser Lys Lys Arg Val Ile Pro Glu Thr Pro Pro Asn
            660                 665                 670

Ser Pro Val Ser Arg Gln Ser Leu Ser Ser Phe Leu Asp Thr Trp Gln
        675                 680                 685

Ser Gln Pro Arg Asp Glu Asp Leu Arg Ile Tyr Glu Ala Gln Ala
    690                 695                 700

Ser Arg Ile Lys Glu Asn Thr Glu Ser Thr Pro Glu Arg Glu Lys Thr
705                 710                 715                 720

Pro Val Gly Glu Pro Gln Glu Ser Gln Ser Glu Pro Asp Pro Thr
                725                 730                 735

Ala Trp Gly Glu Lys Leu Gly Val Tyr Ser Ser Leu Gln Pro Gly Glu
            740                 745                 750

Pro Pro Ile Val Leu His Cys Phe Glu Asp Leu Arg Pro Ser Asp Glu
        755                 760                 765

Asp Glu Gly Glu Asn Ile Gly Gly Glu
    770                 775

<210> SEQ ID NO 52
<211> LENGTH: 215
<212> TYPE: PRT
<213> ORGANISM: Bocavirus

<400> SEQUENCE: 52

Met Ser Ser Glu Ser Met Lys His Arg His Arg Ala Ser Lys Arg Thr
1               5                   10                  15

Pro Ser Pro Leu Arg Arg Glu Arg His Gln Trp Glu Asn His Lys
            20                  25                  30

Lys Ser Arg Ser Arg Ser Pro Ile Arg Gln His Gly Glu Lys Ser Leu
        35                  40                  45

Glu Ser Thr Pro Arg Tyr Asn Gln Glu Ser Arg Gln Ser Ser Tyr Thr
    50                  55                  60

Ala Ser Lys Thr Ser Asp Gln Ala Thr Lys Thr Lys Glu Lys Thr Ser
65                  70                  75                  80

Gly Gly Asn Arg Thr Asn Pro Tyr Thr Val Phe Ser Gln His Arg Ala
                85                  90                  95

Asn His Pro Asp Ala Pro Gly Trp Cys Gly Phe Tyr Trp His Ser Thr
            100                 105                 110

Arg Leu Ala Arg Asp Gly Thr Asn Cys Ile Phe Asn Glu Met Lys Gln
        115                 120                 125

Glu Phe Gln Glu Leu Gln Ile Asn Gly Lys Ile Thr Trp Asp Asn Val
    130                 135                 140

Arg Glu Leu Leu Phe Ser Gln Lys Lys Leu Asp Gln Lys Tyr Arg
145                 150                 155                 160

Asn Met Leu Tyr His Phe Arg His Asn Ala Asp Cys Pro Arg Cys Asp
```

-continued

```
                165                 170                 175
Tyr Trp Asp Asp Val Tyr Arg Lys His Leu Ala His Val Ser Ser Gln
            180                 185                 190

Glu Ser Glu Glu Val Thr Asp Glu Glu Met Leu Ser Ala Val Glu Ser
        195                 200                 205

Met Glu Thr Asn Ala Ser Asn
    210                 215

<210> SEQ ID NO 53
<211> LENGTH: 667
<212> TYPE: PRT
<213> ORGANISM: Bocavirus

<400> SEQUENCE: 53

Met Pro Pro Ile Lys Arg Gln Pro Gly Gly Trp Val Leu Pro Gly Tyr
1               5                   10                  15

Lys Tyr Leu Gly Pro Phe Asn Pro Leu Glu Asn Gly Lys Pro Val Asn
            20                  25                  30

Lys Ala Asp Arg Ala Ala Gln Ala His Asp Lys Ser Tyr Ser Glu Leu
        35                  40                  45

Ile Lys Ser Gly Lys Asn Pro Tyr Leu Tyr Phe Asn Lys Ala Asp Glu
    50                  55                  60

Lys Phe Ile Asp Asp Leu Lys Asn Asp Trp Ser Leu Gly Gly Ile Ile
65                  70                  75                  80

Gly Ser Ser Phe Phe Lys Leu Lys Arg Ala Val Ala Pro Ala Leu Gly
                85                  90                  95

Asn Lys Glu Arg Ala Gln Lys Arg His Phe Tyr Phe Ala Asn Ser Asn
            100                 105                 110

Lys Gly Ala Lys Lys Pro Lys Asn Asn Glu Pro Lys Pro Gly Thr Ser
        115                 120                 125

Lys Met Ser Glu Asn Glu Ile Gln Asp Gln Pro Ser Asp Ser Met
    130                 135                 140

Glu Glu Arg Gly Gly Gly Gly Ala Thr Gly Ser Val Gly Gly
145                 150                 155                 160

Lys Gly Ser Gly Val Gly Ile Ser Thr Gly Gly Trp Val Gly Ser
                165                 170                 175

Tyr Phe Thr Asp Ser Tyr Val Ile Thr Lys Asn Thr Arg Gln Phe Leu
            180                 185                 190

Val Lys Ile Gln Asn Asp His Lys Tyr Arg Thr Glu Asn Ile Ile Pro
        195                 200                 205

Ser Asn Ala Gly Gly Lys Ser Gln Arg Cys Val Ser Thr Pro Trp Ser
    210                 215                 220

Tyr Phe Asn Phe Asn Gln Tyr Ser Ser His Phe Ser Pro Gln Asp Trp
225                 230                 235                 240

Gln Arg Leu Thr Asn Glu Tyr Lys Arg Phe Lys Pro Arg Lys Met His
                245                 250                 255

Val Lys Ile Tyr Asn Leu Gln Ile Lys Gln Ile Leu Ser Asn Gly Ala
            260                 265                 270

Asp Thr Thr Tyr Asn Asn Asp Leu Thr Ala Gly Val His Ile Phe Cys
        275                 280                 285

Asp Gly Glu His Ala Tyr Pro Asn Ala Thr His Pro Trp Asp Glu Asp
    290                 295                 300

Val Met Pro Glu Leu Pro Tyr Glu Thr Trp Tyr Leu Phe Gln Tyr Gly
305                 310                 315                 320

Tyr Ile Pro Val Ile His Glu Leu Ala Glu Met Glu Asp Ala Asn Ala
```

```
                    325                 330                 335
Val Glu Lys Ala Ile Ala Leu Gln Ile Pro Phe Phe Met Leu Glu Asn
                340                 345                 350

Ser Asp His Glu Val Leu Arg Thr Gly Glu Ser Thr Glu Phe Thr Phe
            355                 360                 365

Asp Phe Asp Cys Glu Trp Ile Asn Asn Glu Arg Ala Tyr Ile Pro Pro
        370                 375                 380

Gly Leu Met Phe Asn Pro Lys Val Pro Thr Arg Arg Ala Gln Tyr Ile
385                 390                 395                 400

Arg Gln His Gly Asn Thr Ala Ser Ser Asn Thr Arg Ile Gln Pro Tyr
                405                 410                 415

Ala Lys Pro Thr Ser Trp Met Thr Gly Pro Gly Leu Leu Ser Ala Gln
            420                 425                 430

Arg Val Gly Pro Ala Gly Ser Asp Thr Ala Ser Trp Met Val Val Val
        435                 440                 445

Asn Pro Asp Gly Thr Ala Val Asn Ser Gly Met Ala Gly Val Gly Ser
    450                 455                 460

Gly Phe Asp Pro Pro Ser Gly Ser Leu Arg Pro Thr Asp Leu Glu Tyr
465                 470                 475                 480

Lys Ile Gln Trp Tyr Gln Thr Pro Glu Gly Thr Asn Ser Asp Gly Asn
                485                 490                 495

Ile Ile Ser Asn Pro Pro Leu Ser Met Leu Arg Asp Gln Ala Leu Tyr
            500                 505                 510

Arg Gly Asn Gln Thr Thr Tyr Asn Leu Cys Ser Asp Val Trp Met Phe
        515                 520                 525

Pro Asn Gln Ile Trp Asp Arg Tyr Pro Ile Thr Arg Glu Asn Pro Ile
    530                 535                 540

Trp Cys Lys Lys Pro Arg Ser Asp Lys Asn Thr Ile Ile Asp Pro Phe
545                 550                 555                 560

Asp Gly Thr Leu Ala Met Asp His Pro Pro Gly Thr Ile Phe Ile Lys
                565                 570                 575

Met Ala Lys Ile Pro Val Pro Ser Asn Asn Asn Ala Asp Ser Tyr Leu
            580                 585                 590

Asn Ile Tyr Cys Thr Gly Gln Val Ser Cys Glu Ile Val Trp Glu Val
        595                 600                 605

Glu Arg Tyr Ala Thr Lys Asn Trp Arg Pro Glu Arg Arg His Thr Ala
    610                 615                 620

Leu Gly Leu Gly Ile Gly Gly Glu Glu Asn Ile Asn Pro Thr Tyr His
625                 630                 635                 640

Val Asp Lys Asn Gly Lys Tyr Ile Gln Pro Thr Thr Trp Asp Met Cys
                645                 650                 655

Tyr Pro Ile Lys Thr Asn Ile Asn Lys Val Leu
            660                 665

<210> SEQ ID NO 54
<211> LENGTH: 538
<212> TYPE: PRT
<213> ORGANISM: Bocavirus

<400> SEQUENCE: 54

Met Ser Glu Asn Glu Ile Gln Asp Gln Gln Pro Ser Asp Ser Met Glu
1               5                   10                  15

Glu Arg Gly Gly Gly Gly Gly Ala Thr Gly Ser Val Gly Gly Gly Lys
            20                  25                  30

Gly Ser Gly Val Gly Ile Ser Thr Gly Gly Trp Val Gly Gly Ser Tyr
```

-continued

```
                35                  40                  45
Phe Thr Asp Ser Tyr Val Ile Thr Lys Asn Thr Arg Gln Phe Leu Val
 50                  55                  60
Lys Ile Gln Asn Asp His Lys Tyr Arg Thr Glu Asn Ile Ile Pro Ser
 65                  70                  75                  80
Asn Ala Gly Gly Lys Ser Gln Arg Cys Val Ser Thr Pro Trp Ser Tyr
                 85                  90                  95
Phe Asn Phe Asn Gln Tyr Ser Ser His Phe Ser Pro Asp Trp Gln
                100                 105                 110
Arg Leu Thr Asn Glu Tyr Lys Arg Phe Lys Pro Arg Lys Met His Val
                115                 120                 125
Lys Ile Tyr Asn Leu Gln Ile Lys Gln Ile Leu Ser Asn Gly Ala Asp
130                 135                 140
Thr Thr Tyr Asn Asn Asp Leu Thr Ala Gly Val His Ile Phe Cys Asp
145                 150                 155                 160
Gly Glu His Ala Tyr Pro Asn Ala Thr His Pro Trp Asp Glu Asp Val
                165                 170                 175
Met Pro Glu Leu Pro Tyr Glu Thr Trp Tyr Leu Phe Gln Tyr Gly Tyr
                180                 185                 190
Ile Pro Val Ile His Glu Leu Ala Glu Met Glu Asp Ala Asn Ala Val
                195                 200                 205
Glu Lys Ala Ile Ala Leu Gln Ile Pro Phe Phe Met Leu Glu Asn Ser
210                 215                 220
Asp His Glu Val Leu Arg Thr Gly Glu Ser Thr Glu Phe Thr Phe Asp
225                 230                 235                 240
Phe Asp Cys Glu Trp Ile Asn Asn Glu Arg Ala Tyr Ile Pro Pro Gly
                245                 250                 255
Leu Met Phe Asn Pro Lys Val Pro Thr Arg Arg Ala Gln Tyr Ile Arg
                260                 265                 270
Gln His Gly Asn Thr Ala Ser Ser Asn Thr Arg Ile Gln Pro Tyr Ala
                275                 280                 285
Lys Pro Thr Ser Trp Met Thr Gly Pro Gly Leu Leu Ser Ala Gln Arg
290                 295                 300
Val Gly Pro Ala Gly Ser Asp Thr Ala Ser Trp Met Val Val Asn
305                 310                 315                 320
Pro Asp Gly Thr Ala Val Asn Ser Gly Met Ala Gly Val Gly Ser Gly
                325                 330                 335
Phe Asp Pro Pro Ser Gly Ser Leu Arg Pro Thr Asp Leu Glu Tyr Lys
                340                 345                 350
Ile Gln Trp Tyr Gln Thr Pro Glu Gly Thr Asn Ser Asp Gly Asn Ile
                355                 360                 365
Ile Ser Asn Pro Pro Leu Ser Met Leu Arg Asp Gln Ala Leu Tyr Arg
370                 375                 380
Gly Asn Gln Thr Thr Tyr Asn Leu Cys Ser Asp Val Trp Met Phe Pro
385                 390                 395                 400
Asn Gln Ile Trp Asp Arg Tyr Pro Ile Thr Arg Glu Asn Pro Ile Trp
                405                 410                 415
Cys Lys Lys Pro Arg Ser Asp Lys Asn Thr Ile Ile Asp Pro Phe Asp
                420                 425                 430
Gly Thr Leu Ala Met Asp His Pro Pro Gly Thr Ile Phe Ile Lys Met
                435                 440                 445
Ala Lys Ile Pro Val Pro Ser Asn Asn Asn Ala Asp Ser Tyr Leu Asn
450                 455                 460
```

```
Ile Tyr Cys Thr Gly Gln Val Ser Cys Glu Ile Val Trp Glu Val Glu
465                 470                 475                 480

Arg Tyr Ala Thr Lys Asn Trp Arg Pro Glu Arg His Thr Ala Leu
                485                 490                 495

Gly Leu Gly Ile Gly Gly Glu Glu Asn Ile Asn Pro Thr Tyr His Val
            500                 505                 510

Asp Lys Asn Gly Lys Tyr Ile Gln Pro Thr Thr Trp Asp Met Cys Tyr
        515                 520                 525

Pro Ile Lys Thr Asn Ile Asn Lys Val Leu
        530                 535

<210> SEQ ID NO 55
<211> LENGTH: 5217
<212> TYPE: DNA
<213> ORGANISM: Bocavirus

<400> SEQUENCE: 55
caaggaggag tggttatatg atgtaatcca taaccactcc caggaaatga cgtatgatag      60
ccaatcagaa ttgagtattg aacctatata agctgctgca cttcctgatt caatcagact     120
gcatccggtc tccggcgagt gaacatctct ggaaaaagct ccacgcttgt ggtgagtcta     180
ctatggcttt caatcctcct gtgattagag ctttttctca acctgctttt acttatgtct     240
tcaaatttcc atatccacaa tggaaagaaa agaatggcgc ttcatgca cttttagctc     300 atggaactga caatctatg atacaattaa gaaactgcgc tcctcatccg gatgaagaca     360
taatccgtga tgacttgctt atttctttag aagatcgcca ttttggggct gttctctgca     420
aggctgttta catggcaaca actactctca tgtcacacaa acaaggaat atgtttcctc     480 gttgtgacat catagttcag tctgagctag gagagaaaaa cttacactgc catattatag     540
ttgggggaga aggactaagc aagaggaatg ctaaatcatc ctgtgctcag ttctatggtt     600
taatactagc tgaaataatt caacgctgca atctcttct ggctacacgt cctttttgaac     660 ctgaagaggc tgacatattt cacactttaa aaaggctga gcgagaggca tggggtggag     720
ttactggcgg caacatgcaa atccttcaat atagagatcg cagaggagac cttcatgcac     780
aaacagtgga tcctcttcgc ttcttcaaaa actaccttt acctaaaaat agatgtattt     840
catcttacag caaacctgat gtttgtactt ctcctgacaa ctggttcatt ttagctgaaa     900
aaacttactc tcacactctt attaacgggc tgccgcttcc agaacattac agaaaaaact     960
accacgcaac cctagataac gaagtcattc cagggcctca acaatggcc atggaggac    1020 gtggtccgtg ggaacatctt cctgaggtag gagatcagcg cctagctgcg tcttctgtta    1080
gcactactta taaccctaac aaaaaagaaa aacttatgct aaacttgcta gacaaatgta    1140
aagagctaaa tctattagtt tatgaagact tagtagctaa ttgtcctgaa ctactcctta    1200
tgcttgaagg tcaaccagga ggggcacgcc ttatagaaca agtctgggc atgcaccata    1260 ttaatgtttg ttctaacttt acagctctca catatcttt tcatctacat cctgttactt    1320
cgcttgactc agacaataaa gctttacagc ttttgttgat tcaaggctat aatcctctag    1380
ccgttggtca cgccctgtgc tgtgtcctga acaacaatt cggaaacaa acactgttt    1440 gcttttacgg gcctgcctca acaggtaaaa caaatatggc caaggcaatc gtccaaggga    1500
ttagacttta tgggtgtgtt aatcatttga acaaggatt tgtatttaat gactgcagac    1560
aacgcttagt tgtttggtgg gaggagtgct aatgcacca ggattgggtg aacctgcaa    1620 agtgtatctt gggcgggaca gaatgcagaa ttgacgtcaa gcatagagac agtgtacttt    1680
taactcaaac acctgtaatt atatccacta accacgatat ctacgcggtt gttggtggca    1740
```

```
attctgtttc tcatgttcac gcggctccat taaaagaaag agtgattcag ctaaattta        1800
tgaaacaact tcctcaaaca tttggagaaa tcactgctac tgagattgca gctcttctac        1860
agtggtgttt caatgagtac gactgtactc tgacaggatt taaacaaaaa tggaatttag        1920
ataaaattcc aaactcattt cctcttgggg tcctttgtcc tactcattca caggacttta        1980
cacttcacga aaacggatac tgcactgatt gcggtggtta ccttcctcat agtgctgaca        2040
attctatgta cactgatcgc gcaagcgaaa ctagcacagg agacatcaca ccaagtaagt        2100
aaatacgcat gcgcaagtaa ttcttttact ttcacttcgc tattttttacc aattttact        2160
tttaggtgac ttgggggatt cggacggaga agacaccgag cctgagacat cgcaagtgga        2220
ctattgtcca cccaagaaac gtcgtctaac tgctccagca agtcctccaa actcacctgc        2280
gagctctgta agtactatta ctttctttaa cacttggcac gcacagccac gtgacgaaga        2340
tgagctcagg gaatatgaaa gacaagcatc gctcctacaa aagaaaggg agtccagaaa         2400
gaggggagag gaagagacac tggcagacaa ctcatcacag gagcaggagc cgcagcccga        2460
tccgacacag tggggagaga ggctcgggct catatcatca ggaacaccca atcagccacc        2520
tatcgtcttg cactgcttcg aagacctcag accaagtgat gaagacgagg gagagtacat        2580
cggggaaaaa agacaataga acaaatccat acactgtatt cagtcaacac agagcttcca        2640
atcctgaagc tccagggtgg tgtgggttct actggcactc tactcgcatt gctagagatg        2700
gtactaattc aatctttaat gaaatgaaac aacagtttca acagctacaa attgataata        2760
aaataggatg ggataacact agagaactat tgtttaatca aaagaaaaca ctagatcaaa        2820
aatacagaaa tatgttctgg cactttagaa ataactctga ttgtgaaaga tgtaattact        2880
gggatgatgt gtaccgtagg cacttagcta atgtttcctc acagacagaa gcagacgaga        2940
taactgacga ggaaatgctt tctgctgctg aaagcatgga agcagatgcc tccaattaag        3000
agacagccta gagggtgggt gctgcctgga tacagatatc ttgggccatt taatccactt        3060
gataacggtg aacctgtaaa taacgctgat cgcgctgctc aattacatga tcacgcctac        3120
tctgaactaa taaagagtgg taaaaatcca tacctgtatt tcaataaagc tgatgaaaaa        3180
ttcattgatg atctaaaaga cgattggtca attggtggaa ttattggatc cagttttttt        3240
aaaataaagc gcgccgtggc tcctgctctg ggaaataaag agagagccca aaaaagacac        3300
ttttactttg ctaactcaaa taaggtgca aaaaaaacaa aaaaaagtga acctaaacca         3360
ggaacctcaa aaatgtctga cactgacatt caagaccaac aacctgatac tgtgacgca         3420
ccacagaacg cctcaggggg aggaacagga agtattggag gaggaaaagg atctggtgtg        3480
gggatttcca ctggagggtg ggtcggaggt tctcacttt cagacaaata tgtggttact         3540
aaaaacacaa gacaatttat aaccacaatt cagaatggtc acctctacaa aacagaggcc        3600
attgaaacaa caaccaaag tggaaaatca cagcgctgcg tcacaactcc atggacatac         3660
tttaacttta atcaatacag ctgtcacttc tcaccacaag attggcagcg ccttacaaat        3720
gaatataagc gcttcagacc taaagcaatg caagtaaaga tttacaactt gcaaataaaa        3780
caaatacttt caaatggtgc tgacacaaca tacaacaatg acctcacagc tggcgttcac        3840
atcttttgtg atggagagca tgcttaccca aatgcatctc atccatggga tgaggacgtc        3900
atgcctgatc ttccatacaa gacctggaaa cttttcaat atggatatat tcctattgaa         3960
aatgaactag cagatcttga tggaaatgca gctggaggca atgctacaga aaaagcactt        4020
ctgtatcaga tgccttttt tctacttgaa aacagtgacc accaagtact tagaactggt         4080
gagagcactg aatttacttt taactttgac tgtgaatggg ttaataatga aagagcatac        4140
```

-continued

```
attcctcctg gattgatgtt caatccaaaa gttccaacaa gaagagttca gtacataaga      4200
caaaacggaa gcacagcagc cagcacaggc agaattcagc catactcaaa accaacaagc      4260
tggatgacag gacctggcct gctcagtgca cagagagtag gaccacagtc atcagacact      4320
gctccattca tggtttgcac taacccagaa ggaacacaca taaacacagg tgctgcagga      4380
tttggatctg gctttgatcc tccaagcgga tgtctggcac caactaacct agaatacaaa      4440
cttcagtggt accagacacc agaaggaaca ggaaataatg gaaacataat tgcaaaccca      4500
tcactctcaa tgcttagaga ccaactccta tacaaaggaa accagaccac atacaatcta      4560
gtgggggaca tatggatgtt tccaaatcaa gtctgggaca gatttcctat caccagagaa      4620
aatccaatct ggtgcaaaaa accaagggct gacaaacaca caatcatgga tccatttgat      4680
ggatccattg caatggatca tcctccaggc actattttta taaaaatggc aaaaattcca      4740
gtaccaactg caacaaatgc agactcatat ctaaacatat actgtactgg acaagtcagc      4800
tgtgaaattg tatgggaagt agaaagatac gcaacaaaga actggcgtcc agaaagaaga      4860
catactgcac tcgggatgtc actggggaga gagagcaact acacgcctac ataccacgtg      4920
gatccaacag gagcatacat ccagcccacg tcatatgatc agtgtatgcc agtaaaaaca      4980
aacatcaata agtgttgta atcttataag cctctttttt gcttctgctt acaagttcct      5040
cctcaatgga caagcggaaa gtgaagggtg actgtagtcc tgagctcatg ggttcaagac      5100
cacagcccga tggtagtggt gttaccgtct cgaacctagc cgacagccct tgtacattgt      5160 gggggggagct gttttgtttg cttatgcaat cgcgaaactc tatatctttt aatgtgt          5217
```

<210> SEQ ID NO 56
<211> LENGTH: 639
<212> TYPE: PRT
<213> ORGANISM: Bocavirus

<400> SEQUENCE: 56

```
Met Ala Phe Asn Pro Pro Val Ile Arg Ala Phe Ser Gln Pro Ala Phe
1               5                   10                  15

Thr Tyr Val Phe Lys Phe Pro Tyr Pro Gln Trp Lys Glu Lys Glu Trp
            20                  25                  30

Leu Leu His Ala Leu Leu Ala His Gly Thr Glu Gln Ser Met Ile Gln
        35                  40                  45

Leu Arg Asn Cys Ala Pro His Pro Asp Glu Asp Ile Arg Asp Asp
    50                  55                  60

Leu Leu Ile Ser Leu Glu Asp Arg His Phe Ala Val Leu Cys Lys
65                  70                  75                  80

Ala Val Tyr Met Ala Thr Thr Thr Leu Met Ser His Lys Gln Arg Asn
                85                  90                  95

Met Phe Pro Arg Cys Asp Ile Ile Val Gln Ser Glu Leu Gly Glu Lys
            100                 105                 110

Asn Leu His Cys His Ile Ile Val Gly Gly Glu Gly Leu Ser Lys Arg
        115                 120                 125

Asn Ala Lys Ser Ser Cys Ala Gln Phe Tyr Gly Leu Ile Leu Ala Glu
    130                 135                 140

Ile Ile Gln Arg Cys Lys Ser Leu Leu Ala Thr Arg Pro Phe Glu Pro
145                 150                 155                 160

Glu Glu Ala Asp Ile Phe His Thr Leu Lys Lys Ala Glu Arg Glu Ala
                165                 170                 175

Trp Gly Gly Val Thr Gly Gly Asn Met Gln Ile Leu Gln Tyr Arg Asp
            180                 185                 190
```

```
Arg Arg Gly Asp Leu His Ala Gln Thr Val Asp Pro Leu Arg Phe Phe
            195                 200                 205

Lys Asn Tyr Leu Leu Pro Lys Asn Arg Cys Ile Ser Ser Tyr Ser Lys
            210                 215                 220

Pro Asp Val Cys Thr Ser Pro Asp Asn Trp Phe Ile Leu Ala Glu Lys
225                 230                 235                 240

Thr Tyr Ser His Thr Leu Ile Asn Gly Leu Pro Leu Pro Glu His Tyr
            245                 250                 255

Arg Lys Asn Tyr His Ala Thr Leu Asp Asn Glu Val Ile Pro Gly Pro
            260                 265                 270

Gln Thr Met Ala Tyr Gly Gly Arg Gly Pro Trp Glu His Leu Pro Glu
            275                 280                 285

Val Gly Asp Gln Arg Leu Ala Ala Ser Ser Val Ser Thr Thr Tyr Lys
            290                 295                 300

Pro Asn Lys Lys Glu Lys Leu Met Leu Asn Leu Leu Asp Lys Cys Lys
305                 310                 315                 320

Glu Leu Asn Leu Leu Val Tyr Glu Asp Leu Val Ala Asn Cys Pro Glu
            325                 330                 335

Leu Leu Leu Met Leu Glu Gly Gln Pro Gly Gly Ala Arg Leu Ile Glu
            340                 345                 350

Gln Val Leu Gly Met His His Ile Asn Val Cys Ser Asn Phe Thr Ala
            355                 360                 365

Leu Thr Tyr Leu Phe His Leu His Pro Val Thr Ser Leu Asp Ser Asp
            370                 375                 380

Asn Lys Ala Leu Gln Leu Leu Ile Gln Gly Tyr Asn Pro Leu Ala
385                 390                 395                 400

Val Gly His Ala Leu Cys Cys Val Leu Asn Lys Gln Phe Gly Lys Gln
            405                 410                 415

Asn Thr Val Cys Phe Tyr Gly Pro Ala Ser Thr Gly Lys Thr Asn Met
            420                 425                 430

Ala Lys Ala Ile Val Gln Gly Ile Arg Leu Tyr Gly Cys Val Asn His
            435                 440                 445

Leu Asn Lys Gly Phe Val Phe Asn Asp Cys Arg Gln Arg Leu Val Val
            450                 455                 460

Trp Trp Glu Glu Cys Leu Met His Gln Asp Trp Val Glu Pro Ala Lys
465                 470                 475                 480

Cys Ile Leu Gly Gly Thr Glu Cys Arg Ile Asp Val Lys His Arg Asp
            485                 490                 495

Ser Val Leu Leu Thr Gln Thr Pro Val Ile Ser Thr Asn His Asp
            500                 505                 510

Ile Tyr Ala Val Val Gly Gly Asn Ser Val Ser His Val His Ala Ala
            515                 520                 525

Pro Leu Lys Glu Arg Val Ile Gln Leu Asn Phe Met Lys Gln Leu Pro
            530                 535                 540

Gln Thr Phe Gly Glu Ile Thr Ala Thr Glu Ile Ala Ala Leu Leu Gln
545                 550                 555                 560

Trp Cys Phe Asn Glu Tyr Asp Cys Thr Leu Thr Gly Phe Lys Gln Lys
            565                 570                 575

Trp Asn Leu Asp Lys Ile Pro Asn Ser Phe Pro Leu Gly Val Leu Cys
            580                 585                 590

Pro Thr His Ser Gln Asp Phe Thr Leu His Glu Asn Gly Tyr Cys Thr
            595                 600                 605

Asp Cys Gly Gly Tyr Leu Pro His Ser Ala Asp Asn Ser Met Tyr Thr
```

```
                610                 615                 620
Asp Arg Ala Ser Glu Thr Ser Thr Gly Asp Ile Thr Pro Ser Lys
625                 630                 635

<210> SEQ ID NO 57
<211> LENGTH: 219
<212> TYPE: PRT
<213> ORGANISM: Bocavirus

<400> SEQUENCE: 57

Met Ser Ser Gly Asn Met Lys Asp Lys His Arg Ser Tyr Lys Arg Lys
1               5                   10                  15

Gly Ser Pro Glu Arg Gly Arg Lys Arg His Trp Gln Thr Thr His
            20                  25                  30

His Arg Ser Arg Ser Arg Ser Pro Ile Arg His Ser Gly Glu Arg Gly
        35                  40                  45

Ser Gly Ser Tyr His Gln Glu His Pro Ile Ser His Leu Ser Ser Cys
    50                  55                  60

Thr Ala Ser Lys Thr Ser Asp Gln Val Met Lys Thr Arg Glu Ser Thr
65                  70                  75                  80

Ser Gly Lys Lys Asp Asn Arg Thr Asn Pro Tyr Thr Val Phe Ser Gln
                85                  90                  95

His Arg Ala Ser Asn Pro Glu Ala Pro Gly Trp Cys Gly Phe Tyr Trp
            100                 105                 110

His Ser Thr Arg Ile Ala Arg Asp Gly Thr Asn Ser Ile Phe Asn Glu
        115                 120                 125

Met Lys Gln Gln Phe Gln Gln Leu Gln Ile Asp Asn Lys Ile Gly Trp
    130                 135                 140

Asp Asn Thr Arg Glu Leu Leu Phe Asn Gln Lys Lys Thr Leu Asp Gln
145                 150                 155                 160

Lys Tyr Arg Asn Met Phe Trp His Phe Arg Asn Asn Ser Asp Cys Glu
                165                 170                 175

Arg Cys Asn Tyr Trp Asp Asp Val Tyr Arg Arg His Leu Ala Asn Val
            180                 185                 190

Ser Ser Gln Thr Glu Ala Asp Glu Ile Thr Asp Glu Glu Met Leu Ser
        195                 200                 205

Ala Ala Glu Ser Met Glu Ala Asp Ala Ser Asn
    210                 215

<210> SEQ ID NO 58
<211> LENGTH: 691
<212> TYPE: PRT
<213> ORGANISM: Bocavirus

<400> SEQUENCE: 58

Met Ser Leu His Arg Asn Gln Arg Arg Leu Gln Thr Lys Lys Cys Phe
1               5                   10                  15

Leu Leu Leu Lys Ala Trp Ile Gln Met Pro Pro Ile Lys Arg Gln Pro
            20                  25                  30

Gly Gly Trp Val Leu Pro Gly Tyr Lys Tyr Leu Gly Pro Phe Asn Pro
        35                  40                  45

Leu Glu Asn Gly Glu Pro Val Asn Lys Ala Asp Arg Ala Ala Gln Ala
    50                  55                  60

His Asp Lys Ser Tyr Ser Glu Ile Ile Lys Ser Gly Lys Asn Pro Tyr
65                  70                  75                  80

Leu Tyr Phe Asn Lys Ala Asp Glu Lys Phe Ile Asp Asp Leu Lys Asn
                85                  90                  95
```

```
Asp Trp Ser Leu Gly Gly Ile Ile Gly Ser Ser Phe Lys Leu Lys
            100                 105                 110

Arg Ala Val Ala Pro Ala Leu Gly Asn Lys Glu Arg Ala Gln Lys Arg
        115                 120                 125

His Phe Tyr Phe Ala Asn Ser Asn Lys Gly Ala Lys Lys Pro Lys Asn
    130                 135                 140

Asn Glu Pro Lys Pro Gly Thr Ser Lys Met Ser Glu Asn Glu Ile Gln
145                 150                 155                 160

Asp Gln Gln Pro Ser Gly Ser Met Glu Glu Arg Gly Gly Gly Gly
                165                 170                 175

Ala Val Gly Ser Val Gly Gly Lys Gly Ser Ser Val Gly Ile Ser
            180                 185                 190

Thr Gly Gly Trp Val Gly Ser Tyr Phe Thr Asp Ser Tyr Val Ile
            195                 200                 205

Thr Lys Asn Thr Arg Gln Phe Leu Val Lys Ile Gln Asn Asp His Lys
    210                 215                 220

Tyr Arg Thr Glu Asn Ile Ile Pro Ser Asn Ala Gly Gly Lys Ser Gln
225                 230                 235                 240

Arg Cys Val Ser Thr Pro Trp Ser Tyr Phe Asn Phe Asn Gln Tyr Ser
                245                 250                 255

Ser His Phe Ser Pro Gln Asp Trp Gln His Leu Thr Asn Glu Tyr Lys
            260                 265                 270

Arg Phe Lys Pro Arg Lys Met His Val Lys Ile Tyr Asn Leu Gln Ile
        275                 280                 285

Lys Gln Ile Leu Ser Asn Gly Ala Asp Thr Thr Tyr Asn Asn Asp Leu
290                 295                 300

Thr Ala Gly Val His Ile Phe Cys Asp Gly Glu His Ala Tyr Pro Asn
305                 310                 315                 320

Ala Thr His Pro Trp Asp Glu Asp Val Met Pro Glu Leu Pro Tyr Glu
                325                 330                 335

Thr Trp Tyr Leu Phe Gln Tyr Gly Tyr Ile Pro Val Ile His Glu Leu
            340                 345                 350

Ala Glu Met Glu Asp Ala Asn Ala Val Glu Lys Ala Ile Ala Leu Gln
        355                 360                 365

Ile Pro Phe Phe Met Leu Glu Asn Ser Asp His Glu Val Leu Arg Thr
370                 375                 380

Gly Glu Ser Thr Glu Phe Thr Phe Asp Phe Asp Cys Glu Trp Ile Asn
385                 390                 395                 400

Asn Glu Arg Ala Tyr Ile Pro Pro Gly Leu Met Phe Asn Pro Lys Val
                405                 410                 415

Pro Thr Arg Arg Ala Gln Tyr Ile Arg Gln His Gly Asn Thr Ala Ser
            420                 425                 430

Ser Asn Thr Arg Ile Gln Pro Tyr Ala Lys Pro Thr Ser Trp Met Thr
        435                 440                 445

Gly Pro Gly Leu Leu Ser Ala Gln Arg Val Gly Pro Ala Gly Ser Asp
450                 455                 460

Thr Ala Ser Trp Met Val Val Asn Pro Asp Gly Ala Ala Val Asn
465                 470                 475                 480

Ser Gly Met Ala Gly Val Gly Ser Gly Phe Asp Pro Pro Ser Gly Ser
                485                 490                 495

Leu Arg Pro Thr Asp Leu Glu Tyr Lys Ile Gln Trp Tyr Gln Thr Pro
            500                 505                 510

Ala Gly Thr Asn Ser Asp Gly Asn Ile Ile Ser Asn Pro Pro Leu Ser
```

```
                515                 520                 525
Met Leu Arg Asp Gln Ala Leu Tyr Arg Gly Asn Gln Thr Thr Tyr Asn
    530                 535                 540

Leu Cys Ser Asp Val Trp Met Phe Pro Asn Gln Ile Trp Asp Arg Tyr
545                 550                 555                 560

Pro Ile Thr Arg Glu Asn Pro Ile Trp Cys Lys Pro Arg Ser Asp
                565                 570                 575

Lys Asn Thr Ile Ile Asp Pro Phe Asp Gly Thr Leu Ala Met Asp His
                580                 585                 590

Pro Pro Gly Thr Ile Phe Ile Lys Met Ala Lys Ile Pro Val Pro Ser
            595                 600                 605

Asn Asn Asn Ala Asp Ser Tyr Leu Asn Ile Tyr Cys Thr Gly Gln Val
    610                 615                 620

Ser Cys Glu Ile Val Trp Glu Val Glu Arg Tyr Ala Thr Lys Asn Trp
625                 630                 635                 640

Arg Pro Glu Arg Arg His Thr Ala Leu Gly Leu Gly Ile Gly Gly Glu
                645                 650                 655

Glu Asn Val Asn Pro Thr Tyr His Val Asp Lys Asn Gly Lys Tyr Ile
                660                 665                 670

Gln Pro Thr Thr Trp Asp Met Cys Tyr Pro Ile Lys Thr Asn Ile Asn
            675                 680                 685

Lys Val Leu
    690

<210> SEQ ID NO 59
<211> LENGTH: 671
<212> TYPE: PRT
<213> ORGANISM: Bocavirus

<400> SEQUENCE: 59

Met Pro Pro Ile Lys Arg Gln Pro Arg Gly Trp Val Leu Pro Gly Tyr
1               5                   10                  15

Arg Tyr Leu Gly Pro Phe Asn Pro Leu Asp Asn Gly Glu Pro Val Asn
            20                  25                  30

Asn Ala Asp Arg Ala Ala Gln Leu His Asp His Ala Tyr Ser Glu Leu
        35                  40                  45

Ile Lys Ser Gly Lys Asn Pro Tyr Leu Tyr Phe Asn Lys Ala Asp Glu
    50                  55                  60

Lys Phe Ile Asp Asp Leu Lys Asp Asp Trp Ser Ile Gly Gly Ile Ile
65                  70                  75                  80

Gly Ser Ser Phe Phe Lys Ile Lys Arg Ala Val Ala Pro Ala Leu Gly
                85                  90                  95

Asn Lys Glu Arg Ala Gln Lys Arg His Phe Tyr Phe Ala Asn Ser Asn
            100                 105                 110

Lys Gly Ala Lys Lys Thr Lys Lys Ser Glu Pro Lys Pro Gly Thr Ser
        115                 120                 125

Lys Met Ser Asp Thr Asp Ile Gln Asp Gln Gln Pro Asp Thr Val Asp
    130                 135                 140

Ala Pro Gln Asn Ala Ser Gly Gly Gly Thr Gly Ser Ile Gly Gly Gly
145                 150                 155                 160

Lys Gly Ser Gly Val Gly Ile Ser Thr Gly Gly Trp Val Gly Gly Ser
                165                 170                 175

His Phe Ser Asp Lys Tyr Val Val Thr Lys Asn Thr Arg Gln Phe Ile
            180                 185                 190

Thr Thr Ile Gln Asn Gly His Leu Tyr Lys Thr Glu Ala Ile Glu Thr
```

```
                    195                 200                 205
Thr Asn Gln Ser Gly Lys Ser Gln Arg Cys Val Thr Thr Pro Trp Thr
210                 215                 220

Tyr Phe Asn Phe Asn Gln Tyr Ser Cys His Phe Ser Pro Gln Asp Trp
225                 230                 235                 240

Gln Arg Leu Thr Asn Glu Tyr Lys Arg Phe Arg Pro Lys Ala Met Gln
                245                 250                 255

Val Lys Ile Tyr Asn Leu Gln Ile Lys Gln Ile Leu Ser Asn Gly Ala
                260                 265                 270

Asp Thr Thr Tyr Asn Asn Asp Leu Thr Ala Gly Val His Ile Phe Cys
            275                 280                 285

Asp Gly Glu His Ala Tyr Pro Asn Ala Ser His Pro Trp Asp Glu Asp
290                 295                 300

Val Met Pro Asp Leu Pro Tyr Lys Thr Trp Lys Leu Phe Gln Tyr Gly
305                 310                 315                 320

Tyr Ile Pro Ile Glu Asn Glu Leu Ala Asp Leu Asp Gly Asn Ala Ala
                325                 330                 335

Gly Gly Asn Ala Thr Glu Lys Ala Leu Leu Tyr Gln Met Pro Phe Phe
                340                 345                 350

Leu Leu Glu Asn Ser Asp His Gln Val Leu Arg Thr Gly Glu Ser Thr
            355                 360                 365

Glu Phe Thr Phe Asn Phe Asp Cys Glu Trp Val Asn Asn Glu Arg Ala
370                 375                 380

Tyr Ile Pro Pro Gly Leu Met Phe Asn Pro Lys Val Pro Thr Arg Arg
385                 390                 395                 400

Val Gln Tyr Ile Arg Gln Asn Gly Ser Thr Ala Ala Ser Thr Gly Arg
                405                 410                 415

Ile Gln Pro Tyr Ser Lys Pro Thr Ser Trp Met Thr Gly Pro Gly Leu
                420                 425                 430

Leu Ser Ala Gln Arg Val Gly Pro Gln Ser Ser Asp Thr Ala Pro Phe
            435                 440                 445

Met Val Cys Thr Asn Pro Glu Gly Thr His Ile Asn Thr Gly Ala Ala
450                 455                 460

Gly Phe Gly Ser Gly Phe Asp Pro Pro Ser Gly Cys Leu Ala Pro Thr
465                 470                 475                 480

Asn Leu Glu Tyr Lys Leu Gln Trp Tyr Gln Thr Pro Glu Gly Thr Gly
                485                 490                 495

Asn Asn Gly Asn Ile Ile Ala Asn Pro Ser Leu Ser Met Leu Arg Asp
            500                 505                 510

Gln Leu Leu Tyr Lys Gly Asn Gln Thr Thr Tyr Asn Leu Val Gly Asp
            515                 520                 525

Ile Trp Met Phe Pro Asn Gln Val Trp Asp Arg Phe Pro Ile Thr Arg
530                 535                 540

Glu Asn Pro Ile Trp Cys Lys Lys Pro Arg Ala Asp Lys His Thr Ile
545                 550                 555                 560

Met Asp Pro Phe Asp Gly Ser Ile Ala Met Asp His Pro Pro Gly Thr
                565                 570                 575

Ile Phe Ile Lys Met Ala Lys Ile Pro Val Pro Thr Ala Thr Asn Ala
            580                 585                 590

Asp Ser Tyr Leu Asn Ile Tyr Cys Thr Gly Gln Val Ser Cys Glu Ile
            595                 600                 605

Val Trp Glu Val Glu Arg Tyr Ala Thr Lys Asn Trp Arg Pro Glu Arg
610                 615                 620
```

```
Arg His Thr Ala Leu Gly Met Ser Leu Gly Gly Glu Ser Asn Tyr Thr
625                 630                 635                 640

Pro Thr Tyr His Val Asp Pro Thr Gly Ala Tyr Ile Gln Pro Thr Ser
            645                 650                 655

Tyr Asp Gln Cys Met Pro Val Lys Thr Asn Ile Asn Lys Val Leu
        660                 665                 670
```

<210> SEQ ID NO 60
<211> LENGTH: 30
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (21)..(30)
<223> OTHER INFORMATION: n is a, c, g, or t

<400> SEQUENCE: 60
gccggagctc tgcagatatc nnnnnnnnnn                              30

<210> SEQ ID NO 61
<211> LENGTH: 20
<212> TYPE: DNA
<213> ORGANISM: Artificial Sequence
<220> FEATURE:
<223> OTHER INFORMATION: Primer

<400> SEQUENCE: 61
gccggagctc tgcagatatc                                         20

<210> SEQ ID NO 62
<211> LENGTH: 20
<212> TYPE: DNA
<213> ORGANISM: Artificial Sequence
<220> FEATURE:
<223> OTHER INFORMATION: Primer

<400> SEQUENCE: 62
aacagatggg caagcagaac                                         20

<210> SEQ ID NO 63
<211> LENGTH: 21
<212> TYPE: DNA
<213> ORGANISM: Artificial Sequence
<220> FEATURE:
<223> OTHER INFORMATION: Primer

<400> SEQUENCE: 63
aggacaaagg tctccaagag g                                       21

<210> SEQ ID NO 64
<211> LENGTH: 20
<212> TYPE: DNA
<213> ORGANISM: Artificial Sequence
<220> FEATURE:
<223> OTHER INFORMATION: Primer

<400> SEQUENCE: 64
tgcttcaaca ggcaaaacaa                                         20

<210> SEQ ID NO 65
<211> LENGTH: 21
<212> TYPE: DNA
<213> ORGANISM: Artificial Sequence
<220> FEATURE:
<223> OTHER INFORMATION: Primer

<400> SEQUENCE: 65
tccaagagga aatgagtttg g            21

HUMAN PARVOVIRUS: BOCAVIRUS

RELATED APPLICATION

This application relies for priority under 35 U.S.C. §119(e) upon U.S. Provisional Application Ser. No. 61/045,926 filed Apr. 17, 2008.

GRANT INFORMATION

This invention was made in part with government support under NIH Grant No. R01 HL083254-01A awarded by the National Institutes of Health. The United States government has certain rights in this invention.

FIELD OF THE INVENTION

The present invention relates generally to the discovery of a new human parvovirus and more specifically, to methods of using the virus including methods of detecting the virus and diagnosing viral infection, methods of treating or preventing virus infection, and methods for identifying anti-viral compounds.

BACKGROUND OF THE INVENTION

Parvoviruses are among the smallest DNA-containing viruses that infect animals and man. Parvoviruses range in size from 15 to 28 nm in diameter, lack a lipid membrane (non-enveloped), and contain a single strand of DNA. Parvoviruses are heat stable and generally resistant to chemical deactivating agents, which may account for their prevalence and persistence in the environment. In animals, many diseases such as canine parvovirus and feline panleukopenia exhibit high morbidity and high mortality in affected animal populations and the infections can persist endemically.

The Parvoviridae family is divided into five genera: Parvovirus, Dependovirus, Erythrovirus, Amdovirus and Bocavirus. Animal parvoviruses such as canine parvovirus, feline parvovirus, mink enteritis virus, and porcine parvovirus are responsible for many serious diseases in animals. In humans, the first identified pathogenic member of this family was parvovirus B19, which is a member of genus Erythrovirus. Other B19-related human parvoviruses include A6 and V9. The genomes of A6 and V9 are highly related to that of B19. As with other parvoviruses, B19 is highly contagious and exhibits high morbidity in affected populations. B19 causes fifth disease in normal individuals, transient aplastic crisis in patients with underlying hemolysis, and chronic anemia due to persistent infection in immunocompromised patients. B19 infection in pregnancy can lead to hydrops fetalis and fetal loss. B19 has also been implicated as the cause of chronic arthritis in adults where there is evidence of recent B19 infection, e.g., rheumatoid and inflammatory arthritis.

Parvoviruses are also associated with respiratory tract infections. Lower respiratory tract infections (LRTI) are a leading cause of hospitalization of infants and young children. Animal bocaviruses BPV (bovine parvovirus) and MVC (canine minute virus, or minute virus of canines) are associated with respiratory symptoms and enteritis of young animals. Systemic infection by BPV and MVC appears likely, and there are indications that fetal infection leading to fetal death may occur.

The discovery of a human Bocavirus (HBoV) has been recently reported. (WO2007/057062) HBoV is pathogenic to humans, and is associated with respiratory tract infections in children.

Despite the known pathogenicity of parvoviruses and the urgent need for methods to prevent, diagnose and treat parvovirus infections, other divergent human parvoviruses have not yet been identified. Therefore, a need exists to detect divergent human parvoviruses and to provide a method to diagnose, prevent and treat parvoviruses infection. Moreover, there exists a need to provide methods to identify parvoviruses antiviral compounds.

SUMMARY OF THE INVENTION

The present invention relates to a new human Parvovirus, Bocavirus-2 (HBoV2). Accordingly, the present invention provides the genomic sequences of 9 variants of Bocavirus-2, and the sequences of the viral proteins encoded thereby. The variants have been termed HBoV2A-PK5510, HBoV2A-PK2255, HBoV2A-UK648, HBoV2A-TU114-06, HBoV2B-NI327, HBoV2B-NI213, HBoV3-NI385, HBoV4-TU210-07, and HBoV4-NI374. Also provided are methods of detecting the Bocavirus-2 variants and diagnosing Bocavirus-2 infection in biological samples, methods of treating or preventing Bocavirus-2 infection, and methods for identifying antiviral compounds.

Accordingly, in one embodiment of the present invention there are provided isolated nucleic acid molecules obtained from Bocavirus-2 variants. In certain embodiments, the nucleic acid molecule comprises a nucleotide sequence having at least 80% identity to SEQ ID NO:1, SEQ ID NO:5, SEQ ID NO:9, SEQ ID NO:13, SEQ ID NO:17, SEQ ID NO:21, SEQ ID NO:25, SEQ ID NO:43, SEQ ID NO:49, or a complement thereof. In some embodiments, the nucleic acid molecule comprises a nucleotide sequence having at least 85% identity to SEQ ID NO:1, SEQ ID NO:5, SEQ ID NO:9, SEQ ID NO:13, SEQ ID NO:17, SEQ ID NO:21, SEQ ID NO:25, SEQ ID NO:43, SEQ ID NO:49, or a complement thereof. In other embodiments, the nucleic acid molecule comprises a nucleotide sequence having at least 90% identity to SEQ ID NO:1, SEQ ID NO:5, SEQ ID NO:9, SEQ ID NO:13, SEQ ID NO:17, SEQ ID NO:21, SEQ ID NO:25, SEQ ID NO:43, SEQ ID NO:49, or a complement thereof. In still other embodiments, the nucleic acid molecule comprises a nucleotide sequence having at least 95% identity to SEQ ID NO:1, SEQ ID NO:5, SEQ ID NO:9, SEQ ID NO:13, SEQ ID NO:17, SEQ ID NO:21, SEQ ID NO:25, SEQ ID NO:43, SEQ ID NO:49, or a complement thereof. In one aspect, the nucleic acid molecule comprises a sequence selected from the group consisting of SEQ ID NO:1, SEQ ID NO:5, SEQ ID NO:9, SEQ ID NO:13, SEQ ID NO:17, SEQ ID NO:21, SEQ ID NO:25, SEQ ID NO:43, SEQ ID NO:49, and a complement thereof. In still other embodiments, the nucleic acid molecule is a fragment of at least 12 nucleotides in length of any of the above nucleic acids. In some embodiments, the fragment may be at least 20, 25, 30, 40, 50, 75, 100, or 200 nucleotides in length.

In certain embodiments, the nucleic acid molecule comprises a nucleotide sequence that hybridizes under highly stringent conditions to at least 12 contiguous nucleotides of the nucleotide sequence as set forth in SEQ ID NO:1, SEQ ID NO:5, SEQ ID NO:9, SEQ ID NO:13, SEQ ID NO:17, SEQ ID NO:21, SEQ ID NO:25, SEQ ID NO:43, SEQ ID NO:49, or a complement thereof. In particular embodiments, the nucleotide sequence hybridizes under stringent conditions to at least 25, or at least 50, or at least 100, or at least 150 contiguous nucleotides of the nucleotide sequence as set forth in SEQ ID NO:1, SEQ ID NO:5, SEQ ID NO:9, SEQ ID NO:13, SEQ ID NO:17, SEQ ID NO:21, SEQ ID NO:25, SEQ ID NO:43, SEQ ID NO:49, or a complement thereof. In one aspect, the nucleotide sequence hybridizes under highly stringent conditions over the full length of the nucleotide sequence as set forth in SEQ ID NO:1, SEQ ID NO:5, SEQ ID NO:9, SEQ ID NO:13, SEQ ID NO:17, SEQ ID NO:21, SEQ ID NO:25, SEQ ID NO:43, SEQ ID NO:49, or a complement thereof. In one aspect, the nucleic acid molecule is at least 12 nucleotides in length. In another aspect, the nucleotide sequence comprises at least 80% identity, at least 90% identity, or at least 95% identity to SEQ ID NO:1, SEQ ID NO:5, SEQ ID NO:9, SEQ ID NO:13, SEQ ID NO:17, SEQ ID NO:21, SEQ ID NO:25, SEQ ID NO:43, SEQ ID NO:49, or a complement thereof.

In another embodiment, the nucleic acid molecule hybridizes under highly stringent conditions to at least 12 contiguous nucleotides of an open reading frame of SEQ ID NO:1, SEQ ID NO:5, SEQ ID NO:9, SEQ ID NO:13, SEQ ID NO:17, SEQ ID NO:21, SEQ ID NO:25, SEQ ID NO:43, SEQ ID NO:49, or a complement thereof. In one aspect, the nucleotide sequence comprises an open reading frame encoding a protein selected from the group consisting of SEQ ID NO:2, SEQ ID NO:3, SEQ ID NO:4, SEQ ID NO:6, SEQ ID NO:7, SEQ ID NO:8, SEQ ID NO: 10, SEQ ID NO:11, SEQ ID NO:12, SEQ ID NO:14, SEQ ID NO:15, SEQ ID NO:16, SEQ ID NO:18, SEQ ID NO:19, SEQ ID NO:20, SEQ ID NO:22, SEQ ID NO:23, SEQ ID NO:24, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:44, SEQ ID NO:45, SEQ ID NO:46, SEQ ID NO:47, SEQ ID NO:48, SEQ ID NO:50, SEQ ID NO:51, SEQ ID NO:52, SEQ ID NO:53, SEQ ID NO:54, and conservative variants thereof.

In another embodiment of the invention, there are provided substantially purified proteins encoded by Bocavirus-2 nucleic acid molecules of the invention. In some embodiments, the protein is encoded by a nucleic acid sequence that hybridizes under stringent conditions to at least 12 contiguous nucleotides of the nucleotide sequence as set forth in SEQ ID NO:1, SEQ ID NO:5, SEQ ID NO:9, SEQ ID NO:13, SEQ ID NO:17, SEQ ID NO:21, SEQ ID NO:25, SEQ ID NO:43, SEQ ID NO:49, or a complement thereof. In certain embodiments, the protein is encoded by a nucleic acid sequence that hybridizes under stringent conditions to at least 25, or at least 50, or at least 100, or at least 150 contiguous nucleotides of the nucleotide sequence as set forth in SEQ ID NO:1, SEQ ID NO:5, SEQ ID NO:9, SEQ ID NO:13, SEQ ID NO:17, SEQ ID NO:21, SEQ ID NO:25, SEQ ID NO:43, SEQ ID NO:49, or a complement thereof. In particular embodiments, the invention includes a protein encoded by a nucleotide sequence selected from the group consisting of SEQ ID NO:1, SEQ ID NO:5, SEQ ID NO:9, SEQ ID NO:13, SEQ ID NO:17, SEQ ID NO:21, SEQ ID NO:25, SEQ ID NO:43, and SEQ ID NO:49. In other embodiments, the protein comprises a sequence having about 80%, or 90%, or 95% identity to a sequence selected from the group consisting of SEQ ID NO:2, SEQ ID NO:3, SEQ ID NO:4, SEQ ID NO:6, SEQ ID NO:7, SEQ ID NO:8, SEQ ID NO:10, SEQ ID NO:11, SEQ ID NO:12, SEQ ID NO:14, SEQ ID NO:15, SEQ ID NO:16, SEQ ID NO:18, SEQ ID NO:19, SEQ ID NO:20, SEQ ID NO:22, SEQ ID NO:23, SEQ ID NO:24, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:44, SEQ ID NO:45, SEQ ID NO:46, SEQ ID NO:47, SEQ ID NO:48, SEQ ID NO:50, SEQ ID NO:51, SEQ ID NO:52, SEQ ID NO:53, SEQ ID NO:54, and fragments thereof. In some embodiments, the protein comprises a sequence selected from the group consisting of SEQ ID NO:2, SEQ ID NO:3, SEQ ID NO:4, SEQ ID NO:6, SEQ ID NO:7, SEQ ID NO:8, SEQ ID NO:10, SEQ ID NO:11, SEQ ID NO:12, SEQ ID NO:14, SEQ ID NO:15, SEQ ID NO:16, SEQ ID NO:18, SEQ ID NO:19, SEQ ID NO:20, SEQ ID NO:22, SEQ ID NO:23, SEQ ID NO:24, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:44, SEQ ID NO:45, SEQ ID NO:46, SEQ ID NO:47, SEQ ID NO:48, SEQ ID NO:50, SEQ ID NO:51, SEQ ID NO:52, SEQ ID NO:53, SEQ ID NO:54, and fragments thereof. In certain embodiments the fragment is an antigen or immunogenic fragment.

In one embodiment, the invention includes a composition containing a protein of the invention.

The invention also provides an isolated antibody that specifically binds to a protein of the invention. In one aspect, the antibody is a polyclonal antibody. In another aspect, the antibody is a monoclonal antibody.

In another embodiment, the invention includes purified serum containing polyclonal antibodies that specifically bind to a protein of the invention.

The invention also provides an isolated Bocavirus-2 comprising a nucleic acid molecule of the invention.

In one embodiment, there is provided an expression vector comprising a nucleic acid molecule of the invention. In one aspect, a host cell comprising the expression vector is provided.

In another embodiment, the invention includes a substantially pure preparation of virus which induces respiratory tract infection.

In still another embodiment of the invention, there is provided a method of detecting a Bocavirus-2 nucleic acid molecule by hybridization to a probe. In some embodiments, the method includes contacting, under highly stringent hybridization conditions, a sample suspected of containing a Bocavirus-2 nucleic acid with a nucleotide sequence that hybridizes under highly stringent conditions to a nucleotide sequence as set forth in SEQ ID NO:1, SEQ ID NO: 5, SEQ ID NO:9, SEQ ID NO:13, SEQ ID NO:17, SEQ ID NO:21, SEQ ID NO:25, SEQ ID NO:43, SEQ ID NO:49, or a complement thereof; and detecting the presence or absence of hybridization. In one aspect, the hybridization conditions include hybridizing at 42° C. in a solution comprising 50% formamide, 5×SSC, and 1% SDS and washing at 65° C. in a solution comprising 0.2×SSC and 0.1% SDS.

In yet another embodiment of the invention, there is provided a method of detecting a Bocavirus-2 nucleic acid molecule by detection of a nucleic acid amplification product. In some embodiments the method includes amplifying the nucleic acid of a sample suspected of containing Bocavirus-2 nucleic acid with at least one primer that hybridizes to a nucleotide sequence as set forth in SEQ ID NO:1, SEQ ID NO:5, SEQ ID NO:9, SEQ ID NO:13, SEQ ID NO:17, SEQ ID NO:21, SEQ ID NO:25, SEQ ID NO:43, SEQ ID NO:49, or a complement thereof to produce an amplification product; and detecting the presence of an amplification product, thereby detecting the presence of the Bocavirus-2 nucleic acid. In one aspect, the amplifying includes a denaturation phase of 90° C.-95° C. for 30 sec-2 min., an annealing phase of 50° C. to about 65° C. lasting 30 sec.-2 min., and an extension phase of about 72° C. for 1-2 min., and an extension phase of about 72° C. for 1-2 min for 20-40 cycles.

In another embodiment, there is provided a method of detecting a Bocavirus-2 infection in a subject by detecting a protein of the invention in a sample from the subject. In one aspect the method includes contacting a sample suspected of comprising a Bocavirus-2 protein with an antibody that specifically binds a polypeptide encoded by SEQ ID NO:1, SEQ ID NO:5, SEQ ID NO:9, SEQ ID NO:13, SEQ ID NO:17, SEQ ID NO:21, SEQ ID NO:25, SEQ ID NO:43, or SEQ ID NO:49 to form a protein/antibody complex; and detecting the presence of the protein/antibody complex, thereby detecting the presence of the Bocavirus protein.

The invention also contemplates a kit for detecting a Bocavirus-2 nucleic acid, the kit containing at least one polynucleotide having a nucleotide sequence that hybridizes under highly stringent conditions to a nucleotide sequence as set forth in SEQ ID NO:1, SEQ ID NO:5, SEQ ID NO:9, SEQ ID NO:13, SEQ ID NO:17, SEQ ID NO:21, SEQ ID NO:25, SEQ ID NO:43, SEQ ID NO:49, or a complement thereof.

The invention also contemplates a kit for detecting a Bocavirus-2 nucleic acid, the kit containing at least one oligonucleotide primer that hybridizes to a nucleotide sequence as set forth in SEQ ID NO:1, SEQ ID NO:5, SEQ ID NO:9, SEQ ID NO:13, SEQ ID NO:17, SEQ ID NO:21, SEQ ID NO:25, SEQ ID NO:43, SEQ ID NO:49, or a complement thereof under highly stringent PCR conditions. In one aspect the PCR conditions comprise a denaturation phase of 90° C.-95° C. for 30 sec-2 min., an annealing phase of 50° C. to about 65° C. lasting 30 sec.-2 min., and an extension phase of about 72° C. for 1-2 min., and an extension phase of about 72° C. for 1-2 min for 20-40 cycles.

In another embodiment, the invention describes a kit for detecting a Bocavirus-2 in a sample, where the kit contains an antibody that detects a polypeptide encoded by SEQ ID NO:1, SEQ ID NO:5, SEQ ID NO:9, SEQ ID NO:13, SEQ ID NO:17, SEQ ID NO:21, SEQ ID NO:25, SEQ ID NO:43, or SEQ ID NO:49. In one aspect, the kit contains a monoclonal antibody. In another aspect, the kit contains a polyclonal antibody.

The invention contemplates a method of assaying for an anti-Bocavirus-2 compound by 1) contacting a sample suspected of containing a Bocavirus-2 with a test compound, where the Bocavirus encodes a genome that hybridizes under highly stringent conditions to a nucleotide sequence as set forth in SEQ ID NO:1, SEQ ID NO:5, SEQ ID NO:9, SEQ ID NO: 13, SEQ ID NO:17, SEQ ID NO:21, SEQ ID NO:25, SEQ ID NO:43, SEQ ID NO:49, or a complement thereof, wherein the hybridization reaction is incubated at 42° C. in a solution comprising 50% formamide, 5×SSC, and 1% SDS and washed at 65° C. in a solution comprising 0.2×SSC and 0.1% SDS; and 2) determining whether the test compound inhibits Bocavirus replication, wherein inhibition of Bocavirus replication indicates that the test compound is the anti-Bocavirus compound.

In still other embodiments, there is provided a method of treating or preventing a Bocavirus-2 infection in a subject by administering to the subject an antigen encoded by a Bocavirus, the Bocavirus containing a genome that hybridizes under highly stringent conditions to a nucleotide sequence as set forth in SEQ ID NO:1, SEQ ID NO:5, SEQ ID NO:9, SEQ ID NO:13, SEQ ID NO:17, SEQ ID NO:21, SEQ ID NO:25, SEQ ID NO:43, SEQ ID NO:49, or a complement thereof; thereby treating or prevention infection in the subject.

Another embodiment of the invention provides a vaccine for the prevention of respiratory tract infections in a subject, including a Bocavirus-2 or viral antigen from a Bocavirus-2, which induces respiratory tract infections in a subject and a pharmacologically acceptable carrier. In one aspect, the virus of the vaccine is in a killed form. In another aspect, the virus of the vaccine is in a live but attenuated form.

In one embodiment of the invention, there is provided a method for detecting and serotyping Bocavirus in a sample by 1) contacting a first portion of the sample with a first pair of primers in a first amplification protocol, wherein the first pair of primers have an associated first characteristic amplification product if a Bocavirus is present in the sample; 2) determining whether or not the first characteristic amplification product is present; 3) contacting a second portion of the sample with a second pair of primers in a second amplification protocol, wherein the second pair of primers have an associated second characteristic amplification product if a Bocavirus is present in the sample and wherein the second pair of primers are different from the first pair of primers; 4) determining whether or not the second characteristic amplification product is present; 5) based on whether or not the first and second characteristic amplification product are present, selecting one or more subsequent pair of primers and contacting the one or more subsequent pair of primers with additional portions of the sample in subsequent amplification protocols, wherein each subsequent pair of primers is different from each pair of primers already used and wherein each subsequent pair of primers has an associated subsequent characteristic amplification product if a Bocavirus is present in the sample; 6) determining whether or not the associated characteristic amplification product for each subsequent pair of primers used is present; 7) repeating steps 5 and 6 for one or more subsequent pairs of primers if the Bocavirus cannot be serotyped based on the determinations of steps 2, 4, and 6 until the Bocavirus can be serotyped, wherein the one or more subsequent pairs of primers are different from all pairs of primers used in earlier amplification protocols; and determining the serotype or groups of serotypes of the Bocavirus that may be present in the sample. In one aspect, the sample is a biological sample. In another aspect, the sample is whole blood or a fraction thereof, a bronchial wash, cerebrospinal fluid, an eye swab, a conjunctival swab, a swab or scraping from a lesion, a nasopharyngeal swab, an oral or buccal swab, pericardial fluid, a rectal swab, serum, semen, cerebrospinal fluid, sputum, saliva, stool, a stool extract, a throat swab, urine, brain tissue, heart tissue, intestinal tissue, kidney tissue, liver tissue, lung tissue, pancreas tissue, spinal cord tissue, skin tissue, spleen tissue, thymus tissue, cells from a tissue culture, a supernatant from a tissue culture, and tissue from an experimentally infected animal. In one aspect, the first, second, and any subsequent amplification protocols are polymerase chain reactions or reverse-transcription polymerase chain reactions. In another aspect, detecting and serotyping of the Bocavirus in the sample is used to diagnose a viral disease or medical condition. In yet another aspect, the viral disease or medical condition is a respiratory tract infection.

In still another embodiment of the invention, there is provided a method for detecting the presence of a Bocavirus in a sample by 1) purifying RNA contained in the sample; 2) reverse transcribing the RNA with primers effective to reverse transcribe Bocavirus RNA to provide a cDNA; 3) contacting at least a portion of the cDNA with (i) a composition that promotes amplification of a nucleic acid and (ii) an oligonucleotide mixture wherein the mixture comprises at least one oligonucleotide that hybridizes to a highly conserved sequence of the sense strand of a Bocavirus nucleic acid and at least one oligonucleotide that hybridizes to a highly conserved sequence of the antisense strand of a Bocavirus nucleic acid; 4) carrying out an amplification procedure on the amplification mixture such that, if a Bocavirus is present in the sample, a Bocavirus amplicon is produced whose sequence comprises a nucleotide sequence of at least a portion of the Bocavirus genome; and 5) detecting whether an amplicon is present; wherein the presence of the amplicon indicates that a Bocavirus is present in the sample. In one aspect, the amplification procedure comprises a polymerase chain reaction. In another aspect, the sample is chosen from the group consisting of whole blood or a fraction thereof, a bronchial wash, cerebrospinal fluid, an eye swab, a conjunctival swab, a swab or scraping from a lesion, a nasopharyngeal swab, an oral or buccal swab, pericardial fluid, a rectal swab, serum, semen, cerebrospinal fluid, sputum, saliva, stool, a stool extract, a throat swab, urine, brain tissue, heart tissue, intestinal tissue, kidney tissue, liver tissue, lung tissue, pancreas tissue, spinal cord tissue, skin tissue, spleen tissue, thymus tissue, cells from a tissue culture, a supernatant from a tissue culture, and tissue from an experimentally infected animal. In another aspect, the detection is carried out by a procedure chosen from the group consisting of gel electrophoresis and visualization of amplicons contained in a resulting gel, size separation matrix, capillary electrophoresis and detection of the emerging amplicon, probing for the presence of the amplicon using a labeled probe, sequencing the amplicon, and labeling a PCR primer employed in the method and detecting the label.

BRIEF DESCRIPTION OF THE DRAWINGS

FIG. 1 shows the nucleic acid sequence of the human Bocavirus-type-2 (HBoV2A-PK5510) genome (SEQ ID NO:1).

FIG. 2 shows the amino acid sequences of the HBoV2A-PK5510 nonstructural proteins NS1 (SEQ ID NO:2) and NS2 (SEQ ID NO:29).

FIG. 3 shows the amino acid sequence of the HBoV2A-PK5510 nucleoprotein protein (NP1) (SEQ ID NO:3).

FIG. 4 shows the amino acid sequence of the HBoV2A-PK5510 proteins VP1 (SEQ ID NO:4) and VP2 (SEQ ID NO:30).

FIG. 5 shows the nucleotide alignment between the complete genome of HBoV1 (SEQ ID NO:55) and HBoV2 (SEQ ID NO:1).

FIG. 6 shows the amino acid alignments between HBoV2 and HBoV1 for the a) NS1 protein (SEQ ID NO'S 2 & 56, respectively), b) NP1 protein (SEQ ID NO'S 3 & 57, respectively, and c) VP1 protein (SEQ ID NO'S 58 & 59, respectively).

FIGS. 7A-D show the genomic sequence of HBoV4-TU210-07 (SEQ ID NO:5; FIG. 7A) and the encoded amino acid sequences for NS1 and NS2 (SEQ ID NO:6 and SEQ ID NO:31, respectively; FIG. 7B); NP1 (SEQ ID NO:7; FIG. 7C); and VP1 and VP2 (SEQ ID NO:8 and SEQ ID NO:32, respectively; FIG. 7D).

FIGS. 8A-D show the genomic sequence of HBoV2A-TU114-06 (SEQ ID NO:9; FIG. 8A) and the encoded amino acid sequences for NS1 and NS2 (SEQ ID NO:10 and SEQ ID NO:33, respectively; FIG. 8B); NP1 (SEQ ID NO:11; FIG. 8C); and VP1 and VP2 (SEQ ID NO:12 and SEQ ID NO:34, respectively; FIG. 8D).

FIGS. 9A-D show the genomic sequence of HBoV2B-NI213 (SEQ ID NO:13; FIG. 9A) and the encoded amino acid sequences for NS1 and NS2 (SEQ ID NO:14 and SEQ ID NO:35, respectively; FIG. 9B); NP1 (SEQ ID NO:15; FIG. 9C); and VP1 and VP2 (SEQ ID NO:16 and SEQ ID NO:36, respectively; FIG. 9D).

FIGS. 10A-D show the genomic sequence of HBoV2B-NI327 (SEQ ID NO:17; FIG. 10A) and the encoded amino acid sequences for NS1 and NS2 (SEQ ID NO:18 and SEQ ID NO:37, respectively; FIG. 10B); NP1 (SEQ ID NO:19; FIG. 10C); and VP1 and VP2 (SEQ ID NO:20 and SEQ ID NO:38, respectively; FIG. 10D).

FIGS. 11A-D show the genomic sequence of HBoV4-NI374 (SEQ ID NO:21; FIG. 11A) and the encoded amino acid sequences for NS1 and NS2 (SEQ ID NO:22 and SEQ ID NO:39, respectively; FIG. 11B); NP1 (SEQ ID NO:23; FIG. 11C); and VP1 and VP2 (SEQ ID NO:24 and SEQ ID NO:40, respectively; FIG. 11D).

FIGS. 12A-D show the genomic sequence of HBoV3-NI3853 (SEQ ID NO:25; FIG. 12A) and the encoded amino acid sequences for NS1 and NS2 (SEQ ID NO:26 and SEQ ID NO:41, respectively; FIG. 12B); NP1 (SEQ ID NO:27; FIG. 12C); and VP1 and VP2 (SEQ ID NO:28 and SEQ ID NO:42, respectively; FIG. 12D).

FIGS. 16A-D show the genomic sequence of HBoV2A-PK2255 (SEQ ID NO:43; FIG. 16A) and the encoded amino acid sequences for NS1 and NS2 (SEQ ID NO:44 and SEQ ID NO:45, respectively; FIG. 16B); NP1 (SEQ ID NO:46; FIG. 16C); and VP1 and VP2 (SEQ ID NO:47 and SEQ ID NO:48, respectively; FIG. 16D).

FIGS. 17A-D show the genomic sequence of HBoV2A-UK648 (SEQ ID NO:49; FIG. 17A) and the encoded amino acid sequences for NS1 and NS2 (SEQ ID NO:50 and SEQ ID NO:51, respectively; FIG. 17B); NP1 (SEQ ID NO:52; FIG. 17C); and VP1 and VP2 (SEQ ID NO:53 and SEQ ID NO:54, respectively; FIG. 17D).

DETAILED DESCRIPTION OF THE INVENTION

Figure 13:
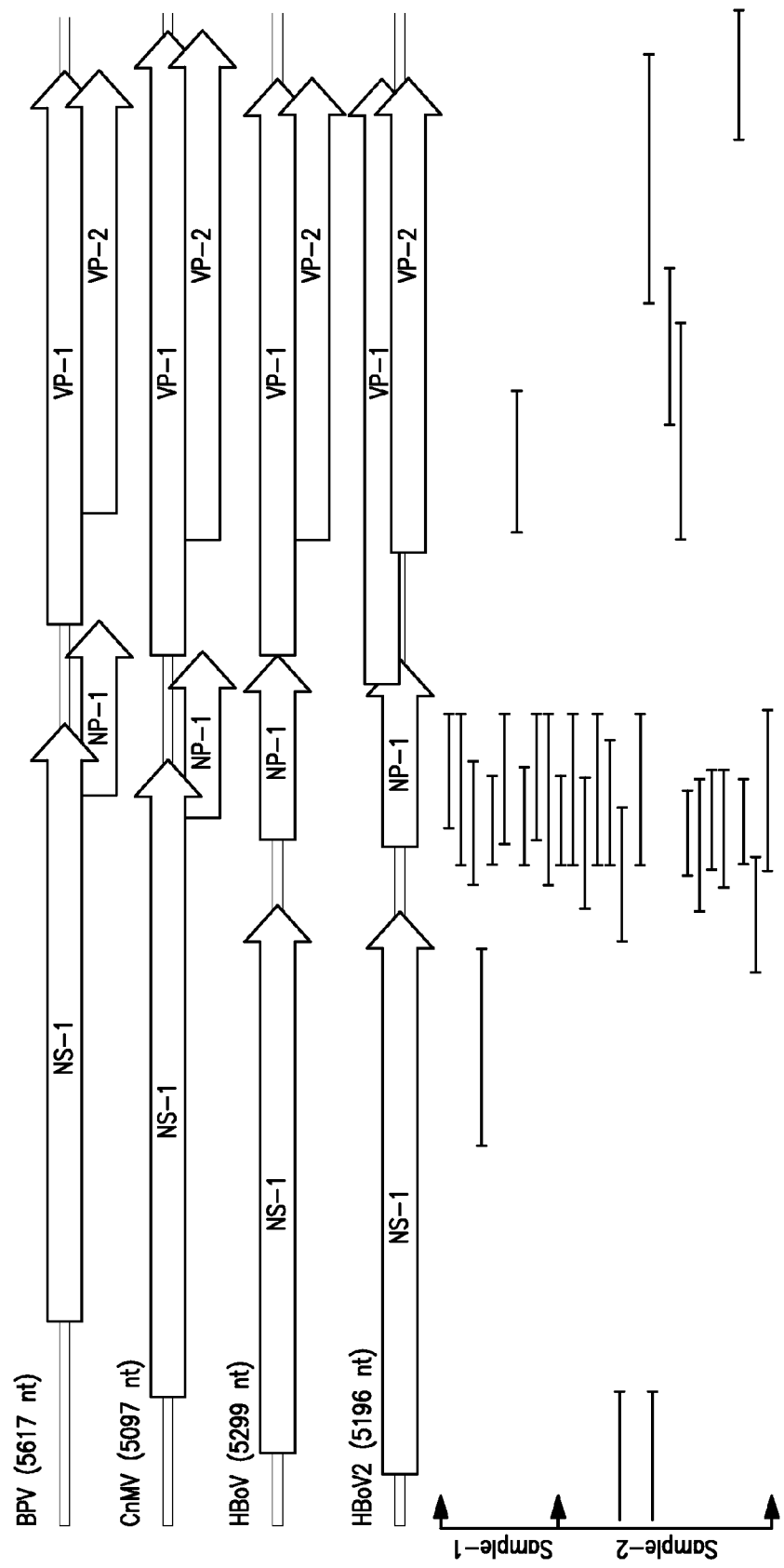
FIG. 13 shows a schematic representation of the genomic organization of HBoV2 and other species of Bocaviruses (BPV, CnMV, and HBoV).

The present invention is based on the discovery of a novel virus, Bocavirus-2, which is associated with respiratory tract infections. There are various molecular methods for discovery of novel human viruses including immunoreactive cDNA expression library screening, representational difference analysis (RDA), DNA microarrays and use of degenerate PCR primers. Other methods include sequence independent single primer amplification of nucleic acids in serum (DNase-SISPA), or "metagenomics shotgun sequencing." For these approaches, DNA can be isolated directly from environmental samples and sequenced, without attempting to culture the organisms from which it comes. The DNase-SISPA method first removes contaminating human DNA in plasma or serum by DNase digestion. Viral nucleic acids protected from DNase digestion by their viral coats are then converted into double stranded DNA (dsDNA) using random primers. The dsDNA is then digested by a four base pair specific restriction endonuclease resulting in two overhanging bases to which are ligated a complementary oligonucleotide linker. A PCR primer complementary to the ligated linker is then used to PCR amplify the sequences between the restriction sites. The PCR products are analyzed by PAGE and distinct DNA bands are extracted, subcloned and sequenced. Similarity to known viruses is then tested using BLASTn (for nucleic acid similarity) and tBLASTx (for protein similarity). The DNase-SISPA method does not require foreknowledge of the viral sequences being amplified and can therefore theoretically amplify more divergent members of known viral families than nucleic acid sequence similarity-dependent approaches using degenerate primers or microarrays.

Accordingly, the present invention provides a new virus, human Bocavirus-2 (HBoV2) and variants thereof, as well as their genomic sequences and the viral proteins encoded thereby. The genome encodes the structural proteins of the virus and non-structural proteins involved in viral replication. The genomic sequence of an exemplary Bocavirus-2 (termed HBoV2A-PK5510) is provided herein. In addition, 8 variant Bocavirus-2 genomes are provided herein, termed. HBoV2A-PK2255, HBoV2A-UK648, HBoV2A-TU114-06, HBoV2B-NI327, HBoV2B-NI213, HBoV3-NI385, HBoV4-TU210-07, and HBoV4-NI374. The genomic sequences of these bocavirus-2 variants are provided in FIG. 1 (HBoV2A-PK5510; SEQ ID NO:1), FIG. 7A (HBoV4-TU210-07; SEQ ID NO:5), FIG. 8A (HBoV2A-TU114-06; SEQ ID NO:9), FIG. 9A (HBoV2B-NI213; SEQ ID NO:13), FIG. 10A (HBoV2B-NI327; SEQ ID NO:17), FIG. 11A (HBoV4-NI374; SEQ ID NO:21), FIG. 12A (HBoV3-NI3853; SEQ ID NO:25), FIG. 16A (HBoV2A-PK2255; SEQ ID NO:43), and FIG. 17A (HBoV2A-UK648; SEQ ID NO:49).

The amino acid sequences of exemplary HBoV2 (HBoV2A-PK5510) nonstructural proteins NS1 and NS2 are shown in FIG. 2 (SEQ ID NO:2 and SEQ ID NO:29, respectively). Additional exemplary amino acid sequences of NS1 proteins are set forth in SEQ ID NOs: 6, 10, 14, 18, 22, 26, 44, and 50. Additional exemplary amino acid sequences of NS2 proteins are set forth in SEQ ID NOs: 31, 33, 35, 37, 39, 41, 45, and 51. FIG. 3 shows the amino acid sequence of an exemplary HBoV2 nucleoprotein protein (NP) (SEQ ID NO:3). Additional exemplary amino acid sequences of NP proteins are set forth in SEQ ID NOs: 7, 11, 15, 19, 23, 27, 46, and 52. Additionally, FIG. 4 shows the amino acid sequences of exemplary HBoV2 VP1 and VP2 proteins (SEQ ID NO:4 and SEQ ID NO:30, respectively). Further exemplary amino acid sequences of VP1 proteins are set forth in SEQ ID NOs: 8, 12, 16, 20, 24, 28, 47, and 53. Further exemplary amino acid sequences of VP2 proteins are set forth in SEQ ID NOs: 30, 32, 34, 36, 38, 40, 42, 48, and 54.

Phylogenetic analysis of HBoV2 establishes it as diverse from HBoV1 (also termed HBoV), containing a 78% amino acid identity to HBoV1 in the non-structural (NS) region. (FIG. 6a) The nucleocapsid protein (NP) of HBoV1 has only a 66% amino acid identity with the NP protein of HBoV-2. (FIG. 6b) Additionally, the capsid protein (CP) of HBoV has only a 66% amino acid identity to the NP protein of HBoV2. (FIG. 6c)

The identification of Bocavirus-2 provides methods of detecting the virus, its genome, transcripts, and proteins including structural and non-structural proteins. Antibodies (polyclonal and monoclonal) made to antigens from any of these viral proteins can be used to detect the antigen or protein as well as to isolate the antigens and to remove virus, proteins, or nucleic acids from a sample, e.g., a blood sample. Antibodies to Bocavirus-2 antigens can be used in diagnostic assays to detect viral infection. Any suitable sample, including blood, saliva, sputum, etc., can be used in a diagnostic assay of the invention. Such antibodies can also be used in therapeutic applications to inhibit or prevent viral infection.

The Bocavirus-2 antigens of the invention can also be used in diagnostic application to detect anti-Bocavirus-2 antigen antibodies in infected or exposed subjects. Bocavirus-2 antigens of the invention can also be used therapeutically, as prophylactic vaccines or vaccines for acute or latent infections, e.g., whole virus vaccines, protein or subunit vaccines, and nucleic acid vaccines encoding viral proteins, ORFs or genomes for intracellular expression and secretion or cell surface display, or can be targeted to specific cell types using promoters and vectors.

The Bocavirus virus, nucleic acids and proteins of the invention can be used to assay for antiviral compounds, including compounds that inhibit (1) viral interactions at the cell surface, e.g., viral transduction (e.g., block viral cell receptor binding or internalization); (2) viral replication and gene expression, e.g., viral replication (e.g., by inhibiting non-structural protein activity, origin activity, or primer binding), viral transcription (promoter or splicing inhibition, non-structural protein inhibition), viral protein translation, protein processing (e.g., cleavage or phosphorylation); and (3) viral assembly and egress, e.g., viral packaging, and virus release.

"Bocavirus" refers to both the genetic components of the virus, e.g., the genome (positive or negative) and RNA transcripts thereof (either sense or antisense), proteins encoded by the genome (including structural and nonstructural proteins), and viral particles. This description includes Bocavirus nucleic acids, alleles, mutants, and interspecies homologs that: (1) have a nucleotide sequence that has greater than about 60% nucleotide sequence identity, 65%, 70%, 75%, 80%, 85%, 90%, preferably 91%, 92%, 93%, 94%, 95%, 96%, 97%, 98% or 99% or greater nucleotide sequence identity, preferably over a region of at least about 25, 50, 100, 200, 500, 1000, or more nucleotides, up to the full length sequence, to the nucleotide sequence as set forth in SEQ ID NO:1, SEQ ID NO:5, SEQ ID NO:9, SEQ ID NO:13, SEQ ID NO:17, SEQ ID NO:21, SEQ ID NO:25, SEQ ID NO:43, SEQ ID NO:49, or a complement thereof; (2) encode a protein that binds to antibodies, e.g., polyclonal or monoclonal antibodies, raised against an antigen or an immunogen from an amino acid sequence of a protein encoded by an open reading frame of SEQ ID NO:1, SEQ ID NO:5, SEQ ID NO:9, SEQ ID NO:13, SEQ ID NO:17, SEQ ID NO:21, SEQ ID NO:25, SEQ ID NO:43, or SEQ ID NO:49; (3) specifically hybridize under stringent hybridization conditions to a nucleic acid sequence as set forth in SEQ ID NO:1, SEQ ID NO:5, SEQ ID NO:9, SEQ ID NO:13, SEQ ID NO:17, SEQ ID NO:21, SEQ ID NO:25, SEQ ID NO:43, SEQ ID NO:49, or a complement thereof; (4) encodes a protein having an amino acid sequence that has greater than about 60% identity, 65%, 70%, 75%, 80%, 85%, 90%, preferably 91%, 92%, 93%, 94%, 95%, 96%, 97%, 98% or 99% or greater sequence identity, preferably over a region of over a region of at least about 25, 50, 100, 200, 500, 1000, or more amino acids, to a protein as set forth in SEQ ID NO:2, SEQ ID NO:3, SEQ ID NO:4, SEQ ID NO:6, SEQ ID NO:7, SEQ ID NO:8, SEQ ID NO:10, SEQ ID NO:11, SEQ ID NO:12, SEQ ID NO:14, SEQ ID NO:15, SEQ ID NO:16, SEQ ID NO:18, SEQ ID NO:19, SEQ ID NO:20, SEQ ID NO:22, SEQ ID NO:23, SEQ ID NO:24, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:44, SEQ ID NO:45, SEQ ID NO:46, SEQ ID NO:47, SEQ ID NO:48, SEQ ID NO:50, SEQ ID NO:51, SEQ ID NO:52, SEQ ID NO:53, or SEQ ID NO:54. Bocavirus-2 nucleic acids may be isolated from an animal host including, but not limited to, primate, e.g., human; rodent, e.g., rat, mouse, hamster; cow, pig, horse, sheep, or any mammal. The nucleic acids and proteins of the invention include both naturally occurring and recombinant molecules.

Bocavirus-2 nucleic acids can be used to produce infectious clones, e.g., for production of recombinant viral particles, including empty capsids or capsids containing a recombinant (e.g., wild type or further comprising a heterologous nucleic acid) or modified (e.g., mutated) Bocavirus genome, which may be replication competent or incompetent, using the methods disclosed in U.S. Pat. Nos. 6,558,676; 6,132,732; 6,001,371; 5,916,563; 5,827,647; 5,508,186; 6,379,885; 6,287,815; 6,204,044; and 5,449,608. Such particles are useful as gene transfer vehicles, and as vaccines, and for use in diagnostic applications and for drug discovery assays for antiviral compounds, as discussed below.

"Protein encoded by Bocavirus" or "protein encoded by Bocavirus open reading frame (ORF)" refers to structural and non-structural Bocavirus proteins that: (1) are encoded by a nucleic acid molecule of the invention such as a nucleic acid molecule that has greater than about 60% nucleotide sequence identity, 65%, 70%, 75%, 80%, 85%, 90%, preferably 91%, 92%, 93%, 94%, 95%, 96%, 97%, 98% or 99% or greater nucleotide sequence identity, preferably over a region of over a region of at least about 25, 50, 100, 200, 500, 1000, or more nucleotides, up to the full length sequence, to the nucleotide sequence as set forth in SEQ ID NO:1, SEQ ID NO:5, SEQ ID NO:9, SEQ ID NO:13, SEQ ID NO:17, SEQ ID NO:21, SEQ ID NO:25, SEQ ID NO:43, SEQ ID NO:49, or a complement thereof; (2) bind to antibodies, e.g., polyclonal or monoclonal antibodies, raised against an immunogen comprising an amino acid sequence of a protein as set forth in SEQ ID NO:2, SEQ ID NO:3, SEQ ID NO:4, SEQ ID NO:6, SEQ ID NO:7, SEQ ID NO:8, SEQ ID NO:10, SEQ ID NO:11, SEQ ID NO:12, SEQ ID NO:14, SEQ ID NO:15, SEQ ID NO:16, SEQ ID NO:18, SEQ ID NO:19, SEQ ID NO:20, SEQ ID NO:22, SEQ ID NO:23, SEQ ID NO:24, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:44, SEQ ID NO:45, SEQ ID NO:46, SEQ ID NO:47, SEQ ID NO:48, SEQ ID NO:50, SEQ ID NO:51, SEQ ID NO:52, SEQ ID NO:53, SEQ ID NO:54, or conservatively modified variants thereof; (3) is encoded by a nucleic acid molecule that specifically hybridizes under stringent hybridization conditions to a nucleic acid sequence as set forth in SEQ ID NO:1, SEQ ID NO:5, SEQ ID NO:9, SEQ ID NO:13, SEQ ID NO:17, SEQ ID NO:21, SEQ ID NO:25, SEQ ID NO:43, SEQ ID NO:49, or a complement thereof, starting with an ATG and ending with a TAA, e.g., nucleotides 2378-5122); (4) have an amino acid sequence that has greater than about 60% identity, 65%, 70%, 75%, 80%, 85%, 90%, preferably 91%, 92%, 93%, 94%, 95%, 96%, 97%, 98% or 99% or greater identity, preferably over a region of at least about 25, 50, 100, 200, 500, 1000, or more amino acids, to a protein as set forth in SEQ ID NO:2, SEQ ID NO:3, SEQ ID NO:4, SEQ ID NO:6, SEQ ID NO:7, SEQ ID NO:8, SEQ ID NO:10, SEQ ID NO:11, SEQ ID NO:12, SEQ ID NO:14, SEQ ID NO:15, SEQ ID NO:16, SEQ ID NO:18, SEQ ID NO:19, SEQ ID NO:20, SEQ ID NO:22, SEQ ID NO:23, SEQ ID NO:24, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:44, SEQ ID NO:45, SEQ ID NO:46, SEQ ID NO:47, SEQ ID NO:48, SEQ ID NO:50, SEQ ID NO:51, SEQ ID NO:52, SEQ ID NO:53, SEQ ID NO:54, or conservatively modified variants thereof.

"Biological sample" includes sections of tissues such as biopsy and autopsy samples, and frozen sections taken for histologic purposes. Such samples include blood and blood fractions or products (e.g., serum, plasma, platelets, red blood cells, and the like), sputum, tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, mouse; rabbit; or a bird; reptile; or fish.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., nucleotide sequence or amino acid sequence of FIGS. 1 and 2, respectively, corresponding to SEQ ID NO:1 and SEQ ID NO:2, respectively), when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

There are several methods available and well known to those skilled in the art to obtain full-length DNAs, or extend short DNAs, for example those based on the method of Rapid Amplification of cDNA Ends (RACE). Another sequencing method is based on detecting the activity of DNA polymerase with a chemiluminescent enzyme. Essentially, the method allows sequencing of a single strand of DNA by synthesizing the complementary strand along it, one base pair at a time, and detecting which base was actually added at each step. The template DNA is immobilized, and solutions of A, C, G, and T nucleotides are added sequentially. Light is produced only when the nucleotide solution compliments the first unpaired base of the template. The sequence of solutions which produce chemiluminescent signals allows the determination of the sequence of the template.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues. The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an αcarbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M).

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. Domains are portions of a polypeptide that form a compact unit of the polypeptide and are typically 15 to 350 amino acids long. Exemplary domains include domains with enzymatic activity. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

For preparation of antibodies, e.g., recombinant, monoclonal, or polyclonal antibodies, many technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* (3d ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121: 210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332: 323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The antibody can be conjugated to an "effector" moiety. The effector moiety can be any number of molecules, including labeling moieties such as radioactive labels or fluorescent labels, or can be a therapeutic moiety. In one aspect the antibody modulates the activity of the protein.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to a Bocavirus, polymorphic variants, alleles, orthologs, and conservatively modified variants, or splice variants, or portions thereof, can be selected to obtain only those polyclonal antibodies that are specifically immunoreactive with Bocavirus and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

By "therapeutically effective dose" herein is meant a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

The phrase "functional effects" in the context of assays for testing compounds that modulate activity of a Bocavirus includes the determination of a parameter that is indirectly or directly under the influence of a Bocavirus, e.g., a phenotypic or chemical effect, such as the ability to increase or decrease viral genome replication, viral RNA and protein production, virus packaging, viral particle production (particularly replication competent viral particle production), cell receptor binding, viral transduction, cellular infection, antibody binding, inducing a cellular or humoral immune response, viral protein enzymatic activity, etc. "Functional effects" include in vitro, in vivo, and ex vivo activities. Such functional effects can be measured by any means known to those skilled in the art, e.g., changes in spectroscopic characteristics (e.g., fluorescence, absorbance, refractive index); hydrodynamic (e.g., shape); chromatographic; or solubility properties for a protein; measuring inducible markers or transcriptional activation of a protein; measuring binding activity or binding assays, e.g. binding to antibodies; measuring changes in ligand or substrate binding activity; measuring viral replication; measuring cell surface marker expression; measurement of changes in protein levels; measurement of RNA stability; identification of downstream or reporter gene expression (CAT, luciferase, β-gal, GFP and the like), e.g., via chemiluminescence, fluorescence, colorimetric reactions, antibody binding, and inducible markers.

"Inhibitors," "activators," and "modulators" of Bocavirus nucleic acid and polypeptide sequences are used to refer to activating, inhibitory, or modulating molecules identified using in vitro and in vivo assays of the Bocavirus nucleic acid and polypeptide sequences. Inhibitors are compounds that, e.g., bind to, partially or totally block activity, decrease, prevent, delay activation, inactivate, desensitize, or down regulate the activity or expression of Bocavirus, e.g., antagonists. "Activators" are compounds that increase, open, activate, facilitate, enhance activation, sensitize, agonize, or up regulate Bocavirus activity, e.g., agonists. Inhibitors, activators, or modulators also include genetically modified versions of Bocavirus, e.g., versions with altered activity, as well as naturally occurring and synthetic ligands, substrates, antagonists, agonists, antibodies, peptides, cyclic peptides, nucleic acids, antisense molecules, ribozymes, small chemical molecules and the like. Such assays for inhibitors and activators include, e.g., expressing Bocavirus in vitro, in cells, or cell membranes, applying putative modulator compounds, and then determining the functional effects on activity, as described above.

Samples or assays comprising Bocavirus that are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition of Bocavirus is achieved when the activity value relative to the control is about 80%, preferably 50%, more preferably 25-0%. Activation of Bocavirus is achieved when the activity value relative to the control (untreated with activators) is 110%, more preferably 150%, more preferably 200-500% (i.e., two to five fold higher relative to the control), more preferably 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, oligonucleotide, etc., to be tested for the capacity to directly or indirectly modulation tumor cell proliferation. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

An "siRNA" molecule or an "RNAi" molecule refers to a nucleic acid that forms a double stranded RNA, which double stranded RNA has the ability to reduce or inhibit expression of a gene or target gene when the siRNA expressed in the same cell as the gene or target gene. "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is 15-50 nucleotides in length, and the double stranded siRNA is about 15-50 base pairs in length, preferable about preferably about 20-30 base nucleotides, preferably about 20-25 or about 24-29 nucleotides in length, e.g., 20, 21, 22, 23, 24, 25, 26, 27, 28, 29, or 30 nucleotides in length. See also PCT/US03/07237, herein incorporated by reference in its entirety.

An siRNA molecule or RNAi molecule is "specific" for a target nucleic acid if it reduces expression of the nucleic acid by at least about 10% when the siRNA or RNAi is expressed in a cell that expresses the target nucleic acid.

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

Bocavirus, polymorphic variants, orthologs, and alleles that are substantially identical to an amino acid sequence encoded by nucleic acids of SEQ ID NO:1 (FIG. 1) can be isolated using nucleic acid probes and oligonucleotides under stringent hybridization conditions, by screening DNA libraries or by using PCR. Genes encoding Bocavirus proteins can be isolated using cDNA libraries. Alternatively, expression libraries can be used to clone the Bocavirus, polymorphic variants, orthologs, and alleles by detecting expressed homologs immunologically with antisera or purified antibodies made against Bocavirus or portions thereof.

Other techniques that can be used to identify known and previously uncharacterized Bocavirus isolates, including representational difference analysis (RDA), DNA microarrays and use of degenerate PCR primers or other methods well known to those of skill in the art. Other methods for determining the sequence of a Bocavirus, are, for example, sequence independent single primer amplification of nucleic acids in serum (DNase-SISPA) can be used. In this method, DNA is isolated directly from environmental samples and sequenced. This method first removes contaminating human DNA in plasma or serum by DNase digestion. Viral nucleic acids protected from DNase digestion by their viral coats are then converted into double stranded DNA (dsDNA) using random primers. The dsDNA is then digested by a 4 base pair specific restriction endonuclease resulting in two overhanging bases to which are ligated a complementary oligonucleotide linker. A PCR primer complementary to the ligated linker is then used to PCR amplify the sequences between the restriction sites. The PCR products are analyzed by PAGE and distinct DNA bands are extracted, subcloned and sequenced. Similarity to known viruses is then tested using BLASTn (for nucleic acid similarity) and tBLASTx (for protein similarity). The DNase-SISPA method does not require foreknowledge of the viral sequences being amplified and can therefore theoretically amplify more divergent members of known viral families than nucleic acid sequence similarity-dependent approaches using degenerate primers or microarrays. There are several methods available and well known to those skilled in the art to obtain full-length DNAs, or extend short DNAs, for example, those based on the method of Rapid Amplification of cDNA Ends (RACE) and large scale sequencing.

To make a cDNA library to clone Bocavirus genes expressed by the genome, the source used should be rich in the RNA of choice. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263-269 (1983); Sambrook et al., supra; Ausubel et al., supra).

For a genomic library, the DNA is extracted from the tissue and optionally mechanically sheared or enzymatically digested. The fragments are then separated by gradient centrifugation from undesired sizes and are constructed in suitable vectors. These vectors are packaged in vitro. Recombinant vectors can be analyzed, e.g., by plaque hybridization as described in Benton & Davis, *Science* 196:180-182 (1977). Colony hybridization is carried out as generally described in Grunstein et al., *Proc. Natl. Acad. Sci. USA.*, 72:3961-3965 (1975).

A preferred method of isolating Bocavirus and orthologs, alleles, mutants, polymorphic variants, splice variants, and conservatively modified variants combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR and RT-PCR) and ligase chain reaction (LCR) can be used to amplify nucleic acid sequences directly from mRNA, from cDNA, from genomic libraries or cDNA libraries. Degenerate oligonucleotides can be designed to amplify homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of Bocavirus encoding mRNA in physiological samples, for nucleic acid sequencing, or for other purposes. Genes amplified by the PCR reaction can be purified from agarose gels and cloned into an appropriate vector.

Gene expression of Bocavirus can also be analyzed by techniques known in the art, e.g., reverse transcription and amplification of mRNA, isolation of total RNA or poly A$^+$ RNA, northern blotting, dot blotting, in situ hybridization, RNase protection, high density polynucleotide array technology, e.g., and the like.

Nucleic acids encoding a Bocavirus genome or protein can be used with high density oligonucleotide array technology to identify Bocavirus, orthologs, alleles, conservatively modified variants, and polymorphic variants in this invention. In the case where the homologs being identified are linked to modulation of the cell cycle, they can be used with oligonucleotide array as a diagnostic tool in detecting the disease in a biological sample, see, e.g., Gunthand et al., *AIDS Res. Hum. Retroviruses* 14: 869-876 (1998); Kozal et al., *Nat. Med.* 2:753-759 (1996); Matson et al., *Anal. Biochem.* 224: 110-106 (1995); Lockhart et al., *Nat. Biotechnol.* 14:1675-1680 (1996); Gingeras et al., *Genome Res.* 8:435-448 (1998); Hacia et al., *Nucleic Acids Res.* 26:3865-3866 (1998).

The gene of choice is typically cloned into intermediate vectors before transformation into prokaryotic or eukaryotic cells for replication and/or expression. These intermediate vectors are typically prokaryote vectors, e.g., plasmids, or shuttle vectors.

To obtain high level expression of a cloned gene or genome, one typically subclones the nucleic acid into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al., and Ausubel et al, supra. Bacterial expression systems for expressing the protein are available in, e.g., *E. coli, Bacillus* sp., and *Salmonella* (Palva et al., *Gene* 22:229-235 (1983); Mosbach et al., Nature 302:543-545 (1983). Kits for such expression systems are commercially available. Eukaryotic expression systems for mammalian cells, yeast, and insect cells are well known in the art and are also commercially available. In one preferred embodiment, retroviral expression systems are used in the present invention.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the nucleic acid in host cells. A typical expression cassette thus contains a promoter operably linked to the nucleic acid sequence encoding the nucleic acid of choice and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc. Sequence tags may be included in an expression cassette for nucleic acid rescue. Markers such as fluorescent proteins, green or red fluorescent protein, β-gal, CAT, and the like can be included in the vectors as markers for vector transduction.

Expression vectors containing regulatory elements from eukaryotic viruses are typically used in eukaryotic expression vectors, e.g., SV40 vectors, papilloma virus vectors, retroviral vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal.

In one embodiment, the vectors of the invention have a regulatable promoter, e.g., tet-regulated systems and the RU-486 system (see, e.g., Gossen & Bujard, PNAS 89:5547 (1992); Oligino et al., Gene Ther. 5:491-496 (1998); Wang et al., Gene Ther. 4:432-441 (1997); Neering et al., Blood 88:1147-1155 (1996); and Rendahl et al., Nat. Biotechnol. 16:757-761 (1998)). These impart small molecule control on the expression of the candidate target nucleic acids. This beneficial feature can be used to determine that a desired phenotype is caused by a transfected cDNA rather than a somatic mutation.

Some expression systems have markers that provide gene amplification such as thymidine kinase and dihydrofolate reductase. Alternatively, high yield expression systems not involving gene amplification are also suitable, such as using a baculovirus vector in insect cells, with a sequence of choice under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of protein, which are then purified using standard techniques (see, e.g., Colley et al., J. Biol. Chem. 264:17619-17622 (1989); Guide to Protein Purification, in Methods in Enzymology, vol. 182 (Deutscher, ed., 1990)). Transformation of eukaryotic and prokaryotic cells are performed according to standard techniques (see, e.g., Morrison, J. Bact. 132:349-351 (1977); Clark-Curtiss & Curtiss, Methods in Enzymology 101:347-362 (Wu et al., eds, 1983).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing Bocavirus proteins and nucleic acids.

After the expression vector is introduced into the cells, the transfected cells are cultured under conditions favoring expression of the protein of choice, which is recovered from the culture using standard techniques identified below.

Either naturally occurring or recombinant Bocavirus proteins can be purified for use in diagnostic assays, for making antibodies (for diagnosis and therapy) and vaccines, and for assaying for anti-viral compounds. As described above, SEQ ID NO: 3 and SEQ ID NO:4 encode structural proteins. Naturally occurring proteins can be purified, e.g., from human tissue samples. Recombinant protein can be purified from any suitable expression system.

The protein may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant protein is being purified. For example, proteins having established molecular adhesion properties can be reversible fused to the protein. With the appropriate ligand or substrate, a specific protein can be selectively adsorbed to a purification column and then freed from the column in a relatively pure form. The fused protein is then removed by enzymatic activity. Finally, protein could be purified using immunoaffinity columns. Recombinant protein can be purified from any suitable source, include yeast, insect, bacterial, and mammalian cells.

Methods for production and purification of recombinant protein from a bacterial or eukaryotic (e.g., yeast, mammalian cell, and the like) system are well known in the art. Recombinant proteins are expressed by transformed host cells, (e.g., bacteria) in large amounts, typically after promoter induction; but expression can be constitutive. Promoter induction with IPTG is one example of an inducible promoter system. Host cells are grown according to standard procedures in the art. Where the host cell is a bacterial cell, fresh or frozen bacteria cells are used for isolation of protein.

Recombinant proteins, particularly when expressed in bacterial host cells, may form insoluble aggregates ("inclusion bodies"). Several protocols are suitable for purification of protein inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. Human proteins are separated from other bacterial proteins by standard separation techniques, e.g., with Ni-NTA agarose resin.

Alternatively, where the host cell is a bacterium, it is possible to purify recombinant protein from bacteria periplasm. After lysis of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

Standard protein separation techniques for purifying proteins are also contemplated in the present invention. Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

The molecular weight of the protein can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

The protein can also be separated from other proteins on the basis of its size, net surface charge, hydrophobicity, and affinity for ligands or substrates. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

In addition to the detection of a Bocavirus gene and gene expression using nucleic acid hybridization technology, one can also use immunoassays to detect Bocavirus proteins, virus, and nucleic acids of the invention. Such assays are useful for, e.g., therapeutic and diagnostic applications. Immunoassays can be used to qualitatively or quantitatively analyze protein, virus, and nucleic acids. A general overview of the applicable technology can be found in Harlow & Lane, *Antibodies: A Laboratory Manual* (1988).

Methods of producing polyclonal and monoclonal antibodies that react specifically with Bocavirus protein, virus and nucleic acids are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495-497 (1975)). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)).

A number of immunogens comprising portions of a Bocavirus protein, virus or nucleic acid may be used to produce antibodies specifically reactive with the Bocavirus. For example, a recombinant Bocavirus protein or an antigenic fragment thereof, can be isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, *Eur. J. Immunol.* 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., *Science* 246:1275-1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-Bocavirus proteins and nucleic acids, using a competitive binding immunoassay. Specific polyclonal antisera and monoclonal antibodies will usually bind with a $K_d$ of at least about 0.1 mM, more usually at least about 1 µM, preferably at least about 0.1 µM or better, and most preferably, 0.01 µM or better. Antibodies specific only for a particular Bocavirus protein can also be made by subtracting out other cross-reacting proteins, e.g., from other human Bocaviruses or other non-human Bocaviruses. In this manner, antibodies that bind only to the protein of choice may be obtained.

Once the specific antibodies against a Bocavirus protein, virus or nucleic acid in are available, the antigen can be detected by a variety of immunoassay methods. In addition, the antibody can be used therapeutically. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in Enzyme Immunoassay (Maggio, ed., 1980); and Harlow & Lane, supra.

Protein, in this case Bocavirus protein which is either associated with or separate from a Bocavirus viral particle, can be detected and/or quantified using any of a number of well recognized immunological binding assays (see, e.g., U.S. Pat. Nos. 4,366,241; 4,376,110; 4,517,288; and 4,837,168). Bocavirus viral particles may be detected based on an epitope defined by the viral proteins as presented in a viral particle and/or an epitope defined by a viral protein that is separate from a viral particle (e.g., such as may be present in an infected cell). As used in this context, then, "antigen" is meant to refer to a Bocavirus polypeptide as well as Bocavirus viral particles. For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice. The antibody may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled Bocavirus protein nucleic acid or a labeled anti-Bocavirus antibody. Alternatively, the labeling agent may be a third moiety, such a secondary antibody, that specifically binds to the antibody/antigen complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111:1401-1406 (1973); Akerstrom et al., *J. Immunol.* 135: 2589-2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Immunoassays for detecting Bocavirus protein, virus and nucleic acid in samples may be either competitive or noncompetitive, and may be either quantitative or non-quantitative. Noncompetitive immunoassays are assays in which antigen is directly detected and, in some instances the amount of antigen directly measured. In a "sandwich" assay, for example, the anti-Bocavirus antibodies can be bound directly to a solid substrate on which they are immobilized. These immobilized antibodies then capture the Bocavirus antigen present in the test sample. Proteins thus immobilized are then bound by a labeling agent, such as a second anti-Bocavirus antigen antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

In competitive assays, Bocavirus antigen present in a sample is detected indirectly by detecting a decrease in a detectable signal associated with a known, added (exogenous) Bocavirus antigen displaced (competed away) from an anti-Bocavirus antigen antibody by the unknown Bocavirus antigen present in a sample. In this manner, such assays can also be adapted to provide for an indirect measurement of the amount of Bocavirus antigen present in the sample. In one competitive assay, a known amount of Bocavirus antigen is added to a sample and the sample is then contacted with an antibody that specifically binds to the Bocavirus antigen. The amount of exogenous Bocavirus antigen bound to the antibody is inversely proportional to the concentration of Bocavirus antigen present in the sample. In a particularly preferred embodiment, the antibody is immobilized on a solid substrate. The amount of Bocavirus antigen bound to the antibody may be determined either by measuring the amount of Bocavirus antigen present in Bocavirus antigen/antibody complex, or alternatively by measuring the amount of remaining uncomplexed protein. The amount of Bocavirus antigen may be detected by providing a labeled Bocavirus antigen.

A hapten inhibition assay is another competitive assay. In this assay the known Bocavirus antigen is immobilized on a solid substrate. A known amount of anti-Bocavirus antigen antibody is added to the sample, and the sample is then contacted with the immobilized Bocavirus antigen. The amount of anti-Bocavirus antigen bound to the known immobilized Bocavirus antigen is inversely proportional to the amount of Bocavirus antigen present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Immunoassays in the competitive binding format can also be used for crossreactivity determinations. For example, a Bocavirus antigen can be immobilized to a solid support. Proteins are added to the assay that compete for binding of the antisera to the immobilized antigen. The ability of the added proteins to compete for binding of the antisera to the immobilized protein is compared to the ability of the Bocavirus antigen to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of a Bocavirus antigen, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the Bocavirus antigen that is required to inhibit 50% of binding, then the second protein is said to specifically bind to the polyclonal antibodies generated to Bocavirus antigen.

Western blot (immunoblot) analysis can be is used to detect and quantify the presence of Bocavirus antigen in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the Bocavirus antigen. The anti-Bocavirus antigen antibodies specifically bind to the Bocavirus antigen on the solid support. These antibodies may be directly labeled or alternatively may be subsequently detected using labeled antibodies (e.g., labeled sheep anti-mouse antibodies) that specifically bind to the anti-Bocavirus antigen antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34-41 (1986)).

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads, fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize Bocavirus antigen, or secondary antibodies that recognize anti-Bocavirus antigen.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by the use of electronic detectors such as charge coupled devices (CCDs) or photomultipliers and the like. Similarly, enzymatic labels may be detected by providing the appropriate substrates for the enzyme and detecting the resulting reaction product. Colorimetric or chemiluminescent labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

The present invention provides diagnostic assays to detect Bocavirus, Bocavirus nucleic acids (genome and genes), Bocavirus antibodies in an infected subject, and Bocavirus proteins. In one embodiment, Bocavirus nucleic acid is detected using a nucleic acid amplification-based assay, such as a PCR assay, e.g., in a quantitative assay to determine viral load. In another embodiment, Bocavirus antigens are detected using a serological assay with antibodies (either monoclonal or polyclonal) to antigens encoded by Bocavirus.

In one embodiment of the present invention, the presence of Bocavirus, Bocavirus nucleic acid, or Bocavirus protein in a sample is determined by an immunoassay. Enzyme mediated immunoassays such as immunofluorescence assays (IFA), enzyme linked immunosorbent assays (ELISA) and immunoblotting (western) assays can be readily adapted to accomplish the detection of the Bocavirus or Bocavirus proteins. An ELISA method effective for the detection of the virus can, for example, be as follows: (1) bind an anti-Bocavirus antibody or antigen to a substrate; (2) contact the bound receptor with a fluid or tissue sample containing the virus, a viral antigen, or antibodies to the virus; (3) contact the above with an antibody bound to a detectable moiety (e.g., horseradish peroxidase enzyme or alkaline phosphatase enzyme); (4) contact the above with the substrate for the enzyme; (5) contact the above with a color reagent; (6) observe color change. The above method can be readily modified to detect presence of an anti-Bocavirus antibody in the sample or a specific Bocavirus protein as well as the virus.

Another immunologic technique that can be useful in the detection of Bocaviruses is the competitive inhibition assay, utilizing monoclonal antibodies (MABs) specifically reactive with the virus. Briefly, serum or other body fluids from the subject is reacted with an antibody bound to a substrate (e.g. an ELISA 96-well plate). Excess serum is thoroughly washed away. A labeled (enzyme-linked, fluorescent, radioactive, etc.) monoclonal antibody is then reacted with the previously reacted Bocavirus virus-antibody complex. The amount of inhibition of monoclonal antibody binding is measured relative to a control. MABs can also be used for detection directly in samples by IFA for MABs specifically reactive for the antibody-virus complex.

Alternatively, a Bocavirus antigen and/or a patient's antibodies to the virus can be detected utilizing a capture assay. Briefly, to detect antibodies to Bocavirus in a patient sample, antibodies to the patient's immunoglobulin, e.g., anti-IgG (or IgM) are bound to a solid phase substrate and used to capture the patient's immunoglobulin from serum. A Bocavirus, or reactive fragments of a Bocavirus, are then contacted with the solid phase followed by addition of a labeled antibody. The amount of patient Bocavirus specific antibody can then be quantitated by the amount of labeled antibody binding.

Additionally, a micro-agglutination test can also be used to detect the presence of Bocavirus in test samples. Briefly, latex beads are coated with an antibody and mixed with a test sample, such that Bocavirus in the tissue or body fluids that are specifically reactive with the antibody crosslink with the receptor, causing agglutination. The agglutinated antibody-virus complexes form a precipitate, visible with the naked eye or by spectrophotometer. Other assays include serologic assays, in which the relative concentrations of IgG and IgM are measured.

In the diagnostic methods described above, the sample can be taken directly from the patient or in a partially purified form. The antibody specific for a particular Bocavirus (the primary reaction) reacts by binding to the virus. Thereafter, a secondary reaction with an antibody bound to, or labeled with, a detectable moiety can be added to enhance the detection of the primary reaction. Generally, in the secondary reaction, an antibody or other ligand which is reactive, either specifically or nonspecifically with a different binding site (epitope) of the virus will be selected for its ability to react with multiple sites on the complex of antibody and virus. Thus, for example, several molecules of the antibody in the secondary reaction can react with each complex formed by the primary reaction, making the primary reaction more detectable.

The detectable moiety can allow visual detection of a precipitate or a color change, visual detection by microscopy, or automated detection by spectrometry, radiometric measurement or the like. Examples of detectable moieties include fluorescein and rhodamine (for fluorescence microscopy), horseradish peroxidase (for either light or electron microscopy and biochemical detection), biotin-streptavidin (for light or electron microscopy) and alkaline phosphatase (for biochemical detection by color change). The detection methods and moieties used can be selected, for example, from the list above or other suitable examples by the standard criteria applied to such selections (Harlow and Lane, (1988)).

As described herein, a Bocavirus infection may also, or alternatively, be detected based on the level of a Bocavirus RNA or DNA in a biological sample. Primers from Bocavirus can be used for detection of Bocavirus, diagnosis, and determination of Bocavirus viral load. Any suitable primer can be used to detect the genome, nucleic acid sub-sequence, ORF, or protein of choice, using, e.g., methods described in US 20030104009. For example, the subject nucleic acid compositions can be used as single- or double-stranded probes or primers for the detection of Bocavirus mRNA or cDNA generated from such mRNA, as obtained may be present in a biological sample (e.g., extracts of human cells). The Bocavirus polynucleotides of the invention can also be used to generate additional copies of the polynucleotides, to generate antisense oligonucleotides, and as triple-strand forming oligonucleotides. For example, two oligonucleotide primers may be employed in a polymerase chain reaction (PCR) based assay to amplify a portion of Bocavirus cDNA derived from a biological sample, wherein at least one of the oligonucleotide primers is specific for (i.e., hybridizes to) the Bocavirus polynucleotide. The amplified cDNA is then separated and detected using techniques well known in the art, such as gel electrophoresis. Similarly, oligonucleotide probes that specifically hybridize to a Bocavirus polynucleotide may be used in a hybridization assay to detect the presence of the Bocavirus polynucleotide in a biological sample. These and other uses are described in more detail below.

Nucleic acid probes specific to Bocavirus-2 can be generated using the polynucleotide sequences disclosed herein. The probes are preferably at least about 12, 15, 16, 18, 20, 22, 24, or 25 nucleotide fragments of a contiguous sequence of SEQ ID NO:1, SEQ ID NO:5, SEQ ID NO:9, SEQ ID NO:13, SEQ ID NO:17, SEQ ID NO:21, SEQ ID NO:25, SEQ ID NO:43, SEQ ID NO:49, or a complement thereof, or other polynucleotide sequence encoding a Bocavirus-2 polypeptide. Nucleic acid probes can be less than about 200, 150, 100, 75, 60, 50, 40, 30, or 25 nucleotides in length, or may be up to 2 kb, 1.5 kb, 1 kb, 0.5 kb, 0.25 kb, 0.1 kb, or 0.05 kb in length. Probes may be 5 to 40 nucleotides in length, or 8 to 35 nucleotides, or 10 to 25 nucleotides. The probes can be produced by, for example, chemical synthesis, PCR amplification, generation from longer polynucleotides using restriction enzymes, or other methods well known in the art.

The polynucleotides of the invention, particularly where used as a probe in a diagnostic assay, can be detectably labeled. Exemplary detectable labels include, but are not limited to, radiolabels, fluorochromes, (e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein, 6-carboxy-X-rhodamine (ROX), 6-carboxy-2',4',7',4,7-hexachlorofluorescein (HEX), 5-carboxyfluorescein (5-FAM) or N,N,N', N'-tetramethyl-6-carboxyrho-damine (TAMRA)), radioactive labels, (e.g. $^{32}$P, $^{35}$S, and $^{3}$H), and the like. The detectable label can involve two stage systems (e.g., biotin-avidin, hapten-anti-hapten antibody, and the like).

The invention also includes solid substrates, such as arrays, comprising any of the polynucleotides described herein. The polynucleotides are immobilized on the arrays using methods known in the art. An array may have one or more different polynucleotides.

Any suitable qualitative or quantitative methods known in the art for detecting specific Bocavirus nucleic acid (e.g., RNA or DNA) can be used. Bocavirus nucleic acid can be detected by, for example, in situ hybridization in tissue sections, using methods that detect single base pair differences between hybridizing nucleic acid (e.g., using the technology described in U.S. Pat. No. 5,846,717), by reverse transcriptase-PCR, or in Northern blots containing poly A+ mRNA, and other methods well known in the art. For detection of Bocavirus polynucleotides in blood or blood-derived samples, the use of methods that allow for detection of single base pair mismatches is preferred.

Using the Bocavirus nucleic acid as a basis, nucleic acid probes (e.g., including oligomers of at least about 8 nucleotides or more) can be prepared, either by excision from recombinant polynucleotides or synthetically, which probes hybridize with the Bocavirus nucleic acid, and thus are useful in detection of Bocavirus virus in a sample, and identification of infected individuals, as well as further characterization of the viral genome(s). The probes for Bocavirus polynucleotides (natural or derived) are of a length or have a sequence which allows the detection of unique viral sequences by hybridization. While about 6-8 nucleotides may be useful, longer sequences may be preferred, e.g., sequences of about 10-12 nucleotides, or about 20 nucleotides or more. Preferably, these sequences will derive from regions which lack heterogeneity among Bocavirus viral isolates.

Nucleic acid probes can be prepared using routine methods, including automated oligonucleotide synthetic methods. A complement to any unique portion of the Bocavirus genome may be used, e.g., a portion of the Bocavirus genome that allows for distinguishing Bocavirus from other viruses that may be present in the sample. For use as probes, complete complementarity is desirable, though it may be unnecessary as the length of the fragment is increased.

For use of such probes as diagnostics, the biological sample to be analyzed, such as blood or serum, may be treated, if desired, to extract the nucleic acids contained therein. The resulting nucleic acid from the sample may be subjected to gel electrophoresis or other size separation techniques; alternatively, the nucleic acid sample may be dot blotted without size separation. The probes are usually labeled with a detectable label. Suitable labels, and methods for labeling probes are known in the art, and include, for example, radioactive labels incorporated by nick translation or kinasing, biotin, fluorescent probes, and chemiluminescent probes. The nucleic acids extracted from the sample are then treated with the labeled probe under hybridization conditions of suitable stringencies.

The probes can be made completely complementary to the Bocavirus genome or portion thereof. Therefore, usually high stringency conditions are desirable in order to prevent or at least minimize false positives. However, conditions of high stringency should only be used if the probes are complementary to regions of the viral genome which lack heterogeneity among Bocavirus viral isolates. The stringency of hybridization is determined by a number of factors during hybridization and during the washing procedure, including temperature, ionic strength, length of time, and concentration of formamide. These factors are outlined in, for example, Sambrook et al. (1989), "Molecular Cloning; A Laboratory Manual", Second Edition (Cold Spring Harbor Press, Cold Spring Harbor, N.Y.).

Generally, it is expected that the Bocavirus sequences will be present in a biological sample (e.g., blood, cells, and the liked) obtained from an infected individual at relatively low levels, e.g., at approximately $10^2$-$10^4$ Bocavirus sequences per $10^6$ cells. This level may require that amplification techniques be used in hybridization assays. Such techniques are known in the art.

For example, the Enzo Biochemical Corporation "Bio-Bridge" system uses terminal deoxynucleotide transferase to add unmodified 3'-poly-dT-tails to a DNA probe. The poly dT-tailed probe is hybridized to the target nucleotide sequence, and then to a biotin-modified poly-A. PCT Publication No. WO84/03520 and European application no. EPA124221 describe a DNA hybridization assay in which: (1) analyte is annealed to a single-stranded DNA probe that is complementary to an enzyme-labeled oligonucleotide; and (2) the resulting tailed duplex is hybridized to an enzyme-labeled oligonucleotide. EPA 204510 describes a DNA hybridization assay in which analyte DNA is contacted with a probe that has a tail, such as a poly-dT tail, an amplifier strand that has a sequence that hybridizes to the tail of the probe, such as a poly-A sequence, and which is capable of binding a plurality of labeled strands.

Non-PCR-based, sequence specific DNA amplification techniques can also be used in the invention to detect Bocavirus sequences. An example of such techniques include, but are not necessarily limited to the Invader assay, see, e.g., Kwiatkowski et al. *Mol. Diagn.* December 1999; 4(4):353-64. See also U.S. Pat. No. 5,846,717.

A particularly desirable technique may first involve amplification of the target Bocavirus sequences in sera approximately 10,000 fold, e.g., to approximately 10 sequences/mL. This may be accomplished, for example, by the polymerase chain reactions (PCR) technique described which is by Saiki et al. (1986), by Mullis, U.S. Pat. No. 4,683,195, and by Mullis et al. U.S. Pat. No. 4,683,202. Other amplification methods are well known in the art. In a preferred embodiment, a sample suspected of comprising the Bocavirus nucleic acid is contacted with at least one primer that hybridizes to a nucleotide sequence of SEQ ID NO:1, SEQ ID NO:5, SEQ ID NO:9, SEQ ID NO:13, SEQ ID NO:17, SEQ ID NO:21, SEQ ID NO:25, SEQ ID NO:43, SEQ ID NO:49, or a complement thereof, said contacting being under conditions suitable for amplification of an amplification product from a Bocavirus nucleic acid in the sample.

The probes, or alternatively nucleic acid from the samples, may be provided in solution for such assays, or may be affixed to a support (e.g., solid or semi-solid support). Examples of supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride, diazotized paper, nylon membranes, activated beads, and Protein A beads.

In one embodiment, the probe (or sample nucleic acid) is provided on an array for detection. Arrays can be created by, for example, spotting polynucleotide probes onto a substrate (e.g., glass, nitrocellulose, and the like) in a two-dimensional matrix or array. The probes can be bound to the substrate by either covalent bonds or by non-specific interactions, such as hydrophobic interactions. Samples of polynucleotides can be detectably labeled (e.g., using radioactive or fluorescent labels) and then hybridized to the probes. Double stranded polynucleotides, comprising the labeled sample polynucleotides bound to probe polynucleotides, can be detected once the unbound portion of the sample is washed away. Techniques for constructing arrays and methods of using these arrays are described in EP 799 897; WO 97/29212; WO 97/27317; EP 785 280; WO 97/02357; U.S. Pat. Nos. 5,593,839; 5,578,832; EP 728 520; U.S. Pat. No. 5,599,695; EP 721 016; U.S. Pat. No. 5,556,752; WO 95/22058; and U.S. Pat. No. 5,631,734. Arrays are particularly useful where, for example a single sample is to be analyzed for the presence of two or more nucleic acid target regions, as the probes for each of the target regions, as well as controls (both positive and negative) can be provided on a single array. Arrays thus facilitate rapid and convenience analysis.

The invention further provides diagnostic reagents and kits comprising one or more such reagents for use in a variety of diagnostic assays, including for example, immunoassays such as ELISA and "sandwich"-type immunoassays, as well as nucleic acid assay, e.g., PCR assays. In a related embodiment, the assay is performed in a flow-through or strip test format, wherein the binding agent is immobilized on a membrane, such as nitrocellulose. Such kits may preferably include at least a first peptide, or a first antibody or antigen binding fragment of the invention, a functional fragment thereof, or a cocktail thereof, or a first oligo pair, and means for signal generation. The kit's components may be pre-attached to a solid support, or may be applied to the surface of a solid support when the kit is used. The signal generating means may come pre-associated with an antibody or nucleic acid of the invention or may require combination with one or more components, e.g., buffers, nucleic acids, antibody-enzyme conjugates, enzyme substrates, or the like, prior to use.

Kits may also include additional reagents, e.g., blocking reagents for reducing nonspecific binding to the solid phase surface, washing reagents, enzyme substrates, enzymes, and the like. The solid phase surface may be in the form of microtiter plates, microspheres, or other materials suitable for immobilizing nucleic acids, proteins, peptides, or polypeptides. An enzyme that catalyzes the formation of a chemiluminescent or chromogenic product or the reduction of a chemiluminescent or chromogenic substrate is one such component of the signal generating means. Such enzymes are well known in the art. Where a radiolabel, chromogenic, fluorogenic, or other type of detectable label or detecting means is included within the kit, the labeling agent may be provided either in the same container as the diagnostic or therapeutic composition itself, or may alternatively be placed in a second distinct container means into which this second composition may be placed and suitably aliquoted. Alternatively, the detection reagent and the label may be prepared in a single container means, and in most cases, the kit will also typically include a means for containing the vial(s) in close confinement for commercial sale and/or convenient packaging and delivery.

Assays for modulators of Bocavirus are also contemplated in the present invention. Modulation of a Bocavirus, and corresponding modulation of the cell cycle, e.g., tumor cell, proliferation, can be assessed using a variety of in vitro and in vivo assays, including cell-based models. Such assays can be used to test for inhibitors and activators of Bocavirus. Modulators of Bocavirus are tested using either recombinant or naturally occurring protein of choice, preferably human Bocavirus.

Preferably, the Bocavirus will have the sequence as shown in SEQ ID NO:1, SEQ ID NO:5, SEQ ID NO:9, SEQ ID NO:13, SEQ ID NO:17, SEQ ID NO:21, SEQ ID NO:25, SEQ ID NO:43, or SEQ ID NO:49. Alternatively, the Bocavirus of the assay will be derived from a eukaryote and encode an amino acid subsequence having substantial amino acid sequence identity to a sequence as shown in SEQ ID NO:2, SEQ ID NO:3, SEQ ID NO:4, SEQ ID NO:6, SEQ ID NO:7, SEQ ID NO:8, SEQ ID NO:10, SEQ ID NO:11, SEQ ID NO:12, SEQ ID NO:14, SEQ ID NO:15, SEQ ID NO:16, SEQ ID NO:18, SEQ ID NO:19, SEQ ID NO:20, SEQ ID NO:22, SEQ ID NO:23, SEQ ID NO:24, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:44, SEQ ID NO:45, SEQ ID NO:46, SEQ ID NO:47, SEQ ID NO:48, SEQ ID NO:50, SEQ ID NO:51, SEQ ID NO:52, SEQ ID NO:53, or SEQ ID NO:54. Generally, the amino acid sequence identity will be at least 60%, preferably at least 65%, 70%, 75%, 80%, 85%, or 90%, most preferably at least 95%.

Measurement of modulation of a Bocavirus or a cell expressing Bocavirus, either recombinant or naturally occurring, can be performed using a variety of assays, in vitro, in vivo, and ex vivo, as described herein. A suitable physical, chemical or phenotypic change that affects activity, e.g., enzymatic activity, cell surface marker expression, viral replication and proliferation can be used to assess the influence of a test compound on the polypeptide of this invention. When the functional effects are determined using intact cells or animals, one can also measure a variety of effects.

Assays to identify compounds with Bocavirus modulating activity can be performed in vitro. Such assays can used full length Bocavirus or a variant thereof, or a mutant thereof, or a fragment thereof, such as a RING domain. Purified recombinant or naturally occurring protein can be used in the in vitro methods of the invention. In addition to purified Bocavirus, the recombinant or naturally occurring protein can be part of a cellular lysate or a cell membrane. As described below, the binding assay can be either solid state or soluble. Preferably, the protein or membrane is bound to a solid support, either covalently or non-covalently. Often, the in vitro assays of the invention are substrate or ligand binding or affinity assays, either non-competitive or competitive. Other in vitro assays include measuring changes in spectroscopic (e.g., fluorescence, absorbance, refractive index), hydrodynamic (e.g., shape), chromatographic, or solubility properties for the protein.

In one embodiment, a high throughput binding assay is performed in which the protein or a fragment thereof is contacted with a potential modulator and incubated for a suitable amount of time. In one embodiment, the potential modulator is bound to a solid support, and the protein is added. In another embodiment, the protein is bound to a solid support. A wide variety of modulators can be used, as described below, including small organic molecules, peptides, antibodies, etc. A wide variety of assays can be used to identify Bocavirus-modulator binding, including labeled protein-protein binding assays, electrophoretic mobility shifts, immunoassays, enzymatic assays, and the like. In some cases, the binding of the candidate modulator is determined through the use of competitive binding assays, where interference with binding of a known ligand or substrate is measured in the presence of a potential modulator. Either the modulator or the known ligand or substrate is bound first, and then the competitor is added. After the protein is washed, interference with binding, either of the potential modulator or of the known ligand or substrate, is determined. Often, either the potential modulator or the known ligand or substrate is labeled.

In another embodiment, the Bocavirus is expressed in a cell, and functional, e.g., physical and chemical or phenotypic, changes are assayed to identify modulators of the cell cycle. Any suitable functional effect can be measured, as described herein. The Bocavirus can be naturally occurring or recombinant. Also, fragments of the Bocavirus or chimeric proteins can be used in cell based assays. In addition, point mutants in essential residues required by the catalytic site can be used in these assays.

The compounds tested as modulators of Bocavirus can be any small organic molecule, or a biological entity, such as a protein, e.g., an antibody or peptide, a sugar, a nucleic acid, e.g., an antisense oligonucleotide or a ribozyme or RNAi, or a lipid. Alternatively, modulators can be genetically altered versions of a Bocavirus. Typically, test compounds will be small organic molecules, peptides, circular peptides, RNAi, antisense molecules, ribozymes, and lipids.

Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial small organic molecule or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274:1520-1522 (1996) and U.S. Pat. No. 5,593,853), small organic molecule libraries (see, e.g., benzodiazepines, Baum C&EN, Jan. 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, 5,288,514, and the like).

Devices for the preparation of combinatorial libraries are commercially available (see, e.g., 357 MPS, 390 MPS, *Advanced Chem Tech*, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

In one embodiment the invention, soluble assays using a Bocavirus, or a cell or tissue expressing an Bocavirus, either naturally occurring or recombinant are provided. In another embodiment, the invention provides solid phase based in vitro assays in a high throughput format, where the Bocavirus is attached to a solid phase. Any one of the assays described herein can be adapted for high throughput screening.

In the high throughput assays of the invention, either soluble or solid state, it is possible to screen up to several thousand different modulators or ligands in a single day. This methodology can be used for Bocavirus in vitro, or for cell-based or membrane-based assays comprising a Bocavirus. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100-about 1500 different compounds. It is possible to assay many plates per day; assay screens for up to about 6,000, 20,000, 50,000, or more than 100,000 different compounds are possible using the integrated systems of the invention.

For a solid state reaction, the protein of interest or a fragment thereof, e.g., an extracellular domain, or a cell or membrane comprising the protein of interest or a fragment thereof as part of a fusion protein can be bound to the solid state component, directly or indirectly, via covalent or non covalent linkage. A tag for covalent or non-covalent binding can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

Within certain aspects, Bocavirus, proteins or peptides and immunogenic fragments thereof, and/or polynucleotides, as well as anti-Bocavirus antibodies and/or T cells, may be incorporated into pharmaceutical compositions or immunogenic compositions (e.g., vaccines). Whole virus vaccine (live and attenuated, or replication incompetent, or killed) or subunit vaccines, such as structural or non-structural Bocavirus proteins or immunogenic fragments thereof, of SEQ ID NO:2, SEQ ID NO:3, SEQ ID NO:4, SEQ ID NO:6, SEQ ID NO:7, SEQ ID NO:8, SEQ ID NO:10, SEQ ID NO:11, SEQ ID NO:12, SEQ ID NO:14, SEQ ID NO:15, SEQ ID NO:16, SEQ ID NO:18, SEQ ID NO:19, SEQ ID NO:20, SEQ ID NO:22, SEQ ID NO:23, SEQ ID NO:24, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:44, SEQ ID NO:45, SEQ ID NO:46, SEQ ID NO:47, SEQ ID NO:48, SEQ ID NO:50, SEQ ID NO:51, SEQ ID NO:52, SEQ ID NO:53, SEQ ID NO:54 or conservatively modified variants thereof, can be used to treat or prevent Bocavirus infections by eliciting an immune response in a subject. Alternatively, a pharmaceutical composition may comprise an antigen-presenting cell (e.g., a dendritic cell) transfected with a Bocavirus polynucleotide such that the antigen-presenting cell expresses a Bocavirus peptide.

Pharmaceutical compositions comprise one or more such vaccine compounds and a physiologically acceptable carrier. Vaccines may comprise one or more such compounds and a non-specific immune response enhancer. A non-specific immune response enhancer may be any substance that enhances an immune response to an exogenous antigen. Examples of non-specific immune response enhancers include adjuvants, biodegradable microspheres (e.g., polylactic galactide) and liposomes (into which the compound is incorporated; see, e.g., U.S. Pat. No. 4,235,877). Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Vaccine preparation is generally described in, for example, Powell and Newman, eds., Vaccine Design (the subunit and adjuvant approach), Plenum Press (NY, 1995). Vaccines may be designed to generate antibody immunity and/or cellular immunity such as that arising from CTL or CD4+ T cells.

Pharmaceutical compositions and vaccines within the scope of the present invention may also contain other compounds, which may be biologically active or inactive. For example, one or more immunogenic portions of other antigens may be present, either incorporated into a fusion polypeptide or as a separate compound, within the composition or vaccine. Polypeptides may, but need not, be conjugated to other macromolecules as described, for example, within U.S. Pat. Nos. 4,372,945 and 4,474,757. Pharmaceutical compositions and vaccines may generally be used for prophylactic and therapeutic purposes.

Nucleic acid vaccines encoding a genome, structural protein or non-structural protein or a fragment thereof of Bocavirus can also be used to elicit an immune response to treat or prevent Bocavirus infection. Numerous gene delivery techniques are well known in the art, such as those described by Rolland (1998) *Crit. Rev. Therap. Drug Carrier Systems* 15:143-198, and references cited therein. Appropriate nucleic acid expression systems contain the necessary DNA sequences for expression in the patient (such as a suitable promoter and terminating signal). In a preferred embodiment, the DNA may be introduced using a viral expression system (e.g., vaccinia, pox virus, retrovirus, or adenovirus), which may involve the use of a non-pathogenic (defective), replication competent virus. Suitable systems are disclosed, for example, in Fisher-Hoch et al. (1989) *Proc. Natl. Acad. Sci. USA* 86:317-321; Flexner et al. (1989) *Ann. NY. Acad. Sci.* 569:86-103; Flexner et al. (1990) *Vaccine* 8:17-21; U.S. Pat. Nos. 4,603,112, 4,769,330, 4,777,127 and 5,017,487; WO 89/01973; GB 2,200,651; EP 0,345,242; WO 91/02805; Berkner (1988) *Biotechniques* 6:616-627; Rosenfeld et al. (1991) *Science* 252:431-434; Kolls et al. (1994) *Proc. Natl. Acad. Sci. USA* 91:215-219; Kass-Eisler et al. (1993) *Proc. Natl. Acad. Sci. USA* 90:11498-11502; Guzman et al. (1993) *Circulation* 88:2838-2848; and Guzman et al. (1993) *Cir. Res.* 73:1202-1207. Techniques for incorporating DNA into such expression systems are well known to those of ordinary skill in the art. The DNA may also be "naked," as described, for example, in Ulmer et al. (1993) *Science* 259:1745-1749 and reviewed by Cohen (1993) *Science* 259:1691-1692. The uptake of naked DNA may be increased by coating the DNA onto biodegradable beads, which are efficiently transported into the cells. It will be apparent that a vaccine may comprise both a polynucleotide and a polypeptide component. Such vaccines may provide for an enhanced immune response.

Vaccines and pharmaceutical compositions may be presented in unit-dose or multi-dose containers, such as sealed ampoules or vials. Such containers are preferably hermetically sealed to preserve sterility of the formulation until use. In general, formulations may be stored as suspensions, solutions or emulsions in oily or aqueous vehicles. Alternatively, a vaccine or pharmaceutical composition may be stored in a freeze-dried condition requiring only the addition of a sterile liquid carrier immediately prior to use.

Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., *Remington's Pharmaceutical Sciences,* $17^{th}$ ed., 1989). Administration can be in any convenient manner, e.g., by injection, oral administration, inhalation, transdermal application, or rectal administration.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of commends can be presented in unit-dose or multi-dose sealed containers, such as ampules and vials.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate. Compounds may also be encapsulated within liposomes using well known technology.

Injection solutions and suspensions can be prepared from sterile powders, granules, and tablets of the kind previously described. Cells transduced by nucleic acids for ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions owing to diminished or aberrant expression of the protein, the physician evaluates circulating plasma levels of the vector, vector toxicities, progression of the disease, and the production of anti-vector antibodies. In general, the dose equivalent of a naked nucleic acid from a vector is from about 1 µg to 100 µg for a typical 70 kilogram patient, and doses of vectors are calculated to yield an equivalent amount of therapeutic nucleic acid.

For administration, compounds and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

EXAMPLE

Using viral metagenomics a novel parvovirus species (termed HBoV2) and variants thereof were identified in human stool, whose closest phylogenetic relative is the human bocavirus (HBoV). HBoV2 has an identical genomic organization to HBoV but shares only 78%, 67%, and 80% identity to its NS1, NP1 and VP1/VP2 proteins. Using PCR HBoV2 sequences were detected in 5/98 Pakistani children stool samples and 3/699 stool samples from the UK. Near full genome sequencing showed the presence of three divergent genotypes and evidence of recombination.

Patients, materials, and methods. Stool samples from 57 children with non-polio AFP (mean age 54.6 months) and 41 from healthy Pakistani children (mean age 39.8 months) were analyzed. Samples were collected as part of the WHO poliovirus eradication program. 699 stool samples from a mixed age population submitted for enteric bacteriology screening in Edinburgh were also analyzed.

Stool supernatants were processed for viral metagenomics as previously described (Kapoor et al., J Virol 82:311-20, 2008) with minor modifications. Briefly, stool samples were suspended in Hanks buffered salt solution (HBSS), centrifuged at 12,000 rpm for 2 minutes in a tabletop microfuge and the supernatant collected. The supernatant was then filtered (Ultrafree-MC HV 0.45 um sterile filter, Millipore, UFC30HV0S). The flow through was then ultracentrifuged at 30,000 rpm for 3 hrs at 10° C. (Beckman Coulter Optima LE-80 ultracentrifuge) to pellet viral particles (and other particles), which were then re-suspended in 100 µl HBBS which was then treated with 14 U of Turbo DNase (Ambion) and 2 µl of 10 mg/ml RNase A at 37 C for 2 hours to digest non-particle protected (naked) nucleic acids. 140 µl total viral nucleic acids (both RNA and DNA) were extracted with QIAAMP Viral RNA Mini Kit and released into 40 µl water plus 20 U recombinant RNase inhibitor (Roche). 11 µl of extracted nucleic acid was treated for viral RNA amplification as described (Kapoor et al., J Virol 82:311-20, 2008). 1 µl was also mixed with 1.5 µl of 10× Ecopol buffer (New England Biolabs), a 1 R1 solution containing each dNTP at 10 mM, and 1 µl of 50 µM primer RA01 (GCCGGAGCTCTG-CAGATATCNNNNNNNNNN) (SEQ ID NO:60). After a denaturation step at 94° C. for 3 min and chilling on ice (to anneal primer RA01 to DNA), 2.5 units of 3'-5' exo-Klenow DNA polymerase (New England Biolabs) was added to extend RA01 and incubated at 37° C. for 1 h. The denaturation, RA01 annealing, Klenow elongation steps was then repeated once with the addition of 2.5 units of fresh 3'-5' exo-Klenow DNA polymerase after chilling followed by 75° C. for 10 min. 7.5 µl of the Klenow-treated product was then used as a template in a subsequent 50 ul PCR consisting of AMPLITAQ GOLD PCR buffer 11 (10 mM Tris-HCl [pH 8.3], 50 mM KCl) (Applied Biosystems), 3 mM $MgCl_2$, each dNTP at 0.3 mM, 1 µM of primer RA02 (GCCGGAGCTCT-GCAGATATC) (SEQ ID NO:61), and 2.5 units of AMPLI-TAQ GOLD DNA polymerase LD (Applied Biosystems). An initial denaturation step for 5 min at 95° C. was followed by 40 cycles of PCR (95° C. for 1 min, 55° C. for 1 min, and 72° C. for 2 min). Random PCR products were then separated on a 1.5% agarose gel, and DNA smears ranging in size from approximately 400 to 1,500 bp were excised and extracted using the QIAQUICK gel extraction kit (Qiagen). Equal volumes of the eluted, purified PCR products generated from nuclease resistant DNA and the randomly amplified PCR product generated from nuclease resistant RNA were mixed together, ligated into the pGEMT-EASY vector (Promega) and introduced into chemically competent *Escherichia coli* TOP-10 cells (Topo One Shot; Invitrogen).

For HBoV and HBoV2 PCR 140 µl of clarified stool supernatant was extracted into 60 µl $H_2O$ using the Qiagen MinElute kit. 12 µl of nucleic acid was used in the PCR. Feces from the UK were tested in pools of ten and then resolved to single sample. HBoV was tested using the nested PCR conditions previously described (Manning et al., J Infect Dis 194:1283-90, 2006). HBoV2 was tested using first round PCR primers: HBoV2-sf1 AACAGATGGGCAAGCA-GAAC (SEQ ID NO:62) and HBoV2-sr1 AGGACAAAG-GTCTCCAAGAGG (SEQ ID NO:63). Second round PCR primers were: HBoV2-sf2 TGCTTCAACAGGCAAAA-CAA (SEQ ID NO:64) and HBoV2-sr2 TCCAAGAG-GAAATGAGTTTGG (SEQ ID NO:65) amplifying a 454 nucleotide region within the NS open reading frame (ORF). PCR were in 50 µl volume at a final $MgCl_2$ concentration of 1.5 mM, using GOTAQ (Promega), and 0.4 µM of each primer. First round cycling was at 95 C for 45 sec., 55 C for 1 min., 72 C for 1 min. for 5 cycles followed by 95 C for 30 sec., 53 C for 30 sec., 72 C for 45 sec. for 35 cycles. Similar conditions were used for the second round except that the first and second annealing temperatures were 53 C and 50 C. The PCR were analyzed by agarose gel electrophoresis and the positive PCR directly sequenced. The sensitivity of the HBoV2 PCR was measured using dilutions of a NS plasmid subclone. 10, 5 and 1 plasmid copies were detected in 10/10, 8/10 and 2/10 PCR respectively.

The resulting random PCR products derived from nuclease resistant, viral-sized particles associated RNA and DNA were subcloned and plasmids inserts sequenced. The resulting sequences were analyzed by tBLASTx against Genbank database. The viral 5' and 3' extremities of HBoV2 were amplified using a modification of RACE (rapid amplification of cDNA ends) (Jones et al., J Virol 79:8230-6, 2005). Conditions for HBoV and HBoV2 PCR are described above.

Sequence distances for different genomic regions were measured using built in functions in the Simmonics2005 sequence editor v1.6. Trees were constructed from pairwise nucleotide and amino acid sequence distances by neighbour-joining in the MEGA2 package. The robustness of groupings was calculated by bootstrap re-sampling of 1000 replicates of the data.

Viral-sized particles were first purified from two consecutive stool samples from a Pakistani child with AFP. Nuclease resistant (i.e. capsid protected) viral nucleic acids were then extracted and randomly amplified (see above). The resulting random amplification products were subcloned and 97 plasmid inserts were sequenced and analyzed by tBLASTx.

Exact sequence matches were found in Genbank to human sequences as well as to *Micrococcus luteus, Pseudomonas fluorescens* and uncultured bacterium sequences. Highly significant but imperfect matches (E score <$10^{-10}$) we also found to *Chlamydophila pneumoniae, Rhodoferax ferrireducens* and numerous bacteriophages. A single perfect sequence match was found to human poliovirus 1 vaccine strain Sabin 1. The detection of a polio Sabin 1 viral sequence likely reflected ongoing replication of orally administered polio vaccine in this child of 36 months who had previously received a total of 14 oral polio vaccinations.

11/47 plasmid sequences from the first stool sample (plus 19/48 from the second time point) gave highly significant tBLASTx E scores to the HBoV genome reference sequence (NC$_{13}$ 007455). PCR was then used to link the different HBoV-like fragments while 5' and 3' RACE were used to amplify the viral extremities. 5196 bases of a novel bocavirus genome were assembled. Based on the ST2 prototype genome sequence of HBoV it is estimated that at least 7 bases may be missing from the 5' end, while the genome described here extends for a further 25 bases at the 3' end. Because the closest genetic relative of this new virus was HBoV, it was termed HBoV2.

The arrangement of ORF's in the prototypic HBoV2 genome was similar to that of HBoV, with three large, coding sequences (FIG. 13). The 5'NS1ORF is required for viral DNA replication and the regulation of viral gene expression. Its protein sequence identity with HBoV was 78% and was co-linear through the gene. The second ORF, NP1, was 4 amino acid shorter and 67% identical. NP1 is a protein of unknown function restricted to bocaviruses (Schwartz et al., Virology 302:219-23, 2002; and Chen et al., J Virol 60:1085-97, 1986). The third large ORF encoded a protein with 80% identity to the VP1/VP2 of HBoV. Relative to the HBoV coding sequence, the VP1 of HBoV2 was preceded by a 25 amino acids methionine initiated ORF stretch and a four amino acid deletion downstream resulting in a slightly larger VP1. Through comparison with HBoV, the VP2 protein of HBoV2 was predicted to start at the 154th amino acid of the third large ORF.

To investigate whether PCR assays for HBoV would be able to amplify HBoV2, the PCR primers from the literature used for HBoV (Allander et al., Proc Natl Acad Sci U S A 102:12891-12896, 2005; Manning et al., J Infect Dis 194: 1283-90, 2006; Sloots et al., J Clin Virol 35:99-102, 2006; Endo et al., J Clin Microbiol 45:3218-23, 2007; Bastien et al., Emerg Infect Dis 12:848-50, 2006; Smuts et al., Emerg Infect Dis 12:1457-8, 2006; Kesebir et al., J Infect Dis 194:1276-82, 2006; Bastien et al., J Clin Microbiol 45:610-3, 2007; Chung et al., Emerg Infect Dis 12:1254-6, 2006; Foulongne et al., Emerg Infect Dis 12:862-3, 2006; Qu et al., Emerg Infect Dis 13:165-8, 2007; and Albuquerque et al., Emerg Infect Dis 13:1756-8, 2007) were aligned with the homologous regions of HBoV2. Most PCR primers contained a substantial number of mismatches with HBoV2 that would preclude or greatly reduce the efficiency of amplification and amplicon detection.

Figure 14:
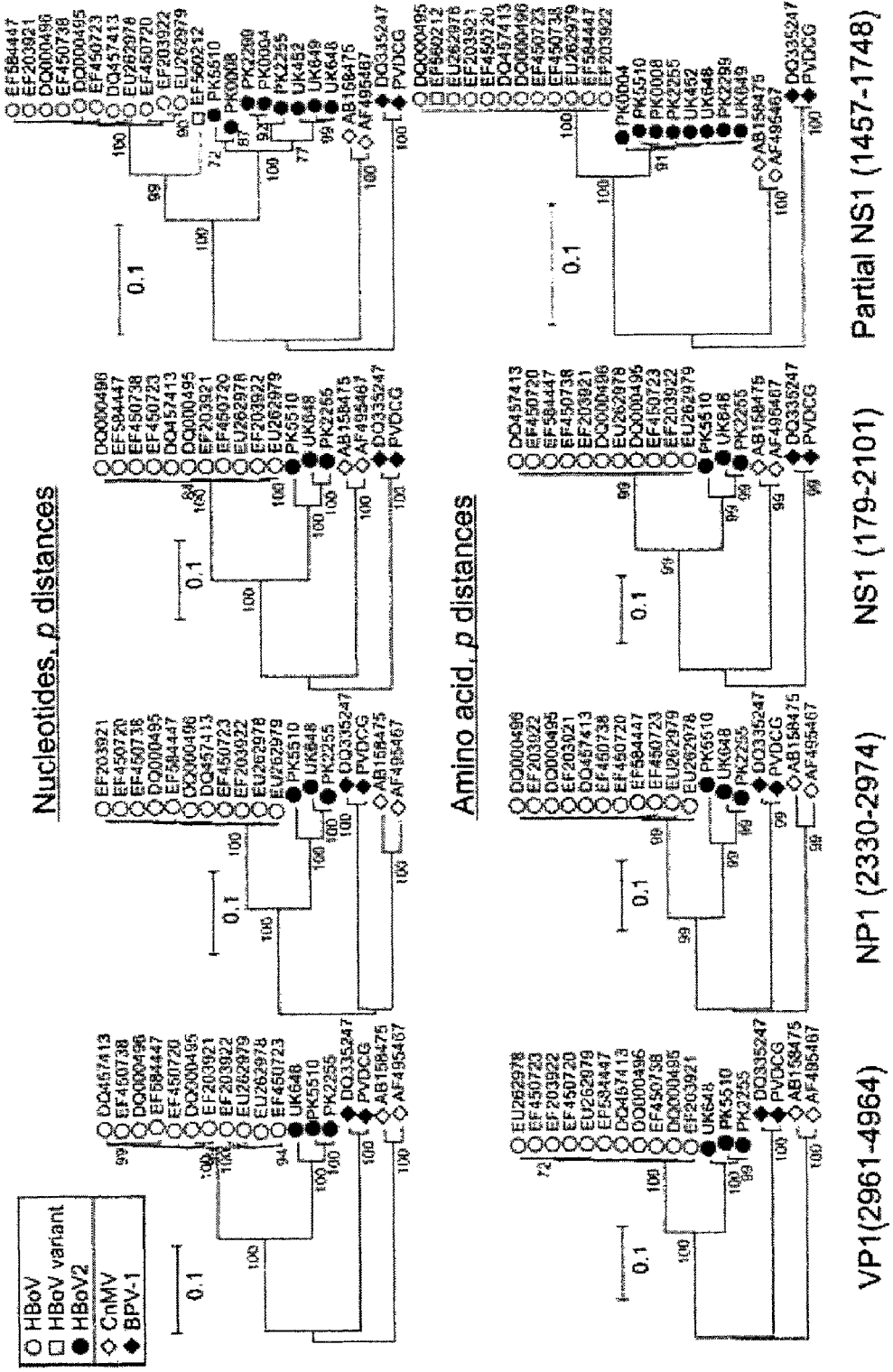
FIG. 14 shows a phylogenetic analysis of Bocaviruses. The 3 major open reading frames were analyzed using both nucleotide and protein sequences of representative variants of HBoV, HParV5, CnMV (Canine minute virus) and BPV-1 (Bovine parvovirus-1). Analysis of the partial sequence of NS1 was used to show phylogenetic relationships of between a larger number of samples amplified by PCR; it also corresponded to the region of the partially sequenced Brazilian HBoV variant (EF560212).

To determine the relationship of HBoV2 to other members of the Bocavirus genus, phylogenetic analyses were performed for the three large ORFs (VP1/2, NP-1 and NS) using both nucleotide and deduced protein sequences (FIG. 14). The prototype HBoV2 variant (PK5510), while more closely related to HBoV than the animal bocaviruses, CnMV and BPV-1, consistently adopted an outlier position to the clade containing all the published HBoV sequences in all three genomic regions. Reflecting this, pairwise nucleotide distances between HBoV2 and HBoV were substantially greater (22-26%) than within the HBoV clade (0.4-0.9%) (Table 1), but less than between HBoV or HBoV2 sequences and animal bocaviruses (46-56%). Similarly, while almost no amino acid sequence variability was observed among HBoV sequences in any genomic region (0.2-0.5%), sequences of all three major genes differed substantially from HBoV2 (20-33%). An unusual partial NS1 HBoV sequence has been reported in Brazil and adopted an intermediate position between HBoV and HBoV2 on phylogenetic analysis (FIG. 14 Partial NS1 EF560212). Interestingly this Brazilian HBoV sequence was derived from the feces of a child with gastrointestinal symptoms (Albuquerque et al., Emerg Infect Dis 13:1756-8, 2007).

TABLE 1

Nucleotide and protein sequence comparisons among and between bocaviruses.

| Comparison Region | Comps. | Nucleotide | Amino acid | dN/dS |
|---|---|---|---|---|
| A) Main ORFs | | | | |
| Within HBoV2: VP1/2 | 3 | 3.1% | 1.1% | 0.094 |
| Within HBoV2: NP1 | 3 | 5.9% | 8.7% | 0.348 |
| Within HBoV2: NS1 | 3 | 5.8% | 4.3% | 0.103 |
| Within HBoV: VP1/2 | 55 | 0.9% | 0.5% | 0.075 |

TABLE 1-continued

Nucleotide and protein sequence comparisons among and between bocaviruses.

| Comparison Region | Comps. | Nucleotide | Amino acid | dN/dS |
|---|---|---|---|---|
| Within HBoV: NP1 | 55 | 0.4% | 0.3% | 0.103 |
| Within HBoV: NS1 | 55 | 0.4% | 0.2% | 0.068 |
| HBoV-HBoV2: VP1/2 | 33 | 22.2% | 20.2% | <0.13* |
| HBoV-HBoV2: NP1 | 33 | 22.9% | 32.9% | <0.38* |
| HBoV-HBoV2: NS1 | 33 | 26.2% | 27.8% | <0.19* |
| HBoV2-B/CnPV: VP1/2 | 12 | 46.2-46.3% | 51.9-53.2% | n.c. |
| HBoV2-B/CnPV: NP-1 | 12 | 47.0-52.3% | 59.7-61.3% | n.c. |
| HBoV2-B/CnPV: NS1 | 12 | 51.3-55.8% | 60.6-65.1% | n.c. |
| B) Partial NS1 region (positions 1457-1748) | | | | |
| Within HBoV2 genotypes: | 7 | 0.9% | 0.3% | 0.022 |
| Within HBoV (main group): | 55 | 0.7% | 0.0% | 0.000 |
| Between HBoV2 genotypes: | 21 | 4.5% | 0.6% | 0.007 |
| HBoV-EF560212: | 11 | 9.0% | 1.1% | 0.003 |
| HBoV-HBoV2: | 88 | 18.0% | 8.3% | 0.071 |

To determine the prevalence of human bocaviruses nested PCR primers specifically targeting HBoV and HBoV2 NS region were used. DNA from the stool samples of 57 Pakistani children with AFP and 41 healthy Pakistani children, plus 699 stool samples submitted for enteric bacteriology screening in Edinburgh were analyzed. A total of three AFP stool samples (including the original patient 5510) and two stools from healthy Pakistani children were positive for HBoV2 DNA sequences (ages were 12, 16, 36, 36, and 96 months). HBoV was not found among the 57 AFP stools. The stool samples from the UK were tested in pools of 10 samples in which two HBoV (ages 1-2 years and 3-5 years) and three HBoV2 (ages 0-3 months, 6-12 months and >65 years) positive samples were identified.

To investigate the genetic diversity of HBoV2, the partial NS region amplicons from the Pakistan and UK samples were sequenced and compared to prototypic HBoV2 and other available human and animal bocavirus sequences (FIG. 14, Partial NS1). Although this initial survey was small, HBoV2 variants fell into 3 groups or genotypes (gts) showing 4.5% sequence divergence from each other in this region of the bocavirus genome (Table 1), a level of diversity much greater than observed between known variants of HBoV (0.7% in this region). HBoV diversity was more comparable to mean diversity seen within any of the three HBoV2 genotype (0.9%).

Figure 15:
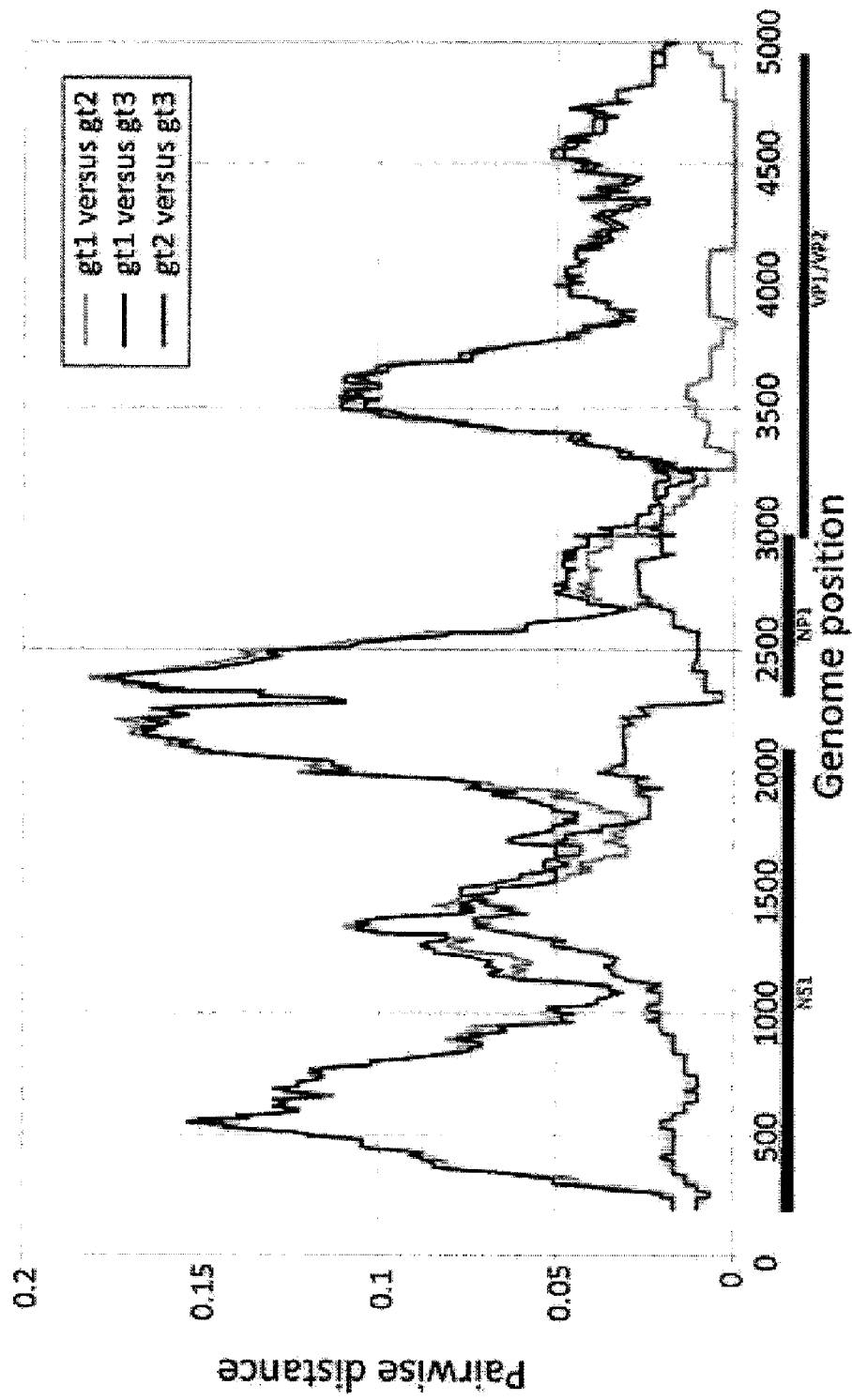
FIG. 15 shows a sequence divergence scan of the complete genome sequences of Bocavirus-2 variants (gt1: HBoV2A-PK5510; gt2: HBoV2A-PK2255; gt3: HBoV2A-UK648).

To further investigate HBoV2 diversity, near complete genome sequences were obtained of representatives of the other two NS1 based genotypes (gt 1: HBoV2 prototype PK5510, gt2: PK2255, and gt3: UK648). Neither HBoV2 variant contained the methionine initiated 25 amino acid stretch seen upstream of VP1 in PK5510 prototype but had otherwise identical length NS1 and NP1 genes (except from NP1 of PK5510 that was one amino acid shorter). As observed for HBoV, sequence divergence within HBoV2 was highly conservative, with very low dN/dS ratios in all three genome regions (Table 1). Despite the approximately equal degrees of sequence divergence between the HBoV2 genotypes in the partial region of NS1 initially sequenced, phylogenetic relationships varied in different genome regions (FIG. 14). The gt1-PK5510 and gt2-PK2255 variants clustered closely in VP1, with gt3-UK648 as a outlier, while gt3-UK648 and gt2-PK2255 clustered in the NP1 and NS1 genes with gt1-PK5510 as the outlier (FIG. 14). Using sliding window analysis of pair-wise nucleotide distances over the HBoV2 genome, gt:2-PK2255 and gt3-UK648 showed a lower level of divergence relative to the other two pair-wise comparisons in the NS1 and NP1 regions (FIG. 15) while gt1-PK5510 and gt2-PK2255 were nearly identical in the VP1/VP2 region (FIG. 15). Discordant phylogenies and inconsistent sequence divergence values between HBoV2 variants is consistent with the occurrence of complex recombination events in the evolution of these viruses. Putative breakpoints were located near the middle and 3' end of NS1 and potentially more recently (i.e., recombinants showing a lower level of divergence) near the beginning of the VP1/VP2.

Based on the VIIth report of the International Committee on Taxonomy of Viruses (ICTV), different bocavirus species should show NS gene nucleotide sequence similarities below 95%. HBoV2, showing 75.6% nucleotide similarity to its closest relative HBoV therefore qualifies as a new human parvovirus and the fourth species in the Bocavirus genus following BPV, CnMV and HBoV. It is believed that this terminology is more appropriate than its alternative possible name as HBoV genotype 2 because genotypes of other parvoviruses, such as those reported for B19 and PARV4 are much less divergent from each other and do not qualify as separate species using ICTV guidelines.

HBoV2 divergence also likely precluded its detection using HBoV based PCR. Thus the epidemiological and clinical information on human bocavirus collected to date refers exclusively to HBoV, and the available sample archives of clinical specimens will have to be screened again with HBoV2-specific primers to investigate its frequency and potential disease associations.

Because parvoviruses are particularly hard to inactivate using heat and detergent treatment they are of special concern in blood product transfusions and some countries screen for parvovirus B19 DNA to exclude highly viremic donations from blood derived products. The development of serological assays, as recently achieved for HBoV (Kantola et al., Clin Infect Dis 46:540-6, 2008; and Endo et al., J Clin Microbiol 45:3218-23, 2007), will allow larger epidemiological studies to measure the rate of seroconversion in different age and geographic cohorts and whether detection of IgM and rise in IgG titers are associated with particular symptoms.

Three genotypes of HBoV2 were characterized whose genetic distances to one another (in partial NS1 sequences) were comparable to those measured between B19 or PARV4 genotypes. The HBoV2 genotype geographic distribution appeared different with all three HBoV2 gt3 being derived from the UK while both genotype 1 and 2 where found in Pakistan. Recombination events among HBoV2 variants were also observed as recently reported for animal parvoviruses (Shackelton et al., J Gen Virol 88:3294-301, 2007). The existence of geographic clustering, further genotypes, and different patterns of recombination will require further screening of samples from a wider geographical base. If HBoV2 is found archived in tissue as shown for B19 and PARV4 (Manning et al., J Infect Dis 195:1345-52, 2007; Hokynar et al. Virology 302:224-8, 2002; Norja et al., PNAS103:7450-3, 2006; and Norja et al., J Virol, 2008) the possibility of past epidemic waves of different HBoV2 genotypes will also be testable using tissues from cohorts of different ages.

Although the detection of HBoV2 was limited to fecal samples in the current study, its detection in stools from 5 Pakistani children lends further supports to the gastrointestinal tract as a site of replication of human bocaviruses. The detection of HBoV2 in the stool of 3 UK residents (2 being less then 12 months old and 1>65years old) also indicates that this virus is not restricted to South Asia nor to young children.

What is claimed is:

1. An isolated nucleic acid molecule comprising a nucleotide sequence having at least 80% identity to SEQ ID NO:1, SEQ ID NO:9, SEQ ID NO:13, SEQ ID NO:17, SEQ ID NO:25, SEQ ID NO:43, SEQ ID NO:49, or a complement thereof.

2. An isolated nucleic acid molecule comprising a nucleotide sequence hybridizes under highly stringent conditions over the full length of SEQ ID NO:1, SEQ ID NO:9, SEQ ID NO:13, SEQ ID NO:17, SEQ ID NO:25, SEQ ID NO:43, SEQ ID NO:49, or a complement thereof, wherein the hybridization reaction is incubated at 42° C. in a solution comprising 50% formamide, 5×SSC, and 1% SDS and washed at 65° C. in a solution comprising 0.2×SSC and 0.1% SDS.

3. The nucleic acid molecule of claim 1, wherein the nucleotide sequence is at least 85% identical to SEQ ID NO:1, SEQ ID NO:9, SEQ ID NO:13, SEQ ID NO:17, SEQ ID NO:25, SEQ ID NO:43, SEQ ID NO:49, or a complement thereof.

4. The nucleic acid molecule of claim 1, wherein the nucleotide sequence is at least 90identical to SEQ ID NO:1, SEQ ID NO:9, SEQ ID NO:13, SEQ ID NO:17, SEQ ID NO:25, SEQ ID NO:43, SEQ ID NO:49, or a complement thereof.

5. The nucleic acid molecule of claim 1, wherein the nucleotide sequence is at least 95% identical to SEQ ID NO:1, SEQ ID NO:9, SEQ ID NO:13, SEQ ID NO:17, SEQ ID NO:25, SEQ ID NO:43, SEQ ID NO:49, or a complement thereof.

6. An isolated nucleic acid molecule comprising a nucleotide sequence selected from the group consisting of SEQ ID NO:1, SEQ ID NO:9, SEQ ID NO:13, SEQ ID NO:17, SEQ ID NO:25, SEQ ID NO:43, SEQ ID NO:49, or a complement thereof.

7. A composition comprising a nucleic acid molecule of claim 1.

8. An isolated Bocavirus comprising a nucleic acid molecule of claim 1.

9. An expression vector comprising a nucleic acid molecule of claim 1.

10. An isolated host cell comprising the expression vector of claim 9.

11. A method of detecting a Bocavirus nucleic acid comprising:
   a) contacting a sample suspected of containing a Bocavirus nucleic acid with a nucleotide sequence that hybridizes under highly stringent conditions to a nucleotide sequence of SEQ ID NO:1, SEQ ID NO:9, SEQ ID NO:13, SEQ ID NO:17, SEQ ID NO:25, SEQ ID NO:43, SEQ ID NO:49, or a complement thereof; and
   b) detecting the presence or absence of hybridization wherein the highly stringent conditions comprise an incubation at 42° C. in a solution comprising 50% formamide, 5X SSC, and 1% SDS and an washing at 65° C. in a solution comprising 0.2X SSC and 0.1% SDS.

* * * * *